US009145354B2

(12) United States Patent
Woodhead et al.

(10) Patent No.: US 9,145,354 B2
(45) Date of Patent: Sep. 29, 2015

(54) PHARMACEUTICAL COMPOUNDS

(71) Applicant: ASTEX THERAPEUTICS LIMITED, Cambridge (GB)

(72) Inventors: Andrew James Woodhead, Cambridge (GB); Christopher Charles Frederick Hamlett, Cambridge (GB); Gilbert Ebai Besong, Bad Duerkheim (DE); Gianni Chessari, Cambridge (GB); Maria Grazia Carr, Cambridge (GB); Alessia Millemaggi, Cambridge (GB); David Norton, Cambridge (GB); Susanne Maria Saalau-Bethell, Cambridge (GB); Hendrika Maria Gerarda Willems, Cambridge (GB); Neil Thomas Thompson, Cambridge (GB); Steven Douglas Hiscock, Royston (GB)

(73) Assignee: ASTEX THERAPEUTICS LIMITED, Cambridge (GB)

(*) Notice: Subject to any disclaimer, the term of this patent is extended or adjusted under 35 U.S.C. 154(b) by 0 days.

(21) Appl. No.: 14/355,786

(22) PCT Filed: Oct. 31, 2012

(86) PCT No.: PCT/EP2012/071573
§ 371 (c)(1),
(2) Date: May 1, 2014

(87) PCT Pub. No.: WO2013/064543
PCT Pub. Date: May 10, 2013

(65) Prior Publication Data
US 2015/0051199 A1 Feb. 19, 2015

Related U.S. Application Data

(60) Provisional application No. 61/554,237, filed on Nov. 1, 2011, provisional application No. 61/554,421, filed on Nov. 1, 2011, provisional application No. 61/625,925, filed on Apr. 18, 2012.

(30) Foreign Application Priority Data

Nov. 1, 2011 (GB) .................................. 1118874.5
Nov. 1, 2011 (GB) .................................. 1118875.2

(51) Int. Cl.
*C07C 225/16* (2006.01)
*C07D 213/73* (2006.01)
(Continued)

(52) U.S. Cl.
CPC ............. *C07C 225/16* (2013.01); *A61K 9/0019* (2013.01); *A61K 9/2018* (2013.01);
(Continued)

(58) Field of Classification Search
None
See application file for complete search history.

(56) References Cited

U.S. PATENT DOCUMENTS 5,212,320 A  5/1993 Okada et al.
6,011,068 A  1/2000 Nemeth et al.
(Continued)

FOREIGN PATENT DOCUMENTS

CA  2111035 A1  6/1994
(Continued)

OTHER PUBLICATIONS

International Search Report on PCT/EP2012/071753 dated Oct. 21, 2013.
(Continued)

*Primary Examiner* — Timothy R Rozof
(74) *Attorney, Agent, or Firm* — Heslin Rothenberg Farley & Mesiti P.C.

(57) ABSTRACT

The invention provides compounds that are useful in the treatment of hepatitis C virus (HCV) infections. The compounds have the formula (1):

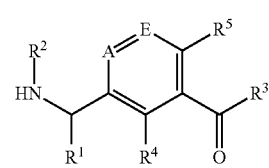

(1)

or a salt, N-oxide, tautomer or stereoisomer thereof, wherein A is CH or N; E is CH or N;
$R^1$ is selected from:
an optionally substituted acyclic $C_{1-8}$ hydrocarbon group wherein one carbon atom of the acyclic $C_{1-8}$ hydrocarbon group may optionally be replaced by O, S, $NR^c$, S(O) or $SO_2$, or two adjacent carbon atoms of the acyclic $C_{1-8}$ hydrocarbon group may optionally be replaced by $CONR^c$, $NR^cCO$, $NR^cSO_2$ or $SO_2NR^c$ provided that in each case at least one carbon atom of the acyclic $C_{1-8}$ hydrocarbon group remains; and
an optionally substituted monocyclic carbocyclic or heterocyclic group of 3 to 7 ring members, of which 0, 1, 2, 3 or 4 are heteroatom ring members selected from O, N and S;
$R^2$ is hydrogen or $X—R^8$;
X is a $C_{1-8}$ alkanediyl group wherein one carbon atom of the $C_{1-8}$ alkanediyl group may optionally be bonded to a $—CH_2—CH_2—$ moiety to form a cyclopropane-1,1-diyl group or two adjacent carbon atoms of the $C_{1-8}$ alkanediyl group may optionally be bonded to a $—(CH_2)_n$ moiety, where n is 1 to 5, to form a $C_{3-7}$-cycloalkane-1,2-diyl group;
$R^3$ is an optionally substituted 3- to 10-membered monocyclic or bicyclic carbocyclic or heterocyclic ring containing 0-3 heteroatom ring members selected from N, O and S;
$R^4$ is hydrogen or $R^{4a}$ wherein $R^{4a}$ is halogen; cyano; $C_{1-4}$ alkyl; fluoro-$_{1-4}$ alkyl; $C_{1-4}$ alkoxy; fluoro-$C_{1-4}$ alkoxy; hydroxy-$C_{1-4}$ alkyl; or $C_{1-2}$ alkoxy-$C_{1-4}$ alkyl;
$R^5$ is hydrogen or $R^{5a}$ wherein $R^{5a}$ is selected from $C_{1-2}$ alkyl optionally substituted with fluorine; $C_{1-3}$ alkoxy optionally substituted with fluorine; halogen; cyclopropyl; and cyano;
$R^8$ is hydroxy or $C(=O)NR^{10}R^{11}$; provided that when $R^8$ is hydroxy, there are at least two carbon atoms in line between the hydroxy group and the nitrogen atom to which X is attached;
$R^{10}$ is hydrogen or $C_{1-4}$ alkyl; and
$R^{11}$ is hydrogen; amino-$C_{2-4}$ alkyl or hydroxy-$C_{2-4}$ alkyl; but excluding the compounds 1-(3-benzoylphenyl)-ethylamine and 1-(3-furan-2-oylcarbonylphenyl)-ethylamine.

18 Claims, 2 Drawing Sheets

(51) Int. Cl.

| | | |
|---|---|---|
| C07D 213/74 | (2006.01) | |
| C07C 255/58 | (2006.01) | |
| C07D 213/79 | (2006.01) | |
| C07D 213/81 | (2006.01) | |
| C07D 213/84 | (2006.01) | |
| C07D 213/89 | (2006.01) | |
| C07D 231/12 | (2006.01) | |
| C07D 401/04 | (2006.01) | |
| C07D 239/26 | (2006.01) | |
| C07D 239/38 | (2006.01) | |
| C07C 225/18 | (2006.01) | |
| C07D 241/20 | (2006.01) | |
| C07D 261/08 | (2006.01) | |
| C07D 277/28 | (2006.01) | |
| C07D 498/04 | (2006.01) | |
| C07D 213/50 | (2006.01) | |
| C07D 213/64 | (2006.01) | |
| C07D 213/65 | (2006.01) | |
| C07C 225/22 | (2006.01) | |
| C07C 229/38 | (2006.01) | |
| C07C 237/06 | (2006.01) | |
| C07C 237/10 | (2006.01) | |
| C07C 237/24 | (2006.01) | |
| C07C 237/30 | (2006.01) | |
| A61K 9/00 | (2006.01) | |
| A61K 9/20 | (2006.01) | |
| A61K 9/48 | (2006.01) | |
| C07C 313/06 | (2006.01) | |
| A61K 31/138 | (2006.01) | |
| A61K 31/277 | (2006.01) | |
| A61K 31/42 | (2006.01) | |
| A61K 31/425 | (2006.01) | |
| A61K 31/44 | (2006.01) | |
| A61K 31/4965 | (2006.01) | |
| A61K 31/505 | (2006.01) | |
| A61K 31/5383 | (2006.01) | |
| A61K 45/06 | (2006.01) | |
| C07C 221/00 | (2006.01) | |
| C07C 253/30 | (2006.01) | |
| C07D 275/02 | (2006.01) | |
| A61K 47/10 | (2006.01) | |
| A61K 47/26 | (2006.01) | |
| A61K 9/19 | (2006.01) | |

(52) U.S. Cl.
CPC ............. *A61K9/4858* (2013.01); *A61K 31/138* (2013.01); *A61K 31/277* (2013.01); *A61K 31/42* (2013.01); *A61K 31/425* (2013.01); *A61K 31/44* (2013.01); *A61K 31/4965* (2013.01); *A61K 31/505* (2013.01); *A61K 31/5383* (2013.01); *A61K 45/06* (2013.01); *C07C 221/00* (2013.01); *C07C 225/18* (2013.01); *C07C 225/22* (2013.01); *C07C 229/38* (2013.01); *C07C 237/06* (2013.01); *C07C 237/10* (2013.01); *C07C 237/24* (2013.01); *C07C 237/30* (2013.01); *C07C 253/30* (2013.01); *C07C 255/58* (2013.01); *C07C 313/06* (2013.01); *C07D 213/50* (2013.01); *C07D 213/64* (2013.01); *C07D 213/65* (2013.01); *C07D 213/73* (2013.01); *C07D 213/74* (2013.01); *C07D 213/79* (2013.01); *C07D 213/81* (2013.01); *C07D 213/84* (2013.01); *C07D 213/89* (2013.01); *C07D 231/12* (2013.01); *C07D 239/26* (2013.01); *C07D 239/38* (2013.01); *C07D 241/20* (2013.01); *C07D 261/08* (2013.01); *C07D 275/02* (2013.01); *C07D 277/28* (2013.01); *C07D 401/04* (2013.01); *C07D 498/04* (2013.01); *A61K 9/19* (2013.01); *A61K 47/10* (2013.01); *A61K 47/26* (2013.01); *C07B 2200/05* (2013.01); *C07C 2101/02* (2013.01)

(56) References Cited

U.S. PATENT DOCUMENTS

| | | |
|---|---|---|
| 6,054,457 A | 4/2000 | Setoi et al. |
| 6,204,293 B1 | 3/2001 | Sebti et al. |
| 6,316,482 B1 | 11/2001 | Setoi et al. |
| 6,586,475 B1 | 7/2003 | Kato et al. |
| 6,639,109 B1 | 10/2003 | Sanpei et al. |
| 6,831,175 B2 | 12/2004 | Li et al. |
| 2003/0096844 A1 | 5/2003 | Kozlowski et al. |
| 2003/0199511 A1 | 10/2003 | Li et al. |
| 2003/0232859 A1 | 12/2003 | Kozlowski et al. |
| 2005/0228020 A1 | 10/2005 | Miyamoto et al. |
| 2007/0099929 A1 | 5/2007 | Thede et al. |
| 2009/0286782 A1 | 11/2009 | Ibrahim et al. |
| 2009/0306086 A1 | 12/2009 | Ibrahim et al. |
| 2010/0021423 A1 | 1/2010 | Brameld et al. |

FOREIGN PATENT DOCUMENTS

| | | |
|---|---|---|
| DE | 4241632 A1 | 6/1994 |
| EP | 0268396 A1 | 5/1988 |
| EP | 0320032 A1 | 6/1989 |
| GB | 2467561 A | 8/2010 |
| WO | 96/41795 A1 | 12/1996 |
| WO | 98/50030 A1 | 11/1998 |
| WO | 99/26614 A1 | 6/1999 |
| WO | 00/31021 A1 | 6/2000 |
| WO | 00/39082 A2 | 7/2000 |
| WO | 01/23350 A1 | 4/2001 |
| WO | 01/87293 A1 | 11/2001 |
| WO | 02/36734 A2 | 5/2002 |
| WO | 02/100846 A1 | 12/2002 |
| WO | 03/051366 A2 | 6/2003 |
| WO | 03/099777 A1 | 12/2003 |
| WO | 2005/009940 A1 | 2/2005 |
| WO | 2005/063734 A2 | 7/2005 |
| WO | 2005/123671 A1 | 12/2005 |
| WO | 2007/022900 A1 | 3/2007 |
| WO | 2007/022901 A1 | 3/2007 |
| WO | 2007/060215 A2 | 5/2007 |
| WO | 2007/066784 A2 | 6/2007 |
| WO | 2008/044667 A1 | 4/2008 |
| WO | 2009/009041 A2 | 1/2009 |

OTHER PUBLICATIONS

European Search Report on EP2634185 dated Jun. 21, 2013.
Database Registry, Chemical Abstracts Service, XP002690955, Accession No. 1259674-97-9, (Jan. 18, 2011).
Database Registry, Chemical Abstracts Service, XP002690954, Accession No. 1259916-62-5, (Jan. 19, 2011).

PHARMACEUTICAL COMPOUNDS

CROSS REFERENCE TO RELATED APPLICATIONS

This application is a U.S. national stage filing under Section 371 of International Application No. PCT/EP2012/071573, filed on Oct. 31, 2012, and published in English as WO 2013/064543 A1 on May 10, 2013, and claims priority to British Application No. 1118874.5 filed on Nov. 1, 2011, to British Application No. 1118875.2 filed on Nov. 1, 2011, to U.S. Provisional Application No. 61/554,237 filed on Nov. 1, 2011, to U.S. Provisional Application No. 61/554,421 filed on Nov. 1, 2011, and to U.S. Provisional Application No. 61/625,925 filed on Apr. 18, 2012. The entire disclosures of each of the prior applications are hereby incorporated herein by reference.

This invention relates to novel substituted benzylamine compounds, their use in medicine, and in particular the treatment of hepatitis C virus (HCV) infections. Also provided are pharmaceutical compositions containing the compounds and processes for making them.

RELATED APPLICATIONS

This application is related to and claims the priority dates of UK patent applications numbers GB1118874.5 and GB1118875.2, both filed on Nov. 1, 2011, US provisional patent application Nos. 61/554,237 and 61/554,421, both filed on Nov. 1, 2011, and U.S. provisional application No. 61/625,925 filed on Apr. 18, 2012, the entire contents of each of which are incorporated herein by reference.

BACKGROUND OF THE INVENTION

Hepatitis C is a chronic liver disease affecting an estimated 3% of the global population, and is caused by the hepatitis C virus. Patients infected with the virus run an 85% risk of developing cirrhosis of the liver and of these, 20% will subsequently progress to hepatocellular carcinoma. HCV is recognized as a major cause of end-stage liver disease and the leading cause of liver transplantation in the developed world [Davila, J. A., et al. (2004) *Gastroenterology*, 127, 1372-1380; Liu, C. L. and Fan, S. T. (1997) *Am. J. Surg.*, 173, 358-365; Garcia-Retortillo, M., et al. (2002) *Hepatology*, 35, 680-687; Brown, R. S. (2005) *Nature*, 436, 973-978]. Transplantation is not curative, since HCV-infected transplant recipients infect their donor livers. The disease burden and mortality related to HCV have risen substantially in the last decade and are predicted by the Centre for Disease Control and Prevention to increase further as the population infected, prior to widespread blood screening, ages.

The HCV genome encodes only 10 viral proteins, namely the structural proteins E1, E2 and C, and the non-structural proteins p7, NS2, NS3, NS4a, NS4b, NS5a and NS5b. The NS3 protein is a bi-functional enzyme with a serine protease domain at the N-terminus and an ATP dependent helicase domain at the C-terminus.

The nomenclature set forth in Simmonds et al., (1993) *J Gen Virol*, 74(Pt. 11):2391-2399 is widely used and classifies HCV isolates into six major genotypes 1 to 6 with two or more related subtypes, e.g., 1a, 1b. Additional genotypes 7-10 and 11 have been proposed but the phylogenetic basis on which this classification is based has been questioned, and thus type 7, 8, 9 and 11 isolates have been reassigned as type 6, and type 10 isolates as type 3 (see Lamballerie et al, *J Gen Virol*, 78(Pt.1):45-51 (1997)). The major genotypes have been defined as having sequence similarities of between 55 and 72% (mean 64.5%), and subtypes within types as having 75%-86% similarity (mean 80%) when sequenced in the NS5 region (see Simmonds et al., *J Gen Virol*, 75(Pt. 5):1053-1061 (1994)).

Of the six known genotypes of HCV, genotypes 1a and 1b are the most prevalent worldwide, followed by 3 and 6. The order of genotypic incidence in the UK is 3a (37.2%), 1a (30.7%), 1b (18.4%) and 2b (6.1%) which account for 92.4% of the reported cases, while in the USA 94.3% of reported infections are caused by the 1a (78.9%) and 1b (15.4%) genotypes [HCV database website at http://hcv.lanl.gov/].

The standard therapy for HCV is under review following the approval of telaprevir and boceprevir. The nature and duration of the treatment is dependent on which genotype being treated. For the treatment of infection with HCV genotype 4, the treatment regime remains a combination of weekly injections of pegylated interferon α and daily oral administration of ribavirin for a period of 48 weeks. For the treatment of infection by HCV genotype 1, the treatment regime comprises the administration of pegylated interferon α and the twice daily oral administration of ribavirin plus the three times daily oral administration of telapravir or boceprevir. For the treatment of infection by HCV genotypes 2 and 3, the treatment regime comprises the administration of pegylated interferon α and twice daily oral administration of 400 mg of ribavirin for twenty four weeks. The treatment of HCV infections is costly and is associated with numerous severe side effects, including psychiatric disorders (depression, headaches), neutropaenia, pancreatitis, diabetes, hypersensitivity reactions, haemolytic anaemia and fatigue. Ribavirin has been shown to be teratogenic in all animals tested and is contraindicated during pregnancy. Moreover, according to NICE, the treatment with pegylated interferon α ribavirin is only successful in 54-56% of patients infected with the 1a and 1b genotypes, leaving a large group of patients with no treatment alternatives.

Host genetic factors have been found to influence treatment outcome. In particular, a single nucleotide polymorphism (SNP) on chromosome 19, rs1297980, has been shown to have a strong association with response to current standard of care. Patients with the CC genotype of rs1297980 had greater than two-fold likelihood to achieve SVR than patients with non CC genotype infected with genotype 1 HCV (Ge et al., Nature 2009; 461:399-401). The trend was also evident in patients infected with GT2 and 3, though the effect was attenuated (Mangia et al, *Gastroenterology* (2010) 139(3): 821-7).

The approval in the US and the European Union of the two NS3/4a active site protease inhibitors, telaprevir and boceprevir, is providing more treatment options to patients, with the National Institute for Clinical Excellence (NICE) issuing guidelines for their use. Both compounds show dramatic and sustained decreases in viral RNA levels in patients, but suffer from poor PK profiles and require high dosing regimes twice or thrice daily. In addition, both compounds lead to the emergence of resistance mutations [Sarrazin, C., et al. (2007) *Gastroenterology*, 132, 1767-1777; Kim, A. Y. and Timm, J. (2008) Expert *Rev Anti Infect Ther.*, 6, 463-478]. As both compounds bind in the same region of the protease enzyme, mutants demonstrate cross resistance. Alternative therapies based on other HCV molecular targets, as well as second wave and second generation protease inhibitors are at earlier stages in clinical trials. Clinical experience suggests that emerging resistance is likely to be a major problem with most agents, with the possible exception of nucleot(s)ide based inhibitors of NS5b polymerase [Le Pogam, S., et al. (2010) *J.*

*Infect Dis.* 202, 1510-9]. First-line therapies are likely to be combinations of effective agents that demonstrate differential cross resistance [Sarrazin, C. and Zeuzem, S (2010) *Gastroenterology,* 138, 447-462].

Inhibition of the NS3/4a protease activity by small active site directed molecules has been shown to halt viral replication in vitro, in the replicon cell-based assay, in the chimeric mouse model and most importantly in the clinic [Lin, C., et al. (2006) *Infect Disord Drug Targets.* 6, 3-16; Venkatraman, S., et al. (2006) *J. Med. Chem.* 49, 6074-6086; Zhou, Y., et al. (2007) *J. Biol. Chem.* 282, 22619-22628; Prongay, A. J., et al. (2007) *J. Med. Chem.* 50, 2310-2318; and Hezode, C., et al. (2009) *N. Engl. J. Med.* 360, 1839-49.

The HCV NS3 NTPase/helicase functions have also been extensively studied and are considered as potential targets for antiviral therapy [Frick, D. N. (2007) *Curr. Issues Mol. Biol.,* 9, 1-20; Serebrov, V., et al. (2009) *J. Biol. Chem.,* 284 (4), 2512-21. However, no agents are reported to be in clinical development (Swan T. and Kaplan, K. (2012) Hepatitis C Drug Development Goes from Pony Ride to Rocket Launch—The pipeline report 2012 at http://www.pipelinereport.org/toc/HCV).

Agents that inhibit helicase function by competing with the nucleic acid substrate have also been reported [Maga, G., et al. (2005) *Biochem.,* 44, 9637-44]. A recent publication by the group of A. M. Pyle, suggests that the full length NS3 protein must undergo a conformational change to facilitate the formation of the functional complex between the enzyme and substrate RNA [Ding, S. C., et al. (2011) *J. Virol.,* 85(9) 4343-4353]. They propose that an extended conformation, also necessary to allow access of substrates to the protease active site, represents the functionally active form of the full length protein for RNA unwinding. Further support for the extended conformation and protease domain interaction with RNA comes from a study that reports the specific interaction of viral RNA with the NS3 protease active site [Vaughan, R. et al. (2012) Virus Research, 169(1), 80-90, RNA binding by the NS3 protease of the hepatitis C virus, available on line at http://dx.doi.org/10.1016/j.virusres.2012.07.007].

Jhoti et al. *Nature Chemical* Biology, volume 8, number 11, pp 920-925, 2012, doi:10.1038/nchembio.1081, available online (the entire contents of which are incorporated herein by reference) reports the discovery of a highly conserved novel binding site located at the interface between the protease and helicase domains of the Hepatitis C Virus (HCV) NS3 protein. This site is reported to have a regulatory function on the protease activity via an allosteric mechanism. Jhoti et al. propose that compounds binding at this allosteric site inhibit the function of the NS3 protein by stabilising an inactive conformation and thus represent a new class of direct acting antiviral agents.

SUMMARY OF THE INVENTION

The present invention provides compounds which are useful in the treatment or prevention of hepatitis C virus (HCV) infection.

DETAILED DESCRIPTION OF THE INVENTION

Figure 1A:
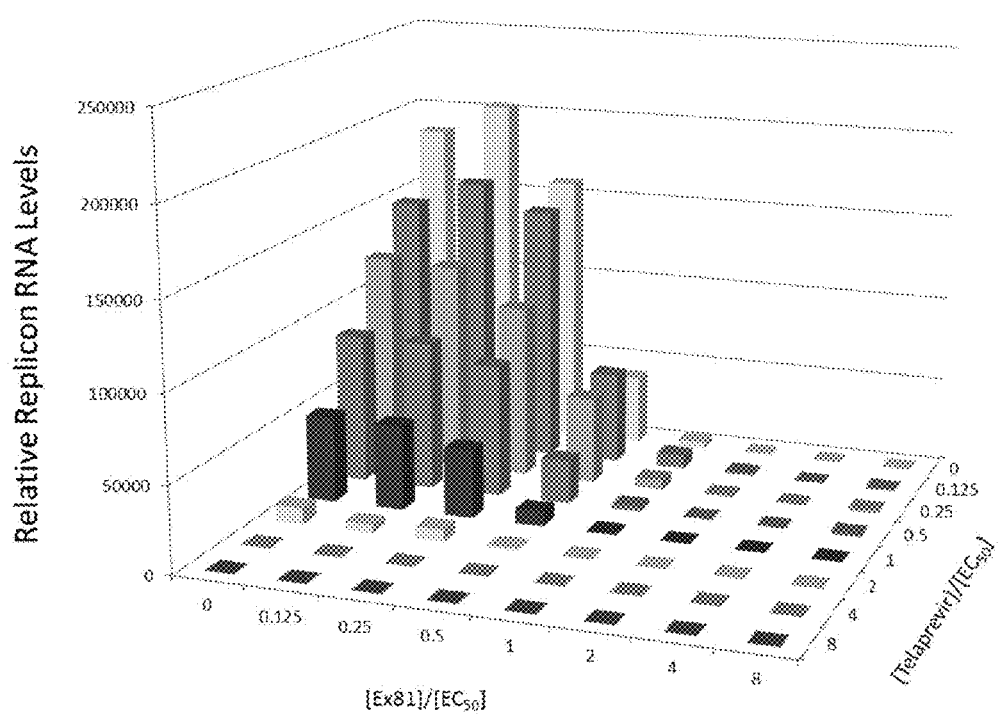
FIG. 1a and 1b are charts that provide $EC_{50}$s of the compound of Example 81, telaprevir and VX-222.

Accordingly, in a first embodiment (Embodiment 1.0), the invention provides a compound of the formula (0):

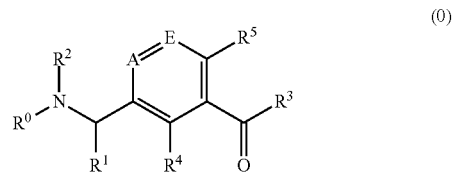

or a salt, N-oxide, tautomer or stereoisomer thereof, wherein:
A is CH or nitrogen;
E is CH or nitrogen;
$R^0$ is hydrogen or $C_{1-2}$ alkyl;
$R^1$ is selected from hydrogen and a group $R^{1a}$:
$R^{1a}$ is selected from;
  $CONH_2$;
  $CO_2H$;
  an acyclic $C_{1-8}$ hydrocarbon group optionally substituted with one or two substituents $R^6$, wherein one carbon atom of the acyclic $C_{1-8}$ hydrocarbon group may optionally be replaced by a heteroatom or group selected from O, S, $NR^c$, S(O) and $SO_2$, or two adjacent carbon atoms of the acyclic $C_{1-8}$ hydrocarbon group may optionally be replaced by a group selected from $CONR^c$, $NR^cCO$, $NR^cSO_2$ and $SO_2NR^c$ provided that in each case at least one carbon atom of the acyclic $C_{1-8}$ hydrocarbon group remains; and
  a monocyclic carbocyclic or heterocyclic group of 3 to 7 ring members, of which 0, 1, 2, 3 or 4 are heteroatom ring members selected from O, N and S, the carbocyclic or heterocyclic group being optionally substituted with one or two substituents $R^{7a}$;
$R^2$ is selected from hydrogen; $R^{2a}$; $-C(=O)R^{2a}$; and $-C(=NH)-NHR^{20}$ where $R^{20}$ is selected from hydrogen and $C_{1-4}$ alkyl;
$R^{2a}$ is selected from an acyclic $C_{1-8}$ hydrocarbon group optionally substituted with one or two substituents $R^8$ wherein one carbon atom of the acyclic $C_{1-8}$ hydrocarbon group may optionally be replaced by a heteroatom or group selected from O and $NR^c$ provided that at least one carbon atom of the acyclic $C_{1-8}$ hydrocarbon group remains; a monocyclic carbocyclic or heterocyclic group of 3 to 7 ring members, of which 0, 1 or 2 ring members are heteroatom ring members selected from O, N and S; and a bicyclic heterocyclic group of 9 or 10 ring members, of which 1 or 2 ring members are nitrogen atoms, one of the rings of the bicyclic heterocyclic group being a non-aromatic nitrogen-containing ring; the monocyclic carbocyclic or heterocyclic group and the bicyclic heterocyclic group each being optionally substituted with one or two substituents $R^{7c}$;
wherein at least one of $R^1$ and $R^2$ is other than hydrogen;
$R^3$ is a 3- to 10-membered monocyclic or bicyclic carbocyclic or heterocyclic ring containing 0, 1, 2 or 3 heteroatom ring members selected from N, O and S, and being optionally substituted with one or more substituents $R^{13}$;
$R^4$ is selected from hydrogen and a substituent $R^{4a}$;
$R^{4a}$ is selected from halogen; cyano; $C_{1-4}$ alkyl optionally substituted with one or more fluorine atoms; $C_{1-4}$ alkoxy optionally substituted with one or more fluorine atoms; hydroxy-$C_{1-4}$ alkyl; and $C_{1-2}$ alkoxy-$C_{1-4}$alkyl;
$R^5$ is selected from hydrogen and a substituent Rya;
$R^{5a}$ is selected from $C_{1-2}$ alkyl optionally substituted with one or more fluorine atoms; $C_{1-3}$ alkoxy optionally substituted with one or more fluorine atoms; halogen; cyclopropyl; cyano; and amino;

$R^6$ is selected from hydroxy; fluorine; carbamoyl; mono- or di-$C_{1-4}$ alkylcarbamoyl; nitro; amino; mono- or di-$C_{1-4}$ alkylamino; a monocyclic carbocyclic or heterocyclic group of 3 to 7 ring members, of which 0, 1 or 2 are heteroatom ring members selected from O, N and S, the carbocyclic or heterocyclic group being optionally substituted with one or two substituents $R^{7b}$;

$R^{7a}$, $R^{7b}$, $R^{7c}$, $R^{7d}$, $R^{7e}$ and $R^7$ are each independently selected from oxo; amino; halogen; cyano; hydroxy; $C_{1-4}$ alkyl; hydroxy-$C_{1-4}$ alkyl; amino-$C_{1-4}$alkyl; mono- and di-$C_{1-4}$ alkylamino-$C_{1-4}$ alkyl;

$R^8$ is selected from hydroxy; halogen; cyano; C(=NH)NHR$^9$; C(=O)NR$^{10}$R$^{11}$; amino; mono- or di-$C_{1-4}$ alkylamino; a non-aromatic monocyclic carbocyclic or heterocyclic group of 3 to 7 ring members, of which 0, 1 or 2 are heteroatom ring members selected from O, N and S, the non-aromatic monocyclic carbocyclic or heterocyclic group being optionally substituted with 1 or 2 substituents $R^{7d}$; and an aromatic heterocyclic group selected from pyrrole, imidazole, pyrazole, indole and pyridone, the aromatic heterocyclic group being optionally substituted with 1 or 2 substituents $R^{7e}$; provided that the carbon atom of the acyclic $C_{1-8}$ hydrocarbon group which is attached directly to the moiety NW cannot be substituted with hydroxy or an N-linked substituent;

$R^9$ is selected from hydrogen, $C_{1-4}$ alkyl and $C_{1-4}$ alkanoyl;

$R^{10}$ is selected from hydrogen and $C_{1-4}$ alkyl;

$R^{11}$ is selected from hydrogen; hydroxy; $C_{1-4}$ alkoxy; amino; mono- or di-$C_{1-4}$ alkylamino; a non-aromatic monocyclic carbocyclic or heterocyclic group of 3 to 7 ring members, of which 0, 1 or 2 are heteroatom ring members selected from O, N and S, the non-aromatic monocyclic carbocyclic or heterocyclic group being optionally substituted with one or two substituents $R^{7f}$; and $C_{1-6}$ alkyl, wherein the $C_{1-6}$ alkyl is optionally substituted with 1, 2 or 3 substituents $R^{12}$;

or NR$^{10}$R$^{11}$ forms a non-aromatic heterocyclic ring having a total of 4 to 7 ring members of which 1 or 2 are nitrogen atoms and the others are carbon atoms, the said non-aromatic heterocyclic ring being optionally substituted with one or more substituents selected from hydroxy, amino and $C_{1-4}$ alkyl;

$R^{12}$ is selected from hydroxy; $C_{1-4}$ alkoxy; cyano; $C_{1-4}$ alkoxycarbonyl; amino; mono- or di-$C_{1-4}$ alkylamino; $C_{3-6}$cycloalkylamino; CONH$_2$; CONH($C_{1-4}$ alkyl); CON($C_{1-4}$alkyl)$_2$ and a group —NH—CH$_2$—Cyc; where Cyc is a benzene, furan, thiophene or pyridine ring;

$R^{13}$ is selected from halogen; cyano; nitro; CH=NOH; and a group $R^a$-$R^b$;

$R^a$ is a bond, O, CO, X$^1$C(X$^2$), C(X$^2$)X$^1$, X$^1$C(X$^2$)X$^1$, S, SO, SO$_2$, NR$^c$, SO$_2$NR$^c$ or NR$^c$SO$_2$;

$R^b$ is hydrogen; a cyclic group $R^d$; or an acyclic $C_{1-8}$ hydrocarbon group optionally substituted with one or more substituents selected from hydroxy, oxo, halogen, cyano, nitro, carboxy, amino, mono- or di-$C_{1-4}$ alkylamino, and a cyclic group $R^d$; wherein one or two but not all of the carbon atoms of the acyclic $C_{1-8}$ hydrocarbon group may optionally be replaced by O, S, SO, SO$_2$, NR$^c$, X$^1$C(X$^2$), C(X$^2$)X$^1$ or X$^1$C(X$^2$)X$^1$; SO$_2$NR$^c$ or NR$^c$SO$_2$;

$R^c$ is hydrogen or $C_{1-4}$ alkyl;

the cyclic group $R^d$ is a monocyclic carbocyclic or heterocyclic group having from 3 to 7 ring members, of which 0, 1, 2 or 3 are heteroatom ring members selected from O, N and S and oxidised forms thereof, the carbocyclic or heterocyclic group being optionally substituted with one or more substituents selected from $R^{14}$; but excluding the combination wherein $R^a$ is a bond and $R^b$ is hydrogen;

$R^{14}$ is selected from oxo; halogen; cyano; and $R^a$-$R^e$;

$R^e$ is hydrogen or an acyclic $C_{1-8}$ hydrocarbon group optionally substituted with one or more substituents selected from phenyl; hydroxy; oxo; halogen; cyano; carboxy; amino; mono- or di-$C_{1-4}$ alkylamino; wherein one or two but not all of the carbon atoms of the acyclic $C_{1-8}$ hydrocarbon group may optionally be replaced by O, S, SO, SO$_2$, NR$^c$, X$^1$C(X$^2$), C(X$^2$)X$^1$ or X$^1$C(X$^2$)X$^1$; SO$_2$NR$^c$ or NR$^c$SO$_2$;

$X^1$ is O or NR$^c$; and $X^2$ is =O or =NR$^c$;

but excluding:

(i) the compounds 1-(3-benzoylphenyl)-ethylamine and 1-(3-furan-2-ylcarbonylphenyl)-ethylamine;

(ii) compounds wherein, in combination, $R^0$, $R^1$ and $R^4$ are all hydrogen and $R^5$ is hydrogen or methoxy;

(iii) compounds wherein, in combination, $R^0$ is methyl, $R^1$ is hydrogen or methyl; $R^4$ is hydrogen and $R^5$ is hydrogen or methoxy;

(iv) compounds wherein, in combination, $R^0$ is hydrogen, $R^1$ is methyl; $R^2$ is benzoyl, furoyl or cyclobutylcarbonyl, $R^3$ is phenyl; and $R^4$ and $R^5$ are both hydrogen; and (v) compounds wherein, in combination, $R^0$ is methyl, $R^1$ is hydrogen, $R^2$ is isobutyl or methyl, $R^3$ is phenyl or aminosulfonylthienyl, $R^4$ is hydrogen or methyl and $R^5$ is hydrogen.

In one embodiment (Embodiment 1.0A), the invention provides a compound as defined in Embodiment 1.0 but excluding compounds wherein, in combination, A is CH or nitrogen; E is CH or nitrogen; $R^0$ is hydrogen; $R^2$ is selected from hydrogen and a group X—R$^{8x}$ wherein X is a $C_{1-8}$ alkylene group, wherein one carbon atom of the $C_{1-8}$ alkylene group may optionally be bonded to a —CH$_2$—CH$_2$— moiety to form a cyclopropane-1,1-diyl group or two adjacent carbon atoms of the $C_{1-8}$ alkylene group may optionally be bonded to a —(CH$_2$)$_n$ moiety, where n is 1 to 5, to form a $C_{3-7}$-cycloalkane-1,2-diyl group; $R^{8x}$ is selected from a hydroxy group and C(=O)NR$^{10x}$R$^{11x}$; provided that when $R^{8x}$ is hydroxy, there are at least two carbon atoms in line between the hydroxy group and the nitrogen atom to which X is attached; $R^{10x}$ is selected from hydrogen and $C_{1-4}$ alkyl; $R^{11x}$ is selected from hydrogen; amino-$C_{2-4}$ alkyl and hydroxy-$C_{2-4}$ alkyl; and $R^1$ is $R^{1a}$ which is selected from;

an acyclic $C_{1-8}$ hydrocarbon group optionally substituted with one or two substituents $R^6$, wherein one carbon atom of the acyclic $C_{1-8}$ hydrocarbon group may optionally be replaced by a heteroatom or group selected from O, S, NR$^c$, S(O) and SO$_2$, or two adjacent carbon atoms of the acyclic $C_{1-8}$ hydrocarbon group may optionally be replaced by a group selected from CONR$^c$, NR$^c$CO, NR$^c$SO$_2$ and SO$_2$NR$^c$ provided that in each case at least one carbon atom of the acyclic $C_{1-8}$ hydrocarbon group remains; and a monocyclic carbocyclic or heterocyclic group of 3 to 7 ring members, of which 0, 1, 2, 3 or 4 are heteroatom ring members selected from O, N and S, the carbocyclic or heterocyclic group being optionally substituted with one or two substituents $R^{7a}$.

In another embodiment (Embodiment 1.1), the invention provides a compound of the formula (1):

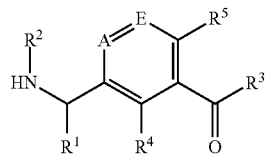

(1)

or a salt, N-oxide, tautomer or stereoisomer thereof, wherein:
A is CH or nitrogen;
E is CH or nitrogen;
$R^1$ is selected from;
  an acyclic $C_{1-8}$ hydrocarbon group optionally substituted with one or two substituents $R^6$, wherein one carbon atom of the acyclic $C_{1-8}$ hydrocarbon group may optionally be replaced by a heteroatom or group selected from O, S, $NR^c$, S(O) and $SO_2$, or two adjacent carbon atoms of the acyclic $C_{1-8}$ hydrocarbon group may optionally be replaced by a group selected from $CONR^c$, $NR^cCO$, $NR^cSO_2$ and $SO_2NR^c$ provided that in each case at least one carbon atom of the acyclic $C_{1-8}$ hydrocarbon group remains; and
  a monocyclic carbocyclic or heterocyclic group of 3 to 7 ring members, of which 0, 1, 2, 3 or 4 are heteroatom ring members selected from O, N and S, the carbocyclic or heterocyclic group being optionally substituted with one or two substituents $R^{7a}$;
$R^2$ is selected from hydrogen and a group $X—R^8$;
X is a $C_{1-8}$ alkanediyl group wherein one carbon atom of the $C_{1-8}$ alkanediyl group may optionally be bonded to a —$CH_2$—$CH_2$— moiety to form a cyclopropane-1,1-diyl group or two adjacent carbon atoms of the $C_{1-8}$ alkanediyl group may optionally be bonded to a —$(CH_2)_n$— moiety, where n is 1 to 5, to form a $C_{3-7}$-cycloalkane-1,2-diyl group;
$R^3$ is a 3- to 10-membered monocyclic or bicyclic carbocyclic or heterocyclic ring containing 0, 1, 2 or 3 heteroatom ring members selected from N, O and S, and being optionally substituted with one or more substituents $R^{13}$;
$R^4$ is selected from hydrogen and a substituent $R^{4a}$;
$R^{4a}$ is selected from halogen; cyano; $C_{1-4}$ alkyl optionally substituted with one or more fluorine atoms; $C_{1-4}$ alkoxy optionally substituted with one or more fluorine atoms; hydroxy-$C_{1-4}$ alkyl; and $C_{1-2}$ alkoxy-$C_{1-4}$ alkyl;
$R^5$ is selected from hydrogen and a substituent Rya;
$R^{5a}$ is selected from $C_{1-2}$ alkyl optionally substituted with one or more fluorine atoms; $C_{1-3}$ alkoxy optionally substituted with one or more fluorine atoms; halogen; cyclopropyl; and cyano;
$R^6$ is selected from hydroxy; fluorine; carbamoyl; mono- or di-$C_{1-4}$ alkylcarbamoyl; nitro; amino; mono- or di-$C_{1-4}$ alkylamino; a monocyclic carbocyclic or heterocyclic group of 3 to 7 ring members, of which 0, 1 or 2 are heteroatom ring members selected from O, N and S, the carbocyclic or heterocyclic group being optionally substituted with one or two substituents $R^{7b}$;
$R^{7a}$ and $R^{7b}$ are each independently selected from (=O); (=S); amino; halogen; cyano; hydroxy; $C_{1-4}$ alkyl; hydroxy-$C_{1-4}$ alkyl; amino-$C_{1-4}$ alkyl; mono- and di-$C_{1-4}$ alkylamino-$C_{1-4}$ alkyl;
$R^8$ is selected from a hydroxy group and C(=O)$NR^{10}R^{11}$; provided that when $R^8$ is hydroxy, there are at least two carbon atoms in line between the hydroxy group and the nitrogen atom to which X is attached;
$R^{10}$ is selected from hydrogen and $C_{1-4}$ alkyl;
$R^{11}$ is selected from hydrogen; amino-$C_{2-4}$ alkyl and hydroxy-$C_{2-4}$ alkyl;
$R^{13}$ is selected from halogen; cyano; (=O); (=S); nitro; CH=NOH; and a group $R^a$-$R^b$;
$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$;
$R^b$ is hydrogen; a cyclic group $R^d$; or an acyclic $C_{1-8}$ hydrocarbon group optionally substituted with one or more substituents selected from hydroxy, oxo, halogen, cyano, nitro, carboxy, amino, mono- or di-$C_{1-4}$ alkylamino, and a cyclic group $R^d$; wherein one or two but not all of the carbon atoms of the acyclic $C_{1-8}$ hydrocarbon group may optionally be replaced by O, S, SO, $SO_2$, $NR^c$, $X^1C(X^2)$, $C(X^2)X^1$ or $X^1C(X^2)X^1$; $SO_2NR^c$ or $NR^cSO_2$;
$R^c$ is hydrogen or $C_{1-4}$ alkyl;
the cyclic group $R^d$ is a monocyclic carbocyclic or heterocyclic group having from 3 to 7 ring members, of which 0, 1, 2 or 3 are heteroatom ring members selected from O, N and S and oxidised forms thereof, the carbocyclic or heterocyclic group being optionally substituted with one or more substituents selected from $R^{14}$;
$R^{14}$ is selected from oxo; halogen; cyano; and $R^a$—$R^e$;
$R^e$ is hydrogen or an acyclic $C_{1-8}$ hydrocarbon group optionally substituted with one or more substituents selected from phenyl; hydroxy; oxo; halogen; cyano; carboxy; amino; mono- or di-$C_{1-4}$ alkylamino; wherein one or two but not all of the carbon atoms of the acyclic $C_{1-8}$ hydrocarbon group may optionally be replaced by O, S, SO, $SO_2$, $NR^c$, $X^1C(X^2)$, $C(X^2)X^1$ or $X^1C(X^2)X^1$; $SO_2NR^c$ or $NR^cSO_2$;
$X^1$ is O or $NR^c$; and
$X^2$ is =O or =$NR^c$;
but excluding the compounds 1-(3-benzoylphenyl)-ethylamine and 1-(3-furan-2-ylcarbonylphenyl)-ethylamine.

Particular and preferred compounds of the formulae (0) and (1) are as defined in the Embodiments 1.2 to 1.303 below.
1.2 A compound according to any one of Embodiments 1.0 to 1.1 wherein A is CH.
1.3 A compound according to any one of Embodiments 1.0 to 1.1 wherein A is N.
1.4 A compound according to any one of Embodiments 1.0 to 1.3 wherein E is CH.
1.5 A compound according to any one of Embodiments 1.0 to 1.3 wherein E is N.
1.6 A compound according to any one of Embodiments 1.0 to 1.5 wherein $R^1$ or $R^{1a}$ is selected from:
  an acyclic $C_{1-8}$ hydrocarbon group optionally substituted with one substituent $R^6$, wherein one carbon atom of the acyclic $C_{1-8}$ hydrocarbon group may optionally be replaced by a heteroatom O; and
  a non-aromatic monocyclic carbocyclic or heterocyclic group of 3, 4, 5, 6 or 7 ring members, of which 0, 1 or 2 are heteroatom ring members selected from N, O and S, the carbocyclic or heterocyclic group being optionally substituted with one or two substituents $R^{7a}$.
1.7 A compound according to Embodiment 1.6 wherein $R^1$ or $R^{1a}$ is selected from:
  an acyclic $C_{1-8}$ hydrocarbon group optionally substituted with one substituent $R^6$, wherein one carbon atom of the acyclic $C_{1-8}$ hydrocarbon group may optionally be replaced by a heteroatom O;

a non-aromatic monocyclic carbocyclic group of 3, 4, 5 or 6 members, the monocyclic carbocyclic group being optionally substituted with one or two substituents $R^{7a}$; and a non-aromatic monocyclic heterocyclic group of 4, 5, 6 or 7 ring members, of which 1 or 2 are heteroatoms selected from N and O, the monocyclic heterocyclic group being optionally substituted with one or two substituents $R^{7a}$.

1.8 A compound according to Embodiment 1.7 wherein $R^1$ or $R^{1a}$ is selected from:
an acyclic $C_{1-8}$ hydrocarbon group optionally substituted with one substituent $R^6$, wherein one carbon atom of the acyclic $C_{1-8}$ hydrocarbon group may optionally be replaced by a heteroatom O;
a monocyclic carbocyclic group of 3 ring members; and
a non-aromatic monocyclic heterocyclic group of 5 or 6 ring members, of which 1 is a nitrogen or oxygen atom, the monocyclic heterocyclic group being optionally substituted with one or two substituents $R^{7a}$.

1.9 A compound according to either of Embodiments 1.7 and 1.8 wherein the monocyclic heterocyclic group is unsubstituted or substituted with one substituent $R^{7a}$.

1.10 A compound according to any one of Embodiments 1.6 to 1.9 wherein the monocyclic group contains a single heteroatom ring member which is an oxygen atom.

1.11 A compound according to Embodiment 1.10 wherein the monocyclic group is a tetrahydropyran or tetrahydrofuran group.

1.12 A compound according to any one of Embodiments 1.6 to 1.9 wherein the monocyclic group contains a single heteroatom ring member which is a nitrogen atom.

1.13 A compound according to Embodiment 1.12 wherein the monocyclic group is a piperidine or pyrrolidine group.

1.14 A compound according to any one of Embodiments 1.0 to 1.13 wherein $R^{7a}$ is selected from oxo, $C_{1-4}$ alkyl, $C_{1-4}$ alkoxy and $C_{1-4}$ acyl.

1.15 A compound according to Embodiment 1.14 wherein $R^{7a}$ is selected from oxo, $C_{1-3}$ alkyl, $C_{1-3}$ alkoxy and $C_{1-3}$ acyl.

1.16 A compound according to Embodiment 1.15 wherein $R^{7a}$ is selected from $C_{1-2}$ alkyl, $C_{1-2}$ alkoxy and $C_{1-2}$ acyl.

1.17 A compound according to Embodiment 1.16 wherein $R^{7a}$ is selected from methyl, ethyl, methoxy and acetyl.

1.18 A compound according to any one of Embodiments 1.0 to 1.17 wherein 0, 1, 2 or 3 substituents $R^{7a}$ are present.

1.19 A compound according to any one of Embodiments 1.0 to 1.18 wherein 0, 1 or 2 substituents $R^{7a}$ are present.

1.20 A compound according to any one of Embodiments 1.0 to 1.19 wherein 0 or 1 substituents $R^{7a}$ are present.

1.21 A compound according to any one of Embodiments 1.0 to 1.8 wherein $R^1$ or $R^{1a}$ is selected from (i) an acyclic $C_{1-8}$ hydrocarbon group optionally substituted with one substituent $R^6$, wherein one carbon atom of the acyclic $C_{1-8}$ hydrocarbon group may optionally be replaced by a heteroatom O; and (ii) a cyclopropyl group.

1.22 A compound according to Embodiment 1.21 wherein $R^1$ or $R^{1a}$ is selected from (i) an acyclic $C_{1-6}$ hydrocarbon group optionally substituted with one substituent $R^6$, wherein one carbon atom of the acyclic $C_{1-6}$ hydrocarbon group may optionally be replaced by a heteroatom 0; and (ii) a cyclopropyl group.

1.23 A compound according to Embodiment 1.21 wherein $R^1$ or $R^{1a}$ is selected from (i) an acyclic $C_{1-4}$ hydrocarbon group optionally substituted with one substituent $R^6$, wherein one carbon atom of the acyclic $C_{1-4}$ hydrocarbon group may optionally be replaced by a heteroatom 0; and (ii) a cyclopropyl group.

1.24 A compound according to any one of Embodiments 1.21 to 1.23, when dependent from Embodiment 1.0, wherein no carbon atom of the acyclic hydrocarbon group is replaced by a heteroatom 0.

1.25 A A compound according to any one of Embodiments 1.0 to 1.8 and 1.21 to 1.24 wherein the optionally substituted acyclic hydrocarbon group is an alkyl group.

1.26 A compound according to any one of Embodiments 1.1 to 1.8 and 1.21 to 1.25 wherein $R^6$ is absent or is selected from hydroxy; fluorine; carbamoyl; mono- or di-$C_{1-2}$ alkylcarbamoyl; amino; mono- or di-$C_{1-2}$ alkylamino; a monocyclic carbocyclic or heterocyclic group of 3 to 7 ring members, of which 0, 1 or 2 are heteroatom ring members selected from O, N and S, the carbocyclic or heterocyclic group being optionally substituted with one or two substituents $R^{7b}$.

1.26A A compound according to any one of Embodiments 1.1 to 1.8 and 1.21 to 1.25 wherein $R^6$ is selected from hydroxy; fluorine; carbamoyl; mono- or di-$C_{1-2}$ alkylcarbamoyl; amino; mono- or di-$C_{1-2}$ alkylamino; a monocyclic carbocyclic or heterocyclic group of 3 to 7 ring members, of which 0, 1 or 2 are heteroatom ring members selected from O, N and S, the carbocyclic or heterocyclic group being optionally substituted with one or two substituents $R^{7b}$;

1.27 A compound according to any one of Embodiments 1.1 to 1.8 and 1.21 to 1.26 wherein $R^6$ is absent or is selected from an aromatic monocyclic carbocyclic or heterocyclic group of 3 to 7 ring members, of which 0 or 1 are heteroatom ring members selected from O and N, halogen, cyano, hydroxy and $C_{1-4}$ alkoxy wherein the $C_{1-4}$ alkoxy is optionally substituted with one or more fluorine atoms or a substituent selected from hydroxy and methoxy.

1.27A A compound according to any one of Embodiments 1.1 to 1.8 and 1.21 to 1.25 and 1.26A wherein $R^6$ is selected from an aromatic monocyclic carbocyclic or heterocyclic group of 3 to 7 ring members, of which 0 or 1 are heteroatom ring members selected from O and N, halogen, cyano, hydroxy and $C_{1-4}$ alkoxy wherein the $C_{1-4}$ alkoxy is optionally substituted with one or more fluorine atoms or a substituent selected from hydroxy and methoxy.

1.27B A compound according to any one of Embodiments 1.1 to 1.8 and 1.21 to 1.26 wherein $R^6$ is absent or is selected from a non-aromatic monocyclic carbocyclic or heterocyclic group of 3 to 7 ring members, of which 0 or 1 are heteroatom ring members selected from O and N, halogen, cyano, hydroxy and $C_{1-4}$ alkoxy wherein the $C_{1-4}$ alkoxy is optionally substituted with one or more fluorine atoms or a substituent selected from hydroxy and methoxy.

1.27C A compound according to any one of Embodiments 1.1 to 1.8 and 1.21 to 1.25 and 1.26A wherein $R^6$ is selected from a non-aromatic monocyclic carbocyclic or heterocyclic group of 3 to 7 ring members, of which 0 or 1 are heteroatom ring members selected from O and N, halogen, cyano, hydroxy and $C_{1-4}$ alkoxy wherein the $C_{1-4}$ alkoxy is optionally substituted with one or more fluorine atoms or a substituent selected from hydroxy and methoxy.

1.28 A compound according to Embodiment 1.27 wherein $R^6$ is absent or is selected from fluorine, cyano, hydroxy and methoxy.

1.28A A compound according to Embodiment 1.27A wherein $R^6$ is absent or is selected from fluorine, cyano, hydroxy and methoxy.

1.29 A compound according to Embodiment 1.28 wherein $R^6$ is absent or is fluorine.

1.30 A compound according to Embodiment 1.28 or 1.28A wherein $R^6$ is fluorine.

1.31 A compound according to Embodiment 1.29 wherein $R^6$ is absent.

1.32 A compound according to any one of Embodiments 1.0 to 1.23 wherein $R^1$ or $R^{1a}$ is selected from cyclopropyl and an unsubstituted $C_{1-4}$ alkyl group.

1.33 A compound according to Embodiment 1.32 wherein $R^1$ or $R^{1a}$ is selected from cyclopropyl and an unsubstituted $C_{2-3}$ alkyl group.

1.34 A compound according to Embodiment 1.33 wherein $R^1$ or $R^{1a}$ is selected from ethyl, isopropyl and cyclopropyl.

1.35 A compound according to Embodiment 1.34 wherein $R^1$ or $R^{1a}$ is selected from ethyl and cyclopropyl.

1.36 A compound according to Embodiment 1.35 wherein $R^1$ or $R^{1a}$ is ethyl.

1.36 A A compound according to Embodiment 1.36 wherein $R^1$ is perdeuteroethyl.

1.37 A compound according to Embodiment 1.35 wherein $R^1$ or $R^{1a}$ cyclopropyl.

1.38 A compound according to Embodiment 1.0 and any Embodiment dependent thereon, wherein $R^1$ is a group $R^{1a}$.

1.39 A compound according to any one of Embodiments 1.0 to 1.38 wherein the moiety:

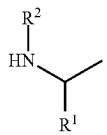

has the configuration:

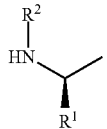

1.40 A compound according to any one of Embodiments 1.0 to 1.38 wherein the moiety:

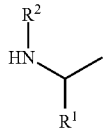

has the configuration:

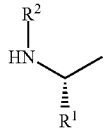

1.41 A compound according to any one of Embodiments 1.0 to 1.40 wherein $R^2$ is hydrogen.

1.42 A compound according to Embodiment 1.1 and any one of Embodiments 1.2 to 1.40 when dependent from Embodiment 1.1, wherein $R^2$ is a group $X-R^8$.

1.43 A compound according to Embodiment 1.42 wherein X is a $C_{1-8}$ alkanediyl group, wherein one carbon atom of the $C_{1-8}$ alkanediyl group may optionally be bonded to a $-CH_2-CH_2-$moiety to form a cyclopropane-1,1-diyl-group or two adjacent carbon atoms of the $C_{1-8}$ alkanediyl group may optionally be bonded to a $-(CH_2)_n-$ moiety, where n is 1 to 5, to form a $C_{3-7}$-cycloalkane-1,2-diyl-group.

1.44 A compound according to Embodiment 1.43 wherein X is a $C_{1-6}$ alkanediyl group, wherein one carbon atom of the $C_{1-8}$ alkanediyl group may optionally be bonded to a $-CH_2-CH_2-$moiety to form a cyclopropane-1,1-diyl-group or two adjacent carbon atoms of the $C_{1-8}$ alkanediyl group may optionally be bonded to a $-(CH_2)_n$ moiety, where n is 1 to 5, to form a $C_{3-7}$-cycloalkane-1,2-diyl-group.

1.45 A compound according to Embodiment 1.1, and any one of Embodiments 1.2 to 1.40 and 1.42 to 1.44 when dependent from Embodiment 1.1, wherein the alkanediyl group of X is a branched chain alkanediylyl group.

1.46 A compound according to Embodiment 1.1, and any one of Embodiments 1.2 to 1.40 and 1.42 to 1.44 when dependent from Embodiment 1.1, wherein the alkanediyl group of X is a straight chain alkanediyl group.

1.47 A compound according to Embodiment 1.1, and any one of Embodiments 1.2 to 1.40 and 1.42 to 1.46 when dependent from Embodiment 1.1, wherein n is 1 to 4.

1.48 A compound according to Embodiment 1.47 wherein n is 1 to 3.

1.49 A compound according to Embodiment 1.48 wherein n is 3.

1.50 A compound according to Embodiment 1.1, and any one of Embodiments 1.2 to 1.40 and 1.42 to 1.49 when dependent from Embodiment 1.1, wherein X is selected from $-(CH_2)_p-$, $(CH_2)_q-CH(Alk)-(CH_2)_r-$, $-CH(Alk)-W-$, $-C(Alk)_2-(CH_2)_r-$ and $-(CH_2)_t-W-(CH_2)_n-$, where W is a cyclopropane-1,1-diyl group; each Alk is independently selected from methyl, ethyl and isopropyl; p is 1, 2, 3 or 4; q is 0 or 1, r is 0, 1, 2 or 3; t is 0, 1 or 2 and u is 0 or 1, provided that the total number of carbon atoms contained within X, excluding two of the carbon atoms of any cyclopropane-1,1-diyl group present, does not exceed 8.

1.50A A compound according to Embodiment 1.1, and any one of Embodiments 1.2 to 1.40 and 1.42 to 1.49 when dependent from Embodiment 1.1, wherein X is selected from $-(CH_2)_p-$, $(CH_2)_q-CH(Alk)-(CH_2)_r-$, $-CH(Alk)-W-$, $-C(Alk)_2-(CH_2)_r-$ and $-(CH_2)_t-W-(CH_2)_u-$, where W is a cyclopropane-1,1-diyl group or cyclopentane-1,2-diyl group; each Alk is independently selected from methyl, ethyl and isopropyl; p is 1, 2, 3 or 4; q is 0 or 1, r is 0, 1, 2 or 3; t is 0, 1 or 2 and u is 0 or 1, provided that the total number of carbon atoms contained within X, excluding two of the carbon atoms of any cyclopropane-1,1-diyl group or cyclopentane-1,2-diyl group present, does not exceed 8.

1.51 A compound according to Embodiment 1.50 or Embodiment 1.50A wherein p is 1 and $R_8$ is other than hydroxy.

1.52 A compound according to Embodiment 1.50 or Embodiment 1.50A wherein p is 2.

1.53 A compound according to Embodiment 1.50 or Embodiment 1.50A wherein p is 3.

1.54 A compound according to Embodiment 1.50 or Embodiment 1.50A wherein q is 0.

1.55 A compound according to Embodiment 1.50 or Embodiment 1.50A wherein q is 1.

1.56 A compound according to any one of Embodiments 1.50, 1.50A, 1.54 and 1.55 wherein r is 0, 1 or 2.

1.57 A compound according to Embodiment 1.56 wherein r is 0 or 1.

1.58 A compound according to Embodiment 1.57 wherein r is 0.

1.59 A compound according to Embodiment 1.57 wherein r is 1.

1.60 A compound according to Embodiment 1.50 or Embodiment 1.50A wherein t is 0.

1.61 A compound according to Embodiment 1.50 or Embodiment 1.50A wherein t is 1.

1.62 A compound according to any one of Embodiments 1.50, 1.50A, 1.60 and 1.61 wherein u is 0.

1.63 A compound according to any one of Embodiments 1.50, 1.50A, 1.60 and 1.61 wherein u is 1.

1.64 A compound according to any one of Embodiments 1.50, 1.50A and 1.54 to 1.63 wherein each Alk is independently selected from methyl and ethyl.

1.65 A compound according to Embodiment 1.64 wherein Alk is methyl.

1.66 A compound according to Embodiment 1.50 or Embodiment 1.50A wherein X is selected from —$CH_2$—, —$CH_2$—$CH_2$—, —$CH_2$—$CH_2$—$CH_2$—, —$CH(CH_3)$—$CH_2$—, —$C(CH_3)_2$—$CH_2$—, —$CH(CH_3)$—W—, and —$CH_2$—$C(CH_3)_2$—.

1.67 A compound according to Embodiment 1.66 wherein X is —$CH(CH_3)$—$CH_2$—.

1.68 A compound according to Embodiment 1.67 wherein X is —*$CH(CH_3)CH_2$— and the asterisk denotes a chiral centre which is in the R-configuration.

1.69 A compound according to Embodiment 1.67 wherein X is —*$CH(CH_3)CH_2$— and the asterisk denotes a chiral centre which is in the S-configuration.

1.70 A compound according to Embodiment 1.1, and any one of Embodiments 1.2 to 1.40 and 1.42 to 1.69 when dependent from Embodiment 1.1, wherein $R^8$ is hydroxy.

1.71 A compound according to Embodiment 1.1, and any one of Embodiments 1.2 to 1.40 and 1.42 to 1.69 when dependent from Embodiment 1.1, wherein $R^8$ is C(=O)$NR^{10}R^{11}$.

1.72 A compound according to Embodiment 1.71 wherein $R^{10}$ is selected from hydrogen and $C_{1-2}$ alkyl.

1.73 A compound according to Embodiment 1.72 wherein $R^{10}$ is hydrogen.

1.74 A compound according to any one of Embodiments 1.71 to 1.73 wherein $R^{11}$ is selected from hydrogen; amino-$C_{2-3}$ alkyl and hydroxy-$C_{2-3}$ alkyl.

1.75 A compound according to Embodiment 1.74 wherein $R^{11}$ is selected from hydrogen; 2-aminoethyl; and 2-hydroxyethyl.

1.76 A compound according to any one of Embodiments 1.71 to 1.73 wherein $R^{11}$ is hydrogen.

1.77 A compound according to any one of Embodiments 1.71 to 1.73 wherein $R^{11}$ is selected from amino-$C_{2-4}$ alkyl and hydroxy-$C_{2-4}$ alkyl.

1.78 A compound according to Embodiment 1.77 wherein $R^{11}$ is selected from amino-$C_{2-3}$ alkyl and hydroxy-$C_{2-3}$ alkyl.

1.79 A compound according to Embodiment 1.77 wherein $R^{11}$ is amino-$C_{2-4}$ alkyl.

1.80 A compound according to Embodiment 1.79 wherein $R^{11}$ is amino-$C_{2-3}$ alkyl.

1.81 A compound according to Embodiment 1.80 wherein $R^{11}$ is 2-aminoethyl.

1.82 A compound according to Embodiment 1.80 wherein $R^{11}$ is 3-aminopropyl.

1.83 A compound according to Embodiment 1.77 wherein $R^{11}$ is hydroxy-$C_{2-4}$ alkyl.

1.84 A compound according to Embodiment 1.83 wherein $R^{11}$ is hydroxy-$C_{2-3}$ alkyl.

1.85 A compound according to Embodiment 1.84 wherein $R^{11}$ is 2-hydroxyethyl.

1.86 A compound according to Embodiment 1.84 wherein $R^{11}$ is 3-hydroxypropyl.

1.87 A compound according to Embodiment 1.1, and any one of Embodiments 1.2 to 1.40 and 1.42 to 1.86 when dependent from Embodiment 1.1, wherein $R^{7a}$ is absent or is selected from amino; hydroxy; $C_{1-4}$ alkyl; hydroxy-$C_{1-3}$ alkyl; and amino-$C_{1-3}$ alkyl.

1.88 A compound according to Embodiment 1.87 wherein $R^{7a}$ is absent or is selected from amino; hydroxy; hydroxymethyl; aminomethyl and methyl.

1.89 A compound according to Embodiment 1.1, and any one of Embodiments 1.2 to 1.40 and 1.42 to 1.86 when dependent from Embodiment 1.1, wherein $R^{7a}$ is absent.

1.90 A compound according to Embodiment 1.1, and any one of Embodiments 1.2 to 1.40 and 1.42 to 1.89 when dependent from Embodiment 1.1, wherein $R^{7b}$ is absent or is selected from amino; hydroxy; $C_{1-4}$ alkyl; hydroxy-$C_{1-3}$ alkyl; and amino-$C_{1-3}$ alkyl.

1.91 A compound according to Embodiment 1.90 wherein $R^{7b}$ is absent or is selected from amino; hydroxy; hydroxymethyl; aminomethyl and methyl.

1.92 A compound according to Embodiment 1.1, and any one of Embodiments 1.2 to 1.40 and 1.42 to 1.91 when dependent from Embodiment 1.1, wherein $R^{7b}$ is absent.

1.93 A compound according to Embodiment 1.0A and any one of Embodiments 1.2 to 1.41 dependent thereon, wherein $R^2$ is selected from $R^{2a}$; —C(=O)$R^{2a}$; and —C(=NH)—$NHR^{20}$.

1.94 A compound according to Embodiment 1.93 wherein $R^{2a}$ is selected from:
an acyclic $C_{1-6}$ hydrocarbon group which is a $C_{1-6}$ alkyl group, a $C_{2-6}$ alkenyl group or a $C_{2-6}$ alkynyl group, the acyclic $C_{1-6}$ hydrocarbon group being optionally substituted with one or two substituents $R^8$ wherein one carbon atom of the acyclic $C_{1-8}$ hydrocarbon group may optionally be replaced by a heteroatom or group selected from O and $NR^c$ provided that at least one carbon atom of the acyclic $C_{1-8}$ hydrocarbon group remains;
a monocyclic carbocyclic or heterocyclic group of 3 to 7 ring members, of which 0, 1 or 2 ring members are heteroatom ring members selected from O, N and S; wherein the monocyclic carbocyclic or heterocyclic group is selected from $C_{3-6}$ cycloalkyl groups; and five and six membered heterocyclic groups containing one or two heteroatom ring members selected from N, O and S; and
a bicyclic heterocyclic group of 9 or 10 ring members, of which 1 or 2 ring members are nitrogen atoms, one of the rings of the bicyclic heterocyclic group being a non-aromatic nitrogen-containing ring;
wherein the monocyclic carbocyclic or heterocyclic group and the bicyclic heterocyclic group are each optionally substituted with one or two substituents $R^{7c}$.

1.95 A compound according to Embodiment 1.93 or Embodiment 1.94 wherein the acyclic $C_{1-6}$ hydrocarbon group of $R^{2a}$ is a $C_{1-6}$ alkyl group which is optionally substituted with one or two substituents $R^8$ and wherein one carbon atom of the $C_{1-6}$ alkyl group may optionally be replaced by a heteroatom or group selected from O and $NR^c$ provided that at least one carbon atom of the $C_{1-6}$ alkyl group remains.

1.96 A compound according to Embodiment 1.95 wherein the acyclic $C_{1-6}$ hydrocarbon group of $R^{2a}$ is a $C_{1-4}$ alkyl group which is optionally substituted with one or two substituents $R^8$ and wherein one carbon atom of the $C_{1-6}$ alkyl group may optionally be replaced by an oxygen atom provided that at least one carbon atom of the $C_{1-4}$ alkyl group remains.

1.97 A compound according to Embodiment 1.96 wherein the optionally substituted $C_{1-4}$ alkyl group is a straight chain alkyl group.

1.98 A compound according to Embodiment 1.96 wherein the optionally substituted $C_{1-4}$ alkyl group is a branched chain alkyl group.

1.99 A compound according to Embodiment 1.96 wherein the optionally substituted $C_{1-4}$ alkyl group is selected from methyl, ethyl, propyl and isopropyl, each of which is optionally substituted with one or two substituents $R^8$.

1.100 A compound according to Embodiment 1.99 wherein the optionally substituted $C_{1-4}$ alkyl group is selected from methyl, ethyl, propyl and isopropyl, each of which is optionally substituted with one substituent $R^8$.

1.101 A compound according to Embodiment 1.100 wherein the optionally substituted $C_{1-4}$ alkyl group is methyl which is optionally substituted with one substituent $R^8$.

1.102 A compound according to Embodiment 1.100 wherein the optionally substituted $C_{1-4}$ alkyl group is ethyl which is optionally substituted with one substituent $R^8$.

1.103 A compound according to Embodiment 1.100 wherein the optionally substituted $C_{1-4}$ alkyl group is isopropyl which is optionally substituted with one substituent $R^8$.

1.104 A compound according to Embodiment 1.93 wherein $R^{2a}$ is an acyclic $C_{1-6}$ hydrocarbon group as defined in any one of Embodiments 1.1 and 1.44 to 1.53.

1.105 A compound according to Embodiment 1.93 or Embodiment 1.94 wherein the monocyclic carbocyclic or heterocyclic group of $R^{2a}$ is selected from:
$C_{3-6}$ cycloalkyl groups;
five or six membered heteroaryl groups having one or two heteroatom ring members selected from N, O and S; and
four, five and six membered non-aromatic heterocyclic groups containing 0, 1 or 2 heteroatom ring members selected from N, O and S;
wherein the monocyclic carbocyclic or heterocyclic groups are each optionally substituted with one or two substituents $R^{7c}$.

1.106 A compound according to Embodiment 1.105 wherein the monocyclic carbocyclic or heterocyclic group of 3 to 7 ring members is selected from:
$C_{3-6}$ cycloalkyl groups;
five membered heteroaryl groups having one or two heteroatom ring members selected from N, O and S; and
five and six membered non-aromatic heterocyclic groups containing 1 or 2 heteroatom ring members selected from N, O and S;
wherein the monocyclic carbocyclic or heterocyclic groups are each optionally substituted with one or two substituents $R^{7c}$.

1.107 A compound according to Embodiment 1.106 wherein the monocyclic carbocyclic or heterocyclic group of 3 to 7 ring members is selected from:
cyclopropyl;
five membered heteroaryl groups selected from imidazole and pyrazole;
five and six membered saturated heterocyclic groups containing 1 or 2 heteroatom ring members selected from N and O;
five and six membered partially unsaturated heterocyclic groups containing 1 or 2 heteroatom ring members selected from N, O and S;
wherein the monocyclic carbocyclic or heterocyclic groups are each optionally substituted with one or two substituents $R^{7c}$.

1.108 A compound according to Embodiment 1.93 wherein $R^{2a}$ is a monocyclic carbocyclic or heterocyclic group of 3 to 7 ring members as defined in any one of Embodiments 1.0A, 1.94 and 1.105 to 1.107.

1.109 A compound according to Embodiment 1.93 or Embodiment 1.94 wherein the bicyclic heterocyclic group of $R^{2a}$ is selected from indole, indazole, azaindole, benzoimidazole, isoquinoline, quinoline, tetrahydroisoquinoline and tetrahydroquinoline, each optionally substituted with one or two substituents $R^{7c}$.

1.110 A compound according to Embodiment 1.109 wherein the bicyclic heterocyclic group is selected from indole and tetrahydroisoquinoline, optionally substituted with one or two substituents $R^{7c}$.

1.111 A compound according to Embodiment 1.93 wherein $R^{2a}$ is a bicyclic heterocyclic group as defined in either of Embodiments 1.109 and 1.110.

1.112 A compound according to Embodiment 1.93 wherein $R^2$ is $R^{2a}$ and $R^{2a}$ is as defined in any one of Embodiments 1.0A and 1.94 to 1.11.

1.113 A compound according to Embodiment 1.93 wherein $R^2$ is —C(=O)$R^{2a}$ and $R^{2a}$ is as defined in any one of Embodiments 1.0A and 1.94 to 1.111.

1.114 A compound according to Embodiment 1.93 wherein $R^2$ is —C(=NH)—NHR$^{20}$.

1.115 A compound according to any one of Embodiment 1.0A, any one of Embodiments 1.2 to 1.91 dependent from Embodiment 1.0A, and Embodiments 1.93 to 1.114 wherein the optional substituents $R^8$ are selected from hydroxy; halogen; amino; C(=NH)NHR$^9$; C(=O)NR$^{10}$R$^{11}$; a non-aromatic monocyclic carbocyclic or heterocyclic group of 3 to 6 ring members, of which 0, 1 or 2 are heteroatom ring members selected from O and N, the carbocyclic or heterocyclic group being optionally substituted with 1 or 2 substituents $R^{7d}$; and an aromatic heterocyclic group selected from pyrrole, imidazole, pyrazole, indole and pyridone, the aromatic heterocyclic group being optionally substituted with 1 or 2 substituents $R^{7e}$.

1.116 A compound according to Embodiment 1.115 wherein the optional substituents $R^8$ are selected from hydroxy; fluorine; amino; C(=O)NR$^{10}$R$^{11}$; a non-aromatic monocyclic carbocyclic or heterocyclic group of 3 to 6 ring members, of which 0, 1 or 2 are heteroatom ring members selected from N, the heterocyclic group being optionally substituted with 1 or 2 substituents $R^{7d}$; and an aromatic heterocyclic group selected from pyrrole, imidazole, pyrazole, indole and pyridone, the aromatic heterocyclic group being optionally substituted with 1 or 2 substituents $R^{7e}$.

1.117 A compound according to Embodiment 1.116 wherein the optional substituents $R^8$ are selected from fluorine; hydroxy; amino; C(=O)NR$^{10}$R$^{11}$; cyclopropyl; a non-aromatic monocyclic heterocyclic group of 5 to 6 ring members selected from piperidine and pyrrolidine; and an aromatic heterocyclic group selected from pyrrole and imidazole.

1.118 A compound according to Embodiment 1.117 wherein $R^8$ is C(=O)NR$^{10}$R$^{11}$.

1.119 A compound according to Embodiment 1.118 wherein $R^{10}$ is selected from hydrogen and $C_{1-2}$ alkyl.

1.120 A compound according to Embodiment 1.119 wherein $R^{10}$ is hydrogen.

1.121 A compound according to any one of Embodiments 1.0A and 1.115 to 1.120 wherein $R^{11}$ is selected from (i) hydrogen; (ii) $C_{1-6}$ alkyl optionally substituted with one or more substituents selected from amino, mono-$C_{1-4}$ alkylamino, di-$C_{1-4}$ alkylamino and hydroxy; and (iii) a monocyclic non-aromatic carbocyclic or heterocyclic group of 3 to 7 ring members, of which 0, 1 or 2 are heteroatom ring members selected from O, N and S, the non-aromatic carbocyclic or heterocyclic group being optionally substituted with one or two substituents $R^{7f}$.

1.122 A compound according to Embodiment 1.121 wherein $R^{11}$ is hydrogen.

1.123 A compound according to Embodiment 1.121 wherein $R^{11}$ is $C_{1-6}$ alkyl optionally substituted with one or more substituents selected from amino, mono-$C_{1-4}$ alkylamino, di-$C_{1-4}$ alkylamino and hydroxy.

1.124 A compound according to Embodiment 1.123 wherein $R^{11}$ is $C_{1-4}$ alkyl substituted with one or more substituents selected from amino, mono-$C_{1-2}$ alkylamino, di-$C_{1-2}$ alkylamino and hydroxy.

1.125 A compound according to Embodiment 1.121 wherein $R^{11}$ is selected from hydrogen, 2-aminoethyl, 2-hydroxyethyl, 2-methylaminoethyl and piperidinyl.

1.126 A compound according to Embodiment 1.125 wherein $R^{11}$ is 2-aminoethyl.

1.127 A compound according to Embodiment 1.93 wherein $R^2$ is selected from $R^{2a}$; —C(=O)$R^{2a}$; —C(=NH)—NHR$^{20}$;
wherein $R^{20}$ is hydrogen; and $R^{2a}$ is selected from:
$C_{1-4}$ alkyl optionally substituted with fluorine;
$C_{3-6}$ cycloalkyl;
$C_{3-6}$ cycloalkyl-$C_{1-4}$ alkyl;
a group $(CH_2)_q$—HET$^1$ where HET$^1$ is a 5 to 6-membered heterocyclic ring containing one or two heteroatom ring members selected from O and N; and q is 0-3;
—CH$_2$—CH(R$^{21}$)NH$_2$ where $R^{21}$ is hydrogen or $C_{1-4}$ alkyl; and
—CH(R$^{22}$)CH$_2$CONHR$^{11b}$ where $R^{22}$ is hydrogen or $C_{1-4}$ alkyl and $R^{11}$ is hydrogen or amino-$C_{1-4}$ alkyl.

1.128 A compound according to Embodiment 1.127 wherein $R^2$ is selected from $R^{2a}$; —C(=O)$R^{2a}$; —C(=NH)—NHR$^{20}$; wherein $R^{20}$ is hydrogen and $R^{2a}$ is selected from methyl; isopropyl; fluoromethyl; cyclopropylmethyl; cyclopropyl; tetrahydrofuranyl; tetrahydropyranyl; pyrrolidinyl; piperidinyl; dihydropyrrolyl; tetrahydropyridinyl; imidazolylmethyl; imidazolylethyl; pyrazolylmethyl; pyrazolylethyl; —CH$_2$—CH(R$^{21}$)NH$_2$ where $R^{21}$ is hydrogen or isopropyl; and —CH(R$^{22}$)CH$_2$CONHR$^{11b}$ where $R^{22}$ is hydrogen or methyl and $R^{11}$ is hydrogen or aminoethyl.

1.129 A compound according to Embodiment 1.127 wherein $R^2$ is selected from —C(=NH)—NH$_2$; methyl; isopropyl; fluoromethyl; cyclopropylmethyl; cyclopropyl; tetrahydrofuranyl; tetrahydropyranyl; —C(=O)-pyrrolidinyl; —C(=O)-piperidinyl; —C(=O)-dihydropyrrolyl; —C(=O)-tetrahydropyridinyl; imidazolylmethyl; imidazolylethyl; pyrazolylmethyl; pyrazolylethyl; and —C(=O)—CH$_2$—CH(R$^{21}$)NH$_2$.

1.130 A compound according to Embodiment 1.0A and any one of Embodiments 1.2 to 1.129 that are dependent from Embodiment 1.0A, wherein $R^{7a}$ is absent or is selected from amino; hydroxy; $C_{1-4}$ alkyl; hydroxy-$C_{1-3}$ alkyl; and amino-$C_{1-3}$ alkyl.

1.131 A compound according to Embodiment 1.130 wherein $R^{7a}$ is absent or is selected from amino; hydroxy; hydroxymethyl; aminomethyl and methyl.

1.132 A compound according to Embodiment 1.0A, and any one of Embodiments 1.2 to 1.131 that are dependent from Embodiment 1.0A, wherein $R^{7a}$ is absent.

1.133 A compound according to Embodiment 1.0A, and any one of Embodiments 1.2 to 1.131 that are dependent from Embodiment 1.0A, wherein $R^{7a}$ is present and is selected from amino; hydroxy; $C_{1-4}$ alkyl; hydroxy-$C_{1-3}$ alkyl; and amino-$C_{1-3}$ alkyl.

1.134 A compound according to Embodiment 1.133 wherein $R^{7a}$ is selected from amino; hydroxy; hydroxymethyl; aminomethyl and methyl.

1.135 A compound according to A compound according to Embodiment 1.0A, and any on of Embodiments 1.2 to 1.134 that are dependent from Embodiment 1.0A, wherein $R^{7c}$ is absent or is selected from amino; hydroxy; $C_{1-4}$ alkyl; hydroxy-$C_{1-3}$ alkyl; and amino-$C_{1-3}$ alkyl.

1.136 A compound according to Embodiment 1.135 wherein $R^{7c}$ is absent or is selected from amino; hydroxy; hydroxymethyl; aminomethyl and methyl.

1.137 A compound according to Embodiment 1.0A, and any one of Embodiments 1.2 to 1.136 that are dependent from Embodiment 1.0A, wherein $R^{7c}$ is absent.

1.138 A compound according to any one of Embodiments 1.1 to 1.137 wherein $R^{7b}$ is absent or is selected from amino; hydroxy; $C_{1-4}$ alkyl; hydroxy-$C_{1-3}$ alkyl; and amino-$C_{1-3}$ alkyl.

1.139 A compound according to Embodiment 1.138 wherein $R^{7b}$ is absent or is selected from amino; hydroxy; hydroxymethyl; aminomethyl and methyl.

1.140 A compound according to Embodiment 1.0A, and any one of Embodiments 1.2 to 1.139 that are dependent from Embodiment 1.0A, wherein $R^{7b}$ is absent.

1.141 A compound according to Embodiment 1.0A, and any one of Embodiments 1.2 to 1.140 that are dependent from Embodiment 1.0A wherein $R^{7d}$ is absent or is selected from amino; hydroxy; $C_{1-4}$ alkyl; hydroxy-$C_{1-3}$ alkyl; and amino-$C_{1-3}$ alkyl.

1.142 A compound according to Embodiment 1.141 wherein $R^{7d}$ is absent or is selected from amino; hydroxy; hydroxymethyl; aminomethyl and methyl.

1.143 A compound according to Embodiment 1.0A, and any one of Embodiments 1.2 to 1.142 that are dependent from Embodiment 1.0A, wherein $R^{7d}$ is absent.

1.144 A compound according to Embodiment 1.0A, and any one of Embodiments 1.2 to 1.143 that are dependent from Embodiment 1.0A, wherein $R^{7e}$ is absent or is selected from amino; hydroxy; $C_{1-4}$ alkyl; hydroxy-$C_{1-3}$ alkyl; and amino-$C_{1-3}$ alkyl.

1.145 A compound according to Embodiment 1.144 wherein $R^{7e}$ is absent or is selected from methyl and ethyl.

1.146 A compound according to Embodiment 1.0A, and any one of Embodiments 1.2 to 1.146 that are dependent from Embodiment 1.0A, wherein $R^{7e}$ is absent.

1.147 A compound according to Embodiment 1.0A, and any one of Embodiments 1.2 to 1.146 that are dependent from Embodiment 1.0A, wherein $R^{7f}$ is absent or is selected from amino; hydroxy; $C_{1-4}$ alkyl; hydroxy-$C_{1-3}$ alkyl; and amino-$C_{1-3}$ alkyl.

1.148 A compound according to Embodiment 1.147 wherein $R^{7f}$ is absent or is selected from amino; hydroxy; hydroxymethyl; aminomethyl and methyl.

1.149 A compound according to Embodiment 1.144 wherein $R^{7f}$ is absent or is hydroxymethyl.

1.150 A compound according to Embodiment 1.0A, and any one of Embodiments 1.2 to 1.149 that are dependent from Embodiment 1.0A, wherein $R^{7f}$ is absent.

1.151 A compound according to any one of Embodiments 1.0 to 1.150 wherein $R^4$ is selected from hydrogen and a substituent $R^{4a}$; wherein $R^{4a}$ is selected from fluorine, chlorine, cyano; $C_{1-2}$ alkyl optionally substituted with one or more fluorine atoms; $C_{1-2}$ alkoxy optionally substituted with one or more fluorine atoms; hydroxy-$C_{1-2}$ alkyl; and $C_{1-2}$ alkoxy-$C_{1-2}$ alkyl.

1.152 A compound according to Embodiment 1.151 wherein $R^{4a}$ is selected from fluorine, chlorine, cyano; methyl, ethyl, difluoromethyl, trifluoromethyl, methoxy, trifluoromethoxy, difluoromethoxy, hydroxymethyl, hydroxyethyl, methoxymethyl and methoxyethyl.

1.153 A compound according to Embodiment 1.152 wherein $R^{4a}$ is selected from fluorine, chlorine, cyano; methyl, ethyl, difluoromethyl, trifluoromethyl and methoxy.

1.154 A compound according to Embodiment 1.153 wherein $R^{4a}$ is selected from fluorine, chlorine and methyl.

1.155 A compound according to Embodiment 1.154 wherein $R^{4a}$ is selected from fluorine and chlorine.

1.156 A compound according to Embodiment 1.155 wherein $R^{4a}$ is fluorine.

1.157 A compound according to Embodiment 1.156 wherein $R^{4a}$ is chlorine.

1.158 A compound according to any one of Embodiments 1.0 to 1.157 wherein $R^4$ is a substituent $R^{4a}$.

1.159 A compound according to any one of Embodiments 1.0 to 1.151 wherein $R^4$ is hydrogen.

1.160 A compound according to any one of Embodiments 1.0 to 1.159 wherein $R^5$ is selected from hydrogen and a substituent $R^{5a}$; and $R^{5a}$ is selected from fluorine, chlorine, cyano, $C_{1-2}$ alkyl optionally substituted with one or more fluorine atoms; $C_{1-2}$ alkoxy optionally substituted with one or more fluorine atoms; cyclopropyl; and amino.

1.161 A compound according to Embodiment 1.160 wherein $R^{5a}$ is selected from fluorine, chlorine, cyano, methyl, ethyl, difluoromethyl, trifluoromethyl, methoxy, trifluoromethoxy and difluoromethoxy.

1.162 A compound according to Embodiment 1.161 wherein $R^{5a}$ is selected from fluorine, chlorine, methyl and ethyl.

1.163 A compound according to Embodiment 1.162 wherein $R^{5a}$ is fluorine or chlorine. 1.164 A compound according to Embodiment 1.163 wherein $R^{5a}$ is chlorine.

1.165 A compound according to Embodiment 1.163 wherein $R^{5a}$ is fluorine.

1.166 A compound according to any one of Embodiments 1.0 to 1.165 wherein $R^5$ is a substituent $R^5a$.

1.167 A compound according to any one of Embodiments 1.1 to 1.160 wherein $R^5$ is hydrogen.

1.168 A compound according to Embodiment 1.0A, and any one of Embodiments 1.2 to 1.167 that are dependent from Embodiment 1.0A, wherein $R^3$ is a 5- to 10-membered monocyclic or bicyclic carbocyclic or heterocyclic ring containing 0, 1, 2 or 3 heteroatom ring members selected from N, O and S, and being optionally substituted with one to three substituents $R^{13}$.

1.169 A compound according to any one of Embodiments 1.1 to 1.168 wherein $R^3$ is selected from optionally substituted (with one or more substituents $R^{13}$) 5- and 6-membered monocyclic aromatic and unsaturated groups containing 0, 1 or 3 heteroatom ring members selected from N, O and S, and optionally substituted (with one or more substituents $R^{13}$) 9- and 10-membered heterocyclic groups containing an aromatic ring fused to a non-aromatic or aromatic ring, the heterocyclic groups containing 1, 2 or 3 heteroatom ring members and being optionally substituted with one or more substituents $R^{13}$.

1.170 A compound according to Embodiment 1.1, and any one of Embodiments 1.2 to 1.169 that are dependent from Embodiment 1.1, wherein $R^3$ is selected from optionally substituted (with one or more substituents $R^{13}$) 5- and 6-membered monocyclic aromatic and unsaturated groups containing 0, 1 or 3 heteroatom ring members selected from N, O and S, and optionally substituted (with one or more substituents $R^{13}$) 9- and 10-membered carbocyclic or heterocyclic groups containing an aromatic ring fused to a non-aromatic or aromatic ring, the heterocyclic groups containing 1, 2 or 3 heteroatom ring members and being optionally substituted with one or more substituents $R^{13}$.

1.171 A compound according to Embodiment 1.1, and any one of Embodiments 1.2 to 1.169 that are dependent from Embodiment 1.1, wherein $R^3$ is selected from phenyl, indanyl, pyridyl, pyrazinyl, pyrimidinyl, oxazolyl, isoxazolyl, thiazolyl, isothiazolyl, pyrazolyl, imidazolyl, pyrrolyl, dihydrobenzofuran, 3,4-dihydro-pyrido-oxazine and 3,4-dihydrobenzoxazine, each being optionally substituted with one or more substituents $R^{13}$.

1.172 A compound according to any one of Embodiments 1.0 to 1.171 wherein $R^3$ is selected from 5- and 6-membered monocyclic aromatic and unsaturated carbocyclic and heterocyclic groups containing 0, 1, 2 or 3 heteroatom ring members selected from N, O and S and being optionally substituted with one or more substituents $R^{13}$.

1.173 A compound according to Embodiment 1.172 wherein $R^3$ is selected from 5- and 6-membered monocyclic aromatic and unsaturated carbocyclic and heterocyclic groups containing 0, 1 or 2 heteroatom ring members selected from N, O and S and being optionally substituted with one or more substituents $R^{13}$.

1.174 A compound according to Embodiment 1.173 wherein $R^3$ is selected from phenyl, pyridyl, pyridonyl, pyrazinyl, pyrimidinyl, oxazolyl, isoxazolyl, thiazolyl, isothiazolyl, pyrazolyl, imidazolyl and pyrrolyl, each being optionally substituted with one or more substituents $R^{13}$.

1.175 A compound according to Embodiment 1.1, and any one of Embodiments 1.2 to 1.169 that are dependent from Embodiment 1.1, wherein $R^3$ is selected from phenyl, pyridyl, pyrazinyl, pyrimidinyl, oxazolyl, isoxazolyl, thiazolyl, isothiazolyl, pyrazolyl, imidazolyl, pyrrolyl, 3,4-dihydro-pyrido-oxazine and 3,4-dihydrobenzoxazine, each being optionally substituted with one or more substituents $R^{13}$.

1.176 A compound according to Embodiment 1.174 wherein $R^3$ is selected from phenyl optionally substituted with one or more substituents $R^{13}$.

1.177 A compound according to Embodiment 1.174 wherein $R^3$ is selected from pyridyl optionally substituted with one or more substituents $R^{13}$.

1.178 A compound according to Embodiment 1.174 wherein $R^3$ is selected from pyridonyl optionally substituted with one or more substituents $R^{13}$.

1.179 A compound according to Embodiment 1.174 wherein $R^3$ is selected from pyrimidinyl optionally substituted with one or more substituents $R^{13}$.

1.180 A compound according to Embodiment 1.174 wherein $R^3$ is selected from pyrazinyl optionally substituted with one or more substituents $R^{13}$.

1.181 A compound according to Embodiment 1.174 wherein $R^3$ is selected from isothiazolyl optionally substituted with one or more substituents $R^{13}$.

1.182 A compound according to Embodiment 1.174 wherein $R^3$ is selected from thiazolyl optionally substituted with one or more substituents $R^{13}$.

1.183 A compound according to Embodiment 1.174 wherein $R^3$ is selected from isoxazolyl optionally substituted with one or more substituents $R^{13}$.

1.184 A compound according to Embodiment 1.174 wherein $R^3$ is selected from pyrazolyl optionally substituted with one or more substituents $R^{13}$.

1.185 A compound according to Embodiment 1.1, and any one of Embodiments 1.2 to 1.184 that are dependent from Embodiment 1.1, wherein the substituents $R^{13}$ are selected from halogen; oxo; cyano; nitro; CH=NOH; and a group $R^a$-$R^b$;
  $R^a$ is a bond, O, CO, $X^1C(X^2)$, $C(X^2)X^1$, $SO_2$, $NR^c$, $SO_2NR^c$ or $NR^cSO_2$;
  $R^b$ is hydrogen; a cyclic group $R^d$; or an acyclic $C_{1-8}$ hydrocarbon group optionally substituted with one or more substituents selected from hydroxy, oxo, halogen, cyano, carboxy, amino, mono- or di-$C_{1-4}$ alkylamino, and a cyclic group $R^d$; wherein one or two but not all of the carbon atoms of the acyclic $C_{1-8}$ hydrocarbon group may optionally be replaced by O, $NR^c$, $X^1C(X^2)$, $C(X^2)X^1$ or $X^1C(X^2)X^1$; $SO_2NR^c$ or $NR^cSO_2$, but excluding the combination wherein $R^a$ is a bond and $R^b$ is hydrogen;
  the cyclic group $R^d$ is a monocyclic carbocyclic or heterocyclic group having from 3 to 7 ring members, of which 0, 1, 2 or 3 are heteroatom ring members selected from O and N, the carbocyclic or heterocyclic group being optionally substituted with one or more substituents selected from $R^{14}$;
  $R^{14}$ is selected from oxo; cyano; and $R^a$-$R^e$;
  $R^e$ is hydrogen or an acyclic $C_{1-8}$ hydrocarbon group optionally substituted with one or more substituents selected from phenyl and hydroxy
  $X^1$ is O or $NR^c$;
  $X^2$ is =O or =$NR^c$; and
  $R^c$ is hydrogen or $C_{1-4}$ alkyl.

1.185 A compound according to Embodiment 1.0A and any one of Embodiments 1.2 to 1.184 that are dependent from Embodiment 1.0A, wherein the substituents $R^{13}$ are selected from halogen; cyano; nitro; CH=NOH; and a group $R^a$—$R^b$;
  $R^a$ is a bond, O, CO, $X^1C(X^2)$, $C(X^2)X^1$, $SO_2$, $NR^c$, $SO_2NR^c$ or $NR^cSO_2$;
  $R^b$ is hydrogen; a cyclic group $R^d$; or an acyclic $C_{1-8}$ hydrocarbon group optionally substituted with one or more substituents selected from hydroxy, oxo, halogen, cyano, amino, mono- or di-$C_{1-4}$ alkylamino, and a cyclic group $R^d$; wherein one or two but not all of the carbon atoms of the acyclic $C_{1-8}$ hydrocarbon group may optionally be replaced by O, $NR^c$, $X^1C(X^2)$, $C(X^2)X^1$ or $X^1C(X^2)X^1$; $SO_2NR^c$ or $NR^cSO_2$, but excluding the combination wherein $R^a$ is a bond and $R^b$ is hydrogen;
  the cyclic group $R^d$ is a monocyclic carbocyclic or heterocyclic group having from 3 to 7 ring members, of which 0, 1, 2 or 3 are heteroatom ring members selected from O and N, the carbocyclic or heterocyclic group being optionally substituted with one or more substituents selected from $R^{14}$;
  $R^{14}$ is selected from cyano; and $R^a$-$R^e$;
  $R^e$ is hydrogen or an acyclic $C_{1-8}$ hydrocarbon group optionally substituted with one or more substituents selected from phenyl and hydroxy
  $X^1$ is O or $NR^c$;
  $X^2$ is =O or =$NR^c$; and
  $R^c$ is hydrogen or $C_{1-4}$ alkyl.

1.186 A compound according to Embodiment 1.1, and any one of Embodiments 1.2 to 1.185 that are dependent from Embodiment 1.1, wherein the substituents $R^{13}$ are selected from halogen; cyano; nitro; CH=NOH; and a group $R^a$-$R^b$;
  $R^a$ is a bond, O, CO, $X^1C(X^2)$, $C(X^2)X^1$, $SO_2$, $NR^c$, $SO_2NR^c$ or $NR^cSO_2$;
  $R^b$ is hydrogen; a cyclic group $R^d$; or an acyclic $C_{1-8}$ hydrocarbon group optionally substituted with one or more substituents selected from hydroxy, oxo, halogen, cyano, amino, mono- or di-$C_{1-4}$ alkylamino, and a cyclic group $R^d$; wherein one or two but not all of the carbon atoms of the acyclic $C_{1-8}$ hydrocarbon group may optionally be replaced by O, $NR^c$, $X^1C(X^2)$, $C(X^2)X^1$ or $X^1C(X^2)X^1$; $SO_2NR^c$ or $NR^cSO_2$, but excluding the combination wherein $R^a$ is a bond and $R^b$ is hydrogen;
  the cyclic group $R^d$ is a monocyclic carbocyclic or heterocyclic group having from 3 to 7 ring members, of which 0, 1, 2 or 3 are heteroatom ring members selected from O and N, the carbocyclic or heterocyclic group being optionally substituted with one or more substituents selected from $R^{14}$;
  $R^{14}$ is selected from cyano; and $R^a$-$R^e$;
  $R^e$ is hydrogen or an acyclic $C_{1-8}$ hydrocarbon group optionally substituted with one or more substituents selected from phenyl and hydroxy
  $X^1$ is O or $NR^c$;
  $X^2$ is =O or =$NR^c$; and
  $R^c$ is hydrogen or $C_{1-4}$ alkyl.

1.187 A compound according to Embodiment 1.186 wherein the substituents $R^{13}$ are selected from halogen; cyano; nitro; CH=NOH; and a group $R^a$-$R^b$;
  $R^a$ is a bond, O, CO, $X^1C(X^2)$, $C(X^2)X^1$, $NR^c$, $SO_2NR^c$ or $NR^cSO_2$;
  $R^b$ is hydrogen; a cyclic group $R^d$; or an acyclic $C_{1-8}$ hydrocarbon group optionally substituted with one or more substituents selected from hydroxy, halogen, cyano, carboxy and a cyclic group $R^d$; wherein one or two but not all of the carbon atoms of the acyclic $C_{1-8}$ hydrocarbon group may optionally be replaced by O, $NR^c$, C(O)O, O(CO), $C(O)NR^c$, $NR^cC(O)$, $OC(O)NR^c$, $SO_2NR^c$ or $NR^cSO_2$, but excluding the combination wherein $R^a$ is a bond and $R^b$ is hydrogen;
  the cyclic group $R^d$ is a monocyclic heterocyclic group having from 3 to 7 ring members, of which 1 or 2 are heteroatom ring members selected from O, N and S and oxidised forms thereof, the carbocyclic or heterocyclic group being optionally substituted with one or more substituents selected from $R^{14}$; and
  $R^{14}$ is oxo or $R^a$-$R^e$; and $R^e$ is hydrogen or an acyclic $C_{1-8}$ hydrocarbon group optionally substituted with one or more substituents selected from phenyl and hydroxy.

1.188 A compound according to any one of Embodiments 1.0 to 1.187 wherein the substituents $R^{13}$ are selected from halogen; cyano; nitro; CH=NOH; and a group $R^a$-$R^b$;
  $R^a$ is a bond, O, CO, $X^1C(X^2)$, $C(X^2)X^1$, $NR^c$, $SO_2NR^c$ or $NR^cSO_2$;
  $R^b$ is hydrogen; a cyclic group $R^d$; or an acyclic $C_{1-8}$ hydrocarbon group optionally substituted with one or more substituents selected from hydroxy, halogen, cyano, and a cyclic group $R^d$; wherein one or two but not all of the carbon atoms of the acyclic $C_{1-8}$ hydrocarbon group may optionally be replaced by O, $NR^c$, $SO_2NR^c$ or $NR^cSO_2$, but excluding the combination wherein $R^a$ is a bond and $R^b$ is hydrogen;
  the cyclic group $R^d$ is a monocyclic heterocyclic group having from 3 to 7 ring members, of which 1 or 2 are heteroatom ring members selected from O, N and S and oxidised forms thereof, the carbocyclic or heterocyclic group being optionally substituted with one or more substituents selected from $R^{14}$; and $R^{14}$ is $R^a$-$R^e$; and $R^e$ is an acyclic $C_{1-8}$ hydrocarbon group substituted with phenyl.

1.189 A compound according to any one of Embodiments 1.0 to 1.188 wherein either no substituents $R^{13}$ are present or 1, 2 or 3 substituents $R^{13}$ are present and are selected from halogen; cyano; nitro; CH=NOH; and a group $R^a$-$R^b$; wherein $R^a$ is a bond, O, CO, $X^1C(X^2)$, $C(X^2)X^1$, $NR^c$, $SO_2NR^c$ or $NR^cSO_2$;

$R^b$ is hydrogen; a cyclic group $R^d$; or an acyclic $C_{1-8}$ hydrocarbon group optionally substituted with one or more substituents selected from hydroxy, halogen, cyano, and a cyclic group $R^d$; wherein one or two but not all of the carbon atoms of the acyclic $C_{1-8}$ hydrocarbon group may optionally be replaced by O, $NR^c$, $SO_2NR^c$ or $NR^cSO_2$, but excluding the combination wherein $R^a$ is a bond and $R^b$ is hydrogen;

the cyclic group $R^d$ is a monocyclic heterocyclic group having from 3 to 7 ring members, of which 1 or 2 are heteroatom ring members selected from O, N and S and oxidised forms thereof, the carbocyclic or heterocyclic group being optionally substituted with one or more substituents selected from $R^{14}$; and $R^{14}$ is $R^a$-$R^e$; and $R^e$ is an acyclic $C_{1-8}$ hydrocarbon group substituted with phenyl.

1.190 A compound according to Embodiment 1.189 wherein either no substituents $R^{13}$ are present or 1, 2 or 3 substituents $R^{13}$ are present and are selected from fluorine; chlorine; cyano; nitro; CH=NOH; and a group $R^a$-$R^b$; wherein $R^a$ is a bond, O, CO, $CONR^c$, $NR^cCO$, $NR^c$, $SO_2NR^c$ or $NR^cSO_2$;

$R^b$ is hydrogen; a cyclic group $R^d$; or a $C_{1-8}$ alkyl group optionally substituted with one or more substituents selected from hydroxy, fluorine, cyano, and a cyclic group $R^d$; wherein one or two but not all of the carbon atoms of the acyclic $C_{1-8}$ hydrocarbon group may optionally be replaced by O, $NR^c$, $SO_2NR^c$ or $NR^cSO_2$;

the cyclic group $R^d$ is a monocyclic heterocyclic group having from 3 to 7 ring members, of which 1 or 2 are heteroatom ring members selected from O, N and S and oxidised forms thereof, the heterocyclic group being optionally substituted with one or more substituents selected from $R^{14}$; and $R^{14}$ is $R^a$-$R^e$; $R^e$; and $R^e$ is benzyl.

1.191 A compound according to Embodiment 1.190 wherein either no substituents $R^{13}$ are present or 1, 2 or 3 substituents $R^{13}$ are present and are selected from fluorine; chlorine; cyano; nitro; CH=NOH; and a group $R^a$-$R^b$; wherein $R^a$ is a bond, O, CO, $CONR^c$, $NR^cCO$, $NR^c$, $SO_2NR^c$ or $NR^cSO_2$;

$R^b$ is a cyclic group $R^d$; $C_{2-3}$ alkynyl; or a $C_{1-6}$ alkyl group optionally substituted with one or more substituents selected from hydroxy, fluorine, cyano, and a cyclic group $R^d$; wherein one or two but not all of the carbon atoms of the $C_{1-6}$ alkyl group may optionally be replaced by $NR^cSO_2$ and wherein the cyclic group $R^d$ is a monocyclic heterocyclic group having from 4-6 ring members, of which 1 or 2 are heteroatom ring members selected from O and N, the heterocyclic group being optionally substituted with one or more substituents selected from $R^{14}$; wherein $R^{14}$ is $R^a$-$R^e$; and $R^e$ is benzyl.

1.192 A compound according to Embodiment 1.1, and any one of Embodiments 1.2 to 1.191 that are dependent from Embodiment 1.1, wherein $R^{13}$ is additionally selected from oxo and hydroxy.

1.193 A compound according to Embodiment 1.1, and any one of Embodiments 1.2 to 1.191 that are dependent from Embodiment 1.1, wherein $R^{13}$ is selected from:

halogen;
cyano;
$C_{1-4}$ alkoxy;
$C_{1-6}$ alkyl optionally substituted with one or more substituents (e.g. one or two) selected from amino, mono- or di-$C_{1-4}$alkylamino, fluorine, cyano, hydroxy, carboxy, $C_{1-2}$ alkoxy, carbamoyloxy, mono- or di-$C_{1-4}$alkylcarbamoyloxy, $C_{1-4}$-alkoxycarbony and $C_{1-4}$alkanoyloxy; wherein one carbon atom of the $C_{1-6}$ alkyl may optionally be replaced by O;
—NH—$C_{1-6}$ alkyl optionally substituted with one or more substituents (e.g. one or two) selected from amino, mono- or di-$C_{1-4}$alkylamino, fluorine, cyano, hydroxy, carboxy, $C_{1-2}$ alkoxy, carbamoyloxy, mono- or di-$C_{1-4}$alkylcarbamoyloxy, $C_{1-4}$-alkoxycarbony and $C_{1-4}$alkanoyloxy; wherein one carbon atom of the $C_{1-6}$ alkyl may optionally be replaced by O;
—O—$C_{1-6}$ alkyl optionally substituted with one or more substituents (e.g. one or two) selected from amino, mono- or di-$C_{1-4}$alkylamino, fluorine, cyano, hydroxy, carboxy, $C_{1-2}$ alkoxy, carbamoyloxy, mono- or di-$C_{1-4}$alkylcarbamoyloxy, $C_{1-4}$-alkoxycarbony and $C_{1-4}$alkanoyloxy; wherein one carbon atom of the $C_{1-6}$ alkyl may optionally be replaced by O;
$C_{1-4}$ alkylthio;
amino;
mono-$C_{1-4}$ alkylamino;
di-$C_{1-4}$ alkylamino;
oxo;
oxido;
carboxy;
carbamoyl;
mono- or di-$C_{1-4}$alkylcarbamoyl;
4-, 5- and 6-membered non-aromatic rings containing a nitrogen heteroatom ring member and optionally a second heteroatom ring member selected from O and N, the non-aromatic rings being optionally substituted with one or more (e.g. one or two) substituents selected from $C_{1-4}$ alkyl and oxo; and
5-membered heteroaryl rings containing a nitrogen heteroatom ring member and optionally a second heteroatom ring member selected from N, O and S, wherein the 5-membered heteroaryl rings are optionally substituted with $C_{1-4}$ alkyl, hydroxy-$C_{1-4}$ alkyl or $C_{1-4}$ alkoxycarbonyl.

1.194 A compound according to Embodiment 1.1, and any one of Embodiments 1.2 to 1.191 that are dependent from Embodiment 1.1, wherein $R^{13}$ is selected from halogen; cyano; $C_{1-4}$ alkoxy; $C_{1-4}$ alkyl optionally substituted with one or more fluorine, cyano, hydroxy or $C_{1-2}$ alkoxy substituents; $C_{1-4}$acyloxy-$C_{1-4}$ alkyl; $C_{1-4}$ alkylthio; amino; mono-$C_{1-4}$ alkylamino; di-$C_{1-4}$ alkylamino; oxo; oxido; carboxy; carbamoyl; mono- or di-$C_{1-4}$alkylcarbamoyl; and 5-membered heteroaryl rings containing a nitrogen heteroatom ring member and optionally a second heteroatom ring member selected from N, O and S, wherein the 5-membered heteroaryl rings are optionally substituted with $C_{1-4}$ alkyl, hydroxy-$C_{1-4}$ alkyl or $C_{1-4}$ alkoxycarbonyl.

1.195 A compound according to Embodiment 1.1, and any one of Embodiments 1.2 to 1.191 that are dependent from Embodiment 1.1, wherein $R^{13}$ is selected from halogen;

cyano; hydroxy; $C_{1-4}$ alkoxy; $C_{1-4}$ alkyl optionally substituted with one or more fluorine, cyano, hydroxy or $C_{1-2}$ alkoxy substituents; $C_{1-4}$acyloxy-$C_{1-4}$ alkyl; $C_{1-4}$ alkylthio; amino; mono-$C_{1-4}$ alkylamino; di-$C_{1-4}$ alkylamino; oxo; oxido; carboxy; carbamoyl; mono- or di-$C_{1-4}$alkylcarbamoyl; and 5-membered heteroaryl rings containing a nitrogen heteroatom ring member and optionally a second heteroatom ring member selected from N, O and S, wherein the 5-membered heteroaryl rings are optionally substituted with $C_{1-4}$ alkyl, hydroxy-$C_{1-4}$ alkyl or $C_{1-4}$ alkoxycarbonyl.

1.196 A compound according to Embodiment 1.194 wherein $R^{13}$ is selected from halogen, cyano, $C_{1-4}$alkoxy, $C_{1-4}$ alkyl, hydroxy-$C_{1-4}$ alkyl, $C_{1-4}$acyloxy-$C_{1-4}$ alkyl, $C_{1-4}$ alkylthio, amino, mono-$C_{1-4}$ alkylamino, di-$C_{1-4}$ alkylamino, oxo, oxido, pyrazolyl, $C_{1-4}$ alkoxycarbonylpyrazolyl, hydroxy-$C_{1-4}$ alkyl-pyrazolyl, carboxy and carbamoyl.

1.197 A compound according to Embodiment 1.195 wherein $R^{13}$ is selected from halogen, cyano; hydroxy, $C_{1-4}$alkoxy; $C_{1-4}$ alkyl, hydroxy-$C_{1-4}$ alkyl, $C_{1-4}$ alkylthio, amino, mono-$C_{1-4}$ alkylamino, di-$C_{1-4}$ alkylamino, oxo, oxido, pyrazolyl, $C_{1-4}$ alkoxycarbonylpyrazolyl, hydroxy-$C_{1-4}$ alkyl-pyrazolyl, carboxy and, carbamoyl.

1.198 A compound according to Embodiment 1.195 wherein $R^{13}$ is selected from halogen, cyano, hydroxy, $C_{1-4}$alkoxy, $C_{1-4}$ alkyl, hydroxy-$C_{1-4}$ alkyl, amino, mono-$C_{1-4}$ alkylamino, di-$C_{1-4}$ alkylamino, oxo, oxido, pyrazolyl, hydroxy-$C_{1-4}$ alkyl-pyrazolyl, carboxy and carbamoyl.

1.199 A compound according to any one of Embodiments 1.0 to 1.91 and 1.196 wherein $R^{13}$ is selected from fluorine, chlorine, cyano, methoxy, methyl, methylthio, oxo, oxido, hydroxymethyl, acetoxymethyl, carboxy, carbamoyl, pyrazolyl, ethoxycarbonyl-pyrazolyl, hydroxymethylpyrazolyl, amino, methylamino and dimethylamino.

1.200 A compound according to Embodiment 1.197 wherein $R^{13}$ is selected from fluorine, chlorine, cyano, hydroxy, methoxy, methyl, oxo, oxido, hydroxymethyl, carboxy, carbamoyl, pyrazolyl, hydroxymethylpyrazolyl, amino, methylamino and dimethylamino.

1.201 A compound according to Embodiment 1.199 wherein $R^{13}$ is selected from fluorine, chlorine, cyano, methyl, oxido, hydroxymethyl, acetoxymethyl, carbamoyl, pyrazolyl, hydroxymethylpyrazolyl, amino and methylamino.

1.202 A compound according to Embodiment 1.201 wherein $R^{13}$ is selected from chlorine, methyl, hydroxymethyl and amino.

1.203 A compound according to Embodiment 1.201 or Embodiment 1.202 wherein $R^{13}$ is amino.

1.204 A compound according to Embodiment 1.202 wherein $R^{13}$ is hydroxymethyl.

1.205 A compound according to Embodiment 1.202 wherein two substituents $R^{13}$ are present and are amino and chlorine.

1.206 A compound according to Embodiment 1.202 wherein two substituents $R^{13}$ are present and are amino and methyl.

1.207 A compound according to any one of Embodiments 1.1 to 1.206 wherein either no substituents $R^{13}$ are present or 1 or 2 substituents $R^{13}$ are present.

1.208 A compound according to Embodiment 1.207 wherein one substituent $R^{13}$ is present.

1.209 A compound according to Embodiment 1.202 wherein two substituents $R^{13}$ are present.

1.210 A compound according to Embodiment 1.207 wherein no substituents $R^{13}$ are present.

1.211 A compound according to Embodiment 1.1 having the isomeric form (1a):

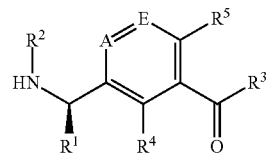

or a salt, N-oxide or tautomer thereof, wherein A, E, $R^1$, $R^2$, $R^3$, $R^4$ and $R^5$ are as defined in Embodiment 1.1 and any one of Embodiments 1.2 to 1.210 that are dependent from Embodiment 1.1.

1.211A A compound according to Embodiment 1.211 wherein:

A is CH;

E is CH;

$R^1$ is ethyl or cyclopropyl;

$R^2$ is X—$R^8$; wherein X is —*CH($CH_3$)$CH_2$— and the asterisk denotes a chiral centre which is in the S-configuration;

$R^8$ is C(=O)$NR^{10}R^{11}$ where $R^{10}$ and $R^{11}$ are both hydrogen;

$R^4$ is fluorine;

$R^5$ is chlorine; and $R^3$ is pyridyl substituted with one substituent which is an $NH_2$ group.

1.212 A compound according to Embodiment 1.1 having the isomeric form (1b):

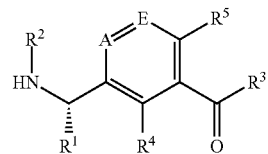

or a salt, N-oxide or tautomer thereof, wherein A, E, $R^1$, $R^2$, $R^3$, $R^4$ and $R^5$ are as defined in Embodiment 1.1 and any one of Embodiments 1.2 to 1.210 that are dependent from Embodiment 1.1.

1.213 A compound according to Embodiment 1.211 having the formula (2):

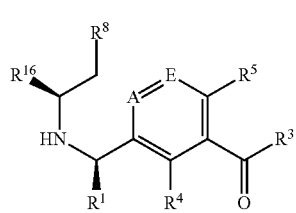

or a salt, N-oxide or tautomer thereof, wherein:

$R^{16}$ is selected from hydrogen and $C_{1-4}$ alkyl; and

A, E, $R^1$, $R^3$, $R^4$, $R^5$ and $R^8$ are as defined in Embodiment 1.1 and any one of Embodiments 1.2 to 1.210 that are dependent from Embodiment 1.1.

1.214 A compound according to Embodiment 1.211 having the formula (3):

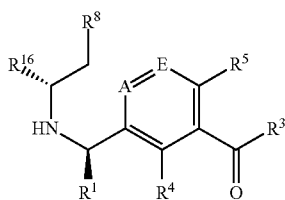

(3)

or a salt, N-oxide or tautomer thereof, wherein:
$R^{16}$ is selected from hydrogen and $C_{1-4}$ alkyl; and
A, E, $R^1$, $R^3$, $R^4$, $R^5$ and $R^8$ are as defined in Embodiment 1.1 and any one of Embodiments 1.2 to 1.210 that are dependent from Embodiment 1.1.

1.215 A compound according to Embodiment 1.212 having the formula (4):

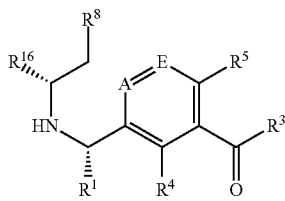

(4)

or a salt, N-oxide or tautomer thereof, wherein:
$R^{16}$ is selected from hydrogen and $C_{1-4}$ alkyl; and A, E, $R^1$, $R^3$, $R^4$, $R^5$ and $R^8$ areas defined in Embodiment 1.1 and any one of Embodiments 1.2 to 1.210 that are dependent from Embodiment 1.1.

1.216 A compound according to Embodiment 1.212 having the formula (5):

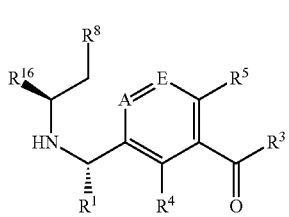

(5)

or a salt, N-oxide or tautomer thereof, wherein:
$R^{16}$ is selected from hydrogen and $C_{1-4}$ alkyl; and
A, E, $R^1$, $R^3$, $R^4$, $R^5$ and $R^8$ are as defined in Embodiment 1.1 and any one of Embodiments 1.2 to 1.210 that are dependent from Embodiment 1.1.

1.217 A compound according to Embodiment 1.1 having the formula (6):

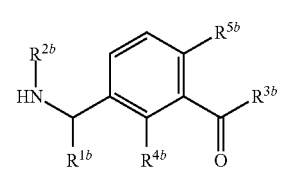

(6)

or a salt, N-oxide, tautomer or stereoisomer thereof, wherein:
$R^{1b}$ is selected from $C_{1-4}$ alkyl, allyl and cyclopropyl;
$R^{2b}$ is selected from hydrogen and a group $X^b$—$R^{8b}$;
$X^b$ is a $C_{1-5}$ alkanediyl group wherein one carbon atom of the $C_{1-4}$ alkanediyl group may optionally be bonded to a —$CH_2$—$CH_2$— moiety to form a cyclopropane-1,1-diyl group or two adjacent carbon atoms of the $C_{1-4}$ alkanediyl group may optionally be bonded to a —$CH_2$—$CH_2$—$CH_2$— moiety to form a cyclopentane-1,2-diylgroup;
$R^{3b}$ is a carbocyclic or heterocyclic ring selected from phenyl, pyridyl, 1-oxypyridyl, pyridonyl, pyrazinyl, pyrimidinyl, pyridazinyl, pyrazolyl, isothiazolyl, thiazolyl, isoxazolyl, pyrido-oxazinonyl and dihydrobenzoxazinyl, each being optionally substituted with one or more substituents $R^{13b}$;
$R^{4b}$ is halogen;
$R^{5b}$ is selected from halogen; hydroxy; $C_{1-2}$alkyl; $C_{1-2}$alkoxy; difluoromethoxy; trifluoromethoxy;
$R^{8b}$ is selected from hydroxy and $C(=O)NHR^{11b}$; provided that when $R^{8b}$ is hydroxy, there are at least two carbon atoms in line between the hydroxy group and the nitrogen atom to which $X^b$ is attached;
$R^{11b}$ is selected from hydrogen and amino-$C_{2-4}$ alkyl; and
$R^{13b}$ is selected from halogen, cyano; hydroxy, $C_{1-4}$ alkyl, oxo, $C_{1-4}$ alkoxy, hydroxy-$C_{1-4}$ alkyl, $C_{1-4}$acyloxy-$C_{1-4}$ alkyl, $C_{1-4}$ alkylsulfanyl, amino, mono-$C_{1-4}$ alkylamino, di-$C_{1-4}$ alkylamino, pyrazolyl, $C_{1-4}$ alkoxycarbonylpyrazolyl, hydroxy-$C_{1-4}$ alkyl-pyrazolyl, carboxy and, carbamoyl.

1.218 A compound according to Embodiment 1.217 wherein:
$R^{1b}$ is selected from $C_{1-4}$ alkyl and cyclopropyl;
$X^b$ is a $C_{1-5}$ alkanediyl group wherein one carbon atom of the $C_{1-4}$ alkanediyl group may optionally be bonded to a —$CH_2$—$CH_2$— moiety to form a cyclopropane-1,1-diyl group;
$R^{3b}$ is a carbocyclic or heterocyclic ring selected from phenyl, pyridyl, 1-oxypyridyl, pyridonyl, pyrazinyl, pyrimidinyl, pyridazinyl, pyrazolyl, isothiazolyl, thiazolyl, isoxazolyl and pyrido-oxazinonyl, each being optionally substituted with one or more substituents $R^{13b}$; and
$R^{13b}$ is selected from halogen, cyano; hydroxy, $C_{1-4}$ alkyl, oxo, $C_{1-4}$ alkoxy, hydroxy-$C_{1-4}$ alkyl, $C_{1-4}$acyloxy-$C_{1-4}$ alkyl, $C_{1-4}$ alkylsulfanyl, amino, mono-$C_{1-4}$ alkylamino, di-$C_{1-4}$ alkylamino, pyrazolyl, $C_{1-4}$ alkoxycarbonylpyrazolyl, hydroxy-$C_{1-4}$ alkyl-pyrazolyl, carboxy and, carbamoyl.

1.219 A compound according to Embodiment 1.217 or Embodiment 1.218, wherein:
$R^{1b}$ is selected from ethyl and cyclopropyl;
$R^{2b}$ is selected from hydrogen and a group $X^b$—$R^{8b}$;
$X^b$ is a $C_{1-5}$ alkanediyl group, which may be optionally substituted with fluorine, wherein one carbon atom of the $C_{1-4}$ alkanediyl group may optionally be bonded to a —$CH_2$—$CH_2$— moiety to form a cyclopropane-1,1-diylgroup;
$R^{3b}$ is a carbocyclic or heterocyclic ring selected from phenyl, pyridyl, 1-oxypyridyl, pyridonyl, pyrazinyl, pyrimidinyl, isothiazolyl, thiazolyl, isoxazolyl, dihydrobenzoxazinyl and pyrido-oxazinonyl, each being optionally substituted with one or more substituents $R^{13b}$;
$R^{4b}$ is fluorine;
$R^{5b}$ is selected from fluorine; chlorine; hydroxy; methyl; and methoxy;
$R^{8b}$ is selected from hydroxy and $C(=O)NHR^{11b}$; provided that when $R^{8b}$ is hydroxy, there are at least two carbon atoms in line between the hydroxy group and the nitrogen atom to which $X^b$ is attached;

$R^{11b}$ is selected from hydrogen and aminoethyl; and $R^{13b}$ is selected from fluorine, chlorine, hydroxy, cyano; methyl, methoxy, hydroxymethyl, acetoxymethyl, methysulfanyl, amino, methylamino, dimethylamino, pyrazolyl, ethoxycarbonyl-pyrazolyl, hydroxymethyl-pyrazolyl, carboxy and carbamoyl.

1.220 A compound according to Embodiment 1.219 wherein $R^{3b}$ is a carbocyclic or heterocyclic ring selected from phenyl, pyridyl, 1-oxypyridyl, pyridonyl, pyrazinyl, pyrimidinyl, isothiazolyl, thiazolyl, isoxazolyl, benzoxazinyl and pyrido-oxazinonyl, each being optionally substituted with one or more substituents $R^{13b}$.

1.221 A compound according to Embodiment 1.219 or Embodiment 220 wherein $R^{1b}$ is ethyl.

1.222 A compound according to Embodiment 1.219 or Embodiment 1.220 wherein $R^{1b}$ is ethyl in which all five hydrogen atoms are $^2H$ (deuterium) isotopes (i.e. $R^{1b}$ is $CD_2CD_3$ where D is deuterium).

1.223 A compound according to Embodiment 1.219 or Embodiment 1.220 wherein $R^{1b}$ is cyclopropyl.

1.224 A compound according to any one of Embodiments 1.217 to 1.223 wherein $R^{5b}$ is chlorine.

1.225 A compound according to any one of Embodiments 1.217 to 1.224 wherein $R^{2b}$ is hydrogen.

1.226 A compound according to one of Embodiments 1.217 to 1.225 wherein $R^{2b}$ is a group $X^b$—$R^{8b}$.

1.227 A compound according to Embodiment 1.226 wherein $R^{8b}$ is $C(=O)NHR^{11b}$; where $R^{11b}$ is selected from hydrogen, 2-hydroxyethyl and 2-aminoethyl.

1.228 A compound according to Embodiment 1.227 wherein $R^{8b}$ is $C(=O)NHR^{11b}$; where $R^{11b}$ is selected from hydrogen and 2-aminoethyl.

1.229 A compound according to Embodiment 1.227 wherein $R^{8b}$ is $C(=O)NH_2$.

1.230 A compound according to Embodiment 1.227 wherein $R^{8b}$ is $C(=O)NH(CH_2)_2NH_2$.

1.231 A compound according to Embodiment 1.227 wherein $R^{8b}$ is $C(=O)NH(CH_2)_2OH$.

1.232 A compound according to any one of Embodiments 1.217 to 1.231 wherein there are 0, 1 or 2 substituents $R^{13b}$ on the carbocyclic or heterocyclic ring.

1.233 A compound according to any one of Embodiments 1.217 to 1.232 wherein $R^{3b}$ is selected from aminopyridyl, phenyl, hydroxyphenyl, difluorophenyl, cyanophenyl, pyridyl, methoxypyridyl, chloropyridyl, carboxypyridyl, fluorophenyl, pyrimidinyl, isothiazolyl, thiazolyl, methyl-isoxazolyl, 1-oxypyridyl, carboxyphenyl, cyanopyridyl, aminopyrazinyl, methylaminopyrazinyl, methylaminopyridyl, dimethylaminopyridyl, pyrazolyl-pyridyl, aminocarbonylpyridyl, aminocarbonylphenyl, pyridonyl, ethoxycarbonylpyrazolyl-pyridyl, hydroxymethylpyrazolyl-pyridyl, acetoxymethylphenyl, hydroxymethylphenyl, methylsulfanylpyrimidinyl, pyrazolyl, pyrido[3,2b][1,4]oxazinonyl, aminopyridazinyl, amino-cyanophenyl, chloropyridazinyl and methoxy-cyanophenyl.

1.234 A compound according to any one of Embodiments 1.217 to 1.232 wherein $R^{3b}$ is selected from aminopyridyl, phenyl, hydroxyphenyl, difluorophenyl, cyanophenyl, pyridyl, methoxypyridyl, chloropyridyl, carboxypyridyl, fluorophenyl, pyrimidinyl, isothiazolyl, thiazolyl, methyl-isoxazolyl, 1-oxypyridyl, carboxyphenyl, cyanopyridyl, aminopyrazinyl, methylaminopyrazinyl, methylaminopyridyl, dimethylaminopyridyl, pyrazolyl-pyridyl, aminocarbonylpyridyl, aminocarbonylphenyl, pyridonyl, ethoxycarbonylpyrazolyl-pyridyl, hydroxymethylpyrazolyl-pyridyl, acetoxymethylphenyl, hydroxymethylphenyl, methylsulfanylpyrimidinyl, pyrazolyl, pyrido[3,2b][1,4]oxazinonyl, aminopyridazinyl, amino-cyanophenyl, chloropyridazinyl, methoxy-cyanophenyl, amino-chlorophenyl, amino-tolyl, benzoxazinyl, dihydrobenzoxazinonyl and amino-methylpyridyl.

1.235 A compound according to Embodiment 1.233 wherein $R^{3b}$ is selected from 6-amino-3-pyridyl; 5-amino-3-pyridyl; 5-amino-2-pyridyl; 2-amino-4-pyridyl; phenyl; 3,4-difluorophenyl; 3-cyanophenyl; 4-cyanophenyl; 2-pyridyl; 3-pyridyl; 4-pyridyl; isothiazolyl-5-yl; 5-methoxypyridin-3-yl; 6-chloropyridin-3-yl; 6-carboxypyridin-3-yl; 3-fluorophenyl; 4-fluorophenyl; pyrimidin-4-yl; pyrimidin-5-yl; isothiazole-5-yl; thiazol-2-yl; 5-methylisoxazol-3-yl; 1-oxypyridin-3-yl; 1-oxypyridin-4-yl; 3-carboxyphenyl; 4-carboxyphenyl; 6-cyanopyridin-3-yl; 5-aminopyrazin-2-yl; 5-methylaminopyrazin-2-yl; 6-methylaminopyridin-3-yl; 6-dimethylaminopyridin-3-yl; 6-(1H)-pyrazol-1-yl)-pyridin-3-yl; 6-aminocarbonylpyridin-3-yl; 4-aminocarbonylphenyl; 6-oxo-1,6-dihydropyridin-3-yl; 6-[4-ethoxycarbonyl-1H-pyrazol-1-yl]-pyridin-3-yl; 6-[4-(hydroxymethyl)-1H-pyrazol-1-yl]-pyridin-3-yl; 4-acetoxymethylphenyl; 3-hydroxymethylphenyl; 4-hydroxymethylphenyl; 2-methylsulfanylpyrimidin-5-yl; 1H-pyrazol-4-yl; 2H,3H,4H-pyrido[3,2-b][1,4]oxazin-3-on-6-yl; 3-hydroxyphenyl; 4-hydroxyphenyl; 6-aminopyridazin-3-yl; 4-amino-3-cyanophenyl; 6-chloropyridazin-3-yl and 3-cyano-4-methoxyphenyl.

1.236 A compound according to Embodiment 1.234 wherein $R^{3b}$ is selected from 6-amino-3-pyridyl; 5-amino-3-pyridyl; 5-amino-2-pyridyl; 5-amino-4-methyl-2-pyridyl; 2-amino-4-pyridyl; phenyl; 3,4-difluorophenyl; 3-cyanophenyl; 4-cyanophenyl; 2-pyridyl; 3-pyridyl; 4-pyridyl; isothiazolyl-5-yl; 5-methoxypyridin-3-yl; 6-chloropyridin-3-yl; 6-carboxypyridin-3-yl; 3-fluorophenyl; 4-fluorophenyl; pyrimidin-4-yl; pyrimidin-5-yl; isothiazole-5-yl; thiazol-2-yl; 5-methylisoxazol-3-yl; 1-oxypyridin-3-yl; 1-oxypyridin-4-yl; 3-carboxyphenyl; 4-carboxyphenyl; 6-cyanopyridin-3-yl; 5-cyanopyridin-2-yl; 5-aminopyrazin-2-yl; 5-methylaminopyrazin-2-yl; 6-methylaminopyridin-3-yl; 6-dimethylaminopyridin-3-yl; 6-(1H)-pyrazol-1-yl)-pyridin-3-yl; 6-aminocarbonylpyridin-3-yl; 4-aminocarbonylphenyl; 6-oxo-1,6-dihydropyridin-3-yl; 6-[4-ethoxycarbonyl-1H-pyrazol-1-yl]-pyridin-3-yl; 6-[4-(hydroxymethyl)-1H-pyrazol-1-yl]-pyridin-3-yl; 4-acetoxymethylphenyl; 3-hydroxymethylphenyl; 4-hydroxymethylphenyl; 2-methylsulfanylpyrimidin-5-yl; 1H-pyrazol-4-yl; 2H,3H,4H-pyrido[3,2-b][1,4]oxazin-3-on-6-yl; 3-hydroxyphenyl; 4-hydroxyphenyl; 6-aminopyridazin-3-yl; 4-amino-3-cyanophenyl; 6-chloropyridazin-3-yl, 3-cyano-4-methoxyphenyl, 4-cyano-3-methoxyphenyl, 4-amino-3-chlorophenyl, 4-amino-3-methylphenyl, benzoxazinyl, 3-oxo-3,4-dihydro-2H-1,4-benzoxazin-7-yl, 3,4-dihydro-2H-1,4-benzoxazin-7-yl and amino-methylpyridyl.

1.237 A compound according to Embodiment 1.233 wherein $R^{3b}$ is selected from aminopyridyl, phenyl, hydroxyphenyl, difluorophenyl, cyanophenyl, pyridyl, fluorophenyl, pyrimidinyl, isothiazolyl, methylisoxazolyl, 1-oxypyridyl, carboxyphenyl, cyanopyridyl, aminopyrazinyl, dimethylaminopyridyl, pyrazolyl-pyridyl, aminocarbonylphenyl, pyridonyl, hydroxymethylpyrazolyl-pyridyl, hydroxymethylphenyl, hydroxyphenyl, aminopyridazinyl, amino-cyanophenyl, chloropyridazinyl and methoxy-cyanophenyl.

1.238 A compound according to Embodiment 1.234 wherein $R^{3b}$ is selected from aminopyridyl, phenyl, hydroxyphenyl, difluorophenyl, cyanophenyl, pyridyl, fluorophenyl, pyrimidinyl, isothiazolyl, methylisoxazolyl, 1-oxypyridyl, carboxyphenyl, cyanopyridyl, aminopyrazinyl, dimethylaminopyridyl, pyrazolyl-pyridyl, aminocarbonylphenyl, pyridonyl, hydroxymethylpyrazolyl-pyridyl, hydroxymethylphenyl, hydroxyphenyl, aminopyridazinyl, aminocyanophenyl, chloropyridazinyl, methoxy-cyanophenyl, amino-methylpyridyl, amino-chlorophenyl, amino-methylphenyl, 3,4-dihydrobenzoxazinyl, 3-oxo-3,4-dihydro-2H-1,4-benzoxazin-7-yl, dihydro-benzoxazinyl and amino-methylpyridyl 1.239 A compound according to Embodiment 1.234 wherein $R^{3b}$ is selected from 6-amino-3-pyridyl; 5-amino-3-pyridyl; 5-amino-2-pyridyl; 2-amino-4-pyridyl; phenyl; 3,4-difluorophenyl; 3-cyanophenyl; 4-cyanophenyl; 2-pyridyl; 3-pyridyl; 4-pyridyl; isothiazolyl-5-yl; 3-fluorophenyl; 4-fluorophenyl; pyrimidin-4-yl, isothiazole-5-yl; 5-methylisoxazol-3-yl; 1-oxypyridin-3-yl; 1-oxypyridin-4-yl; 3-carboxyphenyl; 4-carboxyphenyl; 6-cyanopyridin-3-yl; 5-aminopyrazin-2-yl; 5-methylaminopyrazin-2-yl; 6-dimethylaminopyridin-3-yl; 6-(1H)-pyrazol-1-yl)-pyridin-3-yl; 4-aminocarbonylphenyl; 6-oxo-1,6-dihydropyridin-3-yl; 6-[4-(hydroxymethyl)-1H-pyrazol-1-yl]-pyridin-3-yl; 3-hydroxymethylphenyl; 4-hydroxymethylphenyl; 3-hydroxyphenyl; 4-hydroxyphenyl; 6-aminopyridazin-3-yl; 4-amino-3-cyanophenyl; 6-chloropyridazin-3-yl and 3-cyano-4-methoxyphenyl.

1.240 A compound according to Embodiment 1.234 wherein $R^{3b}$ is selected from 6-amino-3-pyridyl; 5-amino-3-pyridyl; 5-amino-2-pyridyl; 2-amino-4-pyridyl; phenyl; 3,4-difluorophenyl; 3-cyanophenyl; 4-cyanophenyl; 2-pyridyl; 3-pyridyl; 4-pyridyl; isothiazolyl-5-yl; 3-fluorophenyl; 4-fluorophenyl; pyrimidin-4-yl, isothiazole-5-yl; 5-methylisoxazol-3-yl; 1-oxypyridin-3-yl; 1-oxypyridin-4-yl; 3-carboxyphenyl; 4-carboxyphenyl; 6-cyanopyridin-3-yl; 5-aminopyrazin-2-yl; 5-methylaminopyrazin-2-yl; 6-dimethylaminopyridin-3-yl; 6-(1H)-pyrazol-1-yl)-pyridin-3-yl; 4-aminocarbonylphenyl; 6-oxo-1,6-dihydropyridin-3-yl; 6-[4-(hydroxymethyl)-1H-pyrazol-1-yl]-pyridin-3-yl; 3-hydroxymethylphenyl; 4-hydroxymethylphenyl; 3-hydroxyphenyl; 4-hydroxyphenyl; 6-aminopyridazin-3-yl; 4-amino-3-cyanophenyl; 6-chloropyridazin-3-yl, 3-cyano-4-methoxyphenyl, 5-amino-4-methyl-2-pyridyl; 5-cyanopyridin-2-yl; 4-cyano-3-methoxyphenyl, 4-amino-3-chlorophenyl, 4-amino-3-methylphenyl, benzoxazinyl, 3-oxo-3,4-dihydro-2H-1,4-benzoxazin-7-yl, 3,4-dihydro-2H-1,4-benzoxazin-7-yl and amino-methylpyridyl.

1.241 A compound according to Embodiment 1.233 wherein $R^{3b}$ is selected from aminopyridyl, phenyl, difluorophenyl, cyanophenyl, pyridyl, methoxypyridyl, chloropyridyl, carboxypyridyl, carboxyphenyl, fluorophenyl, pyrimidinyl, isothiazolyl, thiazolyl, methylisoxazolyl, 1-oxypyridyl, cyanopyridyl, aminopyrazinyl, methylaminopyridyl, methylaminopyrazinyl, dimethylaminopyridyl, pyrazolyl-pyridyl, aminocarbonylpyridyl, pyridonyl, ethoxycarbonylpyrazolyl-pyridyl, hydroxymethylpyrazolyl-pyridyl, acetoxymethylphenyl, hydroxymethylphenyl, methylsulfanylpyrimidinyl, pyrazolyl and pyrido[3,2b][1,4]oxazinonyl.

1.242 A compound according to Embodiment 1.241 wherein $R^{3b}$ is selected from 6-amino-3-pyridyl; 5-amino-3-pyridyl; 5-amino-2-pyridyl; 2-amino-4-pyridyl; phenyl; 3,4-difluorophenyl; 3-cyanophenyl; 4-cyanophenyl; 2-pyridyl; 3-pyridyl; 4-pyridyl; isothiazolyl-5-yl; 5-methoxypyridin-3-yl; 6-chloropyridin-3-yl; 6-carboxypyridin-3-yl; 3-fluorophenyl; 4-fluorophenyl; pyrimidin-4-yl; pyrimidin-5-yl; isothiazole-5-yl; thiazol-2-yl; 5-methylisoxazol-3-yl; 1-oxypyridin-3-yl; 1-oxypyridin-4-yl; 6-cyanopyridin-3-yl; 5-aminopyrazin-2-yl; 5-methylaminopyrazin-2-yl; 6-methylaminopyridin-3-yl; 6-dimethylaminopyridin-3-yl; 6-(1H)-pyrazol-1-yl)-pyridin-3-yl; 6-aminocarbonylpyridin-3-yl; 6-oxo-1,6-dihydropyridin-3-yl; 6-[4-ethoxycarbonyl-1H-pyrazol-1-yl]-pyridin-3-yl; 6-[4-(hydroxymethyl)-1H-pyrazol-1-yl]-pyridin-3-yl; 4-acetoxymethylphenyl; 3-carboxyphenyl; 3-hydroxymethylphenyl; 4-hydroxymethylphenyl; 2-methylsulfanylpyrimidin-5-yl; 1H-pyrazol-4-yl and 2H,3H,4H-pyrido[3,2-b][1,4]oxazin-3-on-6-yl.

1.243 A compound according to Embodiment 1.234 wherein $R^{3b}$ is selected from 6-amino-3-pyridyl; 5-amino-3-pyridyl; 5-amino-2-pyridyl; 2-amino-4-pyridyl; phenyl; 3,4-difluorophenyl; 3-cyanophenyl; 4-cyanophenyl; 2-pyridyl; 3-pyridyl; 4-pyridyl; isothiazolyl-5-yl; 5-methoxypyridin-3-yl; 6-chloropyridin-3-yl; 6-carboxypyridin-3-yl; 3-fluorophenyl; 4-fluorophenyl; pyrimidin-4-yl; pyrimidin-5-yl; isothiazole-5-yl; thiazol-2-yl; 5-methylisoxazol-3-yl; 1-oxypyridin-3-yl; 1-oxypyridin-4-yl; 6-cyanopyridin-3-yl; 5-aminopyrazin-2-yl; 5-methylaminopyrazin-2-yl; 6-methylaminopyridin-3-yl; 6-dimethylaminopyridin-3-yl; 6-(1H)-pyrazol-1-yl)-pyridin-3-yl; 6-aminocarbonylpyridin-3-yl; 6-oxo-1,6-dihydropyridin-3-yl; 6-[4-ethoxycarbonyl-1H-pyrazol-1-yl]-pyridin-3-yl; 6-[4-(hydroxymethyl)-1H-pyrazol-1-yl]-pyridin-3-yl; 4-acetoxymethylphenyl; 3-carboxyphenyl; 3-hydroxymethylphenyl; 4-hydroxymethylphenyl; 2-methylsulfanylpyrimidin-5-yl; 1H-pyrazol-4-yl, 2H,3H,4H-pyrido[3,2-b][1,4]oxazin-3-on-6-yl, 5-amino-4-methyl-2-pyridyl; 5-cyanopyridin-2-yl; 4-cyano-3-methoxyphenyl, 4-amino-3-chlorophenyl, 4-amino-3-methylphenyl, benzoxazinyl, 3-oxo-3,4-dihydro-2H-1,4-benzoxazin-7-yl, 3,4-dihydro-2H-1,4-benzoxazin-7-yl and amino-methylpyridyl.

1.244 A compound according to any one of Embodiments 1.217 to 1.224 and 1.226 to 1.243 wherein $X^b$ is selected from groups A to M and R.

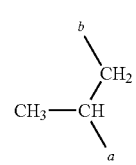

A

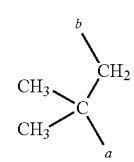

B

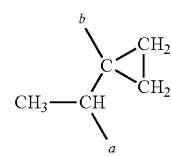

C

D 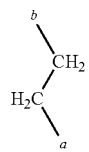
E 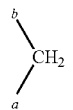
F 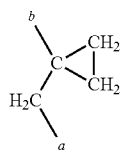
G 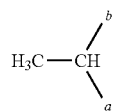
H 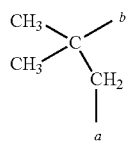
I 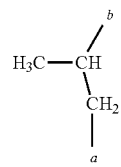
J 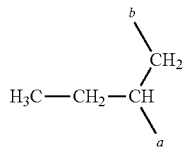
K 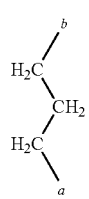
L 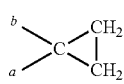
M 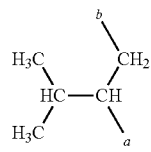
R 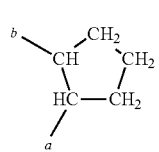
1.244A A compound according to Embodiment 1.244 wherein $X^b$ is selected from groups A to M.
1.245 A compound according to any one of Embodiments 1.217 to 1.224 and 1.226 to 1.243 wherein $X^b$ is selected from groups AA, B, AC, D, E, F, AG, H, AI, J, K, L, M, N, O, P, Q and S below.
AA 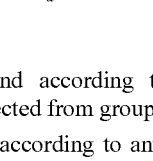
B 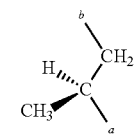
AC 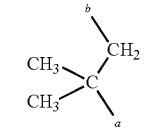
D 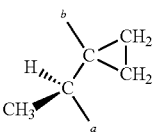
E 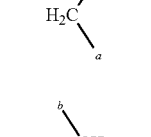
F 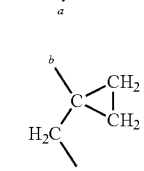
AG 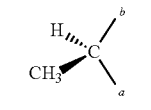

H
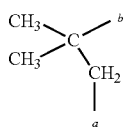
AI
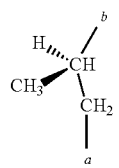
J
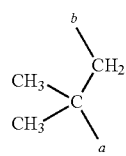
K
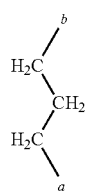
L
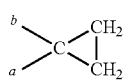
M
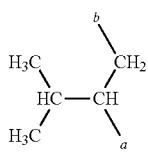
N
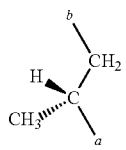
O
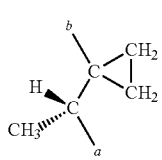
P
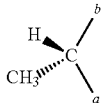
-continued
Q
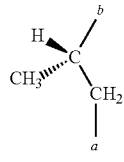
S
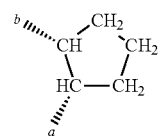
1.246 A compound according to Embodiment 1.245 wherein $X^b$ is selected from groups AA, B, AC, D, E, F, AG, H, AI, J, K, L, M, N, O, P and Q.
1.247 A compound according to any one of Embodiments 1.217 to 1.224 and 1.226 to 1.243 wherein $X^b$ is selected from groups AA, B, AC, D, E, F, AG, H, AI, J, K, L and M below.
AA
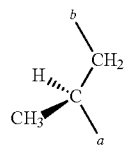
B
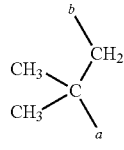
AC
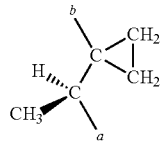
D
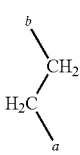
E
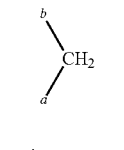
F
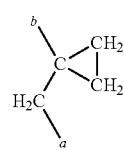

37
-continued

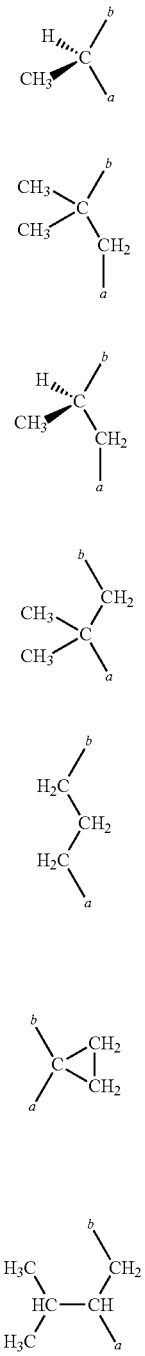

AG

H

AI

J

K

L

M 1.248 A compound according to Embodiment 1.247 wherein $X^b$ is a group AA or B.

1.249 A compound according to Embodiment 1.247 wherein $X^b$ is a group AA, B or D.

1.250 A compound according to Embodiment 1.249 wherein $X^b$ is a group AA.

1.251 A compound according to Embodiment 1.249 wherein $X^b$ is a group B.

1.252 A compound according to Embodiment 1.249 wherein $X^b$ is a group D.

38

1.253 A compound of the formula (7):

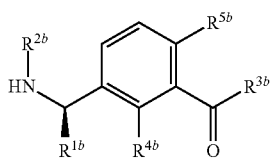

(7)

or a salt, N-oxide, tautomer or stereoisomer thereof, wherein $R^{1b}$, $R^{2b}$, $R^{3b}$, $R^{4b}$ and $R^{5b}$ are as defined in any one of Embodiments 1.217 to 1.252.

1.254 A compound according to Embodiment 1.1 having the formula (8):

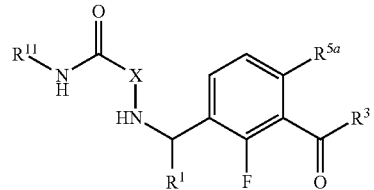

(8)

or a salt, N-oxide, tautomer or stereoisomer thereof, wherein:

$R^{11}$ is selected from hydrogen, amino-$C_{2-4}$alkyl and hydroxy-$C_{2-4}$alkyl;

X is selected from —$(CH_2)_p$—, —$(CH_2)_q$—CH(Alk)-$(CH_2)_r$—, —CH(Alk)-W—, —$(CH_2)_r$—C(CH$_3$)$_2$—$(CH_2)_r$— and —$(CH_2)_t$—W—$(CH_2)_u$—, where W is a cyclopropane-1,1-diyl group or cyclopentane-1,2-diyl group; each Alk is independently selected from methyl, ethyl and isopropyl; p is 1, 2 or 3; q is 0 or 1; r is 0 or 1; t is 0 or 1 and u is 0 or 1; provided that the total number of carbon atoms contained within X, excluding two of the carbon atoms of any cyclopropane-1,1-diyl group or cyclopentane-1,2-diyl group present, does not exceed 8;

$R^1$ is selected from ethyl, propyl, cyclopropyl, cyclopropylmethyl and prop-2-en-1-yl;

$R^{5a}$ is selected from fluorine, chlorine, methyl and methoxy;

$R^3$ is selected from phenyl, pyridyl, pyrazinyl, pyrimidinyl, isoxazolyl, isothiazolyl, pyrazolyl, 3,4-dihydro-pyridooxazine and 3,4-dihydrobenzoxazine, each being unsubstituted or substituted with one or two substituents $R^{13}$; and $R^{13}$ is selected from halogen, cyano, hydroxy, $C_{1-4}$alkoxy, $C_{1-4}$ alkyl, hydroxy-$C_{1-4}$ alkyl, amino, mono-$C_{1-4}$ alkylamino, di-$C_{1-4}$ alkylamino, oxo, oxido, pyrazolyl, hydroxy-$C_{1-4}$ alkyl-pyrazolyl, carboxy and carbamoyl.

1.254A A compound according to Embodiment 1.1 having the formula (8A):

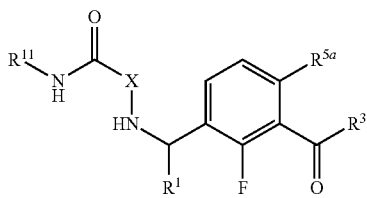

(8A)

or a salt, N-oxide, tautomer or stereoisomer thereof, wherein:

$R^{11}$ is selected from hydrogen and 2-aminoethyl;

X is a group:

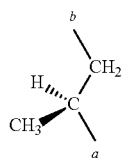

$R^1$ is selected from ethyl, propyl, cyclopropyl, cyclopropylmethyl, 2-methylpropyl and prop-2-en-1-yl;

$R^{5a}$ is chlorine; and $R^3$ is selected from 6-amino-3-pyridyl; 5-amino-2-pyridyl; 4-cyanophenyl; 5-aminopyrazin-2-yl; 6-dimethylaminopyridin-3-yl; 4-hydroxymethylphenyl; 4-amino-3-chlorophenyl; 4-amino-3-methylphenyl; and 3-oxo-3,4-dihydro-2H-1,4-benzoxazin-7-yl.

1.255 A compound according to Embodiment 1.254 wherein $R^{11}$ is selected from hydrogen, 2-aminoethyl and 2-hydroxyethyl.

1.256 A compound according to Embodiment 1.255 wherein $R^{11}$ is hydrogen.

1.257 A compound according to any one of Embodiments 1.254 to 1.256 wherein X is selected from groups A, B and D below:

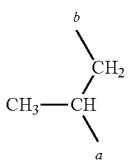

A

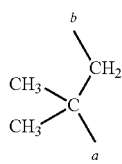

B

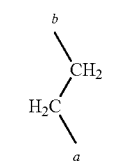

D 1.258 A compound according to Embodiment 1.257 wherein X is selected from groups AA, B and D below:

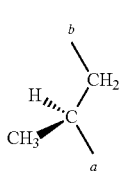

AA

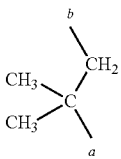

B

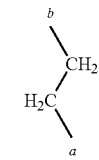

D 1.259 A compound according to Embodiment 1.258 wherein X is a group AA.

1.260 A compound according to any one of Embodiments 1.254 to 1.259 wherein $R^1$ is ethyl or cyclopropyl.

1.261 A compound according to any one of Embodiments 1.254 to 1.260 wherein the moiety:

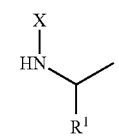

has the configuration:

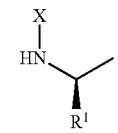

1.262 A compound according to any one of Embodiments 1.254 to 1.261 wherein $R^{5a}$ is chlorine.

1.263 A compound according to any one of Embodiments 1.254 to 1.262 wherein $R^3$ is phenyl or pyridyl, each being unsubstituted or substituted with one or two substituents $R^{13}$.

1.264 A compound according to any one of Embodiments 1.254 to 1.263 wherein 0, 1 or 2 substituents $R^{13}$ are present and, when present, are selected from chlorine, fluorine, cyano, hydroxy, methoxy, methyl, hydroxymethyl, amino, methylamino, dimethylamino, oxo, oxido, pyrazolyl, hydroxymethylpyrazolyl, carboxy and carbamoyl.

1.265 A compound according to Embodiment 1.264 wherein 0, 1 or 2 substituents $R^{13}$ are present and, when present, are selected from chlorine, fluorine, cyano, hydroxy, methoxy, methyl, hydroxymethyl, amino, methylamino, dimethylamino, hydroxymethylpyrazolyl, pyrazolyl and carbamoyl.

1.266 A compound according to Embodiment 1.265 wherein 0, 1 or 2 substituents $R^{13}$ are present and, when present, are selected from chlorine, fluorine, cyano, hydroxy, methyl, hydroxymethyl and amino.

1.267 A compound according to Embodiment 1.254 having the formula (9):

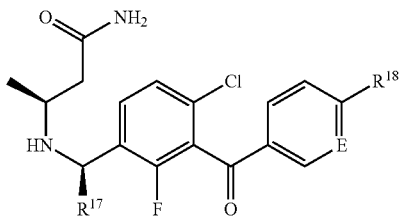

or a salt, N-oxide, tautomer or stereoisomer thereof,
wherein $R^{17}$ is selected from ethyl and cyclopropyl; $R^{18}$ is selected from amino and hydroxymethyl; E is N or C—$R^{19}$; and $R^{19}$ is selected from hydrogen, methyl and chlorine.

1.267 A compound according to Embodiment 1.267 wherein E is N and $R^{18}$ is amino.

1.2678 A compound according to Embodiment 1.1 which is selected from:
(3S)-3-{[(1R)-1-{3-[(6-aminopyridin-3-yl)carbonyl]-4-chloro-2-fluorophenyl}propyl]-amino}butanamide;
(3S)-3-{[(R)-{4-chloro-3-[(4-cyanophenyl)-carbonyl]-2-fluorophenyl}(cyclo-propyl)methyl]amino}-butanamide;
(3S)-3-{[(1R)-1-(4-chloro-3-{[6-(dimethylamino)pyridin-3-yl]carbonyl}-2-fluorophenyl)propyl]-amino}butanamide;
(3S)-3-{[(1R)-1-{3-[(5-aminopyrazin-2-yl)carbonyl]-4-chloro-2-fluorophenyl}propyl]-amino}butanamide;
(3S)-3-{[(1R)-1-{3-[(5-aminopyridin-2-yl)carbonyl]-4-chloro-2-fluorophenyl}propyl]amino}-butanamide;
(3S)-3-{[(R)-{3-[(6-aminopyridin-3-yl)carbonyl]-4-chloro-2-fluorophenyl}(cyclo-propyl)methyl]amino}-butanamide;
(3S)-3-{[(1R)-1-(4-chloro-2-fluoro-3-{[4-(hydroxymethyl)-phenyl]carbonyl}phenyl)propyl]amino}-butanamide;
(3S)-3-{[(R)-{3-[(5-aminopyrazin-2-yl)carbonyl]-4-chloro-2-fluorophenyl}(cyclo-propyl)methyl]amino}-butanamide;
(3S)-3-{[(R)-{3-[(5-aminopyridin-2-yl)carbonyl]-4-chloro-2-fluorophenyl}(cyclopropyl)methyl]-amino}butanamide;
(3S)—N-(2-aminoethyl)-3-{[(1R)-1-{3-[(6-aminopyridin-3-yl)carbonyl]-4-chloro-2-fluorophenyl}propyl]amino}butanamide;
(3S)-3-{[(1R)-1-{4-chloro-2-fluoro-3-[(3-oxo-3,4-dihydro-2H-1,4-benzoxazin-7-yl)carbonyl]phenyl}propyl]amino}butanamide;
(3S)-3-{[(1R)-1-{3-[(6-aminopyridin-3-yl)carbonyl]-4-chloro-2-fluorophenyl}but-3-en-1-yl]amino}butanamide;
(3S)-3-{[(1R)-1-{3-[(6-aminopyridin-3-yl)carbonyl]-4-chloro-2-fluorophenyl}butyl]amino}-butanamide;
(3S)-3-{[(R)-{3-[(4-amino-3-chlorophenyl)carbonyl]-4-chloro-2-fluorophenyl}(cyclopropyl)-methyl]amino}butanamide;
(3S)-3-{[(R)-{3-[(4-amino-3-methylphenyl)carbonyl]-4-chloro-2-fluorophenyl}-(cyclopropyl)-methyl]-amino}butanamide;
(3S)-3-{[(R)-(4-chloro-2-fluoro-3-{[4-(hydroxyl-methyl)phenyl]-carbonyl}phenyl)(cyclo-propyl)-methyl]amino}-butanamide;
(3S)-3-{[(1R)-1-{3-[(6-aminopyridin-3-yl)carbonyl]-4-chloro-2-fluorophenyl}(2,2,3,3,3-deutero)propyl]amino}butanamide;
(3S)-3-{[(1R)-1-{3-[(4-amino-3-methylphenyl)carbonyl]-4-chloro-2-fluorophenyl}(2,2,3,3,3-deutero)propyl]amino}butanamide;
(3S)-3-{[(1R)-1-{3-[(6-aminopyridin-3-yl)carbonyl]-4-chloro-2-fluorophenyl}-3-methylbutyl]amino}butanamide;
(3S)-3-{[(R)-{4-chloro-2-fluoro-3-[(3-oxo-3,4-dihydro-2H-1,4-benzoxazin-7-yl)carbonyl]phenyl}(cyclopropyl)methyl]amino}butanamide;
(3S)-3-{[(1R)-1-{3-[(6-aminopyridin-3-yl)carbonyl]-4-chloro-2-fluorophenyl}-2-cyclopropylethyl]amino}butanamide; and
(3S)-3-{[(1R)-1-{4-chloro-2-fluoro-3-[(3-oxo-3,4-dihydro-2H-1,4-benzoxazin-7-yl)carbonyl]phenyl}(2,2,3,3,3-pentadeuteryl)propyl]amino}butanamide;
and salts thereof.

1.267C A compound according to Embodiment 1.1 which is selected from:
5-({3-[(1R)-1-aminopropyl]-6-chloro-2-fluorophenyl}carbonyl)-pyridin-2-amine;
5-({3-[(1R)-1-aminopropyl]-6-chloro-2-fluorophenyl}carbonyl)-pyrazin-2-amine;
6-({3-[(1R)-1-aminopropyl]-6-chloro-2-fluorophenyl}carbonyl)-pyridin-3-amine;
4-({3-[(R)-amino(cyclopropyl)methyl]-6-chloro-2-fluorophenyl}carbonyl)benzonitrile;
5-({3-[(1R)-1-aminopropyl]-6-chloro-2-fluorophenyl}carbonyl)-N,N-dimethylpyridin-2-amine;
5-({3-[(R)-amino(cyclopropyl)methyl]-6-chloro-2-fluorophenyl}carbonyl)pyridin-2-amine;
[4-({3-[(1R)-1-aminopropyl]-6-chloro-2-fluorophenyl}carbonyl)phenyl]methanol;
5-({3-[(R)-amino(cyclopropyl)methyl]-6-chloro-2-fluorophenyl}carbonyl)pyrazin-2-amine;
7-({3-[(1R)-1-aminopropyl]-6-chloro-2-fluorophenyl}carbonyl)-3,4-dihydro-2H-1,4-benzoxazin-3-one;
6-({3-[(R)-amino(cyclopropyl)methyl]-6-chloro-2-fluorophenyl}carbonyl)pyridin-3-amine;
5-({3-[(1R)-1-aminobutyl]-6-chloro-2-fluorophenyl}carbonyl)pyridin-2-amine;
5-({3-[(1R)-1-aminobut-3-en-1-yl]-6-chloro-2-fluorophenyl}carbonyl)pyridin-2-amine;
[4-({3-[(R)-amino(cyclopropyl)methyl]-6-chloro-2-fluorophenyl}carbonyl)phenyl]methanol;
7-({3-[(1R)-1-amino(2,2,3,3,3-deutero)propyl]-6-chloro-2-fluorophenyl}carbonyl)-3,4-dihydro-2H-1,4-benzoxazin-3-one;
(4-amino-3-chloro-phenyl)-[3-((R)-amino-cyclopropyl-methyl)-6-chloro-2-fluoro-phenyl]-methanone;
[3-((R)-amino-cyclopropyl-methyl)-6-chloro-2-fluoro-phenyl]-(4-amino-3-methyl-phenyl)-methanone;
4-amino-3-methyl-phenyl)-[3-((R)-(1-amino-(2,2,3,3,3-deutero)propyl)-6-chloro-2-fluoro-phenyl]-methanone;
and salts thereof.

1.268 A compound according to Embodiment 1.1 which is selected from:
(3S)-3-{[(1R)-1-(3-benzoyl-4-chloro-2-fluorophenyl)propyl]amino}butanamide;
(3S)-3-{[(1R)-1-{3-[(6-aminopyridin-3-yl)carbonyl]-4-chloro-2-fluorophenyl}propyl]-amino}butanamide; and
(3S)-3-{[(R)-{3-[(6-aminopyridin-3-yl)carbonyl]-4-chloro-2-fluorophenyl}(cyclopropyl)-methyl]amino}butanamide;
(3S)-3-{[(R)-{3-[(4-amino-3-chlorophenyl)carbonyl]-4-chloro-2-fluorophenyl}-(cyclopropyl)methyl]amino}butanamide;

(3S)-3-{[(R)-{3-[(4-amino-3-methylphenyl)carbonyl]-4-chloro-2-fluorophenyl}-(cyclopropyl)methyl]amino}butanamide;

(3S)-3-{[(R)-(4-chloro-2-fluoro-3-{[4-(hydroxymethyl)phenyl]carbonyl}-phenyl)-(cyclopropyl)methyl]amino}butanamide;

and salts thereof.

1.269 A compound according to Embodiment 1.268 which is (3S)-3-{[(1R)-1-(3-benzoyl-4-chloro-2-fluorophenyl)propyl]amino}butanamide; or a salt thereof.

1.270 A compound according to Embodiment 1.268 which is (3S)-3-{[(1R)-1-{3-[(6-aminopyridin-3-yl)carbonyl]-4-chloro-2-fluorophenyl}propyl]-amino}butanamide; or a salt thereof.

1.271 A compound according to Embodiment 1.268 which is (3S)-3-{[(R)-{3-[(6-aminopyridin-3-yl)carbonyl]-4-chloro-2-fluorophenyl}(cyclopropyl)-methyl]amino}-butanamide; or a salt thereof.

1.272 A compound according to Embodiment 1.268 which is (3S)-3-{[(R)-{3-[(4-amino-3-chlorophenyl)carbonyl]-4-chloro-2-fluorophenyl}-(cyclopropyl)methyl]-amino}butanamide; or a salt thereof.

1.273 A compound according to Embodiment 1.268 which is (3S)-3-{[(R)-{3-[(4-amino-3-methylphenyl)carbonyl]-4-chloro-2-fluorophenyl}-(cyclopropyl)methyl]-amino}butanamide; or a salt thereof.

1.274 A compound according to Embodiment 1.268 which is (3S)-3-{[(R)-(4-chloro-2-fluoro-3-{[4-(hydroxymethyl)phenyl]carbonyl}-phenyl)-(cyclopropyl)methyl]amino}-butanamide;

or a salt thereof.

1.275 A compound according to Embodiment 1.1 and any one of Embodiments 1.2 to 1.274 that are dependent from Embodiment 1.1, wherein $R^5$ is other than trifluoromethoxy.

1.276 A compound according to Embodiment 1.1 and any one of Embodiments 1.2 to 1.275 that are dependent from Embodiment 1.1, wherein $R^5$ is other than difluoromethoxy.

1.277 A compound according to any one of Embodiments 1.1 to 173 which is other than 5-({3-[(1R)-1-aminopropyl]-2-fluoro-6-(trifluoromethoxy)phenyl}carbonyl)-pyridin-2-amine.

1.278 A compound according to Embodiment 1.0A having the isomeric form (1a):

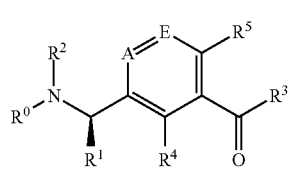

(1a)

or a salt, N-oxide or tautomer thereof, wherein A, E, $R^0$, $R^1$, $R^{1'}$, $R^2$, $R^3$, $R^4$ and $R^5$ are as defined in Embodiment 1.0A and any one of Embodiments 1.2 to 1.210 that are dependent from Embodiment 1.0A.

1.279 A compound according to Embodiment 1.0A having the isomeric form (1b):

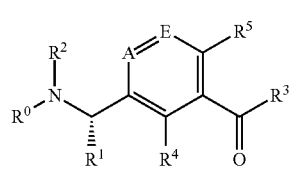

(1b)

or a salt, N-oxide or tautomer thereof, wherein A, E, $R^0$, $R^1$, $R^{1'}$, $R^2$, $R^3$, $R^4$ and $R^5$ are as defined in Embodiment 1.0A and any one of Embodiments 1.2 to 1.210 that are dependent from Embodiment 1.0A.

1.280 A compound according to Embodiment 1.278 having the formula (2):

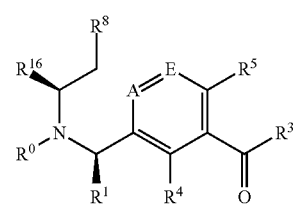

(2)

or a salt, N-oxide or tautomer thereof, wherein:
$R^{16}$ is selected from hydrogen and $C_{1-4}$ alkyl; and
A, E, $R^0$, $R^1$, $R^{1'}$, $R^3$, $R^4$, $R^5$ and $R^8$ are as defined in Embodiment 1.0A and any one of Embodiments 1.2 to 1.210 that are dependent from Embodiment 1.0A.

1.281 A compound according to Embodiment 1.278 having the formula (3):

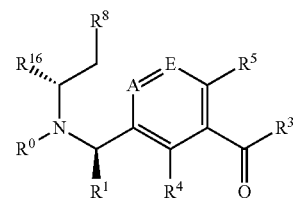

(3)

or a salt, N-oxide or tautomer thereof, wherein:
$R^{16}$ is selected from hydrogen and $C_{1-4}$ alkyl; and
A, E, $R^0$, $R^1$, $R^{1'}$, $R^3$, $R^4$, $R^5$ and $R^8$ are as defined in Embodiment 1.0A and any one of Embodiments 1.2 to 1.210 that are dependent from Embodiment 1.0A.

1.282 A compound according to Embodiment 1.279 having the formula (4):

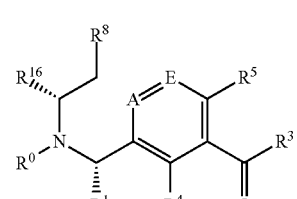

(4)

or a salt, N-oxide or tautomer thereof, wherein:
$R^{16}$ is selected from hydrogen and $C_{1-4}$ alkyl; and
A, E, $R^0$, $R^1$, $R^{1'}$, $R^3$, $R^4$, $R^5$ and $R^8$ are as defined in Embodiment 1.0A and any one of Embodiments 1.2 to 1.210 that are dependent from Embodiment 1.0A.

1.283 A compound according to Embodiment 1.279 having the formula (5):

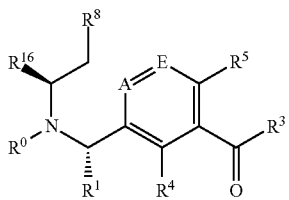

or a salt, N-oxide or tautomer thereof, wherein:
R$^{16}$ is selected from hydrogen and C$_{1-4}$ alkyl; and
A, E, R$^0$, R$^1$, R$^{1'}$, R$^3$, R$^4$, R$^5$ and R$^8$ are as defined in Embodiment 1.0A and any one of Embodiments 1.2 to 1.210 that are dependent from Embodiment 1.0A.

1.284 A compound according to any one of Embodiments 1.0 to 1.283 wherein, when R$^8$ is C(=O)NR$^{10}$R$^{11}$, R$^{11}$ is other than a substituted tetrahydrofuran group or an unsubstituted 2-imidazoline group.

1.285 A compound according to any one of Embodiments 1.0 to 1.284 wherein said compound contains no more than two six membered aromatic rings.

1.286 A compound according to any one of Embodiments 1.0 to 1.285 provided that said compound does not contain a 2-imidazoline group.

1.287 A compound according to any one of Embodiments 1.0 to 1.286 provided that R$^3$ is other than a substituted or unsubstituted cyclohexenone or substituted or unsubstituted 4-pyrazolyl group.

1.288 A compound according to any one of Embodiments 1.0 to 1.287 provided that R$^3$ does not comprise a tetrazole or carboxylic acid group.

1.289 A compound according to any one of Embodiments 1.0 to 1.288 provided that when R$^2$ is hydrogen, then (i) R$^1$ does not contain a hydroxy group; and/or (ii) R$^1$ does not contain a sulphur atom.

1.290 A compound according to any one of Embodiments 1.0 to 1.289 provided that (i) R$^1$ does not contain a hydroxy group; and/or (ii) R$^1$ does not contain a sulphur atom.

1.291 A compound according to any one of Embodiments 1.0 to 1.290 provided that R$^3$ is other than a substituted or unsubstituted pyrimidine-2,4-dione group.

1.292 A compound according to any one of Embodiments 1.0 to 1.291 provided that R$^3$ is other than a pyrrole group bearing amino, carbamoyl and optionally substituted phenyl substituents.

1.293 A compound according to any one of Embodiments 1.0 to 1.292 provided that R$^3$ does not contain a thiophene group bearing a carboxylic acid substituent.

1.294 A compound according to any one of Embodiments 1.0 to 1.293 having a molecular weight of up to 1000.

1.295 A compound according to Embodiment 1.294 having a molecular weight of less than 750.

1.296 A compound according to Embodiment 1.295 having a molecular weight of less than 700.

1.297 A compound according to Embodiment 1.296 having a molecular weight of less than 650.

1.298 A compound according to Embodiment 1.297 having a molecular weight of less than 600 or less than 550.

1.299 A compound according to Embodiment 1.298 having a molecular weight of less than 525, for example, 500 or less.

1.300 A compound selected from the title compounds of any of Examples 1 to 59 (Table 1) and Examples 81 to 222 (Table 2).

1.301 A compound selected from the title compounds of any of Examples 1 to 80 (Table 1) and Examples 81 to 280 (Table 2).

1.302 A compound selected from the title compounds of any of Examples 60 to 80 (Table 1) and Examples 223 to 280 (Table 2).

1.302A A compound selected from the title compounds of any of Examples 81, 129, 136, 138, 149, 154, 186, 194, 237, 240, 247, 256, 258, 261, 262, 263, 265, 268, 269, 270, 278 and 280, and salts thereof.

1.303 A compound selected from the title compounds of any of Examples 281 to 307 (Table 2)

Definitions

In this application, the following definitions apply, unless indicated otherwise.

References to formula (0) include formula (1) and any other subsets of formula (0) unless the context indicates otherwise.

The term "treatment" as used herein in relation to hepatitis C virus infections is used in a general sense to describe any form of intervention where a compound is administered to a subject suffering from, or at risk of suffering from, or potentially at risk of suffering from infection with HCV. Thus the term treatment covers both preventative (prophylactic) treatment (e.g. where there may be a risk of infection but no actual infection has been detected) and treatment where a subject has become infected with HCV. When a subject (e.g. a human subject) has become infected, the treatment may comprise management of the infection or elimination of the infection.

The term "subject" as used herein may refer to a human subject or a non-human subject. In a preferred embodiment, the subject is a human subject. Where the subject is a non-human subject, it may be for example another mammalian species or an avian species. The mammalian species may be, for example, a domestic animal such as a dog or cat, or farmed animals such as cattle, pigs, sheep, horses and goats. Thus, the compounds of the invention may be used in human or veterinary medicine.

As used herein, the term "combination", as applied to two or more compounds and/or agents (also referred to herein as the components), is intended to define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:
    compositions (e.g. unitary formulations) comprising the two or more compounds/agents in admixture (for example within the same unit dose);
    compositions comprising material in which the two or more compounds/agents are chemically/physicochemically linked (for example by crosslinking, molecular agglomeration or binding to a common vehicle moiety);
    compositions comprising material in which the two or more compounds/agents are chemically/physicochemically co-packaged (for example, disposed on or within lipid vesicles, particles (e.g. micro- or nanoparticles) or emulsion droplets);
    pharmaceutical kits, pharmaceutical packs or patient packs in which the two or more compounds/agents are co-packaged or co-presented (e.g. as part of an array of unit doses);

Examples of non-physically associated combined compounds/agents include:

- material (e.g. a non-unitary formulation) comprising at least one of the two or more compounds/agents together with instructions for the extemporaneous association of the at least one compound to form a physical association of the two or more compounds/agents;
- material (e.g. a non-unitary formulation) comprising at least one of the two or more compounds/agents together with instructions for combination therapy with the two or more compounds/agents;
- material comprising at least one of the two or more compounds/agents together with instructions for administration to a patient population in which the other(s) of the two or more compounds/agents have been (or are being) administered;
- material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Administration simultaneously in the same formulation would involve administration of a unitary formulation whereas administration simultaneously in different pharmaceutical formulations would involve non-unitary formulations. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions The term "acyclic hydrocarbon group" (as in "acyclic $C_{1-8}$ hydrocarbon group" or "acyclic $C_{1-6}$ hydrocarbon group" or "acyclic $C_{1-5}$ hydrocarbon group") refers to a non-cyclic group consisting of carbon and hydrogen atoms. The hydrocarbon group may be fully saturated or may contain one or more carbon-carbon double bonds or carbon-carbon triple bonds, or mixtures of double and triple bonds. The hydrocarbon group may be a straight chain or branched chain group.

Examples of acyclic $C_{1-8}$ hydrocarbon groups are alkyl, alkenyl and alkynyl groups.

In each instance where the term "acyclic $C_{1-8}$ hydrocarbon group" appears in any of Embodiments 1.1 to 1.303, a subset of acyclic $C_{1-8}$ hydrocarbon groups consists of $C_{1-8}$ alkyl, $C_{2-6}$ alkenyl and $C_{2-6}$ alkynyl groups. A particular subset of acyclic $C_{1-8}$ hydrocarbon groups consists of $C_{1-8}$ alkyl groups.

In each instance where the term "acyclic $C_{1-8}$ hydrocarbon group" appears in any of Embodiments 1.1 to 1.303, a subset of acyclic $C_{1-6}$ hydrocarbon groups consists of $C_{1-6}$ alkyl, $C_{2-6}$ alkenyl and $C_{2-6}$ alkynyl groups. A particular subset of acyclic $C_{1-6}$ hydrocarbon groups consists of $C_{1-6}$ alkyl groups.

In each instance where the term "acyclic $C_{1-5}$ hydrocarbon group" appears in any of Embodiments 1.1 to 1.303, a subset of acyclic $C_{1-5}$ hydrocarbon groups consists of $C_{1-5}$ alkyl, $C_{2-5}$ alkenyl and $C_{2-5}$ alkynyl groups. A particular subset of acyclic $C_{1-5}$ hydrocarbon groups consists of $C_{1-5}$ alkyl groups.

A further subset of acyclic $C_{1-8}$ hydrocarbon groups or acyclic $C_{1-6}$ hydrocarbon groups or acyclic $C_{1-5}$ hydrocarbon groups consists of $C_{1-4}$ alkyl, $C_{2-4}$ alkenyl and $C_{2-4}$ alkynyl groups. A particular subset consists of $C_{1-4}$ alkyl groups.

Within each of Embodiments 1.1 to 1.303, preferred subsets of acyclic $C_{1-8}$ hydrocarbon groups or acyclic $C_{1-8}$ hydrocarbon groups or acyclic $C_{1-5}$ hydrocarbon groups are $C_{1-8}$ alkyl groups, or $C_{1-6}$ alkyl groups, or $C_{1-5}$ alkyl groups or $C_{1-4}$ alkyl groups. One particular sub-set of alkyl groups consists of methyl, ethyl, n-propyl, isopropyl, n-butyl, isobutyl and tert-butyl. Another particular subset of alkyl groups consists of methyl, ethyl and isopropyl groups.

The term "unbranched (straight chain) alkyl group" refers to an alkyl group which is of the formula —$(CH_2)_n$—H where n is an integer. In the case of a $C_{1-8}$ alkyl group, n is an integer from 1 to 6. Where stated, the alkyl group may be optionally substituted with one or more defined substituents. In a substituted alkyl group, one or more of the hydrogen atoms may be replaced with a defined substituent.

The term "alkanediyl" as in "$C_{1-8}$ alkanediyl" is used in its conventional sense as recommended by the International Union Pure and Applied Chemistry (IUPAC) to mean a divalent radical that is formally derived by removing two hydrogen atoms from an alkane. Thus the group —$CH_2$—$CH_2$—$CH_2$—, which is formally derived by removing two hydrogen atoms from the 1- and 3-positions of propane, is a propane-1-3-diyl group. Similarly, the group —$CH(CH_3)$—, which is formally derived by removing two hydrogen atoms from the 1-position of an ethyl group, is an ethane-1,1-diyl group.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems.

The carbocyclic and heterocyclic groups may be monocyclic or bicyclic and may contain, for example 3 to 10 ring members.

Examples of monocyclic groups are groups containing 3, 4, 5, 6, 7, and 8 ring members, more usually 3 to 7, and preferably 5 or 6 ring members.

Examples of bicyclic groups are those containing 8, 9, 10, 11 and 12 ring members, and more usually 9 or 10 ring members.

The carbocyclic or heterocyclic groups can be aryl or heteroaryl groups having from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents as defined herein.

The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom.

In one embodiment, the heteroaryl ring contains at least one ring nitrogen atom.

The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:

Examples of heteroaryl groups are monocyclic and bicyclic groups containing from five to ten ring members, and more usually from five to ten ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a a 5- or 6-membered ring containing 1, 2 or 3 ring heteroatoms;
e) a pyrazole ring fused to a a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered ring containing 1, 2 or 3 ring heteroatoms; and
o) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo [2,1-b]thiazole) and imidazoimidazole (e.g. imidazo[1,2-a] imidazole).

Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a] pyrimidine), triazolopyrimidine (e.g. [1,2,4]triazolo[1,5-a] pyrimidine), benzodioxole and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups include heterocyclic groups having from 3 to 12 ring members, typically 4 to 12 ring members, and more usually from 5 to 10 ring members. Such groups can be monocyclic or bicyclic, for example, and typically have from 1 to 5 heteroatom ring members (more usually 1,2,3 or 4 heteroatom ring members) typically selected from nitrogen, oxygen and sulphur.

When sulphur is present, it may, where the nature of the adjacent atoms and groups permits, exist as —S—, —S(O)— or —S(O)$_2$—.

Examples of monocyclic non-aromatic heterocyclic groups include 5-, 6- and 7-membered monocyclic heterocyclic groups. Particular examples include morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Further examples of non-aromatic cyclic groups include bridged ring systems such as bicycloalkanes and azabicycloalkanes although such bridged ring systems are generally less preferred. By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged ring systems include bicyclo[2.2.1]heptane, azabicyclo[2.2.1]heptane, bicyclo[2.2.2]octane, aza-bicyclo[2.2.2]octane, bicyclo[3.2.1]octane and aza-bicyclo[3.2.1]octane. A particular example of a bridged ring system is the 1-aza-bicyclo[2.2.2]octan-3-yl group.

The term "N-linked substituent" as used herein refers to a nitrogen atom-containing substituent such as an amino, methylamino, methylamino, pyrrolidinyl or morpholinyl group which is attached through the nitrogen atom.

The term "alkanoyl" as used herein refers to the acyl residue of an alkanoic acid. Examples of $C_{1-4}$ alkanoyl groups are formyl, acetyl, propanoyl and butanoyl.

The term "non-aromatic heterocyclic group having a total of 4 to 7 ring members of which 1 or 2 are nitrogen atoms and the others are carbon atoms" (e.g. as used in the definition of $NR_{10}R_{11}$ above) refers to both fully saturated and partially unsaturated groups, but typically the groups are fully saturated; i.e. they contain no carbon-carbon or carbon-nitrogen multiple bonds. Examples of the non-aromatic heterocyclic groups are azetidine, pyrrolidine, piperidine, azepine, piperazine, imidazoline, pyrazoline and pyrazolidine groups.

Salts and Free Bases

Many compounds of the formula (0) and formula (1) can exist in the form of salts, for example acid addition salts or, in certain cases salts of organic and inorganic bases such as carboxylate, sulfonate and phosphate salts. All such salts are within the scope of this invention, and references to compounds of the formula (0) and formula (1) include the salt forms of the compounds.

The salts are typically acid addition salts.

Alternatively, the compounds can exist in the free base form.

Accordingly, the invention also provides the following Embodiments 1.304 to 1.306:

1.304 A compound according to any one of Embodiments 1.0 to 1.303 which is in the form of a salt.

1.304A A compound according to any one of Embodiments 1.0 to 1.303 which is in the form of a free base.

1.305 A compound according to Embodiment 1.304 wherein the salt is an acid addition salt.

1.306 A compound according to Embodiment 1.304 or Embodiment 1.305 wherein the salt is a pharmaceutically acceptable salt.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.305) may be formed with a wide variety of acids, both inorganic and organic. Examples of acid addition salts falling within Embodiment 1.305 include (Embodiment 1.307): mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins, and is optionally further selected from O-acetyl-mandelic acid (e.g (+)-O-acetyl-L-mandelic acid).

One particular group of salts (Embodiment 1.308) consists of salts formed from acetic, aspartic (e.g. L-aspartic), hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

Another particular group of salts (Embodiment 1.309) consists of the salts of hydrochloric, sulfuric, phosphoric, methanesulfonic, lactic (e.g. L-lactic), tartaric (e.g. L-tartaric), citric, aspartic (e.g. L-aspartic), salicylic, mandelic and O-acetylmandelic acid (e.g. (+)-O-acetyl-L-mandelic acid.

In a further embodiment (Embodiment 1.309A), there is provided a mandelic acid or fumaric acid salt of a compound of any one of Embodiments 1.0 to 1.303.

If the compound is anionic, or has a functional group which may be anionic (e.g., —COOH may be —COO), then a salt may be formed with an organic or inorganic bases, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (0) contain an amine function, these may form quaternary ammonium salts, for example by reaction with an alkylating agent according to methods well known to the skilled person. Such quaternary ammonium compounds are within the scope of formula (0).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (0) and sub-groups and examples thereof as described herein in the form of a salt in a concentration of greater than 10 mg/ml, typically greater than 15 mg/ml and preferably greater than 20 mg/ml.

N-Oxides

N-Oxides can be formed by treatment of the corresponding amine with an oxidizing agent such as hydrogen peroxide or a per-acid (e.g. a peroxycarboxylic acid), see for example Albini, A.; Pietra, S. Heterocyclic N-Oxides; CRC Press: Boca Raton, Fla., 1991, pp 31 More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Accordingly, the invention also provides:
1.310 A compound according to any one of Embodiments 1.0 to 1.309 which is in the form of an N-oxide.

Tautomers

The compounds of the invention may exist in a number of different tautomeric forms and references to the compounds of formula (0) and their salts and N-oxides as defined in Embodiments 1.0 to 1.310 include all such forms.

For example, when $R^3$ is a pyridine group substituted with hydroxy as shown below, the ring system may exhibit tautomerism between tautomers A and B.

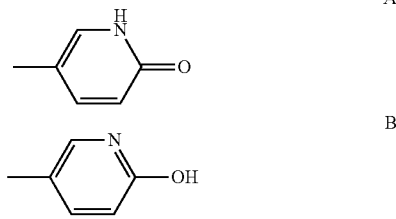

For the avoidance of doubt, where a compound can exist in one of several tautomeric forms and only one is specifically described or shown, all others are nevertheless embraced by Embodiments 1.0 to 1.310.

Accordingly, in another embodiment (Embodiment 1.311), the invention provides a tautomer of a compound according to any one of Embodiments 1.0 to 1.310.

Stereoisomers

Stereoisomers are isomeric molecules that have the same molecular formula and sequence of bonded atoms but which differ only in the three-dimensional orientations of their atoms in space.

The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.312), the invention provides a geometric isomer of a compound according to any one of Embodiments 1.0 to 1.311.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.313) the invention provides an optical isomeric form of a compound according to any one of Embodiments 1.0 to 1.312.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-di-toluoyl-L-tartaric acid, (+)-mandelic acid, (−)-mandelic acid (−)-malic acid, and (−)-camphorsulphonic acid, (−)-camphorsulphonic acid, (−)-N-acetyl-L-leucine, (−)-N-BOC-phenylalanine, (+)-deoxycholic acid, (−)-quinic acid, (+)-camphoric acid, (−)-dibenzoyl-L-tartaric acid, (+)-dibenzoyl-L-tartaric acid, (−)-N-BOC-alanine, (−)-tartaric acid, (−)-2,3,4,6-diisopropylidene-2-ketogluconic, L-(+)-citramalic acid, (+)-S-acetylmandelic acid, (−)-L-acetylglutamic acid, (+)-L-lacic acid, (+)-BOC-isoleucine, (−)-D-isoascorbic acid, (−)-N-(p-toluenesulfonyl)-L-phenylalanine, (+)-N-acetyl-L-phenylalanine, (+)-N-acetyl-L-tyrosine, (−)-N-acetyl-L-proline, (−)-N-BOC-L-tryptophan, (−)-Abietic acid separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.314), the invention provides compositions containing a compound according to any one Embodiments 1.0 to 1.312 having one or more chiral centres, wherein at least 55% (e.g. at least 60%, 65%, 70%, 75%, 80%, 85%, 90% or 95%) of the compound of any one of Embodiments 1.0 to 1.312 is present as a single optical isomer (e.g. enantiomer or diastereoisomer).

In one general embodiment (Embodiment 1.315), 99% or more (e.g. substantially all) of the total amount of the compound (or compound for use) of any one of Embodiments 1.0 to 1.312 is present as a single optical isomer.

For example, in one embodiment (Embodiment 1.316) the compound is present as a single enantiomer.

In another embodiment (Embodiment 1.317), the compound is present as a single diastereoisomer.

The invention also provides mixtures of optical isomers, which may be racemic or non-racemic. Thus, the invention provides:

Embodiment 1.318 A compound according to any one of Embodiments 1.0 to 1.313 which is in the form of a racemic mixture of optical isomers.

Embodiment 1.319: A compound according to any one of Embodiments 1.0 to 1.313 which is in the form of a non-racemic mixture of optical isomers.

Isotopes

The compounds of the invention as defined in any one of Embodiments 1.0 to 1.319 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise.

For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.320), the compound of any one of Embodiments 1.0 to 1.319 contains no radioactive isotopes. Such compounds are preferred for therapeutic use. In another embodiment (Embodiment 1.321), however, the compound of any one of Embodiments 1.0 to 1.319 may contain one or more radioisotopes. Compounds containing such radioisotopes may be useful in a diagnostic context.

Solvates

Compounds of the formula (0) as defined in any one of Embodiments 1.0 to 1.321 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

Accordingly, in further embodiments 1.322 and 1.323, the invention provides:

1.322 A compound according to any one of Embodiments 1.0 to 1.321 in the form of a solvate.

1.323 A compound according to Embodiment 1.322 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.324), the invention provides a compound as defined in any one of Embodiments 1.0 to 1.321 in a non-solvated. e.g. anhydrous form (for example an anhydrous crystalline form).

Crystalline and Amorphous Forms

The compounds of any one of Embodiments 1.0 to 1.324 may exist in a crystalline or non-crystalline (e.g. amorphous) state.

Whether or not a compound exists in a crystalline state can readily be determined by standard techniques such as X-ray powder diffraction (XRPD).

Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD.

Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal.

In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.325 A compound according to any one of Embodiments 1.0 to 1.324 in a crystalline form.
1.326 A compound according to any one of Embodiments 1.0 to 1.324 which is:
(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.
1.327 A compound according to any one of Embodiments 1.0 to 1.324 which is in an amorphous form.

Prodruqs

The compounds of the formula (0) as defined in any one of Embodiments 1.0 to 1.327 may be presented in the form of a pro-drug. By "prodrugs" is meant for example any compound that is converted in vivo into a biologically active compound of the formula (0), as defined in any one of Embodiments 1.0 to 1.327.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.328), the invention provides a pro-drug of a compound as defined in any one of Embodiments 1.0 to 1.327 wherein the compound contains a functional group which is convertable under physiological conditions to form a hydroxyl group or amino group.

Complexes and Clathrates

Also encompassed by formula (0) in Embodiments 1.0 to 1.328 are complexes (e.g. inclusion complexes or clathrates with compounds such as cyclodextrins, or complexes with metals) of the compounds of Embodiments 1.0 to 1.328.

Accordingly, in another embodiment (Embodiment 1.329), the invention provides a compound according to any one of Embodiments 1.0 to 1.328 in the form of a complex or clathrate.

Methods for the Preparation of Compounds of the Formula (0)

Compounds of the formula (0) and subsets thereof, as defined in Embodiments 1.0 to 1.329, can be prepared in accordance with synthetic methods well known to the skilled person and as described herein.

Compounds of the formula (0) wherein $R^0$ and $R^2$ are hydrogen can be prepared by the reaction of a compound of the formula (10):

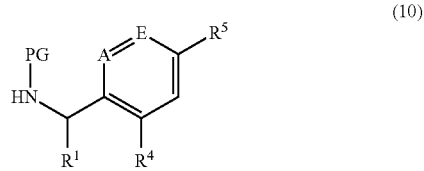

where PG is a protecting group such as a tert-butyloxycarbonyl (Boc) group, with a basic reagent such as an alkyl lithium (e.g. butyl lithium), followed by reaction with a compound of the formula $R^3$—C(=O)-LG, where LG is a leaving group such as a methoxy or ethoxy group or chloride (i.e. acid chloride), to give a compound of the formula: (11):

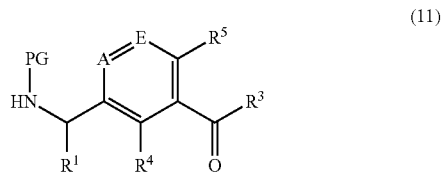

The reaction is typically carried out in a polar aprotic solvent such as tetrahydrofuran at low temperature (e.g. −78° C.). In this reaction, the substituents $R^4$ and $R^5$ are typically selected so that they do not react with the alkyl lithium but provide regioselective control of lithiation. For example, $R^4$ may be fluorine and $R^5$ may be chlorine.

Compounds of the formula (11) can also be prepared by the oxidation of a compound of the formula (30):

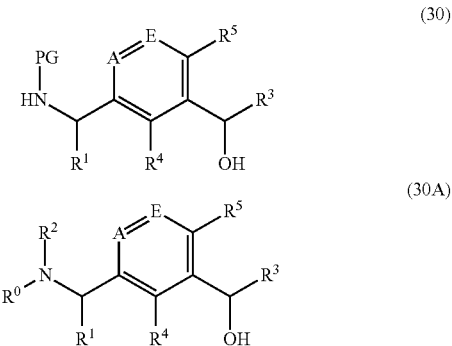

with a suitable oxidising agent such as manganese dioxide or Dess-Martin periodinane. The reaction can conveniently be carried out at room temperature in an aprotic solvent such as dichloromethane. This oxidation reaction may be also be used more generally to prepare compounds of the (0) by using a compound of the formula (30A) or a protected form thereof as the starting material.

Compounds of the formula (30) can be obtained by the reaction of a compound of the formula (10) with an alkyl lithium such as butyl lithium (e.g. at a low temperature such as −78° C. in a dry aprotic solvent such as tetrahydrofuran)

followed by the addition of an aldehyde R³—CHO or a protected derivative thereof. The compounds of formula (30A) where R⁰ and/or R² are other than hydrogen can be made in an analogous manner.

Once formed, compound (11) may be converted to the corresponding compound of formula (1) wherein R⁰ and R² are hydrogen by deprotection using suitable deprotection conditions, such as treatment with acid (e.g. HCl in dioxane).

Alternatively, the N-protected compound of formula (11) may be converted to another compound of formula (11).

For example, when R⁵ is chlorine, the compound of formula (11) can be reacted with an alkyl boronic acid (such as methyl boronic acid) in the presence of a palladium catalyst (such as palladium (II) acetate) and a ligand (such as S-Phos) to give the corresponding compound wherein R⁵ is an alkyl group.

Alternatively, a compound of formula (0) wherein R⁰ is hydrogen and R⁵ is chlorine can be converted to an intermediate compound of the formula (12):

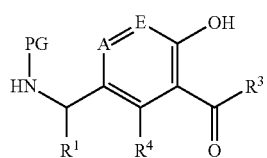

by reaction with potassium hydroxide in the presence of 2-di-tert-butylphosphino-2',4',6'-triisopropylbiphenyl and a palladium catalyst such as tris(dibenzylideneacetone)-palladium(0) in a polar solvent mixture such as dioxane/water.

The intermediate compound of formula (12) can then be converted to compounds of the formula (0) wherein R⁵ is an alkoxy group such as $C_{1-3}$ alkoxy (for example by reaction with an alkylating agent such as iodomethane in the presence of a phase transfer catalyst such as cetyltrimethylammonium bromide) or R⁵ is a fluoroalkoxy group such as difluoromethoxy (for example by reaction with (bromodifluoromethyl)-phosphonate in the presence of potassium hydroxide).

Alternatively, or additionally, compounds of the formula (11) can be converted into other compounds of the formula (11) by interconversion of functional groups within the moiety R³. Examples of such interconversions are described in the Experimental section below.

Compounds of the formula (11) wherein R³ is an aminopyridine, aminopyrazine or similar amino-azine, can be prepared from the corresponding halo-azine compound by reaction with ammonia or an amino-group precursor. For example, compounds of the formula (31):

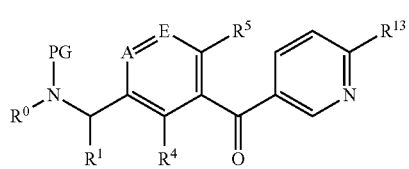

wherein R¹³ is bromine or chlorine, can be converted into the corresponding compound wherein R¹³ is amino by reaction with ammonia. When R¹³ is chlorine, the reaction with ammonia may be carried out by heating the compound with ammonia in methanol (e.g. 7M ammonia in methanol) at an elevated temperature (e.g. approximately 100° C.) in a sealed vessel. When R¹³ is bromine, the reaction may be carried out using aqueous ammonia (e.g. about 29%) in a solvent such as N-methylpyrrolidone at an elevated temperature (e.g. about 80° C.) in the presence of a copper (I) oxide catalyst.

Similar displacement reactions may be carried on the compounds of formulae (32), (33), (34) and (35) below, where R¹³ in each case is bromine or chlorine to give the corresponding compounds wherein R¹³ is an amino group.

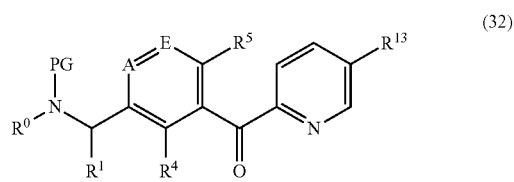

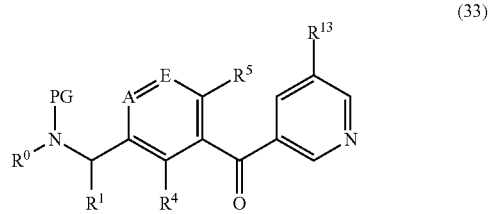

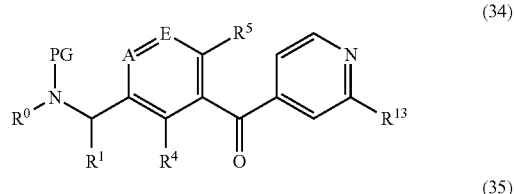

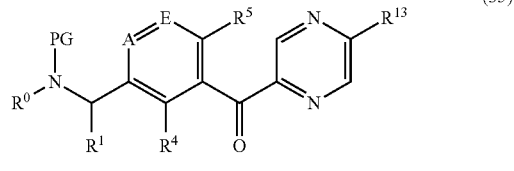

When, as in intermediates (32) and (33), the substituent group R¹³ is not attached to a carbon atom adjacent a nitrogen ring member, more forcing conditions or the assistance of a catalyst (e.g. a copper (I) oxide catalyst) may be required.

Additionally, other interconversions could be utilised. For example, nucleophilic addition of a masked ammonia equivalent followed by deprotection would be suitable for activated heterocyclic electrophiles (e.g. halo-pyridyl and halo-pyrazinyl groups).

For example, in the case of the pyrazine (35), the compound wherein R¹³ is chlorine can be converted into the corresponding compound wherein R¹³ is amino by reaction with p-methoxybenzylamine followed by removal of the p-methoxybenzy group using trifluoroacetic acid.

Further examples of nucleophilic addition of a masked ammonia equivalent include the addition of azide followed by Staudinger reduction (with triphenylphosphine); addition of hydroxylamine or an alkylhydroxylamine followed by reductive cleavage; or addition of a silylated ammonia equivalent (e.g. lithium hexamethyldisilazide) and acidic workup.

Further examples of such interconversions are described in the Experimental section below.

Compounds of the formula (10) wherein A and E are both CH can be prepared by the sequence of reactions shown in Schemes 1 to 3 below.

Scheme 1

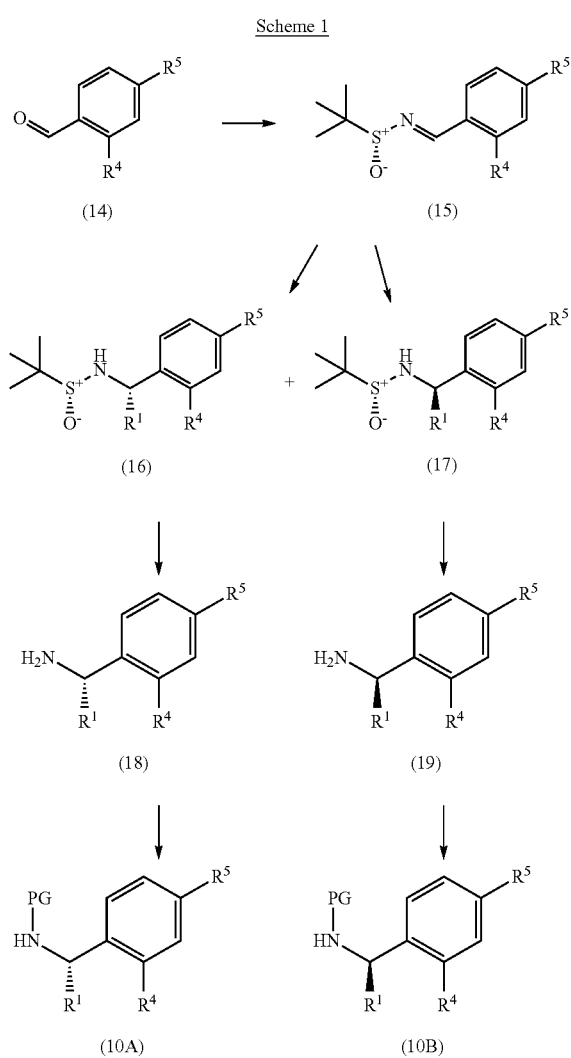

In Scheme 1, the aldehyde starting material (14), which is commercially available or can be made by well known methods, is converted to the chiral sulphinylimine (15) by reaction with the (R) chiral form of tert-butyl sulphinimide in the presence of a promoter such as titanium (IV) ethoxide or caesium carbonate. The chiral sulphinylimine intermediate (15) is then reacted with a nucleophilic reagent suitable for introducing the group $R^1$ or a precursor to the group $R^1$. For example, the intermediate (15) can be reacted at low temperature with a nucleophilic reactant such as a Grignard reagent (e.g. ethyl magnesium bromide or cyclopropyl magnesium bromide), an alkyl anion (such as isopropyl lithium), or nitromethane (with tetra-n-butylammonium fluoride) to give the diastereomeric sulphinic acid amides (16) and (17).

The relative amounts of the two isomeric forms (16) and (17) produced by the reaction with the nucleophilic reactant typically depends on the nature of the nucleophilic reactant. For example, under the conditions (solvent, temperature and dilution) described in the Experimental section, when the nucleophilic reactant is ethylmagnesium bromide, the stereoisomer (17) typically predominates. However, if cyclopropyl magnesium bromide is used as the nucleophilic reactant, stereoisomer (16) predominates.

The diastereoisomers may be separated by conventional means, for example by chromatography on silica, before treating with hydrochloric acid in a polar solvent such as dioxane (e.g. at room temperature under nitrogen) to give the individual amines (18) and (19). Each amine (18) and (19) may then be reacted with a reagent suitable for introducing an amine-protecting group PG. For example, the amines (18) and (19) may each be reacted with di-tert-butyl-dicarbonate in a polar solvent such as tetrahydrofuran (THF) to give the Boc-protected amines (10A) and (10B).

An analogous series of reactions, but using the (S) chiral form of tert-butyl sulphinimide as the starting material, is shown in Scheme 2.

Scheme 2

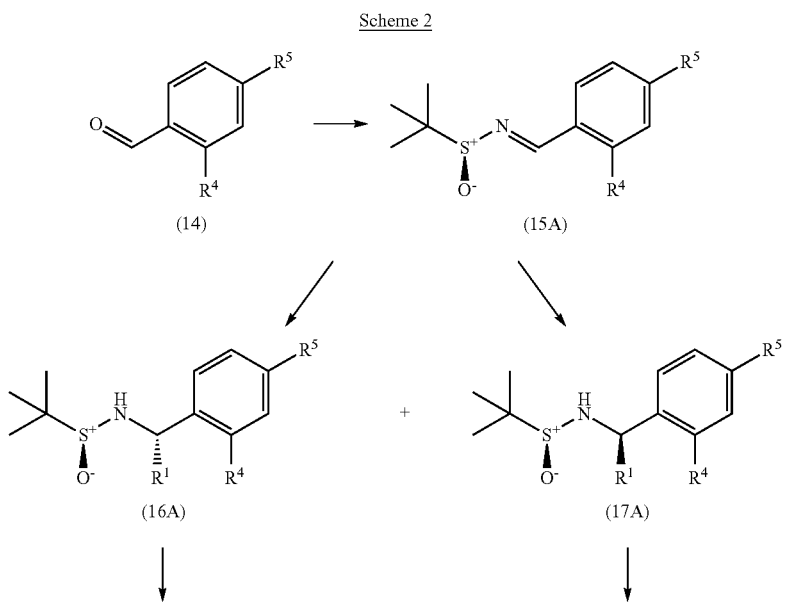

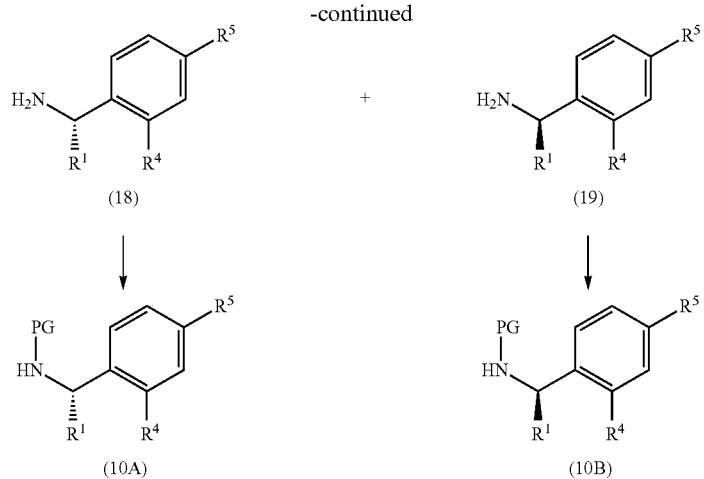

The reaction conditions and reagents used in Scheme 2 are essentially the same as those used in the sequence of reactions shown in Scheme 1. As in Scheme 1, the relative concentrations of stereoisomers (16A) and (17A) formed by reaction of the imine (15A) with the nucleophilic reagent will depend on the nature of the reagent, as well as the solvent used, the reaction temperature and the concentrations of reactants.

Under the specific conditions described in the Examples, the reaction of cyclopropyl magnesium bromide with (15A) gives rise predominantly to the stereoisomer (17A).

Compounds of the formula (1) wherein $R^2$ is hydrogen can also be prepared by the sequence of reactions shown in Scheme 3.

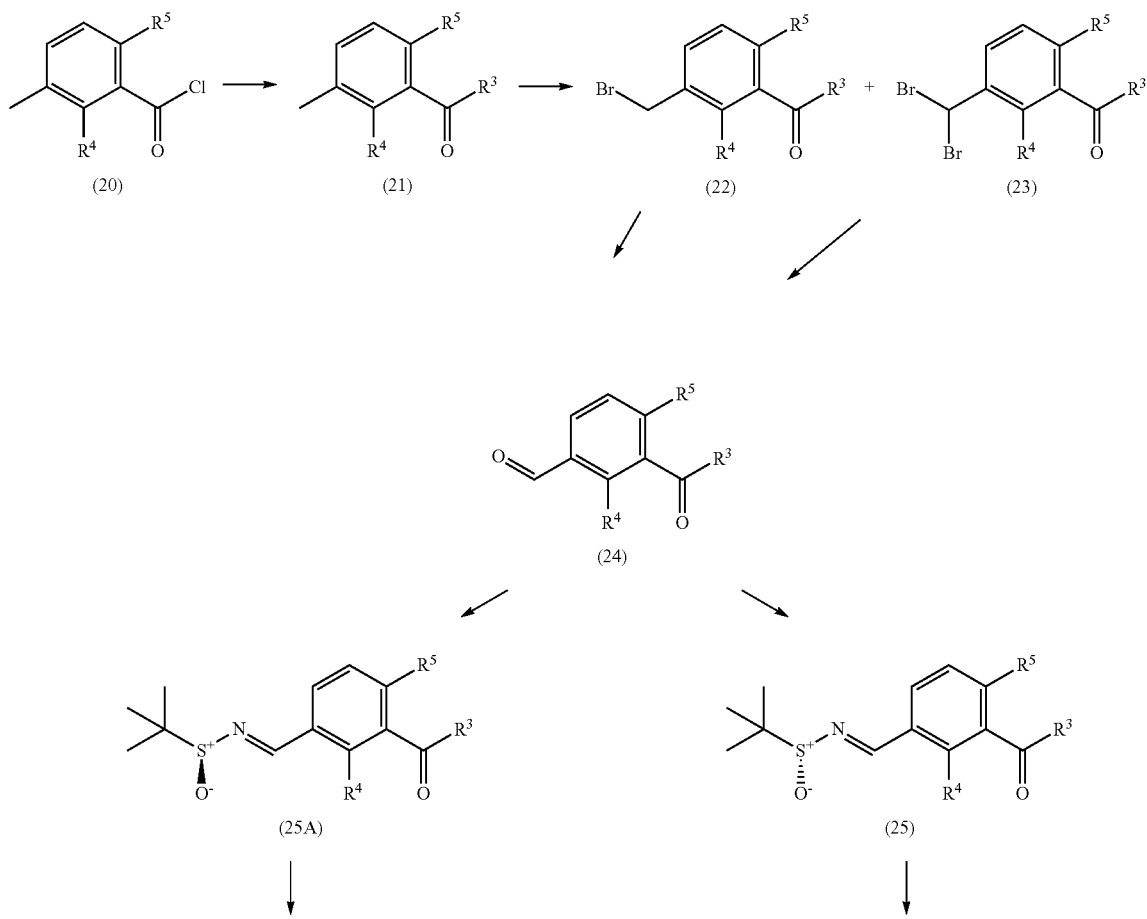

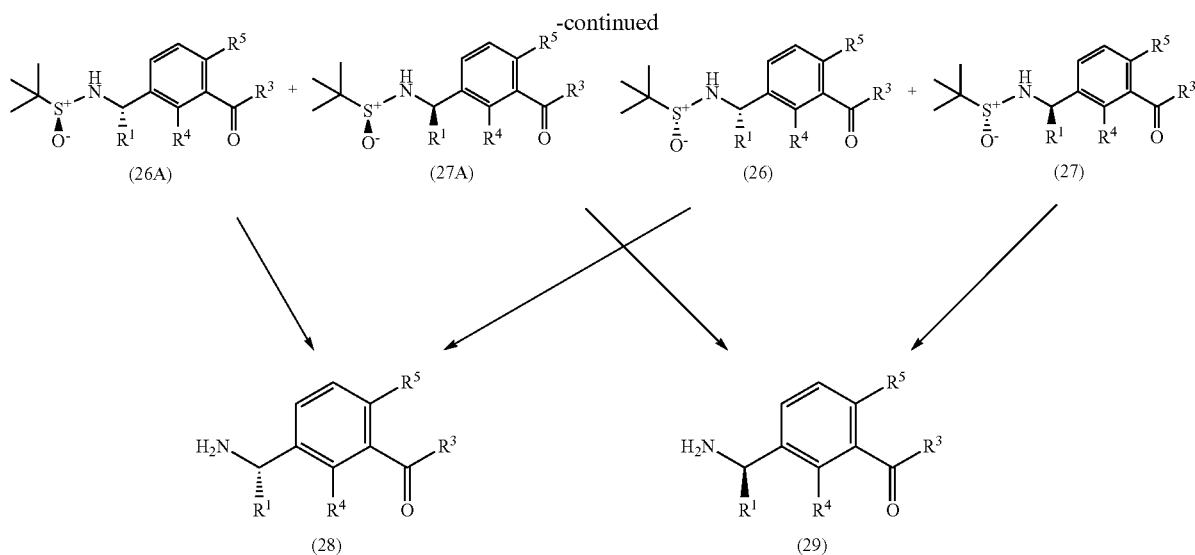

In Scheme 3, the methylbenzoyl chloride (20), which is either commercially available or can be formed from the corresponding methylbenzoic acid by standard methods, is reacted with a Grignard reagent $R^3MgBr$ optionally in the presence of tributyl phosphine in a polar aprotic solvent such as THF, usually with cooling of the reaction mixture, for example in an acetone/$CO_2$ bath. The resulting aryl/heteroaryl ketone (21) is then brominated using N-bromosuccinimide (NBS) in carbon tetrachloride in the presence of a radical initiator (azobisisobutyronitrile) to give a mixture of monobromo (22) and dibromo (23) compounds which can be separated by column chromatography on silica.

The monobromo-compound (22) can be converted to the substituted benzaldehyde (24) by heating with dimethylsulphoxide and sodium bicarbonate and the dibromo-compound (23) can be converted to the substituted benzaldehyde (24) by reaction with silver nitrate in aqueous isopropanol.

The benzaldehyde (24) may be converted to the chiral sulphinylimines (25) and (25A) by reaction with, respectively, the (R) or (S) chiral forms of tert-butyl sulphinimide in the presence of a Lewis acid promoter such as titanium (IV) ethoxide. The chiral sulphinylimines (25) and (25A) can then be reacted with nucleophilic reagent suitable for introducing the group $R^1$ or a precursor to the group $R^1$ using the general reaction conditions described in relation to Scheme 1 to give the N-protected diastereomeric sulphinic acid amide compounds (26) and (27), or (26A) and (27A), which can then be deprotected as described in relation to Scheme 1 to give the amines (28) and (29).

As with the reactions described in Schemes 1 and 2, the ratios of the intermediate compounds (26):(27) or (26A): (27A) produced by the reaction of the imine (25) or the imine (25A) with a nucleophilic reagent will typically depend on the nature of the nucleophilic reagent. Thus, when the imine (25) is reacted with ethylmagnesium bromide, the steroisomeric form (27) is formed predominantly.

Compounds of the formula (1) wherein $R^2$ is hydrogen can be converted into compounds of the formula (1) wherein $R^2$ is other than hydrogen (for example wherein $R^2$ is a group $X—R^8$) by a wide variety of synthetic methods well known to the skilled person or methods analogous thereto. Such methods include:

(i) standard alkylation procedures—e.g. reacting the compound of formula (1) wherein $R^2$ is hydrogen with an alkylating agent of the formula $LG^1$-X—$R^8$, where $LG^1$ is a leaving group, typically in the presence of a base;

(ii) reductive alkylations—e.g. reacting the compound of formula (1) wherein $R^2$ is hydrogen with an aldehyde or ketone X"-C(=O)—X'—$R^8$ or $R^{2a'}$i-K C(=O) where X" and X' are residues of the group X and $R^{2a'}$ and $R^{2a''}$ constitute the residue of the group $R^{2a}$; in the presence of a reducing agent; and (iii) when $R^8$ is C(=O)$NR^{10}R^{11}$, a Michael type reaction of a compound of formula (1) wherein $R^2$ is hydrogen with a compound X'''—C(=O)$NR^{10}R^{11}$ or X'''—C(=O)$M^a$ wherein $R^{10}$ and $R^{11}$ are as defined herein and $M^a$ is a masked amino group or an amino group precursor and X''' contains a double bond conjugated with the carbonyl group of C(=O)$NR^{10}R^{11}$.

In addition, any of the foregoing methods may be used to introduce a group X—$R^{8prec}$ where $R^{8prec}$ is a precursor group of $R^8$, and thereafter converting $R^{8prec}$ to $R^8$. The $R^{8prec}$ group could be, for example, a carboxylic acid group, or cyano group or ester group which can be converted into the corresponding amide by standard methods well known to the skilled person.

Reductive alkylations of they type described in (ii) above are typically carried out using a borohydride reducing agent such as sodium cyanoborohydride; or sodium triacetoxyborohydride in the presence of glacial acetic acid. By synthetic equivalent is meant a reagent or molecule that can replace an aldehyde or ketone in the reaction of interest. For example, the synthetic equivalent can be an acetal or ketal derivative such as (1-ethoxycyclopropoxy)trimethylsilane (equivalent to cyclopropanone) or paraformaldehyde (a polyacetal polymer of formaldehyde).

More particular examples of such methods are set out in the following paragraphs and specific examples are described in the Experimental section below.

For example, where the group $R^8$ is a moiety C(=O) $NR^{10}R^{11}$, the compounds of formula (1) can be prepared by reacting the corresponding compound wherein $R^2$ is hydrogen with a compound of the formula $LG^3$-X—C(=O) $NR^{10}R^{11}$ where $LG^3$ is a leaving group such as a bromine atom. The reaction is typically carried out with heating, for example to a temperature of over 100° C. in a microwave heater. A reaction of this type is particularly suitable when the group X is a straight chain alkanediyl group.

For compounds wherein X is a branched chain alkanediyl group, the compound of formula (1) wherein $R^2$ is hydrogen can be reacted with a compound of the formula (13):

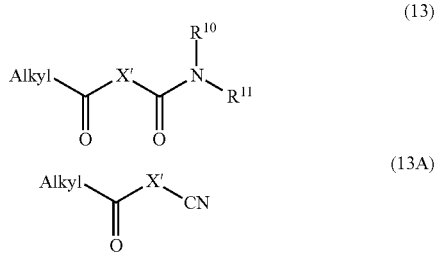

wherein Alkyl is an alkyl group and X' is the residue of the group X, under reductive amination conditions, for example in the presence of acetic acid and sodium triacetoxyborohydride. In a variation of this approach, the compound of formula (1) wherein $R^2$ is hydrogen can be reacted with a compound of the formula (13A) to under reductive amination conditions, or by formation of an imine and then reduction of the imine, to give a nitrile intermediate of the formula (36):

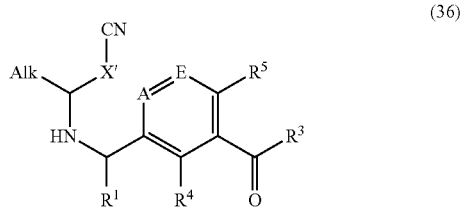

The nitrile intermediate (36) can then be hydrolysed to give a compound of formula (1) by treatment with a mineral acid such as sulphuric acid, for example at room temperature.

When X—$R^8$ is a group —CH(Alk)CH$_2$—CONR$^{10}$R$^{11}$ (wherein "Alk" is an alkyl group) or —CH$_2$CH$_2$—CONR$^{10}$R$^{11}$, the compound can be prepared by a Michael addition reaction between a compound of the formula (1) wherein $R^2$ is hydrogen with an acrylamide or 3-alkyl-acrylamide compound of the formula R"HC=CH—CONR$^{10}$R$^{11}$ (where R" is hydrogen or an alkyl group) or a protected form thereof. When R" is hydrogen, the reaction can conveniently be carried out in the presence of a manganese chloride catalyst.

Alternatively, when X—$R^8$ is a group —CH(Alk)CH$_2$—CONH$_2$ (wherein "Alk" is an alkyl group) or —CH$_2$CH$_2$—CONH$_2$ the compound can be prepared by a Michael addition reaction between a compound of the formula (1) wherein $R^2$ is hydrogen with a compound of the formula R"HC=CH—COM$^a$ wherein M$^a$ is a masked amine or an amine precursor such as a 4-benzyl-1,3-oxazolidin-2-one group, and then converting the masked amine or amine precursor to an amino group. The masked amine or amine precursor may be a chiral moiety, the chirality being chosen so as to induce a particular stereochemical orientation of the "Alk" group in the product of the Michael reaction.

Compounds of the formula (1) wherein $R^2$ is X—CONR$^{10}$R$^{11}$ can also be prepared from compounds of the formula (1) wherein $R^2$ is hydrogen by reaction with an aldehyde or ketone of the formula R"'—C(=O)—X'—CONR$^{10}$R$^{11}$ or a protected derivative thereof, wherein R" is hydrogen or alkyl and X' is the residue of the group X, under reductive amination conditions, for example using sodium cyanoborohydride or sodium triacetoxy-borohydride/glacial acetic acid in a solvent such as dichloromethane or dichloroethane. Alternatively, an imine formed by reaction between the compounds of the formula (1) wherein $R^2$ is hydrogen and the aldehyde or ketone of the formula R"'—C(=O)—X'—CONR$^{10}$R$^{11}$ or a protected derivative thereof, may be isolated and then subjected to reduction using a borane or borohydride reducing agent as described above.

Compounds of the formula (1) wherein $R^2$ is X—CONR$^{10}$R$^{11}$ can also be prepared from compounds of the formula (1) wherein $R^2$ is hydrogen by reaction with a compound of the formula LG$^3$-X—CONR$^{10}$R$^{11}$ or a protected derivative thereof, wherein LG$^3$ is a leaving group or atom such as a bromine atom. The reaction may be carried out with heating, for example in a microwave tube.

In a further method of making compounds wherein $R^2$ is —CH(Alk)CH$_2$—CONR$^{10}$R$^{11}$, the corresponding compound wherein $R^2$ is —CH(Alk)CH$_2$—CO$_2$H is reacted with a compound of the formula HNR$^{10}$R$^{11}$ under amide-forming conditions.

The amide-forming reation is preferably carried out in the presence of a reagent of the type commonly used in the formation of peptide linkages. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC) (Sheehan et al, *J. Org. Chem.,* 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters,* 1990, 31, 205).

Carbodiimide-based coupling agents are advantageously used in combination with 1-hydroxy-7-azabenzotriazole (HOAt) (L. A. Carpino, *J. Amer. Chem. Soc.,* 1993, 115, 4397) or 1-hydroxybenzotriazole (HOBt) (Konig et al, *Chem. Ber.,* 103, 708, 2024-2034). Preferred coupling reagents include HATU, or EDC (EDAC) and DCC in combination with HOAt or HOBt.

The coupling reaction is typically carried out in a non-aqueous, non-protic solvent such as acetonitrile, dioxane, dimethylsulphoxide, dichloromethane, dimethylformamide or N-methylpyrrolidinone, or in an aqueous solvent optionally together with one or more miscible co-solvents. The reaction can be carried out at room temperature, typically in the presence of a non-interfering base, for example a tertiary amine such as triethylamine or N,N-diisopropylethylamine.

The compound wherein $R^2$ is —CH(Alk)CH$_2$—CO$_2$H can be prepared by a Michael addition reaction of a compound of the formula (1) wherein $R^2$ is hydrogen with the chiral compound (N-crotonyl)-(2R)-bornane-10,2-sultam to give an intermediate amide (see Example 1) which is then hydrolysed in the presence of lithium hydroxide to give the lithium carboxylate salt which may be used directly in the amide-forming reaction.

Compounds of the formula (1) wherein $R^8$ is hydroxy can be prepared by the reductive alkylation of a compound wherein $R^2$ is hydrogen with a compound X"-C(=O)—X'—O-PG$^2$, where X" and X' are residues of the group X, and PG$^2$ is a protecting group such as tert-butyl-dimethylsilyl, in the presence of a reducing agent such as sodium triacetoxy-borohydride/glacial acetic acid in a solvent such as dichloromethane or dichloroethane followed by removal of the protecting group (for example by treatment with tetrabutylammonium fluoride in the case of a tert-butyl-dimethylsilyl protecting group.

For example, in order to prepare a compound of the formula (1) wherein $R^2$ is 2-hydroxyethyl, the compound of formula X"-C(=O)—X'—O-PG$^2$ can be the commercially available tert-butyldimethylsilyloxy)acetaldehyde (X"=H, X'=CH$_2$, PG$^2$=tert-butyl-dimethylsilyl).

In some of the methods for converting compounds of the formula (1) wherein $R^2$ is hydrogen to compounds of the formula (1) wherein $R^2$ is X—$R^8$, chiral auxiliaries may be used to induce the formation of a particular desired stereochemical form.

Compounds of the formula (0) in which $R^2$ is a group —C(=O)$R^{2a}$ can be prepared by the reaction of a compound of the formula (0) wherein $R^2$ is hydrogen, or a protected form thereof, with a compound of the formula $R^2$—CO$_2$H, or an activated derivative thereof, under amide-forming conditions, for example the amide-forming conditions described above.

Compounds of the formula (0) wherein $R^2$ is —C(=NH)—NHR$^{20}$ can be prepared by the reaction of a compound of the formula (0) wherein $R^2$ is hydrogen with a guanylating agent such as 1H-pyrazole-1-carboximidamide hydrochloride. The reaction is typically carried out in a polar aprotic solvent such as dimethylformamide in the presence of a non-interfering base such as diisopropylamine.

Alternative guanylating agents are described in the review by A. R. Katritzky et al. in *ARKIVOC*, 2005 (iv) 49-87.

The starting materials for the syntheses set out in Schemes 1, 2 and 3 above can be obtained commercially or by using standard synthetic methods well known to the skilled person or analogous thereto, see for example *Advanced Organic Chemistry* by Jerry March, 4$^{th}$ Edition, John Wiley & Sons, 1992, and *Organic Syntheses*, Volumes 1-8, John Wiley, edited by Jeremiah P. Freeman (ISBN: 0-471-31192-8), 1995, and see also the methods described in the experimental section below.

Once formed, one compound of the formula (1), or a protected derivative thereof, can be converted into another compound of the formula (1) by methods well known to the skilled person. Examples of synthetic procedures for converting one functional group into another functional group are set out in standard texts such as *Advanced Organic Chemistry* and *Organic Syntheses* (see references above) or *Fiesers' Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

Methods of Purification

The compounds of the invention may be isolated and purified by a number of methods well known to those skilled in the art and examples of such methods include chromatographic techniques such as column chromatography (e.g. flash chromatography) and HPLC. Preparative LC-MS is a standard and effective method used for the purification of small organic molecules such as the compounds described herein. The methods for the liquid chromatography (LC) and mass spectrometry (MS) may be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

Alternatively, normal phase preparative LC based methods might be used in place of reverse phase methods. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above may alternatively be used to purify the compounds.

Where products or intermediates are chiral, individual optical isomers may be separated by methods well know to the skilled person, for example by:

(i) chiral chromatography (chromatography on a chiral support); or (ii) forming a salt with an optically pure chiral acid, separating the salts of the two diastereoisomers by fractional crystallisation and then releasing the actieve compound from the salt; or (iii) forming a derivative (such as an ester) with an optically pure chiral derivatising agent (e.g. esterifying agent), separating the resulting epimers (e.g. by chromatography) and then converting the derivative to the compound of formula (0).

Intermediates

Many of the synthetic intermediates described above are themselves novel and, as such, form part of the present application. Accordingly, in a further embodiment (Embodiment 2.1) of the invention, there is provided:

2.1 An intermediate compound selected from compounds (25), (25A), (26), (26A), (27), (27A), (31), (32), (33), (34), (35) and (36) below:

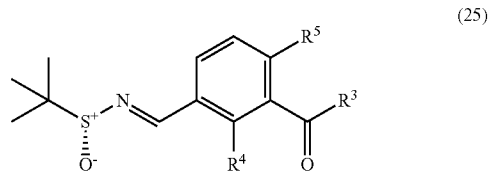

(25)

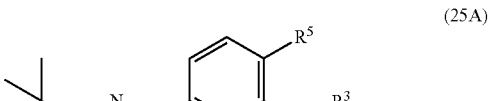

(25A)

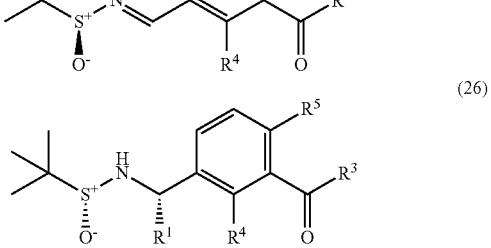

(26)

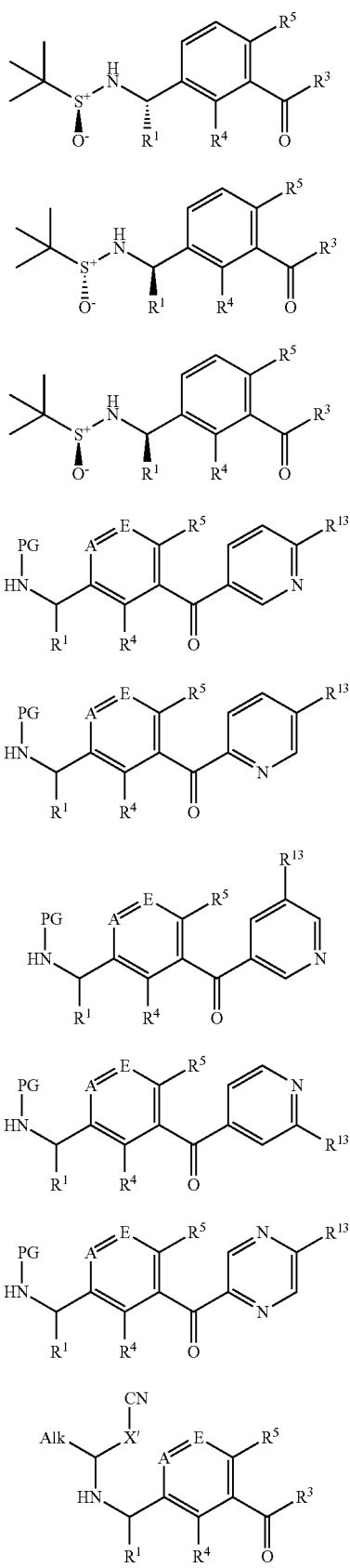

(26A)
(27)
(27A)
(31)
(32)
(33)
(34)
(35)
(36)

2.1A An intermediate compound according to Embodiment 2.1 which is selected from selected from compounds (25), (25A), (26), (26A), (27), (27A), (31), (32), (33), (34) and (35).

2.2 A compound selected from the Key intermediates 6 to 16 described in the experimental section below.

2.3 A compound according to Embodiment 2.2 which is selected from Key Intermediates 12, 13, 14, 15 and 16 described in the experimental section below.

Biological Activity and Therapeutic Uses

The compounds of Embodiments 1.0 to 1.329 are inhibitors of hepatitis C virus NS3 protease and are therefore beneficial in preventing or treating hepatitis C virus infection and virus-related disorders.

In particular, compounds of Embodiments 1.0 to 1.329 are active against multiple HCV genotypes and resistance mutations.

Compounds of Embodiments 1.0 to 1.329 bind to the allosteric site of the NS3 protein described in Jhoti et al. (idem) and therefore inhibit the function of the NS3 protein. Thus, compounds of the invention are allosteric inhibitors of the NS3 protease helicase The activity of the compounds can be determined by means of the HCV NS3 protease assay described in Example A and/or the replicon assay described in Example B below.

Preferred compounds of the formula (0) are those compounds that have $IC_{50}$ values of less than 1 μM against the HCV NS3 protease (when determined according to the assay described in Example A (or an assay analogous thereto).

Thus the compounds of the invention may be used for treating or preventing a viral infection or a virus-related disorder in a patient. In particular, such compounds can be inhibitors of HCV replication, and are thus useful for treating viral diseases such as hepatitis C and disorders related to the activity of a virus. In one embodiment, the hepatitis C infection is acute hepatitis C. In another embodiment, the hepatitis C infection is chronic hepatitis C. The compounds can be useful for treating a patient suffering from infection related to particular HCV genotypes as defined herein. HCV types and subtypes may differ in their antigenicity, level of viremia, severity of disease produced, and response to interferon therapy as well as Direct Acting Antiviral therapy.

The compounds of the invention can also be useful for treating or preventing a disorder related to an HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

The compounds of the invention may also be used for treating subjects who are suffering from co-infection with HCV and another virus such as hepatitis B (HBV) or human immunodeficiency virus (HIV).

The hypervariability of the HCV genome means that emergence of resistance on treatment with direct-acting antiviral agents (DAAs) is a major problem. Therapeutic intervention with agents acting via several mechanisms is required to increase the barrier to resistance during therapy. The addition of an agent with a new mechanism of action to the treatment regime is therefore an important means of further reducing clinical resistance to therapy. Thus, allosteric inhibitors of protease-helicase represent a new class of therapeutics with the potential for: (i) sensitising HCV to other treatments; (ii) alleviating or reducing the incidence of resistance to DAAs or treatments; (ii) reversing resistance to other DAAs or treatments; (iv) potentiating the activity of other DAAs or treatments; and (v) delaying or preventing the onset of resistance to other DAAs or treatments.

Accordingly, in the further embodiments 3.1 to 3.11 set out below, the invention provides:

3.1 A compound as defined in any one of Embodiments 1.0 to 1.329 wherein the compound has an $IC_{50}$ value of less than 1 µM against HCV NS3 protease (e.g. when determined according the assays described herein).

3.2 A compound as defined in any one of Embodiments 1.0 to 1.329 wherein the compound has an $IC_{50}$ value of less than 0.1 µM against HCV NS3 protease (e.g. when determined according the assays described herein).

3.2 A compound as defined in any one of Embodiments 1.0 to 1.329 having inhibitory activity against NS3 helicase.

3.2B A compound as defined in any one of Embodiments 1.0 to 1.329 wherein the compound has an $IC_{50}$ value of less than 50 µM against HCV NS3 helicase (e.g. when determined according the assays described herein).

3.2C A compound as defined in any one of Embodiments 1.0 to 1.329 wherein the compound has an $IC_{50}$ value of less than 10 µM against HCV NS3 helicase (e.g. when determined according the assays described herein).

3.2D A compound as defined in any one of Embodiments 1.0 to 1.329 wherein the compound has an $IC_{50}$ value of less than 5 µM against HCV NS3 helicase (e.g. when determined according the assays described herein).

3.2E A compound as defined in any one of Embodiments 1.0 to 1.329 wherein the compound has an $IC_{50}$ value of less than 1 µM against HCV NS3 helicase (e.g. when determined according the assays described herein).

3.2F A compound as defined in any one of Embodiments 1.0 to 1.329 wherein the compound has an $IC_{50}$ value of less than 0.1 µM against HCV NS3 helicase (e.g. when determined according the assays described herein).

3.3 A compound as defined in any one of Embodiments 1.0 to 1.329 for use in medicine or therapy.

3.4 A compound as defined in any one of Embodiments 1.0 to 1.329 for use in the prevention or treatment of hepatitis C virus infections (e.g. as defined above).

3.5 A compound as defined in any one of Embodiments 1.0 to 1.329 for use in the treatment of hepatitis C virus infections (e.g. as defined above).

3.6 A compound as defined in any one of Embodiments 1.222 for use in the treatment of hepatitis C virus infection in a subject who has been diagnosed as having hepatitis C virus infection (e.g. as defined above).

3.7 The use of a compound as defined in any one of Embodiments 1.0 to 1.329 for the manufacture of a medicament for the prevention or treatment of hepatitis C virus infections (e.g. as defined above).

3.8 The use of a compound as defined in any one of Embodiments 1.0 to 1.329 for the manufacture of a medicament for the treatment of hepatitis C virus infections (e.g. as defined above).

3.9 The use of a compound as defined in any one of Embodiments 1.0 to 1.329 for the manufacture of a medicament for the treatment of hepatitis C virus infection in a subject who has been diagnosed as having hepatitis C virus infection (e.g. as defined above).

3.10 A method of preventing or treating a hepatitis C virus infection in a subject, which method comprises administering to the subject an effective anti-hepatitis C viral amount of a compound as defined in any one of Embodiments 1.0 to 1.329.

3.11 A method of treating a hepatitis C virus infection in a subject, which method comprises administering to the subject an effective anti-hepatitis C viral amount of a compound as defined in any one of Embodiments 1.0 to 1.329.

3.12 A compound as defined in any one of Embodiments 1.0 to 1.329 for use as an allosteric inhibitor of HCV NS3 protease helicase.

3.13 A method of inhibiting HCV NS3 protease helicase by bringing a compound as defined in any one of Embodiments 1.0 to 1.329 into contact with an allosteric binding site on the NS3 protease helicase.

3.14 A compound as defined in any one of Embodiments 1.0 to 1.329 having a therapeutically useful level of activity as an allosteric inhibitor of the NS3 protease helicase for use in treating hepatitis C viral infections.

3.15 The use of a compound as defined in any one of Embodiments 1.0 to 1.329 having a therapeutically useful level of activity as an allosteric inhibitor of the NS3 protease helicase for the manufacture of a medicament for treating hepatitis C viral infections.

3.16 A compound for use, method or use as defined in any one of Embodiments 3.12 to 3.15 wherein the compound binds to the allosteric binding site described in Jhoti et al., Jhoti et al. *Nature Chemical Biology*, 2012, doi:10.1038/nchembio.1081.

3.17 A compound as defined in any one of Embodiments 1.0 to 1.329 for use in treating a subject (e.g. a mammal such as a human) suffering from hepatitis C (HCV) infection by
(i) sensitising the HCV to other treatments; and/or
(ii) alleviating or reducing the incidence of resistance of the HCV to direct-acting anti-viral agents (DAAs) or treatments; and/or
(iii) reversing resistance of the HCV to other DAAs or treatments; and/or
(iv) potentiating the activity against the HCV of other DAAs or treatments; and/or
(v) delaying or preventing the onset of resistance in the HCV to other DAAs or treatments.

3.18 The use of a compound as defined in any one of Embodiments 1.0 to 1.329 for the manufacture of a medicament for treating a subject (e.g. a mammal such as a human) suffering from hepatitis C (HCV) infection by
(i) sensitising the HCV to other treatments; and/or
(ii) alleviating or reducing the incidence of resistance of the HCV to DAAs or treatments; and/or
(iii) reversing resistance of the HCV to other DAAs or treatments; and/or
(iv) potentiating the activity against the HCV of other DAAs or treatments; and/or
(v) delaying or preventing the onset of resistance in the HCV to other DAAs or treatments.

3.19 A method of treating a subject (e.g. a mammal such as a human) suffering from hepatitis C (HCV) infection by:
(i) sensitising the HCV to other treatments; and/or
(ii) alleviating or reducing the incidence of resistance of the HCV to DAAs or treatments; and/or
(iii) reversing resistance of the HCV to other DAAs or treatments; and/or
(iv) potentiating the activity against the HCV of other DAAs or treatments; and/or
(v) delaying or preventing the onset of resistance in the HCV to other DAAs or treatments; which method comprises administering to the subject a therapeutically effective amount of a compound as defined in any one of Embodiments 1.0 to 1.329.

3.19A A compound for use, use or method according to any one of Embodiments 3.6, 3.9, 3.10, 3.11 and 3.17 wherein the subject is one who has been co-infected with HCV and another virus such as HBV or HIV.

3.19B A compound for use, use or method according to any one of Embodiments 3.4 to 3.11 and 3.14 to 3.19 wherein the HCV infection is accompanied by infection with another virus such as HBV or HIV.

3.19C A compound, compound for use, use or method according to any one of Embodiments 3.1 to 3.19B wherein the HCV is selected from genotypes 1a, 1b, 2a, 2b, 3a, 4a, 5a and 6a.

3.19D A compound, compound for use, use or method according to any one of Embodiments 3.1 to 3.19B wherein the HCV is selected from genotypes 1a, 1b, 3a, 5a and 6a.

3.19E A compound, compound for use, use or method according to any one of Embodiments 3.1 to 3.19B wherein the HCV is selected from genotypes 1a, 1b and 3a.

The "other DAAs" referred to in Embodiments 3.17 to 3.19 may be any of the therapeutic agents listed in the section headed "Combination Therapy" below and in Embodiments 3.20 and 3.21.

Posology

The compounds as defined in any one of Embodiments 1.0 to 1.329 are generally administered to a human subject in need of such administration. The human subject will typically have been subjected to tests prior to treatment to establish whether a hepatitis C virus infection is present. The methods of diagnosing the hepatitis C virus infection (e.g. as defined above) may be standard methods well known to the skilled person.

The compounds of the invention will be administered in an effective amount, i.e. an amount which is effective to bring about the desired therapeutic effect The amount of compound of the invention administered to the subject will depend on the nature of the viral infection and on the characteristics of the subject, such as general health, age, sex, body weight, ethnicity, tolerance to drugs and the presence of any other conditions such as diabetes. The skilled person will be able to determine appropriate dosages depending on these and other factors. Effective dosages for commonly used antiviral drugs are well known to the skilled person.

For example, a daily dose of the compound of formula (0) or formula (1) may be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (0) or formula (1) may be administered on a daily basis or on a repeat basis every 2, or 3, or 4, or 5, or 6, or 7, or 10 or 14, or 21, or 28 days for example, the duration of treatment depending on the particular HCV genotype and the potency of the compound of formula (0) or (1) alone or in combination with other therapeutic agents.

The compounds of the invention may be administered orally in a range of doses, for example 1 to 1500 mg (0.6 to 938 mg/m$^2$), or 2 to 800 mg (1.25 to 500 mg/m$^2$), or 5 to 500 mg (3.1 to 312 mg/m$^2$), or 2 to 200 mg (1.25 to 125 mg/m$^2$) or 10 to 1000 mg (6.25 to 625 mg/m$^2$), particular examples of doses including 10 mg (6.25 mg/m$^2$), 20 mg (12.5 mg/m$^2$), 50 mg (31.3 mg/m$^2$), 80 mg (50 mg/m$^2$), 100 mg (62.5 mg/m$^2$), 200 mg (125 mg/m$^2$), 300 mg (187.5 mg/m$^2$), 400 mg (250 mg/m$^2$), 500 mg (312.5 mg/m$^2$), 600 mg (375 mg/m$^2$), 700 mg (437.5 mg/m$^2$), 800 mg (500 mg/m$^2$), 900 mg (562.5 mg/m$^2$) and 1000 mg (625 mg/m$^2$). The compound may be administered once or more than once each day. The compound is typically administered continuously (i.e. taken every day without a break for the duration of the treatment regimen).

In certain circumstances, for example, when used in combination with an anti-cancer drug for treating hepatocellular carcinoma, the compound can be administered continuously or intermittently (i.e. taken continuously for a given period such as a week, then discontinued for a period such as a week and then taken continuously for another period such as a week and so on throughout the duration of the treatment regimen). More usually, the compound of formula (0) will be administered continuously.

Ultimately, however, the quantity of compound administered and the length of the treatment regimen will be at the discretion of a supervising physician.

Combination Therapy

The compounds of Embodiments 1.0 to 1.329 may be used alone or in combination with other therapeutic agents.

Accordingly, in another embodiment (Embodiment 3.20), the invention provides a combination of a compound as defined in any one of Embodiments 1.0 to 1.329 with at least one (e.g. 1, 2, 3 or 4, or more preferably 1, 2 or 3, and most preferably 2 to 3) other therapeutic agents selected from (a) interferons; (b) ribavirin and analogues thereof; (c) other HCV NS3 protease inhibitors; (d) alpha-glucosidase 1 inhibitors; (e) hepatoprotectants; (f) nucleoside or nucleotide inhibitors of HCV NS5B polymerase; (g) non-nucleoside inhibitors of HCV NS5B polymerase; (h) HCV NS5A inhibitors; (i) TLR-7 agonists; (j) cyclophillin inhibitors; (k) HCV IRES inhibitors; (l) pharmacokinetic enhancers; (m) immunoglobulins; (n) immunomodulators; (o) anti-inflammatory agents; (p) antibiotics; (q) HCV NS3 helicase inhibitors; (r) HCV NS4a antagonists; (s) HCV NS4b binding inhibitors; (t) HCV p7 inhibitors; (u) HCV core inhibitors; and (v) HCV entry inhibitors; (w) diacylglycerol acyltransferase type 1 inhibitors (DGAT-1).

Within Embodiment 3.20, examples of other therapeutic agents are as follows:

Examples of interferons are pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-nl (Wellferon), interferon alpha-n3 (Alferon), Interferon alpha 5 (Digna), injectable HDV-interferon, omega interferon (Intarcia), interferon-beta (Avonex, DL-8234), interferon-omega (omega DUROS, Biomed 510), Zalbin (Albuferon, albinterferon alpha-2b), IFN alpha-2b XL, BLX-883 (Locteron), DA-3021, glycosylated interferon alpha-2b (AVI-005), PEG-[iota]nfergen, PEGylated interferon lambda-1 (PEGylated IL-29) and belerofon.

Examples of ribavirin and its analogues include ribavirin per se (Rebetol, Copegus) and taribavirin (Viramidine).

Examples of HCV NS3 protease inhibitors are boceprevir (SCH-503034), telaprevir (VX-950), TMC-435, BI-201335, Vaniprevir (MK-7009), VX-500, VX-985, VX-813, BMS-650032,GS-9451, GS-9256, MK-5172, ACH-1625, ACH-2684, PHX-1766, Danoprevir (ITMN-1911R7227), IDX-320, ABT-450, AVL-181, TG2349, AVL-192.

Examples of alpha-glucosidase 1 inhibitors celgosivir (MX-3253) and Miglitol, UT-231 B.

Examples of hepatoprotectants are IDN-6556, ME 3738, LB-84451, silibilin, MitoQ.

Examples of nucleoside or nucleotide inhibitors of HCV NS5B polymerase are R7128 (RO5024048), IDX-184, BCX-4678, PSI-7977, PSI-938, TMC649128, INX-189, BMS-791325, PSI 353661, ALS2200, ALS2158, GS6620.

Examples of non-nucleoside inhibitors of HCV NS5B polymerase Filibuvir (PF-868554), VX-759, VX-222, B1207127, Tegobuvir (GS-9190), IDX-375, Setrobuvir (ANA-598, VCH-916, MK-3281, VBY-708, A848837, ABT-333, A-48547, VCH-796 (nesbuvir), GSK625433, ABT 072, GS9669, TMC647055.

Examples of HCV NS5A inhibitors Daclatasvir (BMS790052), BMS-824393, AZD-7295, AZD-2836 (A-831), EDP-239, PPI-461, PPI-1301, PP1668, ACH 2928, ACH3102, GS5885, GSK2336805, IDX719.

Examples of TLR-7 agonists are ANA-975, ANA-773 and SM-360320.

Examples of cyclophillin inhibitors are Alisporivir (DEBIO-025), SCY-635 and NIM811.

An example of an HCV IRES inhibitor is MCI-067.

An example of an HCV NS4a antagonist is ACH-1095.

An example of an HCV NS4b binding inhibitor is clemizole (Eiger).

Examples of pharmacokinetic enhancers are BAS-100, SPI-452, PF-4194477, TMC-41629 and roxythromycin.

Examples of immunostimulants include Zadaxin (SciClone).

Examples of HCV entry inhibitors are Pro-206, ITX-5061, SP-30.

An example of an HCV p7 inhibitor is BIT-225.

An example of a DGAT-1 inhibitor is LCQ908.

Examples of other drugs used for treating HCV and which may be combined with the compounds of Embodiments 1.0, 1.00 and 1.1 to 1.329 include nitazoxanide (Alinea, NTZ), BIVN-401 (virostat), PYN-17 (altirex), KPE02003002, actilon (CPG-10101), KRN-7000, civacir, GI-5005, XTL-6865, PTX-111, ITX2865, TT-033i, ANA 971, NOV-205, tarvacin, EHC-18, VGX-410C, EMZ-702, AVI 4065, Bavituximab, MDX-1106 (ONO-4538), Oglufanide and VX-497 (merimepodib), SCV-07, Lenocta, CTS-1027, JKB-122, CF-102, PYN17, PYN18, IMMU-105, CYT-107, GSK-2336805, GSK-2485852.

In a further embodiment (Embodiment 3.21), the invention provides a combination of a compound as defined in any one of Embodiments 1.0 to 1.329 with at least one (e.g. 1, 2, 3 or 4, or more preferably 1, 2 or 3, and most preferably 2 to 3) other therapeutic agents selected from (a) interferons; (b) ribavirin and analogues thereof; (c) other HCV NS3 protease inhibitors; (d) alpha-glucosidase 1 inhibitors; (e) hepatoprotectants; (f) nucleoside or nucleotide inhibitors of HCV NS5B polymerase; (g) non-nucleoside inhibitors of HCV NS5B polymerase; (h) HCV NS5A inhibitors; (i) TLR-7 or TLR-9 agonists; (j) cyclophillin inhibitors; (k) HCV IRES inhibitors; (l) pharmacokinetic enhancers; (m) immunoglobulins; (n) immunomodulators; (o) anti-inflammatory agents; (p) antibiotics; (q) HCV NS3 helicase inhibitors; (r) HCV NS4a antagonists; (s) HCV NS4b binding inhibitors; (t) HCV p7 inhibitors; (u) HCV core inhibitors; and (v) HCV entry inhibitors; (w) diacylglycerol acyltransferase type 1 inhibitors (DGAT-1); (x) TLR-3 agonist vaccine adjuvants; (y) viral assembly inhibitors; (z) HIV inhibitors; (aa) viral serine protease inhibitors; (ab) viral polymerase inhibitors; (ac) viral helicase inhibitors; (ad) immunomodulating agents; (ae) antioxidants; (af) antibacterial agents; (ag) therapeutic vaccines; (ah) hepatoprotectant agents; (ai) antisense agents; and (aj) internal ribosome entry site inhibitors.

Within Embodiment 3.21, examples of other therapeutic agents are as follows:

Examples of interferons are pegylated rIFN-alpha 2b (PEG-Intron, Redipen, Sylatron, C-Pegferon, Cylatron, SCH-054031, PEG-IFN-alfa2b, Peginterferon alfa-2b, Virtron, SCH-54031, ViraferonPeg), pegylated rIFN-alpha 2a (Pegasys), rIFN-alpha 2b (Intron A, IFN-alpha2b, YM-14090, Depolnterferon alpha, Alfratronol; Viraferon, Sch-30500), BIP-48 (Peginterferon alfa 2b 48 kDa), rIFN-alpha 2a (Roferon-A, Canferon A, Alphaferon, Interferon alfa-2a, Ro-22-8181, Roceron-A), interferon alpha (Omniferon, Alfanative, Multiferon), YPEG-IFN-alfa2a (Y-peginterferon alfa-2a) interferon alfacon-1 (Infergen, Advaferon, Inferax), interferon alpha-nl (Wellferon, Sumiferon, Sumiferon MP), interferon alpha 2b (Hanferon, SC Interferon-alpha, HL-143), peg Inerferon alpha 2b (P-1101), InferoXen, interferon alpha-n3 (Alferon Naturaferon, Alferon LDO, Human leukocyte interferon alpha, Alferon N Gel, Cellferon, Altemol, Alferon N Injection), Interferon alpha 5 (NAHE-001), injectable HDV-interferon, omega interferon (Intarcia), interferon-beta (Avonex, DL-8234, rHuIFN-beta, Fibroblast interferon, IFN-beta, DL-8234, R-Frone, Feron, Frone), PEG-interferon beta (PEGylated interferon beta, TRK-560) interferon-omega (omega DUROS, Biomed 510),), Interferon beta-1a (Rebif, IFN-betala, IFN-B-1a) Interferon gamma-1b (Actimmune, Imukin 1, Immukin, DasKloster-1001-01, DasKloster-1001), IFN alpha-2b XL, BLX-883 (Locteron, CR2b), DA-3021, glycosylated interferon alpha-2b (AVI-005), PEG-[iota]nfergen, PEGylated interferon lambda-1 (PEGylated IL-29, BMS-914143, PEG-rIL-29, PEG-Interleukin-29), belerofon, LAPS-IFN alpha (HM-10660A), Alfaferone (Interferon alpha lozenges, BALL-1 IFN-alpha, Natural human lymphoblastoid interferon alfa, Veldona, OPC-18), BBT-012, and Peginterferon alfa-2b/ribavirin (Pegetron).

Examples of ribavirin and its analogues include ribavirin per se (Rebetol, Copegus, C-Virin; Ravanex, Virazide, Virazole, Ribacine, Cotronak, Viramid) and taribavirin (KD-024, AVS-206, Taribavirin hydrochloride, Viramidine hydrochloride, ICN-3142, Ribamidine hydrochloride, AVS-000206, Viramidine).

Examples of HCV NS3 protease inhibitors are boceprevir (SCH-503034, victrelis), telaprevir (VX-950, incivek, incivo), Simeprevir (TMC-435), Faldaprevir (B1-201335), Vaniprevir (MK-7009), VX-985, VX-813, VBY-376, Asunaprevir (BMS-650032),GS-9451, GS-9256 (GS-337152), MK-5172, Sovaprevir (ACH-1625), Neceprevir (ACH-2684), PHX-1766, Danoprevir (ITMN-191/R7227), ABT-450, AVL-181, TG2349, AVL-192, Ossirene (PRX-0002/AS101, PRX-0001/AS101,1VX-Q-101, WAX-120337, AS-101), BL-8030.

Examples of alpha-glucosidase 1 inhibitors celgosivir (VIR-222, MBI-3253, Bucast, MDL-28574, Bu-cast, MX-3253), Brazaves (Zavesca, NB-DNJ, Vevesca, N-Bu-DNJ, N-Butyl-deoxynojirimycin, Miglustat, OGT-918, SC-48334), Miglitol (Diastabol, Glyset, Plumarol, Seibule).

Examples of hepatoprotectants are Emricasan (IDN-6556, PF-03491390, PF-3491390), Nivocasan (LB-84451), silibilin (Siliphos, Silybin-Phytosome, Silipide, Silybin phosphatidylcholine complex, IdB-1016), MitoQ (Mitoubiquinone mesylate, Mitoquinone mesylate), Molixan (BAM-205, NOV-205), Silymarin (Legalon).

Examples of nucleoside or nucleotide inhibitors of HCV NS5B polymerase are Mericitabine (R7128, RO5024048, MCB, R-4048, RG-7128, RO-5024048), IDX-184, IDX-19368, IDX-19370, BCX-5191 BCX-4678, Sofosbuvir (PSI-7977, GS7977), PSI 353661 (PSI-661), ALS2200, ALS2158, GS6620, T-1106).

Examples of non-nucleoside inhibitors of HCV NS5B polymerase Filibuvir (PF-868554), VX-759, Lomibuvir (VX-222, VCH-222), B1207127, Tegobuvir (GS-9190, GS-333126), IDX-375, PPI-383, VLS-732, Setrobuvir (ANA-598, RG-7790), VCH-916, MK-3281, A848837, ABT-333, A-48547, VCH-796 (nesbuvir), GSK625433, GSK-2485852, ABT 072, GS9669, TMC647055, BMS-791325, PPI-383.

Examples of HCV NS5A inhibitors Daclastavir (BMS790052), BMS-824393, AZD-7295, AZD-2836 (A-831), EDP-239, PPI-461, PP1-1301, PPI-668, ABT-267, ACH 2928, ACH3102, GS5885, GSK2336805, IDX719.

Examples of TLR-7 or TLR-9 agonists are ANA-773 (RG-7795), GS-9620, Resiquimod (R-848, VML-600, S-28463), SD-101, ProMune (PF-03512676, CpG B ODN, Agatolimod sodium, Vaxlmmune, CpG ODN 2006, CpG-2006, PF-3512676, CpG-7909), MCT-465.

Examples of cyclophillin inhibitors are Alisporivir (DE-BIO-025, UNIL-025, DEB-025), SCY-635, BC556 and NIM811.

An example of an HCV IRES inhibitor is MCI-067.

An example of an HCV NS4a antagonist is ACH-1095 (ACH-0141095, GS-9525)

An example of an HCV NS4b binding inhibitor is clemizole (Reactrol, Klemidox, Histacuran, Allercur, Clemizole hydrochloride, Eiger).

Examples of pharmacokinetic enhancers are Paradisin C (BAS-100), SPI-452, PF-4194477, GS9350 (Gilead) and ritonavir.

Examples of immunostimulants include Zadaxin (Thymalfasin, Thymosin alpha 1, TA-1), and SM-360320.

Examples of HCV entry inhibitors are ITX-5061, ITX-4520, SP-30, HCV1 MAbM (BL-HCV1), E1E2-VLP and HCV E1E2/MF59C.1 (E1E2/MF59C.1, HCV E1E2MF59).

An example of an HCV p7 inhibitor is BIT-225.

An example of a DGAT-1 inhibitor is Pradigastat (LCQ-908A, LCQ908)

An example of a TLR-3 agonist is Ampligen (Rintatolimod; Atvogen)

Examples of other drugs used for treating HCV and which may be combined with the compounds of Embodiments 1.0 to 1.329 include nitazoxanide (PH-5776, Heliton, Cryptaz, Colufase, Daxon, Alinea, NTZ), PYN-17 (altirex), KPE02003002, KRN-7000, civacir, GI-5005, ITX2865, TT-033i (OBP-701, TT-033), ANA 971, NOV-205, EHC-18, VGX-410C, EMZ-702, Tarvacin (Bavituximab, Ch3G4), Nivolumab (BMS-936558, MDX-1106, ONO-4538,), Oglufanide and VX-497 (merimepodib), Golotide (Golotimod, SCV-07), Lenocta, CTS-1027, JKB-122, CF-102 (CI-IB-MECA), PYN18, IMMU-105, CYT-107, EPB-415, EPB-500, EPB-200, BL-8020, UT-231 B, Nivocasan (GS9450), MK-8742, MK-2748, RO-5466731, RO-5428029, BMS-929075, CH-6808755, JNJ-47910382, VL-01, Vacc-HCV, HS-HIV/SIV, TT-034 (PF-05095808), PHN-121, HCV-003 (AdCh3NSmut/MVA-NSmut), MK-6325, MG-1105, RO-5303253, SB-9200, PerCvax (Ad6NSmut/AdCh3NSmut), TerCvax (AdCh3NSmut/Ad6NSmut), IPH-1201, REP-2055 (REP-9AC), V-5 Immunitor,), Miravirsen (LNA-anti-mRNA-122,SPC-3649, LNA-antimiR-122), HepTide, PF-4136309 (INCB-8761), Pidilizumab (CT-011), (–)-Epicatechin gallate (ECG, (–)-Epicatechin-3-gallate), CYT-107 (CYT-99-007, rhIL-7, Recombinant interleukin-7), ChronVac-C, KPE-00001133, TG-4040 (MVA-HCV), Nurelin (ADS-5102, ADA; ADS-5101, EXP-105-1, Adamantamine hydrochloride, Lysovir, Mantadix, Hofcomant, Cerebramed, Amantadine hydrochloride, NSC-83653, Symmetrel), Teavigo (Sunphenon, Epigallocatechin-3-gallate, (–)-Epigallocatechin gallate, (–)-EGCG, Epigallocatechin gallate), Prevascar (Ilodecakin, Interleukin-10, IL-10, Tenovil, Sch-52000, rIL-10, rhIL-10), Oxocebron (Ryoxon, WF10, Ancloximex, Oxilium, Oxoferin, Oxoviron, Immunokine, Animexan, Oxomexan, Oxovasin, Oxovir, Macrokine, TCDO, WF-10), Thymogen (IM-862, Oglufanide disodium, Glufanide, Timogen), Civacir (Hepatitis C immune globulin (human), Nabi-Civacir), Phosphostim (IPH-1101, BrHPP sodium salt, Bromohydrin pyrophosphate), Transvax™ (IC-41, Peptide Vaccine IC41, hepatitis C vaccine).

In a preferred embodiment (Embodiment 3.13), the invention provides a combination of a compound as defined in any one of Embodiments 1.0 to 1.329 with another therapeutic agent selected from telaprevir and boceprevir and combinations thereof, optionally with a further therapeutic (e.g. antiviral) agent such as interferon and/or ribavarin.

Combinations with Anti-Cancer Agents

One consequence of infection with hepatitis C virus can be the subsequent development of hepatocellular carcinoma. Combinations of compounds of the invention with anti-cancer drugs may be used to treat hepatocellular carcinoma and in particular early stage hepatocarcinoma.

Accordingly, in further embodiments, the invention provides:

3.22 A combination of a compound according to any one of Embodiments 1.0 to 1.329 and an anti-cancer drug, and more particularly an anti-cancer drug effective in treating hepatocellular carcinoma.

3.23 A combination according to Embodiment 3.22 for use in treating hepatocellular carcinoma.

3.24 The use of a combination according to Embodiment 3.23 for the manufacture of a medicament for the treatment of hepatocellular carcinoma.

3.25 A method of treating hepatocellular carcinoma in a subject in need of such treatment, which method comprises administering to the subject a therapeutically effective amount of a combination as defined in Embodiment 3.22.

3.26 A combination, compound for use, use or method according to any one of Embodiments 3.22 to 3.25 wherein the anti-cancer drug is any one or more (e.g. 1, 2 or 3) selected from 1311-metuximab, AEG-35156, alloCIK, ALN-VSP, alpha-fetoprotein cancer vaccine, apatinib mesylate, ARENEGYR (NGR-TNF, NGR-hTNF), avastin, axitinib, AZD-1480, baclofen, bavituximab, (Tarvacin), BCT-100 (PEG-BCT-100), belinostat, bevacizumab, brivanib alaninate, cabozantinib (cabozantinib S-malate, BMS-907351, XL-184), camptothecin, capecitabine, paclitaxel (e.g. cationic lipid complexed paclitaxel nanoparticles), CF-102 (CI-IB-MECA), cisplatin, cixutumumab, CMS-024, CreaVax-HCC, CryoStim, CT-011, curaxin, darinaparsin (Zinapar), dasatinib, dovitinib lactate, doxorubicin, DW-166HC, ENZ-2968 (EZN-2968, SPC-2968), everolimus, EZN-2968 (ENZ-2968; SPC-2968), ficlatuzumab, flavopiridol, foretinib, fotemustine, ganetespib, GC-33 (RG-7686), golvatinib tartrate, GPC3 (114-152)/IFA, GPC3(298-306)/IFA, GWN (ONO-7268MX1), HAP-302 (TH-302), hepacid (Melanocid, Pegylated arginine deiminase 20000), Immuncell-LC, ImmuCyst, kanglaite, KD-018, KD-025, lansoprazole, lenalidomide, lenvatinib mesylate, linifanib, LY-2157299, mapatumumab, MB-07133 (MB-7133), MEDI-573, melphalan, mepacrine (quinacrine), miriplatin, mitomycin, mitoxantrone, MK-2206 (NSC-749607), MS-20, muparfostat, nemorubicin, nimotuzumab, nintedanib, oncolytic HSV, OPB-31121, orantinib, oxiplatin, pidilizumab, pasireotide, PD-0332991, peretinoin, pexastimogene devacirepvec, Poly-ICLC (Hiltonol), provecta (Xantryl, Rose Bengal disodium), ramucirumab, recentin (AZD-2171), refametinib, regorafenib, resminostat, rF-CEA-TRICOM/rV-CEA-TRICOM; CEA-TRICOM, Rose Bengal Sodium, SB-31 (SB Injection, deoxypodophyllotoxin), selumetinib (selumetinib sulfate), sirolimus (Rapamune), sorafenib, tamibarotene, tarceva, talaporfin, TB-403 (Anti-PlGF), temsirolimus, thalidomide, thymalfasin, tigatuzumab, tivantinib, TKM-080301 (PLK1-SNALP; TKM-PLK1), TLC-388, TRC-105, trebananib, tremelimumab, TS-1 (combination of tegafur, gimeracil and oteracil), tyroserleutide (L-Tyrosyl-L-seryl-L-leucine), tyroservaltide (Tyroservatide), vargatef, velcade, veliparib hydrochloride, YN-968D1, zinostatin and zybrestat (Combretastatin A-4).

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (0) as defined in any one of Embodiments 1.0 to 1.329 together with at least one pharmaceutically acceptable excipient.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (0) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface-active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and pre-filled syringes, and may be stored in a freeze-dried (lyophilised) condition requiring only the addition of the sterile liquid carrier, for example water for injections, immediately prior to use.

The pharmaceutical formulation can be prepared by lyophilising a compound of formula (0), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil and corn oil), and injectable organic esters such as ethyl oleate. Proper fluidity can be maintained, for example, by the use of thickening materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or within a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (0) or formula (1) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13$^{th}$ March 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95%, preferably % (w/w) active ingredient and from 99% (w/w) to 5% (w/w) of a pharmaceutically acceptable excipient or combination of excipients. Preferably, the compositions comprise from approximately 20% (w/w) to approximately 90%,% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragees, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allows the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (0) or formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Where the compound of formula (0) or formula (1) is used in combination with another therapeutic agent (such as another antiviral (e.g. anti-HCV) compound as defined above, the active components of the combination can be physically associated or non-physically associated as defined in the "Definitions" section above. Thus, the other therapeutic agent may be formulated separately to the compound of formula (0) or formula (1) or may be formulated together with the compound of formula (0) or formula (1). In one embodiment (Embodiment 4.2), the compound of formula (0) or formula (1) is formulated together with one or more other therapeutic agents.

Accordingly, in another embodiment (Embodiment 4.2) of the invention, there is provided a pharmaceutical composition comprising at least one compound of the formula (0) as defined in any one of Embodiments 1.0 to 1.329 together with at least one other therapeutic agent as defined herein and at least one pharmaceutically acceptable excipient.

The other therapeutic agent or agents can be any one or more of the agents listed under categories (a) to (z) above.

For example, the pharmaceutical compositions may contain 1, 2 or 3 other therapeutic agents, more typically, 1 or 2 other therapeutic agents.

The one or more other therapeutic agents may be intimately mixed with the compound of formula (0) and formulated together to give a homogeneous composition, or they may be presented in discrete sub-units (e.g. granules, layers, beads or minitablets) which are formulated to give a heterogeneous composition.

Thus, the composition may be presented as a multilayer tablet with one layer comprising the compound of formula (0) and optionally one or more other therapeutic agents and one or more further layers each containing one or more other therapeutic agents.

For example, the composition may take the form of a bilayer or trilayer tablet, with one layer containing the compound of formula (0) and the other layer or layers containing other therapeutic agents as hereinbefore defined.

Where tablet contains two or more layers, one or more layers may be provided with a release delaying-coating that delays release of the compound of formula (0) or another therapeutic agent, for example so that it is released at a different time, or at a different rate, or in a different region of the gastrointestinal tract, from other active agents in the composition.

Alternatively, instead of being presented in separate layers, the tablet composition may be formed from compressed granules wherein two or more different types of granule are present, each type of granule containing a different active agent. For example, the tablet may comprise one type of granules containing a compound of formula (0) and one or more further types of granules containing other therapeutic agents.

As an alternative to tablets, the compositions may be presented as capsules. The capsules may contain a solid, semi-solid or liquid filling in which the compound of formula (0) and the other therapeutic agents form a homogeneous mix, or the capsule may contain a filling in which the compound of formula (0) and the other therapeutic agents form a heterogeneous mix. Thus, the capsule may contain two or more different types of granules, beads or minitablets, wherein each type of granule, bead or minitablet contains a different therapeutic agent or combination of therapeutic agents. For example, one type of granule, bead or minitable may contain a compound of formula (0) and one or more further types of granule, bead or minitablet may contain other therapeutic agents. As with the tablet compositions described above, the various different sub-units (e.g. granules, beads of minitablets) may be formulated for release at different times, different rates or in different parts of the gastrointerstinal tract.

The combination of active agents may also be presented as a pharmaceutical kit, pharmaceutical pack or patient pack in which the compound of formula (0) and one or more other therapeutic agents are co-packaged or co-presented (e.g. as part of an array of unit doses); optionally together with instructions for their use.

EXAMPLES

The invention will now be illustrated, but not limited, by reference to the specific embodiments described in the following examples. In the examples, the following abbreviations are used.

Abbreviations
Aq Aqueous
DBU 1,8-Diazabicycloundec-7-ene
DCE 1,2-Dichloroethane
DCM Dichloromethane
DIPEA N,N-Diisopropylethylamine
DMA Dimethylacetamide
DMF N,N-Dimethylformamide
DMSO Dimethylsulfoxide
$Et_2O$ Diethyl ether
EtOAc Ethyl acetate
HATU O-(7-Azabenzotriazol-1-yl)-N,N,N',N'-tetramethyluronium hexafluorophosphate
Hplc High pressure liquid chromatography
IPA Isopropyl alcohol (2-propanol)
MeCN Acetonitrile
MeOH Methanol
Min Minutes
MS Mass Spectrometry
NMP N-Methylpyrrolidinone
NMR Nuclear Magnetic Resonance Spectroscopy
Sat. Saturated
TBME Methyl tert-butyl ether
THF Tetrahydrofuran
TMS-Cl Trimethylsilyl chloride
Analytical LC-MS System and Method Description In the following examples, compounds were characterised by mass spectroscopy using the systems and operating conditions set out below. Where atoms with different isotopes are present and a single mass quoted, the mass quoted for the compound is the monoisotopic mass (i.e. $^{35}Cl$; $^{79}Br$ etc.).

Waters Platform LC-MS System:
HPLC System: Waters 2795
Mass Spec Detector: Micromass Platform LC
PDA Detector: Waters 2996 PDA
  Platform MS Conditions:
Capillary voltage: 3.6 kV (3.40 kV on ES negative)
Cone voltage: 30 V
Source Temperature: 120° C.
Scan Range: 125-800 amu
Ionisation Mode: ElectroSpray Positive or
ElectroSpray Negative or
ElectroSpray Positive & Negative
Waters Fractionlynx LC-MS System:
HPLC System: 2767 autosampler—2525 binary gradient pump
Mass Spec Detector: Waters ZQ
PDA Detector: Waters 2996 PDA
  Fractionlynx MS Conditions:
Capillary voltage: 3.5 kV (3.25 kV on ES negative)
Cone voltage: 40 V (25 V on ES negative)
Source Temperature: 120° C.
Scan Range: 125-800 amu
Ionisation Mode: ElectroSpray Positive or
ElectroSpray Negative or
ElectroSpray Positive & Negative
Agilent 1200SL-6140 LC-MS System—RAPID:
HPLC System: Agilent 1200 series SL
Mass Spec Detector: Agilent 6140 single quadrupole
Second Detector: Agilent 1200 MWD SL
  Agilent MS Conditions:
Capillary voltage: 4000V on ES pos (3500V on ES Neg)
Fragmentor/Gain: 100
Gain: 1
Drying gas flow: 7.0 L/min
Gas Temperature: 345° C.
Nebuliser Pressure: 35 psig
Scan Range: 125-800 amu
Ionisation Mode: ElectroSpray Positive-Negative switching
Agilent 1100 LC-MS System:
HPLC System: Agilent 1100 series
Mass Spec Detector: Bruker Esquire 3000 Plus Ion Trap
  Agilent 1100 MS Conditions:
System: Bruker Esquire 3000 Plus Ion Trap MS
Ion: Polarity Positive
Ion: Source Type ESI
Nebuliser: 50 psi
Dry Gas: 10 l/min
Dry Temperature: 350° C.
Target Mass: 400 m/z
Scan Range: 50 m/z-1000 m/z
Mass Directed Purification LC-MS System Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

Several systems for purifying compounds via preparative LC-MS are described below although a person skilled in the art will appreciate that alternative systems and methods to those described could be used. From the information provided herein, or employing alternative chromatographic systems, a person skilled in the art could purify the compounds described herein by preparative LC-MS.

Preparative LC-MS System Description:
Waters Fractionlynx System:
  Hardware:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
  Waters MS Running Conditions:
Capillary voltage: 3.5 kV (3.2 kV on ES Negative)
Cone voltage: 25 V
Source Temperature: 120° C.
Scan Range: 125-800 amu
Ionisation Mode: ElectroSpray Positive or
ElectroSpray Negative
Agilent 1100 LC-MS Preparative System:
  Hardware:
Autosampler: 1100 series "prepALS"
Pump: 1100 series "PrepPump" for preparative flow gradient and 1100 series "QuatPump" for pumping modifier in prep flow
UV detector: 1100 series "MWD" Multi Wavelength Detector
MS detector: 1100 series "LC-MSD VL"
Fraction Collector: 2×"Prep-FC"
Make Up pump: "Waters RMA"
Agilent Active Splitter Agilent MS Running Conditions:
Capillary voltage: 4000 V (3500 V on ES Negative)
Fragmentor/Gain: 150/1
Drying gas flow: 12.0 L/min
Gas Temperature: 350° C.
Nebuliser Pressure: 50 psig
Scan Range: 125-800 amu
Ionisation Mode: ElectroSpray Positive or
ElectroSpray Negative Columns:

A range of commercially available columns—both achiral and chiral—were used such that, in conjunction with the changes in mobile phase, organic modifier and pH, they enabled the greatest cover in terms of a broad range of selectivity. All columns were used in accordance with the manufacturers recommended operating conditions. Typically 5 micron particle sized columns were used where available. For example, columns from Waters (including but not limited to XBridge™ Prep OBD™ C18 and Phenyl, Atlantis® Prep T3 OBD™ and Sunfire™ Prep OBD C18 5 µm 19×100 mm), Phenomenex (including but not limited to Synergy MAX-RP and LUX™ Cellulose-2), Astec (Chirobiotic™ columns including but not limited to V, V2 and T2) and Diacel® (including but not limited to Chiralpak® AD-H) were available for screening.

Eluents:

Mobile phase eluent was chosen in conjunction with column manufacturers recommended stationary phase limitations in order to optimise a columns separation performance.

Methods:

Achiral Preparative Chromatography

The compound examples described have undergone HPLC purification, where indicated, using methods developed following recommendations as described in Snyder L. R., Dolan J. W., High-Performance Gradient Elution The Practical Application of the Linear-Solvent-Strength Model, Wiley, Hoboken, 2007.

Chiral Preparative Chromatography

Preparative separations using Chiral Stationary Phases (CSPs) are the natural technique to apply to the resolution of enantiomeric mixtures. Equally, it can be applied to the separation of diastereomers and achiral molecules. Methods are well known in the art for optimising preparative chiral separations on CSPs and then using them to purify compounds. Such methods are described in Beesley T. E., Scott R. P. W.; Chiral Chromatography; Wiley, Chichester, 1998.

Salt Formation

Target molecules containing a basic centre were routinely converted to the corresponding hydrochloride salt by treatment with for example sat. HCl in EtOAc or 4M HCl in dioxane, followed by evaporation. Trituration with a suitable solvent such as Et$_2$O and collection by filtration followed by drying under vacuum gave the target molecule as a solid.

Preparation of Key Intermediates

Intermediate 1

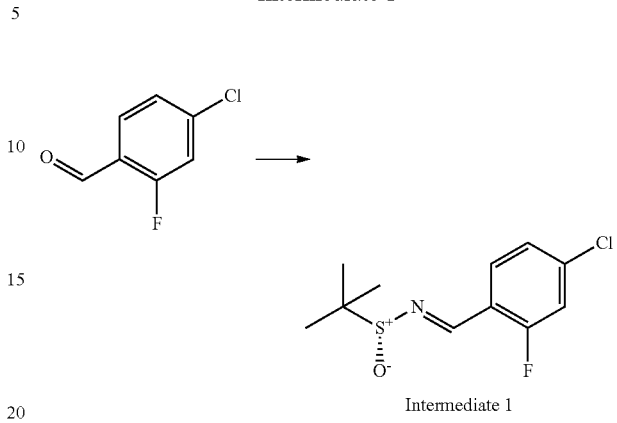

Intermediate 1

To a solution of 4-chloro-2-fluoro-benzaldehyde (198.9 g, 1.254 mol, 1.0 eq) in DCM (2.5 ml) was added (R)-(+)-2-methyl-2-propanesulfinamide (159.6 g, 1.317 mol, 1.1 eq). To this was added a solution of titanium (IV) ethoxide (571.8 g, 2.008 mol, 1.6 eq) in DCM (500 ml) and the reaction was stirred at room temperature overnight. The reaction was diluted with DCM (2 L), Na$_2$SO$_4$.10H$_2$O (2.00 Kg, 6.21 mol, 5.0 eq) was added and the mixture was stirred for 1 h. The mixture was filtered through Celite (1 Kg), eluting with DCM (2×2 L). The filtrate was concentrated in vacuo and the sample dissolved in DCM (2 L). The solution was washed with 10% citric acid solution (2×500 ml) and water (500 ml), dried over MgSO$_4$, filtered and concentrated in vacuo. The residue was slurried in heptanes (200 ml) at 40° C. for 1 hour and then cooled to room temperature and stirred overnight. The stirred suspension was cooled to 0° C. for 1 hour then filtered, washed with cold heptanes (50 ml) and dried in an oven at 40° C. under vacuum overnight to give 237 g of material. The filtrate was concentrated in vacuo, the residue recrystallised from refluxing heptanes (100 ml), cooled to 0° C., filtered and washed with cold heptanes (20 ml). The solids were dried in an oven at 40° C. under vacuum overnight to give 14.1 g of material which was blended with the 237 g previously isolated to give (R)-(+)-2-methyl-propane-2-sulfinic acid 1-(4-chloro-2-fluoro-phenyl)-meth-(E)-ylideneamide (256.7 g, $^1$H NMR>95%, 0.981 mol, 78% yield). 1H NMR (270 MHz, CDCl$_3$): 8.82 (1H, s), 7.96-7.90 (1H, m), 7.25-7.17 (2H, m), 1.25 (9H, s).

Intermediate 2

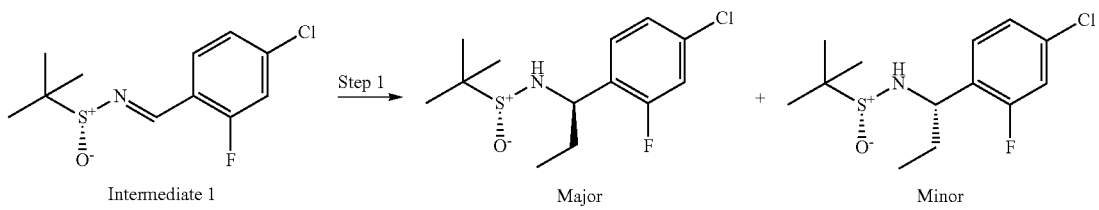

Intermediate 1        Major        Minor

Step 2

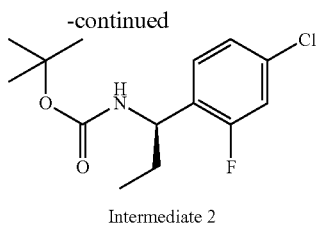 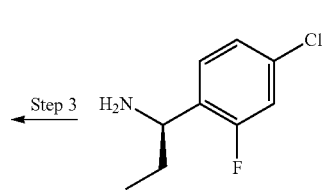

Intermediate 2

Step 1 To a solution of (R)-(+)-2-methyl-propane-2-sulfinic acid 1-(4-chloro-2-fluoro-phenyl)-meth-(E)-ylideneamide (50 g, 0.191 mol, 1.0 eq) in THF (1 L) at −75° C. was added 3M ethylmagnesium bromide in Et$_2$O (127.4 ml, 0.382 mol, 2.0 eq) slowly at <−65° C. over 30 min. The reaction was stirred for 2.5 h at <−65° C. before addition of sat. ammonium chloride solution (500 ml). The solution was diluted with water (250 ml) and the organic layer separated. The aqueous layer was extracted with EtOAc (2×500 ml) and the combined organic layers were washed with brine (500 ml), dried over MgSO$_4$, filtered and concentrated in vacuo to afford 59 g of crude material (3:1 mixture of diastereomers by $^1$H NMR). The crude material was purified by chromatography (silica, 1 Kg) eluting with 20% EtOAc/heptanes up to 30% EtOAc to give (R)-(+)-2-methyl-propane-2-sulfinic acid [(R)-1-(4-chloro-2-fluoro-phenyl)-propyl]-amide (19.9 g, $^1$H NMR>95%, 0.0682 mol, 34% yield). 1H NMR (270 MHz, CDCl$_3$): 7.27-7.21 (1H, m), 7.13-7.04 (2H, m), 4.43 (1H, q), 3.50 (1H, d), 2.02-1.72 (2H, m), 1.21 (9H, s), 0.89 (3H, t).

Step 2 To a solution of (R)-(+)-2-methyl-propane-2-sulfinic acid [(R)-1-(4-chloro-2-fluoro-phenyl)-propyl]-amide (19.9 g, 68.2 mmol, 1.0 eq) in EtOAc (500 ml) was added 2.1M HCl in dioxane (69 ml, 137.1 mmol, 2.0 eq) slowly. The reaction was stirred at room temperature under N$_2$ for 30 min. The solvents were removed in vacuo and the crude material slurried in 3:1 heptane:Et$_2$O (200 ml) for 20 min then filtered and the cake washed with heptanes (2×50 ml). The cake was dried in an oven at 35° C. under vacuum for 30 min to give (R)-1-(4-chloro-2-fluoro-phenyl)-propylamine hydrochloride (19.6 g, $^1$H NMR>95% excluding solvents, 77% active, 67.7 mmol, 99% yield). 1H NMR (270 MHz, DMSO-d$_6$): 8.81 (3H, s), 7.77 (1H, t), 7.52 (1H, dd), 7.41 (1H, dd), 4.33 (1H, q), 2.08-1.76 (2H, m), 0.76 (3H, t).

Step 3 To a suspension of (R)-1-(4-chloro-2-fluoro-phenyl)-propylamine hydrochloride (19.6 g, 67.7 mmol, 1.0 eq) in THF (330 ml) at room temperature was added di-tert-butyl dicarbonate (19.8 g, 90.7 mmol, 1.3 eq) and the reaction was stirred at room temperature overnight. To this was added water (330 ml) and EtOAc (330 ml). The layers were separated, the aqueous layer was extracted with EtOAc (330 ml), the combined organics were washed with brine (330 ml), dried over MgSO$_4$, filtered, and concentrated in vacuo. The residue was dissolved in EtOAc (100 ml) and washed with an aqueous 10% citric acid solution (2×50 ml), dried over MgSO$_4$, filtered and concentrated in vacuo. The residue was triturated with 5:1 heptane/EtOAc (100 ml) to give a white crystaline solid which was slurried in heptanes (100 ml) to give 5 g of material. The liquors were concentrated in vacuo then slurried in heptanes (50 ml) to give 10 g of material. The liquors were concentrated in vacuo and then slurried in heptanes (10 ml) to give 3.9 g of material. The collected solids were oven dried at 45° C. under vacuum for 6 h to give 15.8 g of material. Of this, 9.2 g was dissolved in DCM (200 ml), washed with water (3×100 ml) and brine (100 ml), dried over MgSO$_4$, filtered and concentrated in vacuo to provide [(R)-1-(4-chloro-2-fluoro-phenyl)-propyl]-carbamic acid tert-butyl ester (8.7 g, $^1$H NMR>95%, 30.2 mmol 77% yield). 1H NMR (270 MHz, CDCl$_3$): 7.20-7.03 (3H, m), 4.93 (1H, s), 4.68 (1H, d), 1.77-1.69 (2H, m), 1.40 (9H, s), 0.88 (3H, t). MS: 310.0 ([M+Na]+).

Intermediate 3

[(S)-1-(4-chloro-2-fluoro-phenyl)-propyl]carbamic acid tert-butyl ester can be prepared using the route towards Intermediate 2 using the minor diastereoisomer from Step 1. Analytical data identical to the R-enantiomer.

Intermediate 4

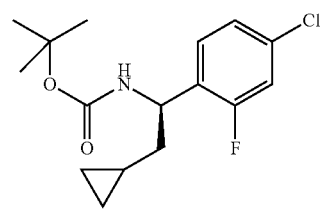 [SMILES: CC(C)(C)OC(=O)N[C@H](CC1CC1)c1ccc(Cl)cc1F]

To a suspension of (1R)-1-(4-chloro-2-fluorophenyl)-2-cyclopropylethan-1-amine hydrochloride (500 mg, 2.0 mmol) in DCM (15 mL) was added triethylamine (0.84 mL, 6 mmol, 3 eq.) followed by Boc anhydride (458 mg, 2.1 mmol, 1.05 eq.) and the reaction mixture was stirred for 4 hours. Further DCM (40 mL) was added and the solution was washed with water (20 mL), 1M HCl (20 mL) and then water (20 mL) followed by brine (20 mL) before the organic layer was dried (MgSO$_4$), filtered and concentrated to give [(R)-1-(4-chloro-2-fluoro-phenyl)-2-cyclopropyl-ethyl]-carbamic acid tert-butyl ester (590 mg, 1.9 mmol, 94%) as a white solid. [M−H]$^-$ 312

Intermediate 5

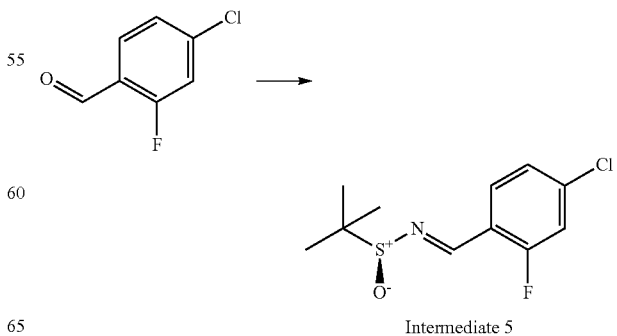

Intermediate 5

To 4-chloro-2-fluorobenzaldehyde (30.64 g, 193.2 mmol, 1.0 eq) in DCM (460 ml) was added (S)-(−)-2-methyl-2-propane sulfinamide (23.41 g, 193.2 mmol, 1.0 eq) followed by titanium (IV) ethoxide (88.1 g, 386 mmol, 2.0 eq). The reaction was stirred overnight before addition of DCM (1 L) and sodium sulfate decahydrate (310 g). After 30 min vigorous stirring, the mixture was filtered through Celite (500 g) and the cake washed with DCM (2×1 L). The organic liquors were dried (MgSO₄), filtered and concentrated in vacuo. The crude compound was dissolved in DCM (500 ml), washed with 10% aq citric acid (200 ml), and saturated brine (100 ml), dried (MgSO₄), filtered and concentrated in vacuo to give (S)-2-methyl-propane-2-sulfinic acid 1-(4-chloro-2-fluoro-phenyl)-meth-(E)-ylideneamide (49.7 g, 1H NMR>95% excluding solvent, 46.7 g active, 178 mmol, 92% yield). 1H NMR (270 MHz, CDCl₃): 8.82 (1H, s), 7.96-7.90 (1H, dd), 7.24-7.16 (2H, m), 1.25 (9H, s).

Intermediate 6

2-methyl-propane-2-sulfinic acid [(R)-(4-chloro-2-fluoro-phenyl)-cyclopropyl-methyl]-amide. 1H NMR (270 MHz, CDCl₃): 7.33 (1H, t), 7.11 (1H, dd), 7.08 (1H, dd), 3.86 (1H, dd), 3.56 (1H, d), 1.28-1.22 (1H, m), 1.18 (9H, s), 0.90-0.80 (1H, m), 0.74-0.64 (1H, m), 0.56-0.35 (2H, m).

Step 2 & 3 To a solution of (S)-(−)-2-methyl-propane-2-sulfinic acid [(R)-(4-chloro-2-fluoro-phenyl)-cyclopropyl-methyl]-amide (6.6 g, 21.7 mmol, 1.0 eq) in EtOAc (150 ml) was added 2.1 M HCl in EtOAc (20.7 ml, 43.4 mmol, 2.0 eq) and the mixture stirred overnight, after which time analysis indicated complete deprotection. The mixture was concentrated in vacuo, the residue slurried in heptane/Et₂O (3/1, 100 ml) for 1 hour, filtered and sucked dry. The HCl salt was partitioned between DCM (100 ml) and sat aq NaHCO₃ (50 ml) and the mixture stirred vigorously for 10 min, the layers separated and the aqueous extracted with DCM. The combined organics were dried (MgSO₄), filtered and concentrated in vacuo.

The resulting amine (3.6 g, 18.0 mmol, 1.0 eq) was dissolved in THF (60 ml) and Et₃N (3.8 ml, 27.0 mmol, 1.5 eq)

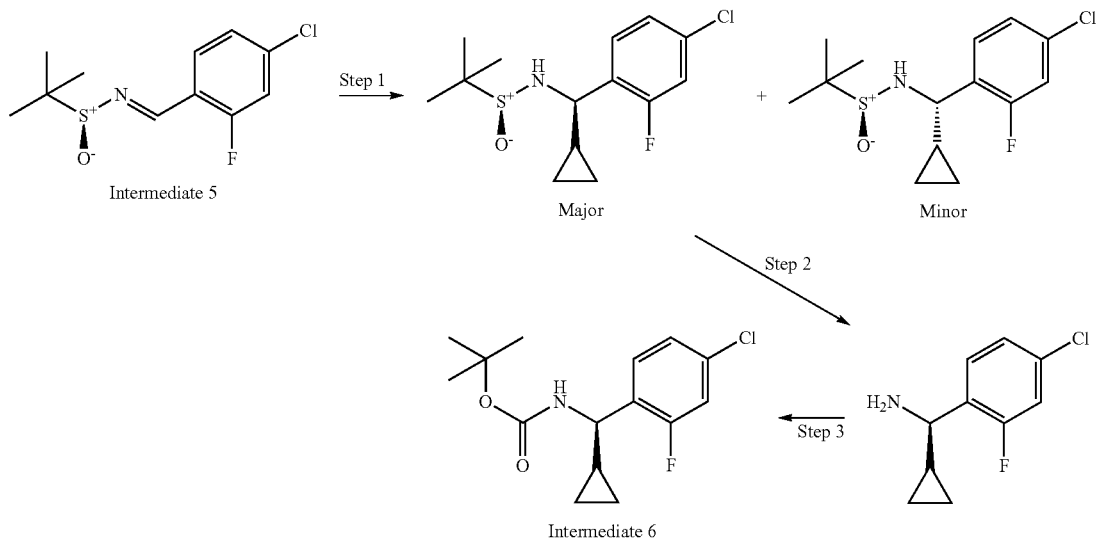

Intermediate 6

Step 1 To a solution of (S)-2-methyl-propane-2-sulfinic acid 1-(4-chloro-2-fluoro-phenyl)-meth-(E)-ylideneamide (26.2 g, 0.1 mol, 1.0 eq) in anhydrous THF (700 ml) at −75° C. was added 0.5M cyclopropylmagensium bromide in THF (400 ml, 0.2 mol, 2.0 eq) dropwise at <−65° C. over 30 min. The reaction was stirred for 2 hours at <−65° C. then allowed to warm to room temperature and stirred for 4 hours. Saturated ammonium chloride solution (300 ml), was added, followed by water (150 ml). The layers were separated and the aqueous extracted with EtOAc (3×200 ml). The combined organic layers were washed with sat. brine (300 ml), dried (MgSO₄), filtered and concentrated in vacuo. The crude material was purified by column chromatography on silica (500 g), eluting with 10% EtOAc/heptanesup to 80% EtOAc. (S)-2-Methyl-propane-2-sulfinic acid [(R)-(4-chloro-2-fluoro-phenyl)cyclopropyl-methyl]-amide was isolated in two batches (combined yield 26.4 g, 86.9 mmol, 87%): 1st batch; 18.4 g ¹H NMR 4:1 mixture of diastereomers in favour of desired isomer, 2nd batch; 8 g ¹H NMR 19:1 mixture of diastereomers in favour of desired isomer. The 2nd batch was repurified by column chromatography on silica (500 g), eluting with 10% EtOAc/heptanesup to 80% EtOAc, to give 6.6 g of pure (S)- added, followed by Boc₂O (5.17 g, 23.4 mmol, 1.3 eq). The mixture was stirred at room temperature for 1 hour, additional Boc₂O (0.5 g) added and the mixture stirred for an additional 1 hour, after which time analysis (LC) indicated complete conversion. Water (60 ml) was added, the layers separated and the aqueous extracted with EtOAc (2×60 ml). The combined organics were dried (MgSO₄), filtered and concentrated. The residue was purified on silica (150 g) eluting with 100% heptanes to 20% EtOAc/heptane. The isolated material was slurried in heptanes(30 ml), the solid filtered, washed with heptanes and sucked dry to give [(R)-(4-chloro-2-fluoro-phenyl)-cyclopropyl-methyl]-carbamic acid tert-butyl ester (1.9 g). The filtrate was concentrated and the solid obtained reslurried in heptanes(10 ml) to provide additional [(R)-(4-chloro-2-fluoro-phenyl)-cyclopropyl-methyl]-carbamic acid tert-butyl ester (1.2 g, combined yield 3.1 g, 10.3 mmol, 47.7%). 1H NMR (400 MHz, DMSO-d6): 7.63 (1H, d), 7.52 (1H, t), 7.37 (1H, dd), 7.31 (1H, d), 4.22 (1H, t), 1.35 (9H, s), 1.16-1.03 (1H, m), 0.56-0.45 (1H, m), 0.45-0.27 (2H, m), 0.26-0.15 (1H, m).

Intermediate 7

[(S)-(4-chloro-2-fluoro-phenyl)-cyclopropyl-methyl]-carbamic acid tert-butyl ester can be prepared using the route outlined towards Intermediate 6 above using the minor diastereoisomer from Step 1 in Step 2. Preferably, the route towards Intermediate 6 is repeated using Intermediate 1 in step 1. Analytical data identical to the R-enantiomer.

Intermediate 8

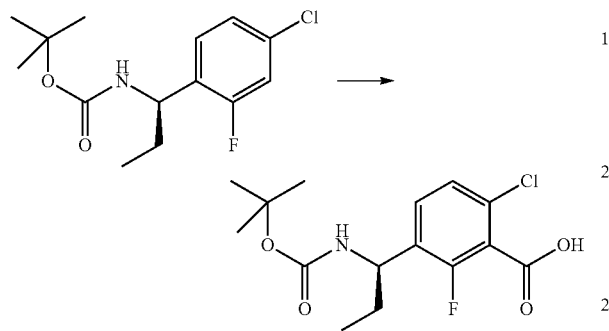

A solution of Intermediate 2 (1.00 g, 3.47 mmol) in THF (30 mL) was cooled under nitrogen to −78 degC and then nBuLi (2.5M in hexanes, 3.2 mL, 8.0 mmol, 2.3 eq.) was added dropwise. After 1 h the solution was poured onto solid $CO_2$ and the resulting mixture warmed to room temperature. The solution was concentrated and then partitioned between EtOAc (50 mL) and water (50 mL) with 1 mL of 5M NaOH. The aqueous phase was acidified with 1M HCl and then extracted with EtOAc (50 mL). The latter organic phase was then washed with brine (10 mL), dried ($MgSO_4$), filtered and concentrated to give 3-((R)-1-tert-butoxycarbonylamino-propyl)-6-chloro-2-fluoro-benzoic acid (980 mg, 2.95 mmol, 85%) as a white solid. [M−H]− 330

Intermediate 9

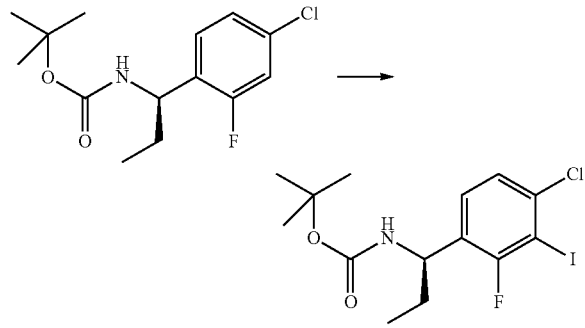

To a flame dried flask under $N_2$ was charged a solution of Intermediate 2 (1.40 g, 4.84 mmol, 1.0 eq) in THF (36 ml). The stirred solution was cooled to −78° C. To this was added 2.5M n-butyllithium in hexane (4.25 ml, 10.64 mmol, 2.2 eq) dropwise<−65° C. over 5 min. The reaction was allowed to warm to −59° C. then cooled to <−65° C. for 1.5 h. To this was added a solution of $I_2$ (1.35 g, 5.32 mmol, 1.1 eq) in THF (6 ml) over 30 seconds. The reaction was stirred at <−65° C. for 30 min then quenched with water (45 ml) and allowed to warm to room temperature. The mixture was diluted with sat. aq. sodium thiosulphate (40 ml) then extracted with EtOAc (2×100 ml). The combined organics were washed with brine (100 ml), dried over $MgSO_4$, filtered and concentrated in vacuo. The residue was purified by chromatography (silica, 220 g) eluting with 1% MeOH/7% EtOAc/92% heptanes to give [(R)-1-(4-Chloro-2-fluoro-3-iodo-phenyl)-propyl]-carbamic acid tert-butyl ester (1.02 g, $^1$H NMR>95%, 2.34 mmol, 48% yield). 1H NMR (270 MHz, $CDCl_3$): 7.25-7.14 (2H, m), 4.93 (1H, bs), 4.71-4.66 (1H, m), 1.80-1.69 (2H, m), 1.40 (9H, s), 0.89 (3H, t).

Intermediate 10

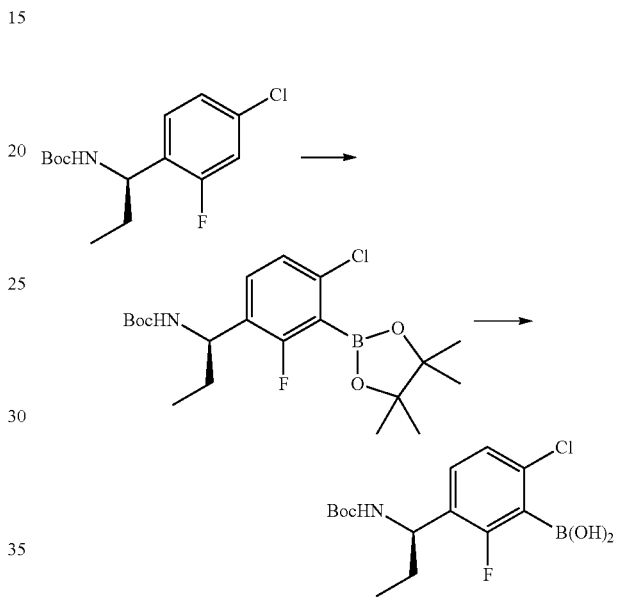

Step 1 To a solution of Intermediate 2 (1.00 g, 3.48 mmol, 1.0 eq) in THF (30 ml) at −70° C. was added n-Butyllithium (2.5M in hexanes, 1.39 ml, 3.48 mmol, 1.0 eq) at <−65° c. over 5 mins. After stirring for 10 mins, sec-Butyllithium (1.4M in cyclohexane, 2.74 ml, 3.84 mmol, 1.1 eq) was added dropwise over 5 mins at <−65° C. After 1 hour, 2-Isopropoxy-4,4,5,5-tetramethyl-1,3,2-dioxaborolane (1.29 g, 6.95 mmol, 2.0 eq) was added as a solution in THF (2 ml) at <−65° C. The reaction was stirred for 3 hours then quenched by addition of sat. ammonium chloride solution (20 ml). The mixture was allowed to warm to 0° C., before addition of water (10 ml) and extraction with $Et_2O$ (2×30 ml). The organic layer was washed with sat. brine (30 ml), dried ($MgSO_4$), filtered and concentrated in vacuo. The crude material was purified by column chromatography on silica (50 g), eluting with 100% DCM. The product fractions were concentrated to give {(R)-1-[4-chloro-2-fluoro-3-(4,4,5,5-tetramethyl-[1,3,2]dioxaborolan-2-yl)-phenyl]-propyl}-carbamic acid tert-butyl ester (490 mg, 1H NMR>95% excluding solvents, 88% active, 1.04 mmol, 30% yield). 1H NMR (270 MHz, $CDCl_3$): 7.20-7.02 (2H, m), 4.90 (1H, bs), 4.65 (1H, bs), 1.80-1.65 (2H, m), 1.45-1.30 (21H, m), 0.84 (3H, t).

Step 2 To {(R)-1-[4-chloro-2-fluoro-3-(4,4,5,5-tetramethyl-[1,3,2]dioxaborolan-2-yl)-phenyl]-propyl}-carbamic acid tert-butyl ester (340 mg, 0.821 mmol, 1.0 eq) in acetone (30 ml) and water (30 ml) was added ammonium acetate (127 mg, 1.642 mmol, 2.0 eq) and then sodium metaperiodate (351 mg, 1.642 mmol, 2.0 eq). After stirring for 2 hour at 20° C., the acetone was removed in vacuo. The pH was adjusted to ~5 with 10% citric acid solution (5 ml) and extracted with DCM (20 ml and 10 ml). The organic layer was washed with sat. brine (5 ml), dried (MgSO4), filtered and concentrated to give a crude material (381 mg). The crude material was combined with a previous batch (350 mg crude) and was purified by column chromatography on silica (9 g) eluting 100% DCM up to 2% MeOH/DCM. The product containing fractions were concentrated to give [(R)-1-(4-chloro-2-fluoro-phenyl-3-boronic acid)-propyl]-carbamic acid tert-butyl ester (330 mg, 1H NMR>95%, 1.00 mmol, 63% yield). 1H NMR (270 MHz, CDCl3): 7.24-7.05 (2H, m), 4.95 (1H, bs), 4.66 (1H, bs), 3.64 (2H, s), 1.82-1.66 (2H, m), 1.39 (9H, bs), 0.87 (3H, t). LCMS: 354.1 (MNa+).

Intermediate 11

3-Benzoyl-4-chloro-2-fluoro-benzaldehyde

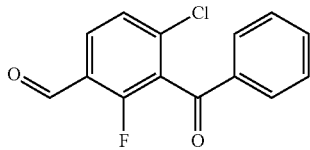 [SMILES: O=Cc1ccc(Cl)c(C(=O)c2ccccc2)c1F]

Step 1 To a solution of 6-chloro-2-fluoro-3-methyl-benzoyl chloride (2.07 g, 10.0 mmol) in anhydrous tetrahydrofuran (50 ml), stirred under nitrogen in an acetonitrile/CO2 bath, was added tributyl phosphine (2.75 ml, 11.0 mmol). The mixture was stirred for 15 minutes before phenylmagnesium bromide (3M in diethyl ether, 3.67 ml, 11.0 mmol) was added dropwise. After 45 minutes, the reaction was quenched by addition of hydrochloric acid (2N, 50 ml). The mixture was extracted with ethyl acetate. The organic liquors were washed with sodium bicarbonate solution and brine, dried (MgSO4) and concentrated in vacuo. The residue was purified by silica chromatography eluting with 0-10% diethyl ether/petroleum ether furnishing (6-chloro-2-fluoro-3-methyl-phenyl)-phenyl-methanone as a yellow oil that slowly crystallised (1.12 g, ca. 80% pure). Trituration with petroleum ether produced an analytically pure sample. MS: [M+H]+ 249

Step 2 A mixture of (6-chloro-2-fluoro-3-methyl-phenyl)-phenyl-methanone (639 mg, 2.57 mmol), N-bromosuccinimide (549 mg, 3.08 mmol) and azobisisobutyronitrile (548 mg, 3.34 mmol) in carbon tetrachloride (10 ml) was heated to 80 degC under nitrogen. After 4 hours starting material plus mono and di-brominated species were evident. An additional 500 mg then 600 mg of both reagents were added over the course of 18 hours; no starting material remained. The mixture was allowed to cool, dichloromethane was added and the mixture was washed with water (×2) before passing through a hydrophobic frit. The organic liquors were concentrated then purified by silica column chromatography eluting with 0-10% diethyl ether/petroleum ether to produce the two products. (6-Chloro-3-dibromomethyl-2-fluoro-phenyl)-phenyl-methanone (582 mg, ca. 85% pure) MS: [M+NH4]+ 242 and (3-bromomethyl-6-chloro-2-fluoro-phenyl)-phenyl-methanone (292 mg, ca. 90% pure) MS: [M+NH4]+ 344

Step 3 A mixture of (3-bromomethyl-6-chloro-2-fluoro-phenyl)-phenyl-methanone (292 mg, 0.896 mmol), sodium bicarbonate (700 mg, 8.33 mmol) and dimethylsulfoxide (10 ml) was heated to 80 degC for 3 hours. The reaction mixture was then allowed to cool, ethyl acetate was added, and the mixture was washed with water, aqueous lithium chloride and brine before drying (MgSO4) and concentrating in vacuo. The residue was purified by silica chromatography eluting with 0-20% ethyl acetate/petroleum ether to furnish 3-benzoyl-4-chloro-2-fluoro-benzaldehyde (115 mg oil, 90% clean). 1H NMR (400 MHz, CDCl3): 10.34 (1H, s), 7.97 (1H, dd), 7.91-7.86 (2H, m), 7.72-7.67 (1H, m), 7.55 (2H, t), 7.44 (1H, d), 7.28 (1H, s). MS: [M+NH4]+ 280

Step 4 A mixture of (6-chloro-3-dibromomethyl-2-fluoro-phenyl)-phenyl-methanone (582 mg, 1.38 mmol), silver nitrate (469 mg, 2.76 mmol), isopropanol (10 ml) and water (2 ml) was stirred at room temperature overnight. Dichloromethane was added and the mixture was filtered under suction washing with isopropanol. The organic liquors were concentrated then purified by silica chromatography eluting with 0-20% ethyl acetate/petroleum ether furnishing 3-benzoyl-4-chloro-2-fluoro-benzaldehyde (222 mg oil, 90% clean). Analytical data as above Intermediate 12 tert-Butyl N-[(1R)-1-(3-benzoyl-4-chloro-2-fluorophenyl)propyl]carbamate

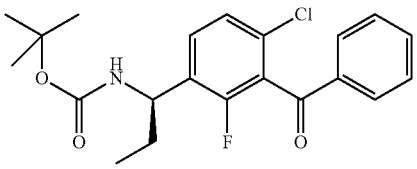 [SMILES: CC[C@@H](NC(=O)OC(C)(C)C)c1ccc(Cl)c(C(=O)c2ccccc2)c1F]

To a stirred solution of Intermediate 2 (1 g, 3.48 mmol) in THF (27.8 mL) at −78° C. was added butyllithium solution (2.5 M in hexanes, 3.2 mL, 7.99 mmol) dropwise. The solution was stirred at −78° C. for 1 hour and then a solution of methyl benzoate (0.478 mL, 3.82 mmol) in THF (7.65 mL) was added dropwise. The reaction was stirred at −78° C. for 2 hours, and then quenched by the addition of saturated NH4Cl solution. Water and EtOAc were added, the phases separated and the aqueous phase was extracted into EtOAc (×2). The combined organic extracts were dried (Na2SO4), filtered and concentrated. Biotage column (25+M) eluting with a gradient of 0% EtOAc/petrol to 20% EtOAc/petrol gave tert-butyl N-[(1R)-1-(3-benzoyl-4-chloro-2-fluorophenyl)propyl]carbamate, 0.62 g, 46%. MS: [M−H]− 390.

Intermediate 13 tert-Butyl N-[(1R)-1-(3-benzoyl-2-fluoro-4-methylphenyl)-propyl]carbamate

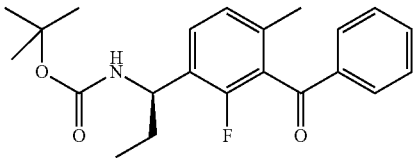 [SMILES: CC[C@@H](NC(=O)OC(C)(C)C)c1ccc(C)c(C(=O)c2ccccc2)c1F]

To a stirred mixture of Intermediate 12 (0.2 g, 0.51 mmol), methylboronic acid (0.183 g, 3.06 mmol), S-Phos (0.021 g, 0.051 mmol), palladium(II) acetate (0.00573 g, 0.0255 mmol) and K3PO4 (0.217 g, 1.02 mmol) under vacuum, was added toluene (1.66 mL). The microwave vial was filled with nitrogen, evacuated and refilled with nitrogen twice before the tube was sealed and heated in the microwave at 120° C. for 40 minutes. The mixture was then diluted with EtOAc, filtered, and concentrated. Biotage column (25+M) eluting with a gradient of 0% EtOAc/petrol to 25% EtOAc/petrol gave tert-butyl N-[(1R)-1-(3-benzoyl-2-fluoro-4-methylphenyl)-propyl]carbamate, 0.178 g, 94%. MS: [M−H]− 370.

Intermediate 14

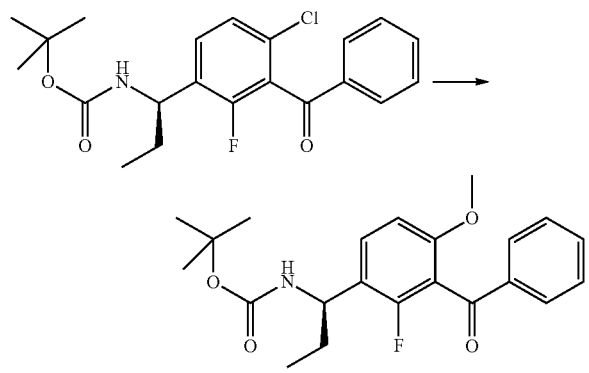

To a stirred mixture of Intermediate 12 (0.3 g, 0.766 mmol), potassium hydroxide (0.202 g, 3.06 mmol), 2-di-tert-butylphosphino-2',4',6'-triisopropylbiphenyl (0.026 g, 0.0612 mmol) and tris(dibenzylideneacetone)dipalladium(0) (0.014 g, 0.0153 mmol) under vacuum, was added 1,4-dioxane (0.919 mL) followed by water (0.612 mL). The microwave vial was filled with nitrogen, evacuated and refilled with nitrogen twice before the tube was sealed and heated in the microwave at 120° C. for 40 minutes. Cetyltrimethylammonium bromide (0.0279 g, 0.0766 mmol) and iodomethane (0.0715 mL, 1.15 mmol) were added and the vial was heated in the microwave at 100° C. for 1.5 hours. The mixture was then diluted with EtOAc, filtered, washed with water, dried (Na2SO4), filtered and concentrated. Biotage column (25+M) eluting with a gradient of 10% EtOAc/petrol to 35% EtOAc/petrol gave tert-butyl N-[(1R)-1-(3-benzoyl-2-fluoro-4-methoxyphenyl)propyl]carbamate, 0.144 g, 49%. MS: [M−H]− 386.

Intermediate 15

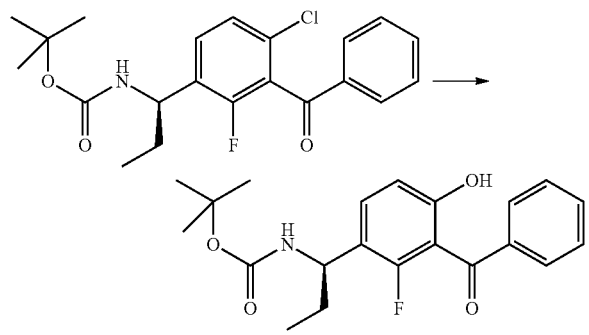

To a stirred mixture of Intermediate 12 (0.5 g, 1.28 mmol), potassium hydroxide (0.253 g, 3.83 mmol), 2-di-tert-butylphosphino-2',4',6'-triisopropylbiphenyl (0.0433 g, 0.102 mmol) and tris(dibenzylideneacetone)dipalladium(0) (0.0234 g, 0.0255 mmol) under vacuum, was added 1,4-dioxane (1.53 mL) followed by water (1.02 mL). The microwave vial was filled with nitrogen, evacuated and refilled with nitrogen twice before the tube was sealed and heated in the microwave at 120° C. for 40 minutes. The mixture was then diluted with EtOAc, filtered, washed with 5% citric acid solution, dried (Na2SO4), filtered and concentrated. The residue was triturated with Et2O giving tert-butyl N-[(1R)-1-(3-benzoyl-2-fluoro-4-hydroxyphenyl)propyl]-carbamate, 0.383 g, 80%. MS: [M−H]− 372.

Preparation of Compounds of the Formula (0)

The preparation of Examples of compounds of the formula (0) is set out in Sections A and B below.

Section A describes the synthesis of compounds of the formula (0) wherein $R^2$ is hydrogen whereas Section B mainly describes the synthesis of compounds of formula (0) wherein $R^2$ is other than hydrogen. In addition to having anti-HCV activity in their own right, the compounds of formula (0) wherein $R^2$ is hydrogen serve as intermediates for the preparation of compounds wherein $R^2$ is X—$R^8$.

A. Preparation of Compounds of the Formula (0) in which $R^2$ is Hydrogen

Example 1

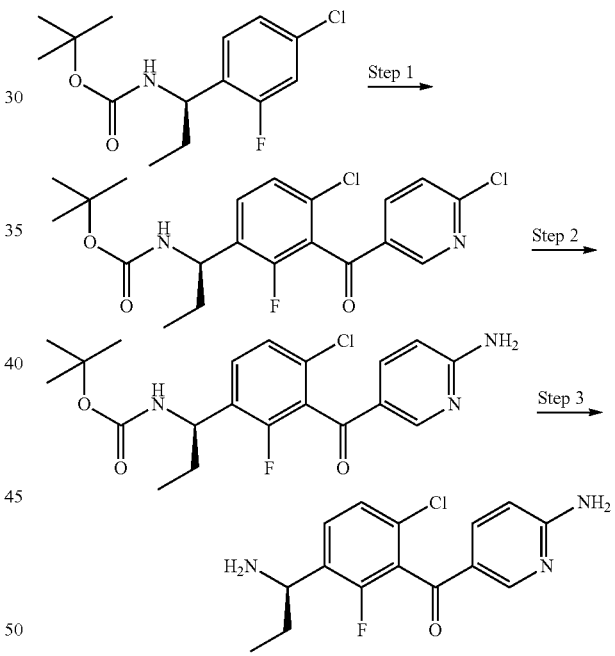

Step 1 To a solution of Intermediate 2 (8 g, 27.8 mmol) in dry THF (200 mL) under nitrogen at −78 degC was added n-BuLi (2.5M in hexanes, 24.5 mL, 61.2 mmol, 2.2 eq.) dropwise and the solution stirred at −78 degC for 1 h. Ethyl 6-chloronicotinate (4.3 mL, 30.6 mmol, 1.1 eq.) was added quickly and the reaction stirred for a further 30 min before it was quenched with NH4Cl (aq.). Once warmed to room temperature, the mixture was partitioned between EtOAc (200 mL) and water (200 mL). The organic phase was washed with water (200 mL) and brine (100 mL) before it was dried (MgSO4), filtered and concentrated. The material was triturated with Et2O twice to give 2 crops of {(R)-1-[4-chloro-3-(6-chloro-pyridine-3-carbonyl)-2-fluoro-phenyl]-propyl}-carbamic acid tert-butyl ester, totalling (6.4 g, 15 mmol, 54%) between them. [MH]+ 371

Step 2 {(R)-1-[4-Chloro-3-(6-chloro-pyridine-3-carbonyl)-2-fluoro-phenyl]-propyl}-carbamic acid tert-butyl ester (6.4 g, 15 mmol) was suspended in 7M NH$_3$ in MeOH (32 mL) and split over 4 Reacti-vials and all heated at 100 degC overnight. The mixture was then evaporated down and purified by silica column, eluting 20-100% EtOAc in petroleum ether to give {(R)-1-[3-(6-amino-pyridine-3-carbonyl)-4-chloro-2-fluoro-phenyl]-propyl}-carbamic acid tert-butyl ester (3.1 g, 7.6 mmol, 51%). [MH]+ 408

Step 3 To a solution of {(R)-1-[3-(6-amino-pyridine-3-carbonyl)-4-chloro-2-fluoro-phenyl]-propyl}-carbamic acid tert-butyl ester (2.18 g, 4.43 mmol) in DCM (50 mL) was added 4M HCl in dioxane (7.75 mL, 31 mmol, 7 eq) and the reaction stirred for 18 h. Complete conversion. Mixture was concentrated and then triturated with diethyl ether (50 mL) and the solid filtered off and dried in a vacuum oven to give [3-((R)-1-amino-propyl)-6-chloro-2-fluoro-phenyl]-(6-amino-pyridin-3-yl)-methanone (1.54 g, 4.35 mmol, 98%) as a beige solid and the HCl salt Example 2

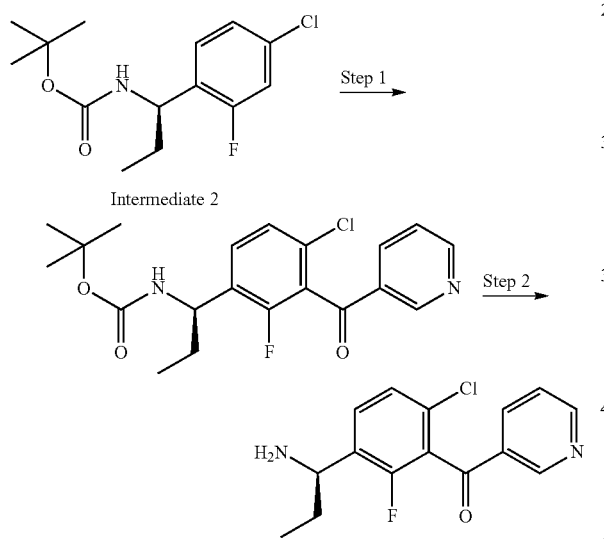

Step 1 To a solution of Intermediate 2 (13.7 g, 147.6 mmol) in dry THF (330 mL) under nitrogen at −78 degC was added nBuLi (2.5M in hexanes, 43.8 mL, 110 mmol, 2.3 eq.) dropwise and the solution stirred at −78 degC for 1 h. Ethyl nicotinate (9.6 mL, 61.9 mmol, 1.3 eq.) was then added. Reaction left at −78 degC for 45 minutes and was then quenched first with MeOH (~10 mL) and then water (~20 mL). Concentrated and then partitioned between EtOAc (400 mL) and water (300 mL). Organic phase was washed with water (300 mL) and brine (100 mL) before it was dried (MgSO$_4$), filtered and concentrated to give crude material (~23 g). Purified by silica column (65M on Biotage SP4) eluting 20-35% EtOAc in petroleum ether over 15 column volumes to give {(R)-1-[4-chloro-2-fluoro-3-(pyridine-3-carbonyl)-phenyl]-propyl}-carbamic acid tert-butyl ester (16.0 g, 40.7 mmol, 86%). [MH]+ 393

Step 2 To a solution of {(R)-1-[4-chloro-2-fluoro-3-(pyridine-3-carbonyl)-phenyl]-propyl}-carbamic acid tert-butyl ester (16.0 g, 40.7 mmol) in DCM (300 mL) was added 4M HCl in dioxane (41 mL, 162 mmol, 4 eq) and the reaction stirred for 18 h. The mixture was concentrated and then triturated with diethyl ether (~200 mL) and the pale green solid filtered off and dried in a vacuum oven to give [3-((R)-1-Amino-propyl)-6-chloro-2-fluoro-phenyl]-pyridin-3-yl-methanone (15.0 g) as the HCl salt. Material contains about 1.3 g dioxane (from NMR ratio), which was not removed from vacuum oven drying.

Example 3

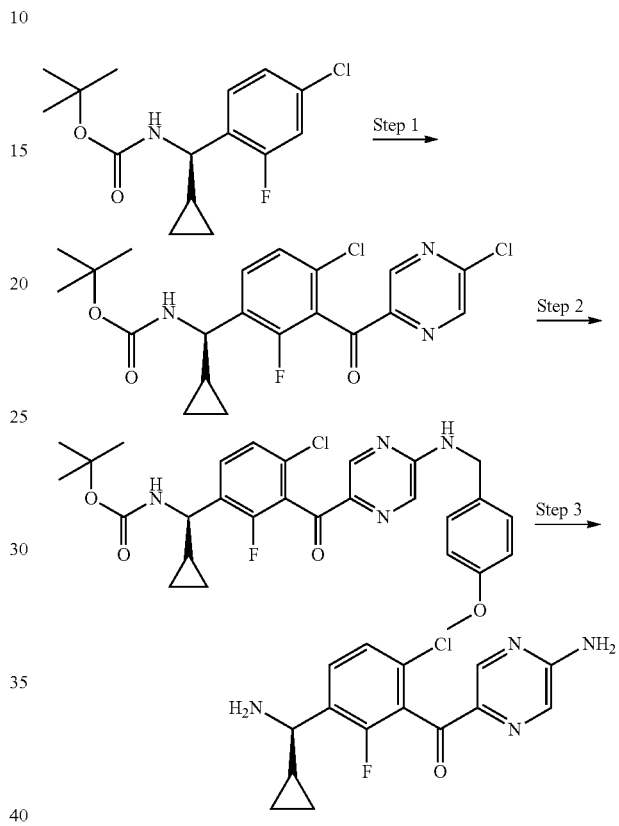

Step 1 Conducted as Step 1 towards Example 1 using Intermediate 6 and methyl 5-chloropyrazine-2-carboxylate. [M−H]− 438

Step 2 {(R)-[4-Chloro-3-(5-chloro-pyrazine-2-carbonyl)-2-fluoro-phenyl]-cyclopropyl-methyl}-carbamic acid tert-butyl ester (709 mg, 1.61 mmol), 4-methoxybenzylamine (0.232 ml, 1.77 mmol), triethylamine (0.448 ml, 3.22 mmol) and dimethylformamide (5 ml) was heated to 80 deg C for 3 hours. The reaction was allowed to cool, ethyl acetate was added, and the mixture was washed with 10% aqueous lithium chloride solution and brine. The organic liquors were dried (MgSO$_4$) and concentrated. The residue was purified by column chromatography eluting with 10-50% ethyl acetate/petroleum ether furnishing ((R)-{4-Chloro-2-fluoro-3-[5-(4-methoxy-benzylamino)-pyrazine-2-carbonyl]-phenyl}-cyclopropyl-methyl)-carbamic acid tert-butyl ester (512 mg) as a yellow oil. [M+H]+ 541

Step 3 The product from Step 2 (512 mg) was heated to 60 deg C in a solution of trifluoroacetic acid (3 ml) and CDCl3 (1 ml). After 2 hours the reaction was allowed to cool and was then cautiously added to 75 ml water. The aqueous mixture was washed with ethyl acetate (×2) then basified with potassium hydroxide pellets (pH~9). This mixture was extracted with dichloromethane (×2). These organic liquors were dried and concentrated to furnish the target compound as an oil (78 mg). Further material was obtained from the ethyl acetate

Example 4

(1R)-1-(3-Benzoyl-4-chloro-2-fluorophenyl)propan-1-amine

Example 4 was prepared from Intermediate 11 according to the procedures used in the synthesis of Intermediates 1 & 2.

Example 5

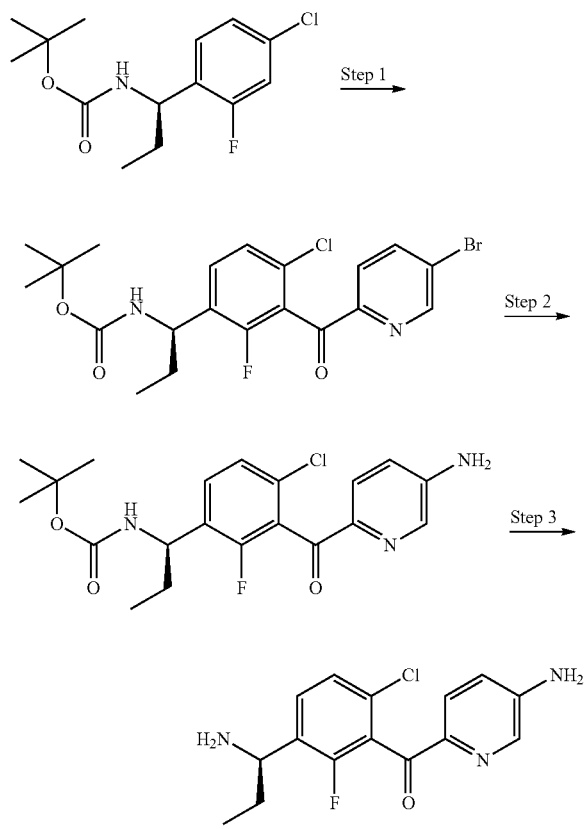

Step 1 Conducted according to Example 1 Step 1 using methyl 5-bromopyridine-2-carboxylate. [M+H]+ 471

Step 2 To a solution of {(R)-1-[3-(5-bromo-pyridine-2-carbonyl)-4-chloro-2-fluoro-phenyl]-propyl}-carbamic acid tert-butyl ester (371 mg, 0.79 mmol) in NMP (2 mL) was added copper (I) oxide (23 mg, 0.16 mmol, 0.2 eq.) and ammonium hydroxide (~29% in water, 2 mL) in a Reacti-vial and the mixture heated at 80° C. for 4 h. The mixture was partitioned between EtOAc (20 mL) and water (20 mL) and the organic phase extracted with further EtOAc (10 mL). Combined organic phase was washed with water (3×20 mL) and brine (10 mL) before it was dried (MgSO4), filtered and concentrated. Purified by silica column, 25 M, eluting 25-80% EtOAc in petrol to give {(R)-1-[3-(5-amino-pyridine-2-carbonyl)-4-chloro-2-fluoro-phenyl]-propyl}-carbamic acid tert-butyl ester (226 mg, 0.55 mmol, 70%). [M+H]+ 408

Step 3 The BOC group was removed using the procedure outlined in Example 1 Step 3.

Example 11

(R)-(3-Benzoyl-4-chloro-2-fluorophenyl)(cyclopropyl)methanamine (R)-(3-benzoyl-4-chloro-2-fluorophenyl)(cyclopropyl) methanamine was prepared from Intermediate 11 according to the procedures used in the synthesis of Intermediates 1 & 6.

Example 19

5-[3-((R)-1-Amino-propyl)-6-chloro-2-fluoro-benzoyl]-pyridine-2-carboxylic acid

To a stirred solution of Intermediate 2 (0.4 g, 1.39 mmol) in THF (10 mL) at −78° C. was added butyllithium solution (2.5 M in hexanes, 1.28 mL, 3.19 mmol) dropwise. The solution was stirred at −78° C. for 1 hour and then a solution of 5-(methoxycarbonyl)pyridine-2-carboxylic acid (0.252 g, 1.39 mmol) in THF (10 mL) pretreated with 60% NaH (0.061 g, 1.59 mmol) for 15 mins was added dropwise. The reaction was stirred at −78° C. for 45 mins, and then quenched by the addition of saturated NH4Cl solution. Water and EtOAc were added and the phases were separated. The organic extract was dried (Na2SO4), filtered and concentrated. Biotage column eluting with a gradient of 0%-50% EtOAc/petrol gave 5-[3-((R)-1-tert-butoxycarbonylamino-propyl)-6-chloro-2-fluoro-benzoyl]-pyridine-2-carboxylic acid (0.06 g), MS: [M+H] 437. 5-[3-((R)-1-tert-Butoxycarbonylamino-propyl)-6-chloro-2-fluoro-benzoyl]-pyridine-2-carboxylic acid (0.06 g, 0.137 mmol) was treated with saturated HCl/EtOAc and stirred at ambient temperature for 1 hour. The resulting solid was filtered off and washed with ether to give 5-[3-((R)-1-amino-propyl)-6-chloro-2-fluoro-benzoyl]-pyridine-2-carboxylic acid (0.03 g).

Example 22

5-[3-((R)-1-Amino-propyl)-6-chloro-2-fluoro-benzoyl]-pyridine-2-carboxylic acid amide To a solution of 5-[3-((R)-1-tert-Butoxycarbonylamino-propyl)-6-chloro-2-fluoro-benzoyl]-pyridine-2-carboxylic acid (Example 19)) in dichloromethane (8 ml) was added ammonium chloride (0.057 g, 0.65 mmol), DIPEA (0.137 mL, 0.78 mmol) and then HATU (0.06 g, 0.156 mmol) and the reaction stirred for 1 h. Further HATU totalling (0.12 g, 0.312 mmol) added. The reaction performed on a further (57 mg), both reactions combined and diluted with dichloromethane washed with water. The organic extract was dried (Na2SO4), filtered and concentrated. Purified by Prep HPLC to give {(R)-1-[3-(6-Carbamoyl-pyridine-3-carbonyl)-4-chloro-2-fluoro-phenyl]-propyl}-carbamic acid tert-butyl ester (0.042 g) MS: [M+H] 436 {(R)-1-[3-(6-Carbamoyl-pyridine-3-carbonyl)-4-chloro-2-fluoro-phenyl]-propyl}-carbamic acid tert-butyl ester (0.042 g, 0.137 mmol) treated with saturated HCl/EtOAc stirred at ambient for 1 hour, precipitate filtered and washed with ether to give 5-[3-((R)-1-amino-propyl)-6-chloro-2-fluoro-benzoyl]-pyridine-2-carboxylic acid amide (0.025 g).

Example 25

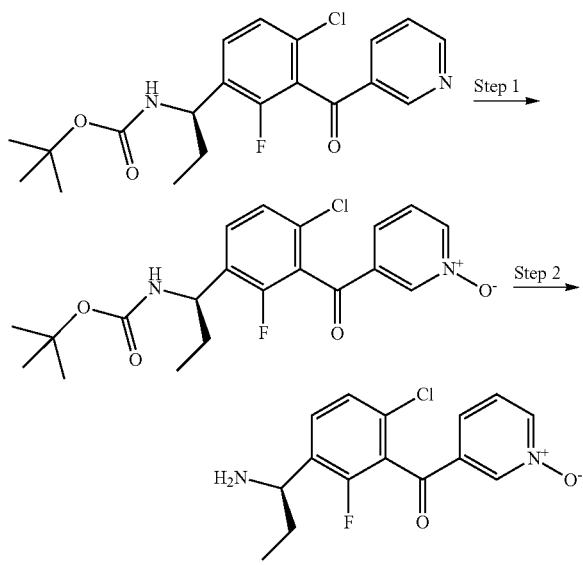

Step 1 To a solution of {(R)-1-[4-chloro-2-fluoro-3-(pyridine-3-carbonyl)-phenyl]-propyl}-carbamic acid tert-butyl ester (intermediate towards Example 2, 460 mg, 1.2 mmol) in dichloromethane (10 ml) was cautiously added m-chloroperoxybenzoic acid (355 mg, 2.1 mmol). After stirring for 90 minutes, a spatula tip of additional reagent was added. After a further 90 minutes the reaction was washed with dilute sodium bicarbonate solution and sodium thiosulfate solution and was dried by hydrophobic frit. The organic liquors were concentrated then purified by column chromatography eluting with 0-20% methanol/ethyl acetate to furnish the product of Step 1 as an oil (420 mg). [M+H]+ 409

Step 2 The BOC group from {(R)-1-[4-chloro-2-fluoro-3-(1-oxy-pyridine-3-carbonyl)-phenyl]-propyl}-carbamic acid tert-butyl ester (420 mg) was removed according to Example 1 Step 3 to furnish the desired product as a white solid (300 mg). [M+H]+ 309

Example 37

(1R)-1-(4-chloro-2-fluoro-3-{[6-(1H-pyrazol-1-yl)pyridin-3-yl]carbonyl}phenyl)propan-1-amine To Pyrazole (0.016 g, 0.23 mmol) in DMF (2 ml) added sodium hydride (60%) (0.01 g, 0.25 mmol) then stirred at ambient for 15 minutes. {(R)-1-[4-Chloro-3-(6-chloro-pyridine-3-carbonyl)-2-fluoro-phenyl]-propyl}-carbamic acid tert-butyl ester [from Example 1, step 1] (0.1 g, 0.23 mmol) in DMF (2 ml) added dropwise, stirred at ambient for 1 hour, reaction quenched using water and extracted with EtOAc. The organic extract was dried (Na2SO4), filtered and concentrated, MS: [M+H] 459. Residue treated with saturated HCl/EtOAc stirred at ambient for 1 hour. Mixture was concentrated, solid triturated with EtOAc, filtered and washed with EtOAC to give (1R)-1-(4-chloro-2-fluoro-3-{[6-(1H-pyrazol-1-yl)pyridin-3-yl]carbonyl}phenyl)propan-1-amine (0.06 g).

Example 38

5-({3-[(1R)-1-aminopropyl]-6-chloro-2-fluorophenyl}carbonyl)-1,2-dihydropyridin-2-one Step 1
{(R)-1-[4-Chloro-3-(6-chloro-pyridine-3-carbonyl)-2-fluoro-phenyl]-propyl}-carbamic acid tert-butyl ester (prepared as step 1, Example 1) (90.0 mg, 0.21 mmol) was dissolved in MeOH (2 mL) then sodium methoxide (25% w/w in MeOH) (50.0 mg, 0.23 mmol, 1.1 eq.) was added and the mixture was stirred at rt for 30 min. The mixture was then evaporated down and the crude tert-butyl N-[(1R)-1-{4-chloro-2-fluoro-3-[(6-methoxypyridin-3-yl)carbonyl]phenyl}propyl]-carbamate (~90.0 mg) was used in the next step. m/z: 422.

Step 2 Tert-butyl N-[(1R)-1-{4-chloro-2-fluoro-3-[(6-methoxypyridin-3-yl)carbonyl]phenyl}-propyl]carbamate (90.0 mg, 0.21 mmol) was dissolved in 6M HCl in water (5.0 mL) and the reaction was heated at reflux for 8 h. Complete conversion. Mixture was quenched with NaOH (5M) until pH~5, then extracted with 4:1 CHCl3:IPA (3×20 mL). Combined organic extracts were dried (Na2SO4), filtered and concentrated in vacuo to give 5-({3-[(1R)-1-aminopropyl]-6-chloro-2-fluorophenyl}carbonyl)-1,2-dihydropyridin-2-one (56.2 mg, 88% yield).

Example 39

(1R)-1-(3-Benzoyl-2-fluoro-4-methylphenyl)propan-1-amine

A solution of Intermediate 13 (0.178 g, 0.479 mmol) in 4M HCl in 1,4-dioxane (0.958 mL) and DCM (2.4 mL) was stirred at room temperature for 2 hours giving a white precipitate. EtOAc was added, the solid was collected by filtration, washed with EtOAc (×2) and dried under vacuum to give (1R)-1-(3-benzoyl-2-fluoro-4-methylphenyl)propan-1-amine as the HCl salt, 0.109 g, 74%.

Example 43

(1R)-1-(3-Benzoyl-2,4-difluorophenyl)propan-1-amine

Prepared in a manner analogous to example 2, starting from 2,4-difluorobenzaldehyde and using benzoyl chloride in place of ethyl nicotinate in step 1.

Example 46

{1-[5-({3-[(1R)-1-aminopropyl]-6-chloro-2-fluorophenyl}carbonyl)pyridin-2-yl]-1H-pyrazol-4-yl}methanol To ethyl 1-[5-({3-[(1R)-1-aminopropyl]-6-chloro-2-fluorophenyl}carbonyl)pyridin-2-yl]-1H-pyrazole-4-carboxylate (Example 41) (0.154 g, 0.358 mmol) in THF (4 ml) at 0° C. was added 1M DiBAL-H/THF (0.78 ml, 0.787 mmol) stirred at 0° C. for 15 minutes allowed to warm to ambient, further 1M DiBAL-H/THF (0.78 ml, 0.787 mmol) added left further 30 minutes at ambient. Reaction quenched with Rochelles salt and extracted with EtOAc. The organic phase was dried (Na2SO4), filtered and concentrated, purified by Prep HPLC to give {1-[5-({3-[(1R)-1-aminopropyl]-6-chloro-2-fluorophenyl}carbonyl)pyridin-2-yl]-1H-pyrazol-4-yl}methanol (0.015 g).

Example 47

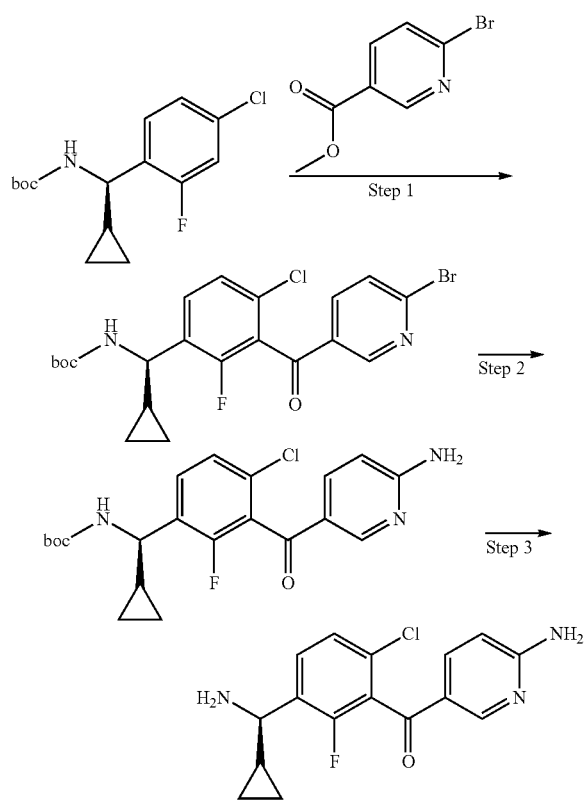

Step 1 To a solution of tert-butyl N—[(R)-(4-chloro-2-fluorophenyl)(cyclopropyl)methyl]-carbamate (Intermediate 6, 6.0 g, 20 mmol) in tetrahydrofuran (100 ml) stirred under nitrogen in a dry ice/acetone bath was added n-butyl lithium (2.5M in hexanes, 18.5 ml, 46 mmol) keeping the temperature below −70° C. The mixture was stirred at low temperature for 75 minutes before addition of methyl 6-bromonicotinate (4.3 g, 20 mmol) in tetrahydrofuran (24 ml) in one portion. The resultant mixture was stirred at low temperature for 30 minutes before quenching with saturated ammonium chloride solution and warming to room temperature. The reaction was diluted with water and was extracted twice with ethyl acetate. The organic liquors were washed with brine, dried (MgSO₄) and concentrated to an orange gum. The residue was purified on silica eluting with 0-40% ethyl acetate/petrol furnishing the desired product (5.4 g). [M−H] 481

Step 2 To each of 6 pressure vessels was added tert-butyl N—[(R)-{3-[(6-bromopyridin-3-yl)carbonyl]-4-chloro-2-fluorophenyl}(cyclopropyl)methyl]carbamate (1.0 g, 2.0 mmol), N-methylpyrrolidin-2-one (4 ml), copper II oxide (59 mg, 0.4 mmol) and 29% aqueous ammonia solution (4 ml). The vessels were sealed and heated to 80° C. for 4 hours. The reaction mixtures were combined, water was added and the combined mixture was extracted twice with ethyl acetate. The combined organic liquors were washed with brine, dried (MgSO₄) and concentrated. The residue was purified by a combination of purification on silica eluting with ethyl acetate/petrol/methanol mixtures and crystallisation from dichloromethane furnishing 2.67 g of the desired material. [M+H] 420

Step 3 tert-butyl N—[(R)-{3-[(6-aminopyridin-3-yl)carbonyl]-4-chloro-2-fluorophenyl}-(cyclopropyl)methyl]carbamate (0.463 g, 1.1 mmol) was treated with a saturated hydrogen chloride solution in ethyl acetate at room temperature. The mixture was stirred for 3 hours then concentrated to furnish the target molecule as a hydrochloride salt as a white solid (0.38 g).

Examples 49 & 50

Step 1 4-(tert-Butyl-dimethyl-silanyloxymethyl)-benzoic acid methyl ester (prepared from methyl 4-hydroxymethyl benzoate as Organic Letters, 11(21), 4882-4885; 2009) and Intermediate 2 were coupled as Step 1 in the preparation of Example 2. [M−H]− 534

Step 2 ((R)-1-{3-[4-(tert-Butyl-dimethyl-silanyloxymethyl)-benzoyl]-4-chloro-2-fluoro-phenyl}-propyl)-carbamic acid tert-butyl ester was deprotected as Step 2 in the preparation of Example 2. A mixture of the doubly deprotected product [3-((R)-1-amino-propyl)-6-chloro-2-fluoro-phenyl]-(4-hydroxymethyl-phenyl)-methanone (=Example 50) and the trans-esterified product acetic acid 4-[3-((R)-1-amino-propyl)-6-chloro-2-fluoro-benzoyl]-benzyl ester (=Example 49) was obtained. Separation was achieved by column chromatography with 0-8% ammonia in methanol/dichloromethane.

Example 51

(1R)-1-(4-chloro-2-fluoro-3-{[2-(methylsulfanyl)pyrimidin-5-yl]carbonyl}phenyl)propan-1-amine Step 1 To a solution of Intermediate 2 (400 mg, 1.39 mmol) in dry THF (10.0 mL) under nitrogen at −78° C. was added nBuLi (1.5 mL, 3.76 mmol, 2.7 eq.) dropwise and the solution stirred at −78° C. for 1 h. 2-(methylsulfanyl)pyrimidine-5-carbaldehyde (236 mg, 1.53 mmol, 1.1 eq.) was dissolved in dry THF (2.0 mL) and then added. Reaction left at −78° C. for 45 minutes and was then quenched with water (~20 mL). Concentrated and then partitioned between EtOAc (30 mL) and water (30 mL). Organic phase was washed with water (30 mL) and brine (10 mL) before it was dried (MgSO₄), filtered and concentrated to give crude material (~520 mg), which was used in Step 2 without further purification. m/z: 441.

Step 2 Dess-Martin periodinane (243 mg, 0.572 mmol) was dissolved in dry CH₂Cl₂ (1 mL) and then added dropwise to a solution of tert-butyl N-[(1R)-1-(4-chloro-2-fluoro-3-{hydroxy[2-(methylsulfanyl)pyrimidin-5-yl]methyl}phenyl)propyl]carbamate (194 mg, 0.439 mmol) in dry CH₂Cl₂ (1 mL) and the solution was stirred at rt for 8 h. After this time the reaction mixture was diluted with CH₂Cl₂ (10 mL) and washed with saturated NaHCO₃ (10 mL). The aqueous phase was extracted with CH₂Cl₂ (3×10 mL) and the combined organic extracts were washed with saturated Na₂SO₃ (10 mL) and brine (10 mL), dried (Na₂SO₄), filtered and concentrated in vacuo to give crude material (~200 mg). Purified by silica column (25M on Biotage SP4) eluting 20-40% EtOAc in petroleum ether over 15 column volumes to give tert-butyl N-[(1R)-1-(4-chloro-2-fluoro-3-{[2-(methylsulfanyl)pyrimidin-5-yl]carbonyl}phenyl)propyl]-carbamate (100 mg, 0.23 mmol, 0.52%). m/z: 439.

Step 3 To a solution of tert-butyl N-[(1R)-1-(4-chloro-2-fluoro-3-{[2-(methylsulfanyl)pyrimidin-5-yl]carbonyl}phenyl)propyl]carbamate (20.0 mg, 0.04 mmol) in DCM (1 mL) was added 4M HCl in dioxane (0.04 mL, 0.16 mmol, 4 eq) and the reaction stirred for 18 h. The mixture was concentrated and then triturated with diethyl ether (~5 mL) and the pale green solid filtered off and dried in a vacuum oven to give (1R)-1-(4-chloro-2-fluoro-3-{[2-(methylsulfanyl)pyrimidin-5-yl]carbonyl}phenyl)propan-1-amine (17.0 mg).

Example 55

[3-((R)-1-Amino-propyl)-6-chloro-2-fluoro-phenyl]-(1H-pyrazol-4-yl)-methanone

Step 1 To a mixture of Intermediate 10 (50 mg, 0.15 mmol), dimethylsulfamoylpyrazole-4-carboxylic acid (40 mg, 018 mmol, 1.2 eq.), Pd(PPh$_3$)$_4$ (5 mg, 0.005 mmol, 3 mol %) and K$_3$PO$_4$ (64 mg, 0.30 mmol, 2 eq.) in dioxane was added diethyldicarbonate (33 uL, 0.23 mmol, 1.5 eq.). The mixture was purged with N$_2$ via a needle through the solution and then heated in the microwave at 120° C. for 30 min. Mixture was partitioned between EtOAc (15 mL) and water (15 mL) and the organic phase washed with water (10 mL) and brine (10 mL) before it was dried (MgSO$_4$), filtered and the solvent removed in vacuo. Purified by silica column, 12M, eluting 10-60% EtOAc in petrol over 20 column volumes. Concentrated to give {(R)-1-[4-Chloro-3-(1-dimethylsulfamoyl-1H-pyrazole-4-carbonyl)-2-fluoro-phenyl]-propyl}-carbamic acid tert-butyl ester (34 mg, 0.07 mmol, 46%). [MH]– 487 LCMS showed about 13% boronic acid present.

Step 2 {(R)-1-[4-Chloro-3-(1-dimethylsulfamoyl-1H-pyrazole-4-carbonyl)-2-fluoro-phenyl]-propyl}-carbamic acid tert-butyl ester (34 mg) was dissolved in MeOH (2 mL) and cHCl (0.2 mL) added. The solution was heated to 70° C. for 2 h then concentrated and the salt formed by addition of 1.1 eq. of HCl in ether to a solution in DCM. Evaporated down, but NMR shows impurity. Purified by prep-HPLC, formic acid method 1. Concentrated and the HCl salt formed by addition of 5 eq. HCl in ether (2M) to a solution of the compound in DCM/MeOH. Evaporated and triturated with ether to give [3-((R)-1-Amino-propyl)-6-chloro-2-fluoro-phenyl]-(1H-pyrazol-4-yl)-methanone (4 mg) as a white solid.

Example 59

3-[3-((R)-1-Amino-propyl)-6-chloro-2-fluoro-benzoyl]-benzoic acid

Step 1 To a solution of Intermediate 2 (300 mg, 1.04 mmol) in dry THF (9 mL) under nitrogen at –78° C. was added nBuLi (2.5M in hexanes, 0.96 mL, 2.4 mmol, 2.3 eq.) dropwise and the solution stirred at –78° C. for 1 h. A solution of the isophthalic acid 1-tert-butyl ester 3-methyl ester (271 mg, 1.15 mmol, 1.1 eq.) in THF (2 mL) was added and the reaction kept at –78° C. for 40 minutes. The reaction was quenched with water and allowed to warm to room temperature. Further water and ethyl acetate (20 mL) was added and the layers separated. The organic phase was washed with water (20 mL) and brine (10 ml) before it was dried (MgSO$_4$), filtered and concentrated. Purified by silica column (25M), eluting 0-15% EtOAc in petrol to give 3-[3-((R)-1-tert-Butoxycarbonylamino-propyl)-6-chloro-2-fluoro-benzoyl]-benzoic acid tert-butyl ester (223 mg, 0.56 mmol, 54%) as a colourless oil. Put straight on to next reaction—NMR/LCMS not taken.

Step 2 To a solution of 3-[3-((R)-1-tert-Butoxycarbonylamino-propyl)-6-chloro-2-fluoro-benzoyl]-benzoic acid tert-butyl ester (219 mg, 0.45 mmol) in DCM (5 mL) was added 4M HCl in dioxane (0.445 mL, 1.78 mmol, 4 eq) and the reaction stirred for 18 h. Complete conversion. Mixture was concentrated and then triturated with diethyl ether (~1 mL) and the solid filtered off to give 3-[3-((R)-1-aminopropyl)-6-chloro-2-fluoro-benzoyl]-benzoic acid (154 mg, 0.41 mmol, 92%). [M+H]+ 336

Example 60

7-({3-[(1R)-1-Aminopropyl]-6-chloro-2-fluorophenyl}-carbonyl)-3,4-dihydro-2H-1,4-benzoxazin-3-one Steps 1-2 The method of Example 51 was followed using 4-nitro-3-(phenylmethoxy)-benzylaldehyde as the starting material in Step 1, to give tert-butyl N-[(1R)-1-(3-{[3-(benzyloxy)-4-nitrophenyl]carbonyl}-4-chloro-2-fluorophenyl)propyl]carbamate [M–H]⁻ 541

Step 3 A mixture of tert-butyl N-[(1R)-1-(3-{[3-(benzyloxy)-4-nitrophenyl]carbonyl}-4-chloro-2-fluorophenyl)propyl]carbamate (obtained from Step 2 above) (185 mg, 0.341 mmol), iron powder (190 mg, 3.41 mmol), ammonium chloride (182 mg, 3.41 mmol), methanol (5 ml) and water (2 ml) was heated to 80 deg C for 45 minutes. The reaction was allowed to cool and was then filtered through GF-A paper washing with methanol. The liquors were concentrated and water was added to the residue. The mixture was extracted with dichloromethane. The organic liquors were passed through a hydrophobic frit and concentrated to furnish an oil (144 mg). [M+H]+ 513

Step 4 Chloroacetyl chloride (0.323 ml, 4.05 mmol) was added to a mixture of tert-butyl N-[(1R)-1-(3-{[4-amino-3-(benzyloxy)phenyl]carbonyl}-4-chloro-2-fluorophenyl)propyl]carbamate (1.6 g, 3.12 mmol), triethylamine (0.651 ml, 4.68 mmol) and dichloromethane (30 ml) at room temperature. After 30 minutes a small additional portion of chloroacetyl chloride was added and in 60 minutes the reaction was complete. The reaction mixture was washed with dilute citric acid solution and dilute sodium bicarbonate and then concentrated. The residue was purified on silica eluting with 30-70% ethyl acetate/petrol to furnish tert-butyl N-[(1R)-1-(3-{[3-(benzyloxy)-4-(2-chloroacetamido)-phenyl]-carbonyl}-4-chloro-2-fluorophenyl)propyl]carbamate as a yellow oil (1.754 g). [M–H]–=587

Step 5 Boron trichloride (1 M in dichloromethane, 8.7 ml, 8.7 mmol) was cautiously added to a solution of tert-butyl N-[(1R)-1-(3-{[3-(benzyloxy)-4-(2-chloroacetamido)-phenyl]-carbonyl}-4-chloro-2-fluorophenyl)propyl]carbamate (1.7 g, 2.88 mmol) in dichloromethane (40 ml) stirred in an ice/water bath. After 75 minutes the reaction was poured onto ice water and saturated sodium bicarbonate solution was added. After the ice had dissolved, the volatiles were removed under vacuum and the aqueous mix was extracted with twice with ethyl acetate. The combined organic liquors were washed with brine, dried (MgSO$_4$) and concentrated to furnish a yellow oil (1.1 g), [M+H]+ 399, which was used without purification in Step 5.

Step 6 To the crude oil from Step 5 was added dimethylformamide (20 ml) and potassium carbonate (571 mg, 4.14 mmol). The mixture was heated to 60 deg C for 30 minutes. The reaction was allowed to cool and then was concentrated. Water was added and the residue was extracted with ethyl acetate (×2). The combined organic liquors were washed with brine, dried (MgSO$_4$) and concentrated. The residue was purified on silica eluting with 0-20% ammonia in methanol/dichloromethane. Further purification by prep HPLC furnished clean 7-({3-[(1R)-1-aminopropyl]-6-chloro-2-fluorophenyl}-carbonyl)-3,4-dihydro-2H-1,4-benzoxazin-3-one.

Example 62

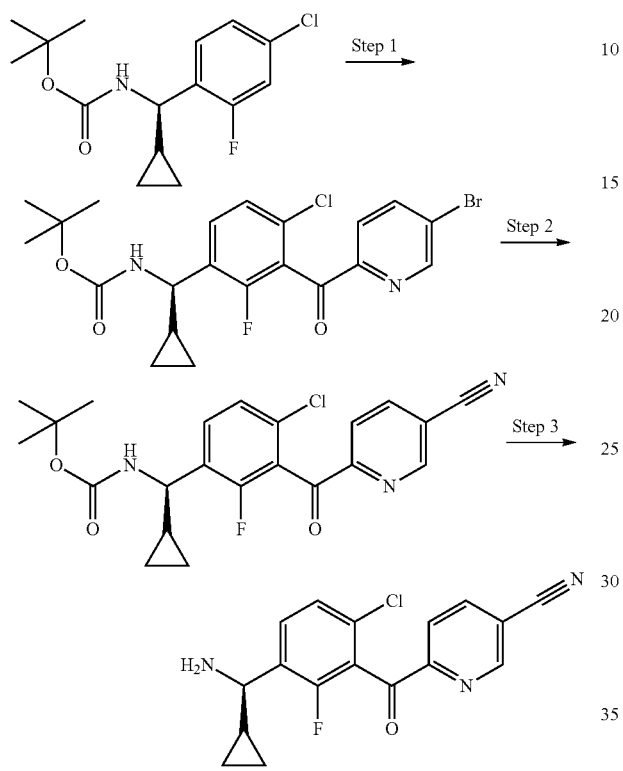

Step 1 Conducted according to Example 1 Step 1 from Intermediate 6 using methyl 5-bromopyridine-2-carboxylate. [M+H]+ 483

Step 2 A mixture of aryl bromide (423 mg, 0.87 mmol) from Step 1, zinc cyanide (51 mg, 0.44 mmol, 0.5 eq.), Pd$_2$(dba)$_3$ (40 mg, 0.04 mmol, 0.05 eq.), dppf (48 mg, 0.09 mmol, 0.1 eq.) and poly(methylhydrosiloxane) (0.06 mL) in dry DMF (12 mL) under a flush of nitrogen was heated at 100° C. for 1.5 h. Cooled and concentrated before it was partitioned between EtOAc (150 mL) and aqueous sodium bicarbonate (150 mL). Organic phase washed with further aqueous sodium bicarbonate (100 mL) then water (100 mL) and brine (50 mL) before it was dried (MgSO$_4$), filtered and concentrated. Purified by silica chromatography, 25M, eluting 10-60% EtOAc in petrol to give {(R)-[4-chloro-3-(5-cyano-pyridine-2-carbonyl)-2-fluoro-phenyl]-cyclopropyl-methyl}-carbamic acid tert-butyl ester (189 mg, 0.44 mmol). 1H NMR (400 MHz, Me-d3-OD): 8.97 (1H, s), 8.46 (1H, dd), 8.34 (1H, d), 7.59 (1H, t), 7.34 (1H, d), 4.31 (1H, s), 1.41 (9H, s), 1.24-1.11 (1H, m), 0.63 (1H, s), 0.58-0.47 (1H, m), 0.47-0.38 (1H, m), 0.38-0.27 (1H, m)

Step 3 The BOC group was removed using the procedure outlined in Example 1 Step 3.

Example 63

6-(4-Methoxy-benzylamino)-nicotinic acid methyl ester (0.6 g, 2.2 mmol) was dissolved in DCM (60 ml) and DMAP (30 mg) was added, followed by Boc$_2$O 2.4 g, 11 mmol). The mixture was stirred at room temperature overnight. Reaction diluted with DCM then washed with sat. bicarbonate then brine The organics were dried (Na$_2$SO$_4$), filtered and concentrated. The residue was purified on Biotage eluting from 0-10% EtOAc/petrol to give 6-[tert-Butoxycarbonyl-(4-methoxy-benzyl)-amino]-nicotinic acid methylester (0.68 g). [MH]+ 373

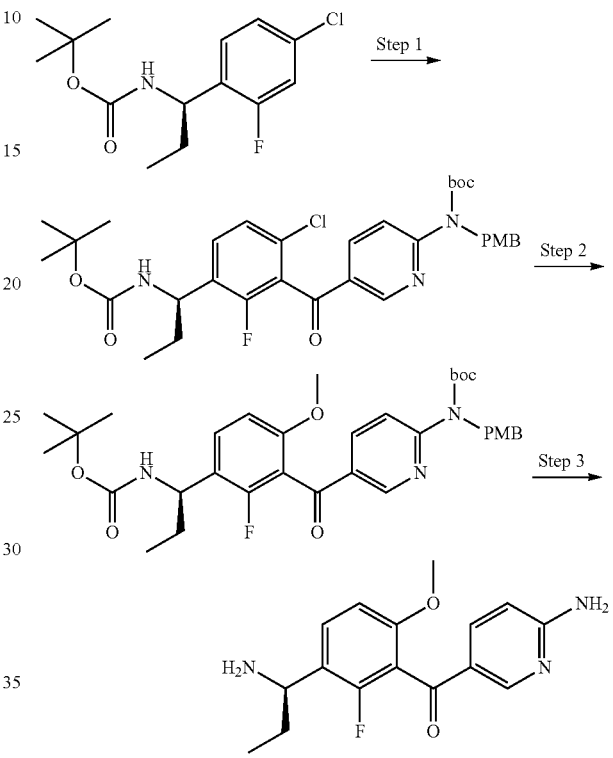

Step 1 Step 1 was carried out following the procedures described for Example 1 step 1 using 6-[tert-butoxycarbonyl-(4-methoxy-benzyl)-amino]nicotinic acid methylester Step 2 Carried out using the method described for Intermediate 14.

Step 3 {5-[3-((R)-1-tert-Butoxycarbonylamino-propyl)-2-fluoro-6-methoxy-benzoyl]-pyridin-2-yl}-(4-methoxy-benzyl)-carbamic acid tert-butyl ester (0.063 g, 0.1 mmol) treated with TFA (2 ml) in DCM (3 ml) over 48 hours, still PMB group present heated at 70° C. for 3 hours. Reaction evaporated to dryness then triturated with diethyl ether to give [3-((R)-1-Amino-propyl)-2-fluoro-6-methoxy-phenyl]-(6-amino-pyridin-3-yl)-methanone (0.018 g). [M-NH$_2$]+287

Example 65

[3-(1-Amino-propyl)-6-chloro-2-fluoro-phenyl]-(3,4-dihydro-2H-benzo[1,4]oxazin-7-yl)-ethanone To a solution of Example 50 (431 mg, 1.19 mmol) in tetrahydrofuran (10 ml) was added borane-tetrahydrofuran complex (1 M in tetrahydrofuran, 4.2 ml) and the mixture was heated to 60° C. After 90 minutes further borane (3 ml) was added and the mixture was stirred for a further 30 minutes. The mixture was then allowed to cool and was quenched cautiously with methanol. The mixture was heated for 5 minutes and was then concentrated in vacuo. The residue was treated with methanol and 2N aqueous hydrochloric acid and heated to 60° C. for 30 minutes.

The mixture was then concentrated to remove methanol then poured into saturated sodium bicarbonate solution. This was extracted twice with ethyl acetate. The organic liquors were washed with brine, dried (MgSO$_4$) and concentrated. The residue was purified on silica eluting with 0-20% methanol/dichloromethane but required further purification by prep HPLC to give clean material.

Example 68

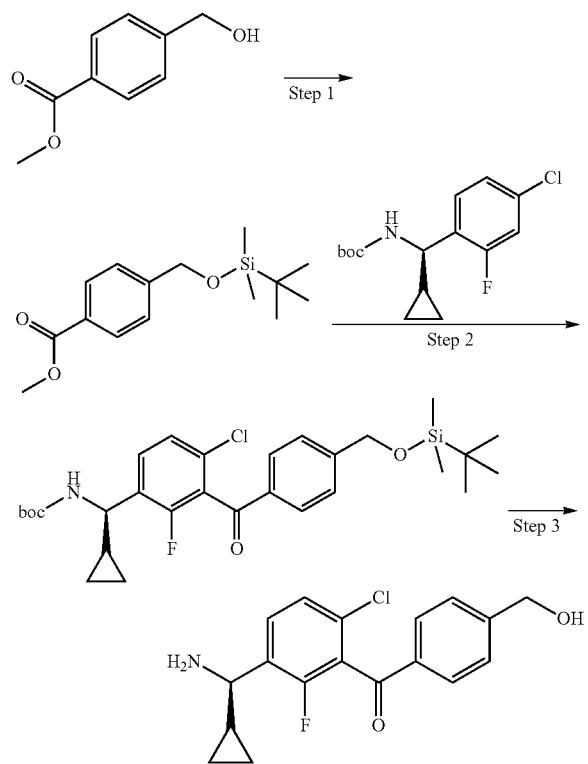

Step 1 To a solution of methyl 4-(hydroxymethyl)benzoate (1.0 g, 6.02 mmol) and 1H-imidazole (533 mg, 7.83 mmol) in N,N-dimethylformamide (10 ml) stirred at room temperature was added tert-butyl(chloro)dimethylsilane (1.09 g, 7.23 mmol). After 60 minutes, aqueous bicarbonate solution was added and the mixture was extracted twice with ethyl acetate. The combined organic liquors were washed with brine, dried (MgSO$_4$) and concentrated. The residue was purified on silica eluting 0-15% ethyl acetate/petrol. The product-containing fractions were concentrated and re-concentrated from toluene to furnish the desired compound as a colourless oil (1.7 g). [M+H] 281

Step 2 n-Butyl lithium (2.5M in hexanes, 2.0 ml, 5.0 mmol) was added slowly to a solution of tert-butyl N—[(R)-(4-chloro-2-fluorophenyl)(cyclopropyl)methyl]carbamate (Intermediate 6, 600 mg, 2.0 mmol) in tetrahydrofuran (20 ml) stirred under nitrogen in a dry ice/acetone bath. The anion was allowed to form over 60 minutes and then a solution of the product from Step 1 (methyl 4-{[(tert-butyldimethylsilyl) oxy]-methyl}benzoate, 673 mg, 2.4 mmol) in tetrahydrofuran (5 ml). The mixture was stirred for a further 60 minutes before the reaction was quenched by addition of saturated ammonium chloride solution and allowed to warm to room temperature. The mixture was extracted twice with ethyl acetate; the combined liquors were washed with brine, dried (MgSO$_4$) and concentrated. The residue was purified on silica eluting with 0-25% ethyl acetate/petrol furnishing the desired product as a colourless oil (91 mg). [M+NH$_4^+$] 565

Step 3 tert-Butyl N—[(R)-{3-[(4-{[(tert-butyldimethylsilyl)oxy]methyl}phenyl)carbonyl]-4-chloro-2-fluorophenyl}(cyclopropyl)methyl]carbamate (265 mg, 0.48 mmol) was treated with a 4M hydrogen chloride solution in 1,4-dioxane (5 ml) at room temperature for 60 minutes. Material that had precipitated out was re-dissolved by the addition of methanol before the mixture was concentrated in vacuo. The residue was re-concentrated from methanol before the addition of a small amount of ethyl acetate and diethyl ether to elicit precipitation. The solids were collected by filtration and were dried in a vacuum oven furnishing [4-({3-[(R)-amino(cyclopropyl)methyl]-6-chloro-2-fluorophenyl}carbonyl)phenyl] methanol hydrochloride as a white solid (138 mg)

Example 72 and 73

5-[3-((R)-1-Amino-propyl)-6-chloro-2-fluoro-benzoyl]-2-methoxy-benzonitrile

Step 1 Example 1 Step 1 but using methyl 4-chloro-3-bromobenzoate to give {1-[3-(3-bromo-4-chloro-benzoyl)-4-chloro-2-fluoro-phenyl]-propyl}-carbamic acid tert-butyl ester Step 2 Procedure described for Example 62, step 2 to give {1-[4-Chloro-3-(4-chloro-3-cyano-benzoyl)-2-fluoro-phenyl]-propyl}-carbamic acid tert-butyl ester. [M−H]$^-$ 449

Step 3 Step 3 was carried out using the procedure described for Example 1, step 2. Both ammonia and methanol displacement products were obtained and separated by column chromatography (eluting 10-50% EtOAc in petroleum ether) in a roughly 1:1 mixture of {(R)-1-[3-(4-amino-3-cyano-benzoyl)-4-chloro-2-fluoro-phenyl]-propyl}-carbamic acid tert-butyl ester ([M−H]$^-$ 430) and {(R)-1-[4-chloro-3-(3-cyano-4-methoxy-benzoyl)-2-fluoro-phenyl]-propyl}-carbamic acid tert-butyl ester ([M−H]$^-$ 445)

Step 4 To a solution of {(R)-1-[3-(4-amino-3-cyano-benzoyl)-4-chloro-2-fluoro-phenyl]-propyl}-carbamic acid tert-butyl ester (66 mg, 0.15 mmol) in DCM (2 mL) was added 4M HCl in dioxane (0.19 mL, 0.76 mmol, 5 eq.) and the reaction mixture was stirred for 60 hours. The mixture was partitioned between DCM (10 mL) and water (10 mL) made basic with 5M NaOH. The aqueous phase was extracted with further DCM (10 mL) and then the combined organics were dried (MgSO$_4$), filtered and concentrated to give 2-Amino-5-[3-((R)-1-amino-propyl)-6-chloro-2-fluoro-benzoyl]-benzonitrile (46 mg, 0.14 mmol) as a viscous gum.

Step 5 To a solution of {(R)-1-[4-Chloro-3-(3-cyano-4-methoxy-benzoyl)-2-fluoro-phenyl]-propyl}-carbamic acid tert-butyl ester (59 mg, 0.13 mmol) in DCM (2 mL) was added 4M HCl in dioxane (0.17 mL, 0.66 mmol, 5 eq.) and the reaction mixture was stirred for 60 hours. The mixture was partitioned between DCM (10 mL) and water (10 mL) made basic with 5M NaOH. The aqueous phase was extracted with further DCM (10 mL) and then the combined organics were dried (MgSO$_4$), filtered and concentrated to give 5-[3-((R)-

1-amino-propyl)-6-chloro-2-fluoro-benzoyl]-2-methoxy-benzonitrile (41 mg, 0.12 mmol) as a viscous gum.

Example 74

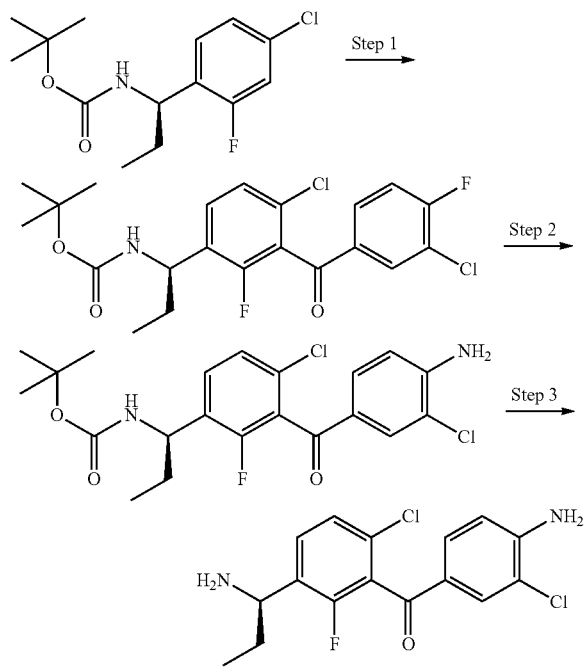

Step 1 Step 1 was carried out using the procedure described for Example 1 Step 1 using methyl 4-fluoro-3-chlorobenzoate. [M−H]⁻ 442

Step 2 Procedure as for Example 1, step 2. [M−H]⁻ 439

Step 3 Procedure as for Example 72, Step 4.

Example 77

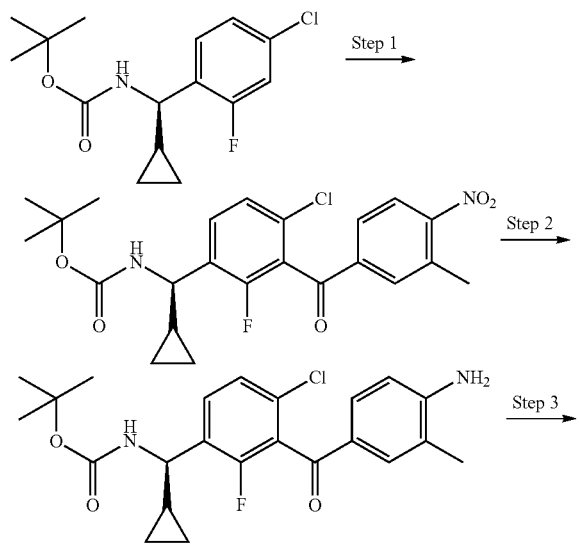

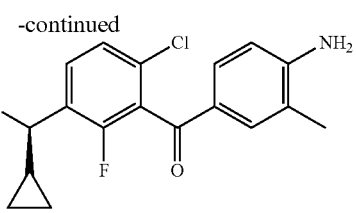

Step 1 Conducted according to Example 1 Step 1, from Intermediate 6 using methyl 4-nitro-3-methylbenzoate. [M−H]⁻ 461

Step 2 To a solution of {(R)-[4-Chloro-2-fluoro-3-(3-methyl-4-nitro-benzoyl)-phenyl]-cyclopropyl-methyl}-carbamic acid tert-butyl ester (608 mg, 1.31 mmol) from step 1 in acetic acid (15 mL) was added zinc dust (859 mg, 13.1 mmol, 10 eq.) and the reaction stirred for 45 minutes. The reaction mixture was filtered and then the filtrate concentrated. The residue was partitioned between EtOAc (30 mL) and sat. aq. sodium bicarbonate (20 mL). The organic phase then washed with water (20 mL) and brine (10 mL) before it was dried (MgSO₄), filtered and then concentrated to give {(R)-[3-(4-amino-3-methyl-benzoyl)-4-chloro-2-fluoro-phenyl]-cyclopropyl-methyl}-carbamic acid tert-butyl ester (570 mg, 1.31 mmol, 100%) as a yellow gum. [M−H]⁻ 431

Step 3 To a solution of {(R)-[3-(4-amino-3-methyl-benzoyl)-4-chloro-2-fluoro-phenyl]-cyclopropyl-methyl}-carbamic acid tert-butyl ester (570 mg, 1.32 mmol) in DCM (6 mL) was added 4M HCl in dioxane (1.65 mL, 6.58 mmol, 5 eq) and the reaction stirred for 18 hours. The resulting mixture was partitioned between DCM (50 mL) and water (20 mL) and basified with NaOH. Not all of the compound dissolved and so the aqueous phase was extracted with 4:1 CHCl₃:IPA (2×30 mL). The combined organics were washed with brine (20 mL) and then dried (MgSO₄), filtered and concentrated to give [3-((R)-amino-cyclopropyl-methyl)-6-chloro-2-fluoro-phenyl]-(4-amino-3-methyl-phenyl)-methanone (451 mg).

Example 80

3-[3-((R)-1-Amino-propyl)-2-fluoro-6-methoxy-benzoyl]-benzonitrile

Step 1 The BOC derivative of Example 18 (0.5 g, 0.96 mmol) (prepared according to the method of Benzylamine 2 step1 but using methyl 3-cyanobenzoate) was treated according to the conditions described for the preparation of Intermediate 14 to replace the chlorine atom with a methoxy group. The resulting mixture of ester, acid and amide was used without purification in Step 2.

Step 2 The mixture formed in Step 1 was taken up in THF/H₂O [4:1] (10 ml), treated with LiOH (120 mgs) and stirred at RT overnight, after which no ester was visible. The reaction mixture was evaporated to dryness and used without purification in Step 3.

Step 3 The mixture from Step 2 was taken up in DMF (20 ml), cooled to 0° C., treated with DIPEA (2 ml), ammonium chloride (0.257 g) and HATU (0.548 g) and the resulting mixture stirred at RT for 48 hours. After this time, approximately 50% of the acid still remained and therefore the same quantities of reagents were added and the mixture was stirred at RT overnight. The reaction mixture was then diluted with water and extracted with EtOAc (×2), the organic phases were combined, dried (Na₂SO₄), filtered and concentrated. The crude product was passed through a Biotage column eluting with a gradient of 0% EtOAc/petrol to 100% EtOAc/petrol to give {(R)-1-[3-(3-Carbamoyl-benzoyl)-2-fluoro-4-methoxy-phenyl]-propyl}-carbamic acid tert-butyl ester (360 mg)) MS: [M+NH$_4$]$^+$ 374

Step 4 A mixture of {(R)-1-[3-(3-carbamoyl-benzoyl)-2-fluoro-4-methoxy-phenyl]-propyl}-carbamic acid tert-butyl ester (269 mg, 0.62 mmol) from Step 3, ethyl dichlorophosphate (0.14 mL, 1.25 mmol, 2 eq.) and DBU (0.28 mL, 1.87 mmol, 3 eq.) in DCM (3 mL) was stirred for 24 hours. The mixture was then diluted with DCM (15 mL) and water (15 mL) and the organic phase was washed with brine, isolated by phase separation and concentrated to give crude {(R)-1-[3-(3-cyano-benzoyl)-2-fluoro-4-methoxy-phenyl]-propyl}-carbamic acid tert-butyl ester which was used in the next step. [M−H]$^−$ 411

Step 5 {(R)-1-[3-(3-Cyano-benzoyl)-2-fluoro-4-methoxy-phenyl]-propyl}-carbamic acid tert-butyl ester (200 mg) was dissolved in DCM (5 mL), 4M HCl in dioxane (485 uL, 1.94 mmol, 4 eq) was added and the reaction mixture was stirred for 5 hours. Water was then added and the mixture was made basic with 1M NaOH. The organic phase was isolated by phase separator and combined and concentrated to give 3-[3-((R)-1-amino-propyl)-2-fluoro-6-methoxy-benzoyl]-benzonitrile.

Characterising Data

By following the methods described above or methods similar or analogous thereto, the compounds of Examples 1 to 80 were prepared, Characterising data for each of the examples, and details of the synthetic methods used to prepare the compounds, are set out in Table 1 below.

The numbers in the first column of the table are the Example numbers.

The MS data refer to the molecular ion [M+H]$^+$ unless stated otherwise.

TABLE 1

| Ex. | Structure | Name | Salt |
|-----|-----------|------|------|
| 1 | 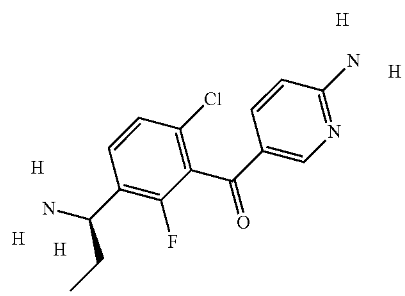 | 5-({3-[(1R)-1-aminopropyl]-6-chloro-2-fluorophenyl}carbonyl)-pyridin-2-amine | Hydrochloride (1:1) |
| 2 | 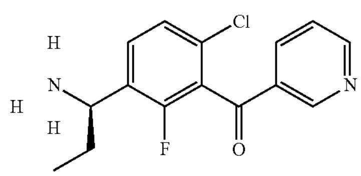 | (1R)-1-{4-chloro-2-fluoro-3-[(pyridin-3-yl)carbonyl]phenyl}-propan-1-amine | HCl (1:1) |
| 3 | 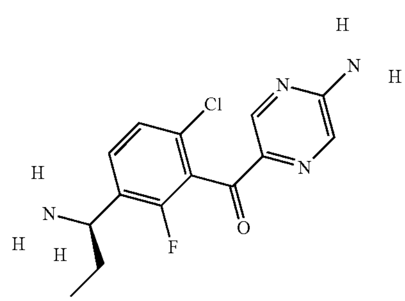 | 5-({3-[(1R)-1-aminopropyl]-6-chloro-2-fluorophenyl}carbonyl)-pyrazin-2-amine | HCl (1:1) |
| 4 | 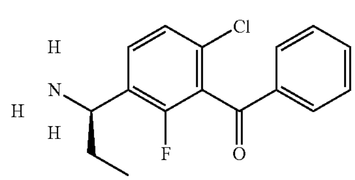 | (1R)-1-(3-benzoyl-4-chloro-2-fluorophenyl)propan-1-amine | HCl (1:1) |

TABLE 1-continued

| Examples | | | |
|---|---|---|---|
| 5 | (structure) | 6-({3-[(1R)-1-aminopropyl]-6-chloro-2-fluorophenyl}carbonyl)-pyridin-3-amine | HCl (1:1) |
| 6 | (structure) | (1S)-1-(3-benzoyl-4-chloro-2-fluorophenyl)propan-1-amine | HCl (1:1) |
| 7 | (structure) | (1R)-1-{4-chloro-2-fluoro-3-[(3-fluorophenyl)carbonyl]-phenyl}propan-1-amine | HCl (1:1) |
| 8 | (structure) | (1R)-1-{4-chloro-2-fluoro-3-[(4-fluorophenyl)carbonyl]-phenyl}propan-1-amine | HCl (1:1) |
| 9 | (structure) | 4-({3-[(1R)-1-aminopropyl]-6-chloro-2-fluorophenyl}carbonyl)-benzonitrile | HCl (1:1) |
| 10 | (structure) | (1R)-1-{4-chloro-2-fluoro-3-[(pyrimidin-4-yl)carbonyl]phenyl}-propan-1-amine | HCl (1:1) |
| 11 | (structure) | (R)-(3-benzoyl-4-chloro-2-fluorophenyl)-(cyclopropyl)-methanamine | HCl (1:1) |

TABLE 1-continued

| | | Examples | | |
|---|---|---|---|---|
| 12 | 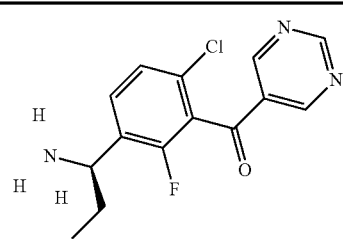 | (1R)-1-{4-chloro-2-fluoro-3-[(pyrimidin-5-yl)carbonyl]phenyl}-propan-1-amine | HCl (1:1) | |
| 13 | 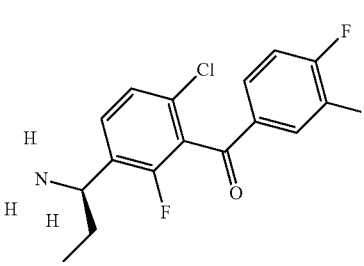 | (1R)-1-{4-chloro-3-[(3,4-difluorophenyl)carbonyl]-2-fluorophenyl}propan-1-amine | HCl (1:1) | |
| 14 | 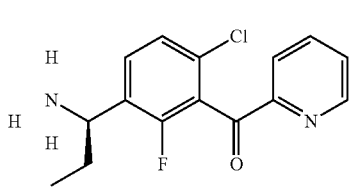 | (1R)-1-{4-chloro-2-fluoro-3-[(pyridin-2-yl)carbonyl]phenyl}propan-1-amine | HCl (1:1) | |
| 15 | 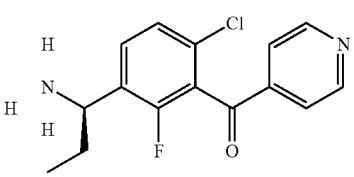 | (1R)-1-{4-chloro-2-fluoro-3-[(pyridin-4-yl)carbonyl]phenyl}propan-1-amine | HCl (1:1) | |
| 16 | 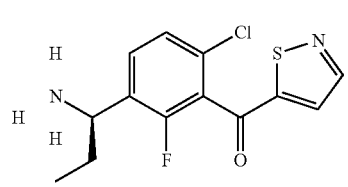 | (1R)-1-{4-chloro-2-fluoro-3-[(1,2-thiazol-5-yl)carbonyl]phenyl}propan-1-amine | HCl (1:1) | |
| 17 | 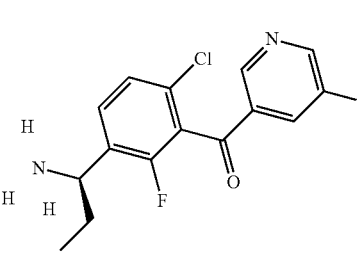 | (1R)-1-{4-chloro-2-fluoro-3-[(5-methoxypyridin-3-yl)carbonyl]phenyl}propan-1-amine | HCl (1:1) | |
| 18 | 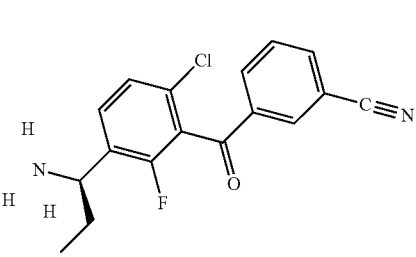 | 3-({3-[(1R)-1-aminopropyl]-6-chloro-2-fluorophenyl}carbonyl)benzonitrile | HCl (1:1) | |

TABLE 1-continued

| | Examples | | |
|---|---|---|---|
| 19 | 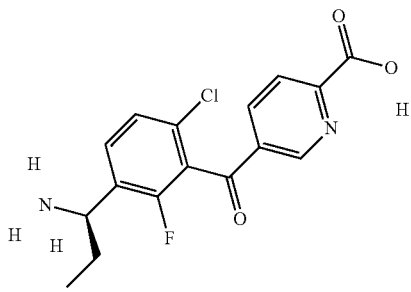 | 5-({3-[(1R)-1-aminopropyl]-6-chloro-2-fluorophenyl}carbonyl)pyridine-2-carboxylic acid | HCl (1:1) |
| 20 | 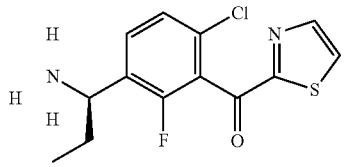 | (1R)-1-{4-chloro-2-fluoro-3-[(1,3-thiazol-2-yl)carbonyl]phenyl}propan-1-amine | HCl (1:1) |
| 21 | 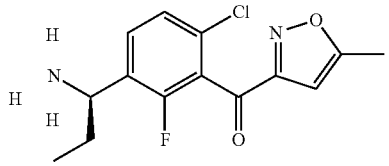 | (1R)-1-{4-chloro-2-fluoro-3-[(5-methyl-1,2-oxazol-3-yl)carbonyl]phenyl}propan-1-amine | HCl (1:1) |
| 22 | 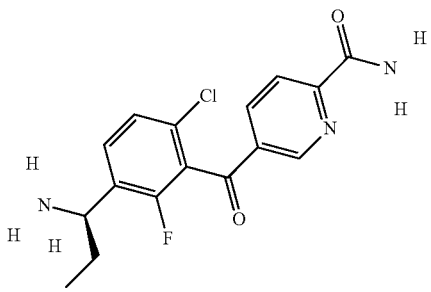 | 5-({3-[(1R)-1-aminopropyl]-6-chloro-2-fluorophenyl}carbonyl)pyridine-2-carboxamide | HCl (1:1) |
| 23 | 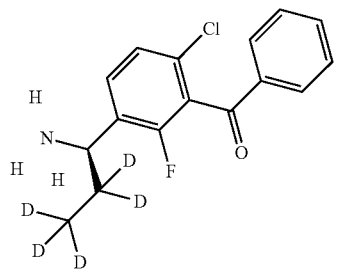 | (1R)-1-(3-benzoyl-4-chloro-2-fluorophenyl)(2,2,3,3,3-D)propan-1-amine | HCl (1:1) |
| 24 | 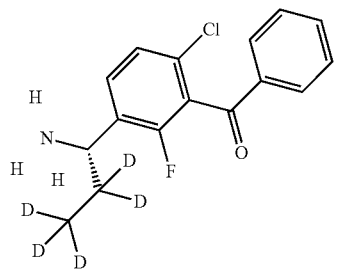 | (1S)-1-(3-benzoyl-4-chloro-2-fluorophenyl)(2,2,3,3,3-D)propan-1-amine | HCl (1:1) |

TABLE 1-continued

| | | Examples | | |
|---|---|---|---|---|
| 25 | | | [3-((R)-1-Amino-propyl)-6-chloro-2-fluoro-phenyl]-(1-oxy-pyridin-3-yl)-methanone | HCl (1:1) |
| 26 | | | (1S)-1-{4-chloro-2-fluoro-3-[(pyridin-3-yl)carbonyl]phenyl}propan-1-amine | HCl (1:1) |
| 27 | | | (R)-{4-chloro-2-fluoro-3-[(4-fluorophenyl)carbonyl]phenyl}(cyclopropyl)methanamine | HCl (1:1) |
| 28 | | | (R)-{4-chloro-2-fluoro-3-[(pyridin-3-yl)carbonyl]phenyl}(cyclopropyl)methanamine | HCl (1:1) |
| 29 | | | (1R)-1-{4-chloro-3-[(6-chloropyridin-3-yl)carbonyl]-2-fluorophenyl}propan-1-amine | HCl (1:1) |
| 30 | | | (1S)-1-{4-chloro-3-[(6-chloropyridin-3-yl)carbonyl]-2-fluorophenyl}propan-1-amine | None |
| 31 | | | 5-({3-[(1S)-1-aminopropyl]-6-chloro-2-fluorophenyl}carbonyl)pyridin-2-amine | HCl (1:1) |

TABLE 1-continued

Examples

| | | | |
|---|---|---|---|
| 32 | 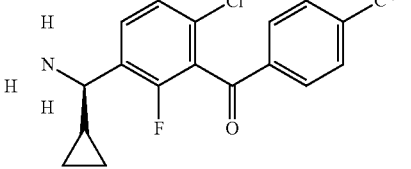 | 4-({3-[(R)-amino(cyclopropyl)methyl]-6-chloro-2-fluorophenyl}carbonyl)benzonitrile | HCl (1:1) |
| 33 | 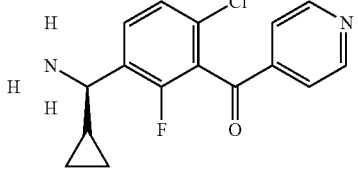 | (R)-{4-chloro-2-fluoro-3-[(pyridin-4-yl)carbonyl]phenyl}(cyclopropyl)methanamine | HCl (1:1) |
| 34 | 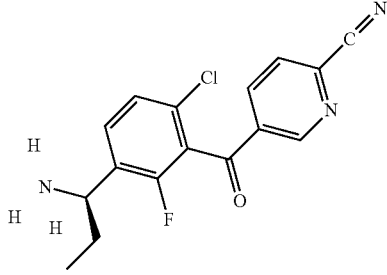 | 5-({3-[(1R)-1-aminopropyl]-6-chloro-2-fluorophenyl}carbonyl)pyridine-2-carbonitrile | Trifluoroacetate (1:1) |
| 35 | 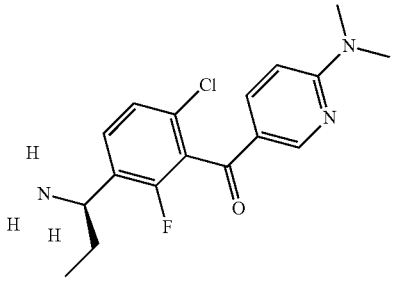 | 5-({3-[(1R)-1-aminopropyl]-6-chloro-2-fluorophenyl}carbonyl)-N,N-dimethylpyridin-2-amine | HCl (1:1) |
| 36 | 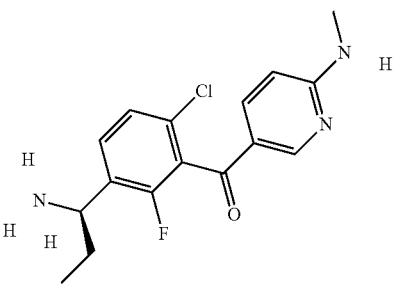 | 5-({3-[(1R)-1-aminopropyl]-6-chloro-2-fluorophenyl}carbonyl)-N-methylpyridin-2-amine | HCl (1:1) |
| 37 | 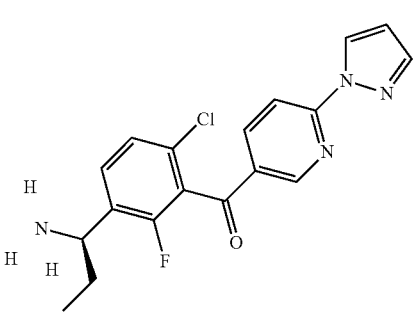 | (1R)-1-(4-chloro-2-fluoro-3-{[6-(1H-pyrazol-1-yl)pyridin-3-yl]carbonyl}phenyl)propan-1-amine | HCl (1:1) |

TABLE 1-continued

| | | Examples | |
|---|---|---|---|
| 38 | 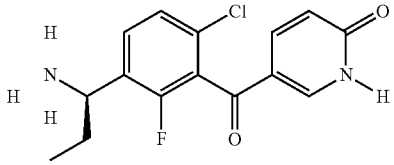 | 5-({3-[(1R)-1-aminopropyl]-6-chloro-2-fluorophenyl}carbonyl)-1,2-dihydropyridin-2-one | HCl (1:1) |
| 39 |  | (1R)-1-(3-benzoyl-2-fluoro-4-methylphenyl)propan-1-amine | HCl (1:1) |
| 40 | 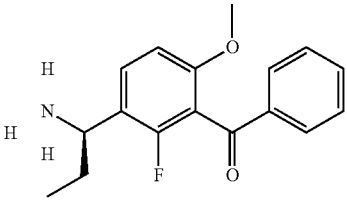 | (1R)-1-(3-benzoyl-2-fluoro-4-methoxyphenyl)propan-1-amine | HCl (1:1) |
| 41 | 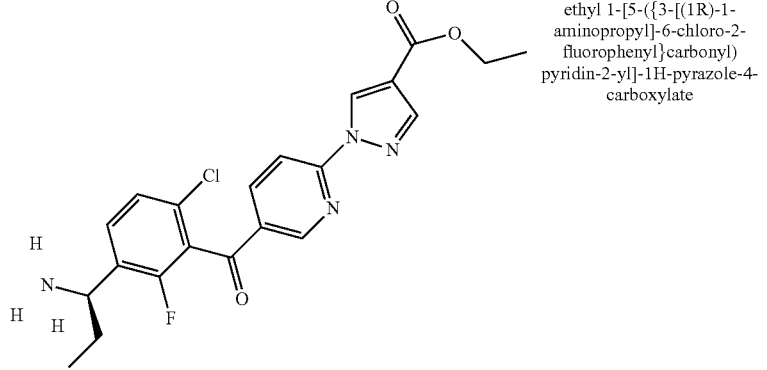 | ethyl 1-[5-({3-[(1R)-1-aminopropyl]-6-chloro-2-fluorophenyl}carbonyl)pyridin-2-yl]-1H-pyrazole-4-carboxylate | HCl (1:1) |
| 42 | 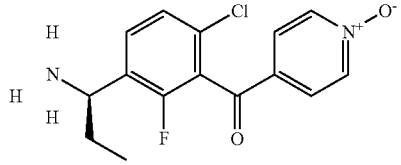 | [3-((R)-1-Amino-propyl)-6-chloro-2-fluoro-phenyl]-(1-oxy-pyridin-4-yl)-methanone | HCl (1:1) |
| 43 | 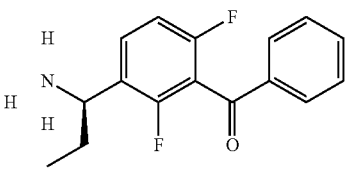 | (1R)-1-(3-benzoyl-2,4-difluorophenyl)propan-1-amine | HCl (1:1) |
| 44 | 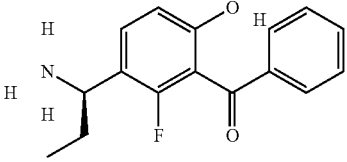 | 4-[(1R)-1-aminopropyl]-2-benzoyl-3-fluorophenol | HCl (1:1) |

TABLE 1-continued

Examples

| | Structure | Name | Salt |
|---|---|---|---|
| 45 | | 5-({3-[(1R)-1-aminopropyl]-6-chloro-2-fluorophenyl}carbonyl)pyridin-3-amine | HCl (1:1) |
| 46 | | {1-[5-({3-[(1R)-1-aminopropyl]-6-chloro-2-fluorophenyl}carbonyl)pyridin-2-yl]-1H-pyrazol-4-yl}methanol | HCl (1:1) |
| 47 | | 5-({3-[(R)-amino(cyclopropyl)methyl]-6-chloro-2-fluorophenyl}carbonyl)pyridin-2-amine | HCl (1:1) |

There is no Example 48

| | Structure | Name | Salt |
|---|---|---|---|
| 49 | | [4-({3-[(1R)-1-aminopropyl]-6-chloro-2-fluorophenyl}carbonyl)phenyl]methyl acetate | HCl (1:1) |
| 50 | | [4-({3-[(1R)-1-aminopropyl]-6-chloro-2-fluorophenyl}carbonyl)phenyl]methanol | HCl (1:1) |

TABLE 1-continued

Examples

| 51 | 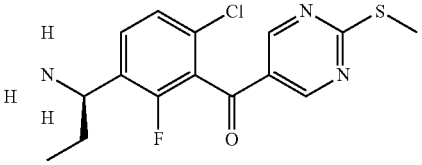 | (1R)-1-(4-chloro-2-fluoro-3-{[2-(methylsulfanyl)pyrimidin-5-yl]carbonyl}phenyl)propan-1-amine | HCl (1:1) |
|---|---|---|---|
| 52 | 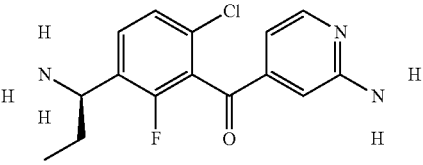 | 4-({3-[(1R)-1-aminopropyl]-6-chloro-2-fluorophenyl}carbonyl)pyridin-2-amine | HCl (1:1) |

There is no Example 53

| 54 | 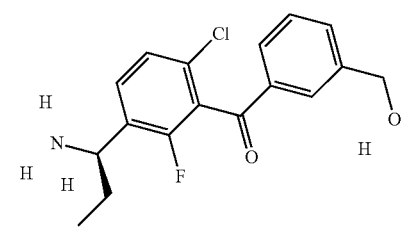 | [3-({3-[(1R)-1-aminopropyl]-6-chloro-2-fluorophenyl}carbonyl)phenyl]methanol | HCl (1:1) |
|---|---|---|---|
| 55 | 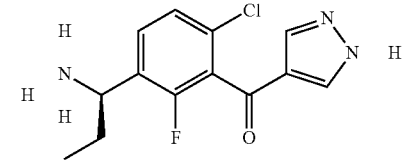 | (1R)-1-{4-chloro-2-fluoro-3-[(1H-pyrazol-4-yl)carbonyl]phenyl}propan-1-amine | HCl (1:1) |
| 56 | 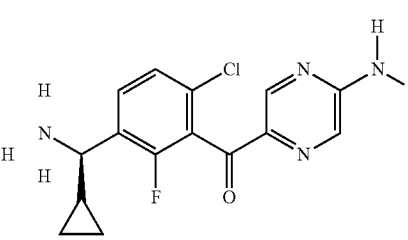 | 5-({3-[(R)-amino(cyclopropyl)methyl]-6-chloro-2-fluorophenyl}carbonyl)pyrazin-2-amine | HCl (1:1) |
| 57 | 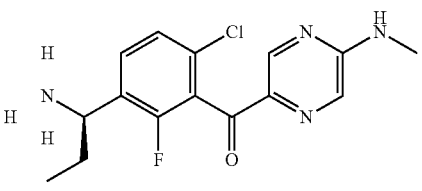 | 5-({3-[(1R)-1-aminopropyl]-6-chloro-2-fluorophenyl}carbonyl)-N-methylpyrazin-2-amine | HCl (1:1) |
| 58 | 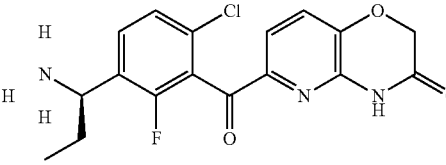 | 6-({3-[(1R)-1-aminopropyl]-6-chloro-2-fluorophenyl}carbonyl)-2H,3H,4H-pyrido[3,2-b][1,4]oxazin-3-one | HCl (1:1) |
| 59 | 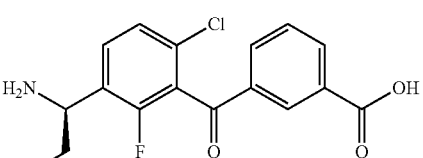 | 3-[3-((R)-1-Amino-propyl)-6-chloro-2-fluoro-benzoyl]-benzoic acid | HCl (1:1) |

TABLE 1-continued

| | Examples | | |
|---|---|---|---|
| 60 | 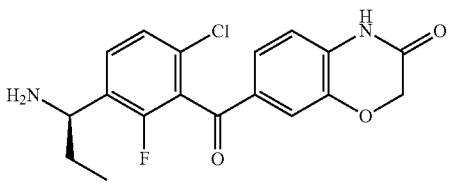 [SMILES: CC[C@@H](N)c1ccc(Cl)c(C(=O)c2ccc3c(c2)OCC(=O)N3)c1F] | 7-({3-[(1R)-1-aminopropyl]-6-chloro-2-fluorophenyl}carbonyl)-3,4-dihydro-2H-1,4-benzoxazin-3-one | Hydrochloride (1:1) |
| 61 | 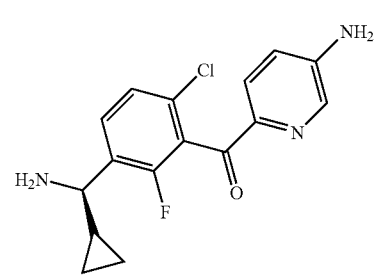 [SMILES: Nc1ccc(C(=O)c2c(Cl)ccc([C@H](N)C3CC3)c2F)nc1] | 6-({3-[(R)-amino(cyclopropyl)methyl]-6-chloro-2-fluorophenyl}carbonyl)pyridin-3-amine | Hydrochloride (1:1) |
| 62 | 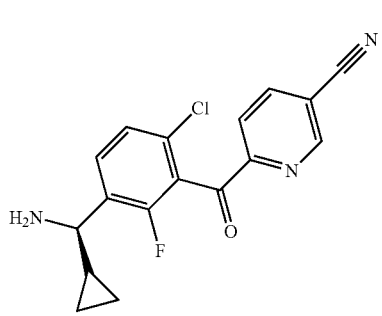 [SMILES: N#Cc1ccc(C(=O)c2c(Cl)ccc([C@H](N)C3CC3)c2F)nc1] | 6-({3-[(R)-amino(cyclopropyl)methyl]-6-chloro-2-fluorophenyl}carbonyl)pyridine-3-carbonitrile | Hydrochloride (1:1) |
| 63 | 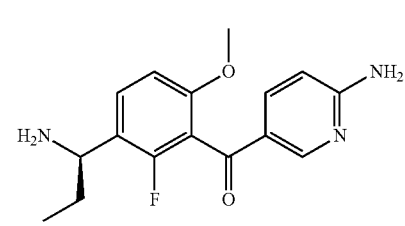 [SMILES: CC[C@@H](N)c1ccc(OC)c(C(=O)c2ccc(N)nc2)c1F] | 5-({3-[(1R)-1-aminopropyl]-2-fluoro-6-methoxyphenyl}carbonyl)pyridin-2-amine | Trifluoro-acetate (1:1) |
| 64 | 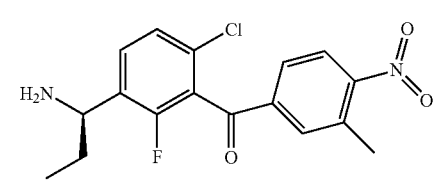 [SMILES: CC[C@@H](N)c1ccc(Cl)c(C(=O)c2ccc([N+](=O)[O-])c(C)c2)c1F] | (1R)-1-{4-chloro-2-fluoro-3-[(3-methyl-4-nitrophenyl)carbonyl]phenyl}propan-1-amine | HCl (1:1) |
| 65 | 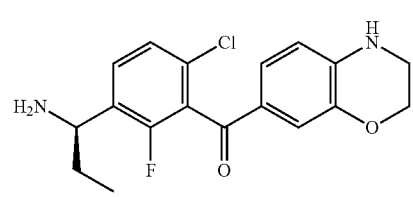 [SMILES: CC[C@@H](N)c1ccc(Cl)c(C(=O)c2ccc3c(c2)OCCN3)c1F] | (1R)-1-{4-chloro-3-[(3,4-dihydro-2H-1,4-benzoxazin-7-yl)carbonyl]-2-fluorophenyl}propan-1-amine | HCl (1:1) |
| 66 | 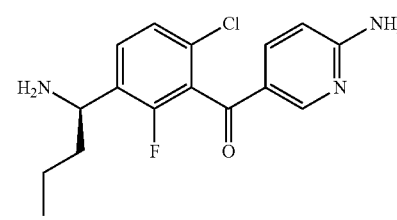 | 5-({3-[(1R)-1-aminobutyl]-6-chloro-2-fluorophenyl}carbonyl)pyridin-2-amine | HCl (1:1) |

TABLE 1-continued

Examples

| 67 | 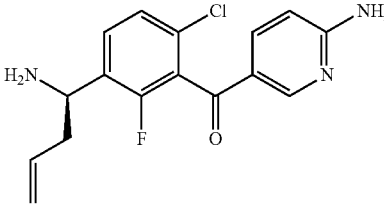 | 5-({3-[(1R)-1-aminobut-3-en-1-yl]-6-chloro-2-fluorophenyl}carbonyl)pyridin-2-amine | HCl (1:1) |
|---|---|---|---|
| 68 | 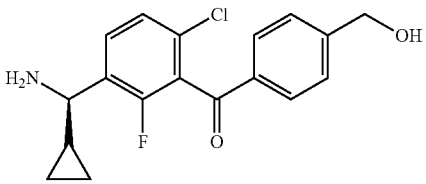 [SMILES: N[C@@H](c1ccc(Cl)c(C(=O)c2ccc(CO)cc2)c1F)C1CC1] | [4-({3-[(R)-amino(cyclopropyl)methyl]-6-chloro-2-fluorophenyl}carbonyl)phenyl]methanol | HCl (1:1) |
| 69 | 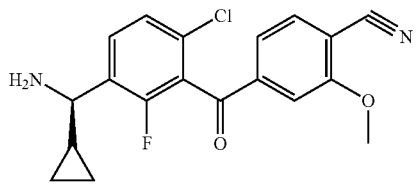 [SMILES: COc1cc(C(=O)c2c(Cl)ccc([C@H](N)C3CC3)c2F)ccc1C#N] | 4-({3-[(R)-amino(cyclopropyl)methyl]-6-chloro-2-fluorophenyl}carbonyl)-2-methoxybenzonitrile | HCl (1:1) |
| 70 | 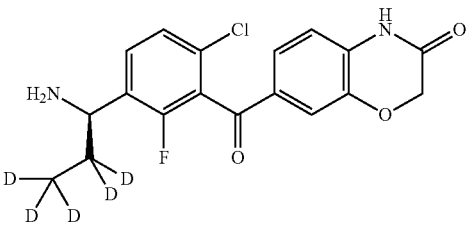 [SMILES: [2H]C([2H])([2H])C([2H])([2H])[C@@H](N)c1ccc(Cl)c(C(=O)c2ccc3c(c2)OCC(=O)N3)c1F] | 7-({3-[(1R)-1-amino(2,2,3,3,3-deutero)propyl]-6-chloro-2-fluorophenyl}carbonyl)-3,4-dihydro-2H-1,4-benzoxazin-3-one | None |
| 71 | 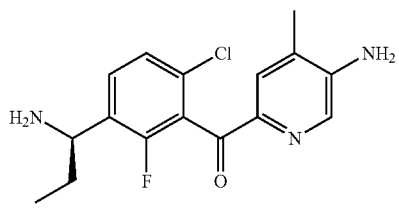 [SMILES: CC[C@@H](N)c1ccc(Cl)c(C(=O)c2cc(C)c(N)cn2)c1F] | (5-Amino-4-methyl-pyridin-2-yl)-[3-((R)-1-amino-propyl)-6-chloro-2-fluoro-phenyl]-methanone | — |
| 72 | 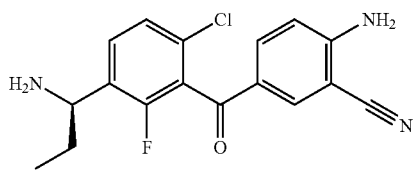 [SMILES: CC[C@@H](N)c1ccc(Cl)c(C(=O)c2ccc(N)c(C#N)c2)c1F] | 2-Amino-5-[3-((R)-1-amino-propyl)-6-chloro-2-fluoro-benzoyl]-benzonitrile | — |
| 73 | 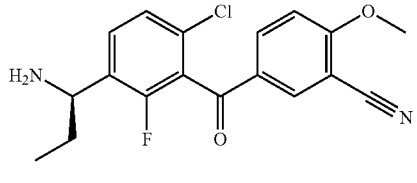 [SMILES: CC[C@@H](N)c1ccc(Cl)c(C(=O)c2ccc(OC)c(C#N)c2)c1F] | 5-[3-((R)-1-Amino-propyl)-6-chloro-2-fluoro-benzoyl]-2-methoxy-benzonitrile | — |
| 74 | 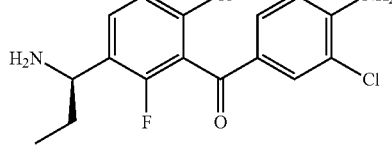 | (4-Amino-3-chloro-phenyl)-[3-((R)-1-amino-propyl)-6-chloro-2-fluoro-phenyl]-methanone | — |

TABLE 1-continued

Examples

| 75 | 2-Amino-5-[3-((R)-amino-cyclopropyl-methyl)-6-chloro-2-fluoro-benzoyl]-benzonitrile | — |
| 76 | (4-Amino-3-chloro-phenyl)-[3-((R)-amino-cyclopropyl-methyl)-6-chloro-2-fluoro-phenyl]-methanone | — |
| 77 | [3-((R)-Amino-cyclopropyl-methyl)-6-chloro-2-fluoro-phenyl]-(4-amino-3-methyl-phenyl)-methanone | — |
| 78 | (4-Amino-3-chloro-phenyl)-[3-((R)-(1-amino-(2,2,3,3,3-deutero)propyl)-6-chloro-2-fluoro-phenyl]-methanone | — |
| 79 | 4-Amino-3-methyl-phenyl)-[3-((R)-(1-amino-(2,2,3,3,3-deutero)propyl)-6-chloro-2-fluoro-phenyl]-methanone | — |
| 80 | 3-[3-((R)-1-Amino-propyl)-2-fluoro-6-methoxy-benzoyl]-benzonitrile | — |

| Ex. | NMR Data | MS Data | Method |
| --- | --- | --- | --- |
| 1 | 1H NMR (400 MHz, Me-d3-OD): 8.42-8.30 (2H, m), 7.74 (1H, t), 7.60 (1H, d), 7.19 (1H, d), 4.55(1H, dd), 2.20-2.04 (2H, m), 1.00 (3H, t). | m/z: 308 | Example 1 |
| 2 | NMR (400 MHz, DMSO-d6): 9.00-8.86 (2H, m), 8.86-8.65 (3H, m), 8.27 (1H, d), 7.94 (1H, t), 7.76-7.64 (2H, m), 4.5 (1H, under water peak) 2.12-1.99 (1H, m), 1.99-1.84 (1H, m), 0.84 (3H, t). | m/z: 293 | Example 2 |

TABLE 1-continued

| Examples | | | |
|---|---|---|---|
| 3 | 1H NMR (400 MHz, DMSO-d6): 8.87-8.65 (4H, m), 8.01-7.72 (4H, m), 7.56 (1H, d), 4.38 (1H, s), 2.10-1.95 (1H, m), 1.92-1.73 (1H, m), 0.87-0.70 (3H, m). | m/z: 309 | Example 3 |
| 4 | 1H NMR (400 MHz, DMSO-d6): 8.72 (3H, s), 7.91 (1H, t), 7.81 (3H, dd), 7.72-7.55 (3H, m), 4.41 (1H, dd), 2.12-1.97 (1H, m), 1.97-1.81 (1H, m), 0.83 (3H, t). | m/z: 292 | Example 4 |
| 5 | 1H NMR (400 MHz, Me-d3-OD): 8.24 (1H, d), 7.94 (1H, d), 7.76 (1H, t), 7.61 (1H, d), 7.53 (1H, dd), 4.55 (1H, dd), 2.20-1.97 (2H, m), 1.00 (3H, t). | m/z: 308 | Example 5 |
| 6 | 1H NMR (400 MHz, DMSO-d6): 8.72 (3H, s), 7.91 (1H, t), 7.81 (3H, dd), 7.72-7.55 (3H, m), 4.41 (1H, dd), 2.12-1.97 (1H, m), 1.97-1.81 (1H, m), 0.83 (3H, t). | m/z: 292 | Isolated as a byproduct during the synthesis of Example 4 |
| 7 | 1H NMR (400 MHz, DMSO-d6): 8.67 (3H, s), 7.91 (1H, t), 7.74-7.56 (5H, m), 4.41 (1H, dd), 2.11-1.98 (1H, m), 1.98-1.82 (1H, m), 0.84 (3H, t). | m/z: 310 | Prepared as Example 2 using 3-fluorobenzoyl chloride |
| 8 | 1H NMR(400 MHz, Me-d3-OD): 7.98-7.87 (2H, m), 7.68 (1H, t), 7.57 (1H, d), 7.38-7.26 (2H, m), 4.53 (1H, dd), 2.18-2.01 (2H, m), 0.99 (3H, t). | m/z: 310 | As Example 4 using 4-fluorophenyl-magnesium bromide in step 1, intermediate 11 |
| 9 | 1H NMR (400 MHz, Me-d3-OD): 8.05-7.92 (4H, m), 7.72 (1H, t), 7.60 (1H, d), 4.54 (1H, dd), 2.17-1.97 (2H, m), 0.99 (3H, t) | m/z: 317 | As Example 2 using 4-cyanobenzoyl chloride |
| 10 | 1H NMR (400 MHz, DMSO-d6): 9.42 (1H, s), 9.28 (1H, d), 8.68 (3H, s), 8.21 (1H, d), 7.92 (1H, t), 7.66 (1H, d), 4.42 (1H, s), 2.10-1.96 (1H, m), 1.93-1.79 (1H, m), 0.83 (3H, t). | m/z: 294 | Prepared as Example 2 using Methyl 1,3-pyrimidine-4-carboxylate |
| 11 | 1H NMR (400 MHz, Me-d3-OD): 7.91-7.81 (2H, m), 7.81-7.70 (2H, m), 7.65-7.47 (3H, m), 3.89 (1H, d), 1.57-1.43 (1H, m), 0.96-0.83 (1H, m), 0.83-0.72 (1H, m), 0.72-0.61 (1H, m), 0.53-0.41 (1H, m). | m/z: 287 [M − NH$_2$]$^+$ | Example 11 |
| 12 | 1H NMR (400 MHz, Me-d3-OD): 9.45 (0.5H, s), 9.17 (1H, s), 8.79 (0.5H, d), 7.80-7.51 (2.5H, m), 6.06 (0.5H, s), 4.55 (1H, q), 2.18-2.04 (2H, m), 1.06-0.94 (3H, m). | m/z: 294 | As Example 2 using ethyl -5-pyrimidine carboxylate |
| 13 | 1H NMR (DMSO-d6): 8.56 (3H, s), 7.98-7.82 (2H, m), 7.75-7.63 (3H, m), 4.42 (1H, dd), 2.07-1.95 (1H, m), 1.95-1.83 (1H, m), 0.84 (3H, t). | m/z: 328 | Prepared as for Example 2, but using methyl 3,4-difluorobenzoate in step 1 |
| 14 | 1H NMR (400 MHz, Me-d3-OD): 8.64 (1H, d), 8.25 (1H, d), 8.19-8.05 (1H, m), 7.76-7.56 (2H, m), 7.51 (1H, d), 4.51 (1H, dd), 2.18-1.94 (2H, m), 0.99 (3H, t). | m/z: 293 | Prepared as Example 2 using methyl pyridine-2-carboxylate Prepared as |

TABLE 1-continued

| | Examples | | |
|---|---|---|---|
| 15 | 1H NMR (400 MHz, Me-d3-OD): 9.14-9.04 (2H, m), 8.31-8.22 (2H, m), 7.81 (1H, t), 7.65 (1H, d), 4.56 (1H, dd), 2.19-1.99 (2H, m), 1.01 (3H, t). | m/z: 293 | Example 2 using methyl pyridine-4-carboxylate |
| 16 | 1H NMR (400 MHz, Me-d3-OD): 8.69 (1H, d), 7.73 (1H, t), 7.66 (1H, d), 7.61 (1H, dd), 4.55 (1H, dd), 2.19-1.95 (2H, m), 1.00 (3H, t). | m/z: 299 | As for Example 2 using isothiazole-5-carboxylic acid methyl ester in step 1. |
| 17 | 1H NMR (400 MHz, Me-d3-OD): 8.59 (1H, d), 8.38 (1H, s), 7.86 (1H, t), 7.73 (1H, t), 7.60 (1H, d), 4.53 (1H, dd), 3.99 (3H, s), 2.17-1.95 (2H, m), 0.99 (3H, t). | m/z: 323 | As Example 2 using methyl-5-methoxypyridine-3-carboxylate |
| 18 | 1H NMR (400 MHz, Me-d3-OD): 8.20-8.13 (2H, m), 8.13-8.06 (1H, m), 7.85-7.76 (1H, m), 7.72 (1H, t), 7.61 (1H, d), 4.54 (1H, t), 2.17-1.98 (2H, m), 1.00 (3H, t). | m/z: 317 | As Example 2 using methyl-3-cyanobenzoate |
| 19 | 1H NMR (400 MHz, Me-d3-OD): 8.98 (1H, s), 8.45 (1H, d), 8.35 (1H, d), 7.75 (1H, t), 7.62 (1H, d), 4.59-4.52 (1H, m), 2.18-1.98 (2H, m), 1.06-0.95 (3H, m) | m/z: 337 | Example 19 |
| 20 | 1H NMR (400 MHz, DMSO-d6): 8.65 (3H, s), 8.48 (1H, d), 8.27-8.20 (1H, m), 7.90 (1H, t), 7.67 (1H, d), 4.43 (1H, dd), 2.07-1.96 (1H, m), 1.91-1.80 (1H, m), 0.87-0.75 (3H, m). | m/z: 299 | Prepared as Example 2 using ethyl thiazole-2-carboxylate |
| 21 | 1H NMR (400 MHz, DMSO-d6): 8.66 (3H, s), 7.92 (1H, t), 7.67 (1H, d), 6.91 (1H, s), 4.47-4.35 (1H, m), 2.54 (3H, s), 2.10-1.93 (1H, m), 1.92-1.76 (1H, m), 0.87-0.69 (3H, m). | m/z: 297 | Prepared as Example 2 using Methyl 5-methyl-3-isoxazole carboxylate |
| 22 | 1H NMR (400 MHz, Me-d3-OD): 9.04 (1H, s), 8.41-8.34 (1H, m), 8.31 (1H, d), 7.73 (1H, t), 7.62 (1H, d), 4.55 (1H, t), 2.16-2.04 (2H, m), 1.01 (3H, t). | m/z: 336 | Example 22 |
| 23 | 1H NMR (400 MHz, DMSO-d6): 8.55 (3H, s), 7.90-7.74 (4H, m), 7.72-7.58 (3H, m), 4.41 (1H, s). | | Prepared as for Example 4 but using D5-ethyl magnesium bromide in step 2. |
| 24 | 1H NMR (400 MHz, DMSO-d6): 8.54 (3H, s), 7.90-7.74 (4H, m), 7.74-7.57 (3H, m), 4.41 (1H, s). | | Prepared as for Example 4 but using D5-ethyl magnesium bromide in step 2. |
| 25 | 1H NMR (400 MHz, DMSO-d6): 8.66 (3H, s), 8.56 (1H, dd), 8.45 (1H, s), 7.93 (1H, t), 7.76-7.62 (3H, m), 4.42 (1H, d), 2.09-2.00 (1H, m), 1.95-1.86 (1H, m), 0.85 (3H, t). | m/z: 309 | Example 25 |
| 26 | 1H NMR (400 MHz, Me-d3-OD): 9.20 (1H, s), 9.05 (1H, d), 8.72 (1H, d), 8.10-7.99 (1H, m), 7.78 (1H, t), 7.64 (1H, d), 4.56 (1H, dd), 2.19-2.00 (2H, m), 1.01 (3H, t). | m/z: 293 | Prepared as Example 2 using Intermediate 3 |

TABLE 1-continued

| | Examples | | |
|---|---|---|---|
| 27 | 1H NMR (270 MHz, DMSO-d$_6$): 8.72 (3H, br s), 7.98-7.87 (3H, m), 7.66 (1H, d), 7.48-7.42 (2H, m), 3.82 (1H, d), 1.48-1.35 (1H, m), 0.69-0.53 (3H, m), 0.34-0.29 (1H, m). | m/z: 305 [M − NH$_2$]$^+$ | Prepared according to Example 2 using Intermediate 6 and ethyl 4-fluorobenzoate |
| 28 | 1H NMR (270 MHz, DMSO-d$_6$): 8.92 (2H, m), 8.88 (3H, brs), 8.30-8.26 (1H, m), 8.03 (1H, t), 7.73-7.66 (2H, m), 3.79 (1H, dd), 1.48-1.44 (1H, m), 0.73-0.65 (2H, m), 0.59-0.52 (1H, m), 0.36-0.29 (1H, m). | m/z: 305 | Prepared according to Example 2 using Intermediate 6 and ethyl nicotinate |
| 29 | 1H NMR (270 MHz, Me-d3-OD): 8.70 (1H, m), 8.27 (1H, dd), 7.80-7.67 (2H, m), 7.56 (1H, d), 4.50 (1H, m), 2.19-1.96 (2H, m), 0.97 (3H, t) | m/z: 327 | Prepared according to Example 2 using methyl 6-chloronicotinate |
| 30 | 1H NMR (400 MHz, Me-d3-OD): 8.73 (1H, d), 8.29 (1H, dd), 7.77 (1H, t), 7.71 (1H, d), 7.60 (1H, d), 4.55 (1H, dd), 2.22-1.96 (2H, m), 0.99 (3H, t). | m/z: 326 | Prepared as Example 2 using Intermediate 3 and ethyl 6-chloropyridine-3-carboxylate |
| 31 | 1H NMR (400 MHz, Me-d3-OD): 8.36-8.32 (2H, m), 7.73 (1H, t), 7.60 (1H, d), 7.16 (1H, dd), 4.55 (1H, dd), 2.20-1.97 (2H, m), 1.00 (3H, t). | m/z: 308 | Prepared as Example 1 using Intermediate 3 |
| 32 | 1H NMR (270 MHz, DMSO-d$_6$): 8.76 (3H, br s), 8.11 (2H, d), 8.02-7.96 (3H, m), 7.69 (1H, d), 3.82 (1H, dd), 1.46-1.38 (1H, m), 0.86-0.53 (3H, m), 0.35-0.29 (1H, m). | m/z: 329 | Prepared according to Example 2 using Intermediate 6 and ethyl 4-cyanobenzoate |
| 33 | 1H NMR (270 MHz, DMSO-d$_6$): 8.94 (2H, m), 8.86 (3H, br s), 8.05 (1H, t), 7.79-7.69 (3H, m), 3.90-3.80 (1H, m), 1.52-1.39 (1H, m), 0.79-0.66 (2H, m), 0.60-0.55 (1H, m), 0.36-0.29 (1H, m). | m/z: 305 | Prepared according to Example 2 using Intermediate 6 and methyl isonicotinate |
| 34 | 1H NMR (400 MHz, Me-d3-OD): 9.06 (1H, d), 8.44 (1H, dd), 8.16-8.07 (1H, m), 7.74 (1H, t), 7.63 (1H, d), 4.54 (1H, dd), 2.16-2.00 (2H, m), 1.00 (3H, t). | m/z: 318 | As Example 2 using 2-cyano-5-ethoxycarbonyl-pyridine |
| 35 | 1H NMR (400 MHz, Me-d3-OD): 8.31-8.21 (2H, m), 7.71 (1H, t), 7.59 (1H, d), 7.24 (1H, d), 4.54 (1H, dd), 3.37 (6H, s), 2.17-1.99 (2H, m), 1.00 (3H, t). | m/z: 336 | As Example 1 using dimethylamine in step 2 |
| 36 | 1H NMR (400 MHz, Me-d3-OD): 8.25 (2H, s), 7.74 (1H, t), 7.60 (1H,d), 7.27-7.03 (1H, m), 4.55 (1H, dd), 3.15 (3H, s), 2.18-1.98 (2H, m), 1.00 (3H, t) | m/z: 322 | As Example 1 using methylamine in step 2 |
| 37 | 1H NMR (400 MHz, Me-d3-OD): 8.81 (1H, d), 8.70 (1H, d), 8.39 (1H, dd), 8.17 (1H, d), 7.87 (1H, d), 7.72 (1H, t), 7.61 (1H, d), 6.62 (1H, dd), 4.55 (1H, dd), 2.18-2.00 (2H, m), 1.01 (3H, t). | m/z: 359 | Example 37 |
| 38 | 1H NMR (400 MHz, Me-d3-OD): 8.03 (1H, dd), 7.91 (1H, d), 7.68 (1H, t), 7.57 (1H, d), 6.62 (1H, d), 4.53 (1H, dd), 2.18-1.96 (2H, m), 1.05-0.84 (3H, m). | m/z: 309 | Example 38 |

TABLE 1-continued

Examples

| | | | |
|---|---|---|---|
| 39 | 1H NMR (400 MHz, Me-d3-OD): 7.86-7.81 (2H, m), 7.72 (1H, tt), 7.56 (3H, q), 7.33 (1H, d), 4.48 (1H, dd), 2.23 (3H, s), 2.16-1.94 (2H, m), 0.97 (3H, t). | m/z: 272 | Example 39 |
| 40 | 1H NMR (400 MHz, Me-d3-OD): 7.85-7.79 (2H, m), 7.69 (1H, tt), 7.63 (1H, t), 7.57-7.50 (2H, m), 7.13 (1H, dd), 4.45 (1H, dd), 3.81 (3H, s), 2.16-1.95 (2H, m), 0.98 (3H, t). | m/z: 271 $[M - NH_2]^+$ | As for Example 39 starting with intermediate 14. |
| 41 | 1H NMR (400 MHz, Me-d3-OD): 9.16 (1H, s), 8.87 (1H, d), 8.46 (1H, dd), 8.29-8.18 (2H, m), 7.74 (1H, t), 7.63 (1H, d), 4.56 (1H, dd), 4.37 (2H, q), 2.18-2.04 (2H, m), 1.40 (3H, t), 1.01 (3H, t). | m/z: 431 | As Example 37 using ethyl-4-pyrazole carboxylate |
| 42 | 1H NMR (400 MHz, DMSO-d6): 8.71 (3H, s), 8.39 (2H, d), 7.92 (1H, t), 7.79 (2H, d), 7.70 (1H, d), 4.41 (1H, s), 2.10-1.96 (1H, m), 1.96-1.82 (1H, m), 0.83 (3H, t). | m/z: 309 | Prepared as Example 25 using intermediate from step 1 towards Example 15 |
| 43 | 1H NMR (400 MHz, Me-d3-OD): 7.88 (2H, d), 7.83-7.68 (2H, m), 7.59 (2H, t), 7.38-7.29 (1H, m), 4.53 (1H, dd), 2.19-1.95 (2H, m), 1.05-0.84 (3H, m). | m/z: 276 | Example 43 |
| 44 | 1H NMR (400 MHz, Me-d3-OD): 7.86 (2H, dd), 7.68 (1H, tt), 7.57-7.50 (2H, m), 7.47 (1H, t), 6.89 (1H, dd), 4.41 (1H, dd), 2.15-1.93 (2H, m), 0.97 (3H, t). | m/z: 272 $[M - H]^-$ | As for Example 39 starting with Intermediate 15. |
| 45 | 1H NMR (400 MHz, DMSO-d6): 8.63 (3H, s), 8.24 (1H, d), 8.09 (1H, s), 7.87 (1H, t), 7.69 (1H, d), 7.52 (1H, s), 4.49-4.37 (1H, m), 3.55 (3H, s), 2.09-1.95 (1H, m), 1.95-1.81 (1H, m), 0.83 (3H, t). | m/z: 308 | Prepared as Example 5 using methyl 5-bromonicotinate |
| 46 | 1H NMR (400 MHz, Me-d3-OD): 8.78 (1H, d), 8.65 (1H, s), 8.37 (1H, dd), 8.17-8.08 (1H, m), 7.85 (1H, s), 7.68 (1H, t), 7.46 (1H, d), 4.62 (2H, s), 4.13 (1H, t), 1.90-1.70 (2H, m), 0.92 (3H, t). | m/z: 389 | Example 46 |
| 47 | 1H NMR (400 MHz, Me-d3-OD): 8.42-8.29 (2H, m), 7.84 (1H, t), 7.60 (1H, d), 7.18 (1H, d), 3.90 (1H, d), 1.60-1.45 (1H, m), 0.97-0.83 (1H, m), 0.82-0.63 (2H, m), 0.54-0.40 (1H, m). | m/z: 303 $[M - NH_2]^+$ | Example 47 |
| | There is no Example 48 | | |
| 49 | 1H NMR (400 MHz, DMSO-d6): 8.63 (3H, s), 7.87 (1H, t), 7.81 (2H, d), 7.67 (1H, d), 7.59 (2H, d), 5.20 (2H, s), 4.41 (1H, dd), 2.11 (3H, s), 2.08-1.96 (1H, m), 1.96-1.82 (1H, m), 0.83 (3H, t). | m/z: 364 | Example 49 |
| 50 | 1H NMR (400 MHz, DMSO-d6):8.70 (3H, s), 7.89 (1H, t), 7.77 (2H, d), 7.66 (1H, d), 7.54 (2H, d), 5.45 (1H, s), 4.61 (2H, s), 4.41 (1H, t), 2.11-1.97 (1H, m), 1.97-1.81 (1H, m), 0.83 (3H, t). | m/z: 322 | Example 50 |
| 51 | 1H NMR (400 MHz, Me-d3-OD): 8.90 (2H, s), 7.72 (1H, t), 7.61 (1H, d), 4.54 (1H, dd), 2.66 (3H, s), 2.18-1.98 (2H, m), 0.99 (3H, t). | m/z: 340 | Example 51 |

TABLE 1-continued

| | Examples | | |
|---|---|---|---|
| 52 | 1H NMR (400 MHz, Me-d3-OD): 8.07 (1H, d), 7.79 (1H, t), 7.63 (1H, d), 7.45 (1H, s), 7.22 (1H, dd), 4.56 (1H, dd), 2.20-1.98 (2H, m), 1.06-0.87 (3H, m). | m/z: 308 | Prepared as Example 5 using methyl 2-bromopyridine-4-carboxylate |
| | There is no Example 53 | | |
| 54 | 1H NMR (400 MHz, DMSO-d6): 8.68 (3H, s), 7.89 (1H, t), 7.81 (1H, s), 7.73-7.62 (3H, m), 7.57 (1H, t), 5.39 (1H, s), 4.57 (2H, s), 4.42 (1H, s), 2.11-1.95 (1H, m), 1.95-1.81 (1H, m), 0.83 (3H, t). | m/z: 322 | Prepared as Example 50 using methyl 3-hydroxymethyl benzoate |
| 55 | 1H NMR (400 MHz, Me-d3-OD): 8.05 (2H, s), 7.63 (1H, t), 7.54 (1H, d), 4.58-4.46 (1H, m), 2.17-1.96 (2H, m), 0.99 (3H, t). | m/z: 282 | Example 55 |
| 56 | 1H NMR (400 MHz, DMSO-d6): 8.80 (3H, d), 8.72 (1H, d), 7.99-7.69 (3H, m), 7.55 (1H, d), 3.84 (1H, d), 1.46-1.33 (1H, m), 0.75-0.61 (2H, m), 0.61-0.49 (1H, m), 0.31 (1H, dd). | m/z: 641 [2M + H]$^+$ | Prepared as Example 3 using Intermediate 6 |
| 57 | 1H NMR (400 MHz, DMSO-d6): 8.77 (1H, d), 8.65 (3H, s), 8.46 (1H, d), 7.90 (1H, d), 7.78 (1H, t), 7.55 (1H, d), 2.92 (3H, d), 2.08-1.94 (1H, m), 1.94-1.77 (1H, m), 0.81 (3H, t). | m/z: 323 | Prepared as Example 3 using 8M methylamine in ethanol in step 2 |
| 58 | 1H NMR (400 MHz, Me-d3-OD): 7.93 (1H, d), 7.68-7.55 (1H, m), 7.55-7.41 (2H, m), 4.81-4.76 (2H, m), 4.51 (1H, dd), 2.17-1.95 (2H, m), 1.01 (3H, t). | m/z: 364 | Prepared as Example 51 using 3-oxo-2H,3H,4H-pyrido[3,2-b][1,4]oxazine-6-carbaldehyde |
| 59 | 1H NMR (400 MHz, Me-d3-OD): 8.42-8.28 (2H, m), 8.13 (1H, d), 7.78-7.65 (2H, m), 7.60 (1H, d), 4.54 (1H, dd), 2.19-1.96 (2H, m), 0.99 (3H, t). | m/z: 336 | Example 59 |
| 60 | 1H NMR (400 MHz, DMSO-d6): 11.23 (1H, s), 8.56 (3H, s), 7.83 (1H, t), 7.65 (1H, d), 7.43 (1H, dd), 7.28 (1H, d), 7.07 (1H, d), 4.69 (2H, s), 4.42 (1H, s), 2.08-1.99 (1H, m), 1.95-1.81 (1H, m), 0.83 (3H, t). | m/z: 363 | Example 60 |
| 61 | 1H NMR (400 MHz, Me-d3-OD): 8.08 (1H, d), 7.96 (1H, d), 7.74 (1H, t), 7.54 (1H, d), 7.32 (1H, dd), 3.88 (1H, d), 1.57-1.44 (1H, m), 0.96-0.83 (1H, m), 0.82-0.61 (2H, m), 0.53-0.41 (1H, m) | m/z: 318 [M − H]$^-$ | Prepared according to Example 5 from intermediate 6 |
| 62 | 1H NMR (400 MHz, Me-d3-OD): 8.97 (1H, d), 8.50 (1H, dd), 8.38 (1H, d), 7.74 (1H, t), 7.52 (1H, d), 3.89 (1H, d), 1.54-1.41 (1H, m), 0.95-0.83 (1H, m), 0.82-0.60 (2H, m), 0.52-0.40 (1H, m). | m/z: 313 [M − NH$_2$]$^+$ | Example 62 |
| 63 | 1H NMR (400 MHz, Me-d3-OD): 8.21 (1H, s), 8.11 (1H, d), 7.63 (1H, t), 7.14 (1H, d), 6.86 (1H, d), 4.45 (1H, dd), 3.85 (3H, s), 2.13-1.98 (2H, m), 0.97 (3H, t). | m/z: 287 [M − NH$_2$]$^+$ | Example 63 |
| 64 | 1H NMR (400 MHz, Me-d3-OD): 8.07 (1H, d), 7.92 (1H, s), 7.83 (1H, dd), 7.73 (1H, t), 7.60 (1H, d), 4.54 (1H, dd), 2.60 (3H, s), 2.20-1.96 (2H, m), 1.00 (3H, t). | m/z: 350 | Prepared according to Example 77, step 1 and then Example 1, step 3 |

TABLE 1-continued

| | Examples | | |
|---|---|---|---|
| 65 | 1H NMR (400 MHz, DMSO-d6): 8.61 (3H, d), 7.78 (1H, t), 7.58 (1H, d), 7.31 (1H, d), 7.14 (1H, d), 6.99 (1H, s), 6.63 (1H, d), 4.40 (1H, s), 4.12 (2H, s), 3.40 (2H, s), 2.08-1.96 (1H, m), 1.93-1.79 (1H, m), 0.82 (3H, t). | m/z: 349 | Example 65 |
| 66 | 1H NMR (400 MHz, Me-d3-OD): 8.33 (2H, d), 7.73 (1H, t), 7.59 (1H, d), 7.15 (1H, d), 4.62 (1H, t), 2.09-2.01 (2H, m), 1.48-1.29 (2H, m), 1.01 (3H, t). | m/z: 322 | As intermediate 2 using n-PrMgCl in step 1 then as Example 1 |
| 67 | 1H NMR (400 MHz, Me-d3-OD): 8.36-8.25 (2H, m), 7.73 (1H, t), 7.59 (1H, d), 7.14 (1H, d), 5.83-5.71 (1H, m), 5.31-5.20 (2H, m), 4.76-4.66 (1H, m), 2.88-2.74 (2H, m). | m/z: 320 (Fragment) | As intermediate 2 using allyMgBr in step 1 then as Example 1 |
| 68 | 1H NMR (400 MHz, DMSO-d6): 8.62 (3H, s), 7.90 (1H, t), 7.77 (2H, d), 7.73-7.63 (1H, m), 7.56 (2H, d), 5.48 (1H, t), 4.62 (2H, d), 3.86 (1H, d), 1.46-1.35 (1H, m), 0.76-0.68 (1H, m), 0.68-0.52 (2H, m), 0.38-0.29 (1H, m). | m/z: 317 [M − NH$_2$]$^+$ | Example 68 |
| 69 | 1H NMR (400 MHz, Me-d3-OD): 7.88-7.76 (2H, m), 7.71 (1H, s), 7.59 (1H, d), 7.36 (1H, d), 4.06 (3H, s), 3.92-3.86 (1H, m), 1.58-1.40 (1H, m), 0.98-0.83 (1H, m), 0.81-0.61 (2H, m), 0.55-0.38 (1H, m). | m/z: 342 [M − NH$_2$]$^+$ | As example 62 using methyl 4-bromo-3-methoxybenzoate in step 1 |
| 70 | 1H NMR (400 MHz, Me-d3-OD): 7.61 (1H, t), 7.46-7.36 (3H, m), 7.01 (1H, d), 4.67 (2H, s), 4.12 (1H, s). | m/z: 368 | As intermediate 2 using D5-ethyl magnesium bromide in step 1 then as Example 60 |
| 71 | | m/z: 322 | Prepared according to Example 5 using methyl 4-methyl-5-bromopyridine-2-carboxylate. Last step according to Example 72, step 4 |
| 72 | | m/z: 332 | Example 72 |
| 73 | | m/z: 347 | Example 73 |
| 74 | | m/z: 339 [M − H]$^-$ | Example 74 |
| 75 | | m/z: 342 [M − H]$^-$ | Prepared according to Example 72 from Intermediate 6 |
| 76 | | m/z: 351 [M − H]$^-$ | Prepared according to Example 74 from Intermediate 6. Final step as per Example 77, step 3. |
| 77 | | m/z: 331 [M − H]$^-$ | Example 77. |
| 78 | | m/z: 344 [M − H]$^-$ | Prepared according to Example 74 except deuterated ethyl Grignard used to make equivalent of Intermediate 2 |

TABLE 1-continued

Examples

| | | |
|---|---|---|
| 79 | m/z 326 | Prepared according to Example 77 except deuterated ethyl Grignard used to make equivalent of Intermediate 2 |
| 80 | m/z: 296 [M − NH$_2$]$^+$ | Example 80 |

B. Preparation of Compounds of Formula (0) in which R$^2$ is a Group X—R$^8$

This section mainly describes the preparation of compounds of the formula (0) wherein R$^2$ is X—R$^8$ from the compounds of the formula (0) in which R$^2$ is hydrogen.

Example 81

(3S)-3-{[(1R)-1-{3-[(6-aminopyridin-3-yl)carbonyl]-4-chloro-2-fluorophenyl}propyl]-amino}butanamide

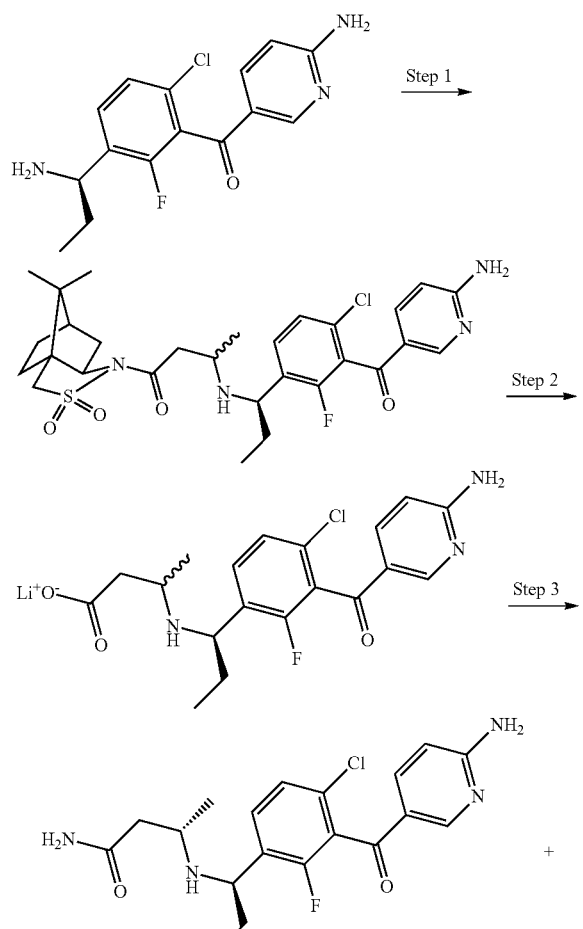

Example 81

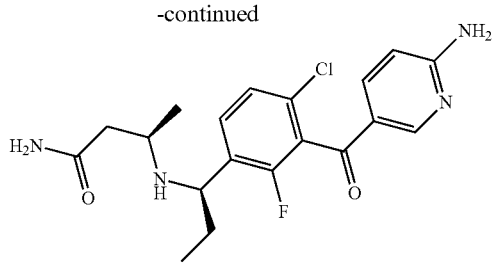

Example 82

Step 1 The benzylamine hydrochloride compound of Example 1 (300 mg, 0.87 mmol) was partitioned between DCM (15 mL) and water (15 mL) with enough NaOH (5M) added to bring the pH to ~12. Organic layer was isolated by phase separator and concentrated. The residue was dissolved in THF (1 mL) and lithium perchlorate (130 mg, 1.09 mmol, 1.4 eq.) and the (N-crotonyl)-(2R)-bornane-10,2-sultam (296 mg, 1.05 mmol, 1.2 eq.) were added. The reaction was stirred at room temperature for 3 days. Partitioned between EtOAc (30 mL) and water (20 mL) and the organic phase washed with brine (10 mL) before it was dried (MgSO4), filtered and concentrated to give crude product (507 mg) which was used directly in the next reaction. [MH]+ 591

Step 2 The residue from step 1 (507 mg) was dissolved in THF (4 mL) before addition of LiOH (72 mg) dissolved in water (1 mL). Reaction stirred for 4 h. Concentrated to dryness and then used directly in next step. [MH]+ 394

Step 3 To a solution of 3-{(R)-1-[3-(6-amino-pyridine-3-carbonyl)-4-chloro-2-fluoro-phenyl]-propylamino}-butyric acid lithium salt (570 mg) in DMF (7 mL) was added ammonium chloride (233 mg, 4.3 mmol), DIPEA (1.05 mL, 6 mmol) and then HATU (491 mg, 2.07 mmol) and the reaction stirred for 3 h. The mixture was partitioned between EtOAc (20 mL) and water (15 mL). The aqueous phase was extracted with further EtOAc (20 mL). The combined organic phase was washed with water (20 mL) and brine (10 mL) before it was dried (MgSO4), filtered and concentrated. Purified by SCX, washing with MeOH and eluting with about 0.2M NH3 in MeOH and concentrated. The (semi-)preparative stereoselective chromatography was carried out using a pre-packed Chiralpak AD-H column (250 mm×20 mm I.D., d$_p$=5 μm), produced by Chiral Technologies Europe (IIIkirch, France). Mobile phase elution was made isocratically using n-heptane/2-propanol/Diethylamine (80/20/0.2 v/v) at a flow of 19 ml/min. The main diastereoisomer was dissolved in DCM and then 1.1 eq. 2M HCl in ether was added to form the mono-hydrochloride salt. The solid was filtered off to give the title compound (36 mg) [M+H]+ 393 for $^{35}$Cl. Further title compound (13 mg) was isolated by flushing the sinter with MeOH, concentrating and drying in a vacuum oven.

Example 81

Alternative Synthesis

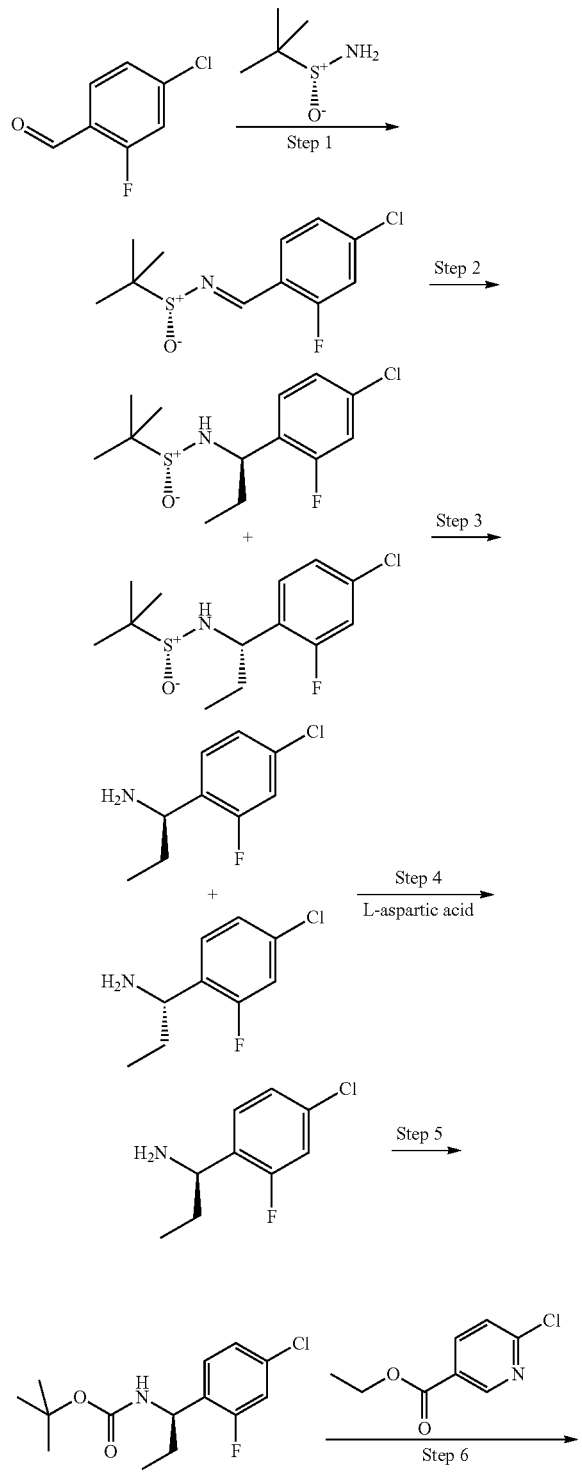

Step 1—To a mixture of 4-chloro-2-fluorobenzaldehyde (1340 g, 8.45 moles, 1.0 eq), dichloromethane (7.0 L) and (R)-(+)-2-methyl-2-propanesulfinamide (1073 g, 8.87 moles, 1.05 eq) was added $Cs_2CO_3$ (3028 g, 9.29 mol, 1.1 eq) and the reaction mixture was stirred overnight at room temperature, after which time NMR confirmed the reaction to be complete. The reaction mixture was then filtered through a Celite pad and the solids retained by the filter were washed several times with dichloromethane before concentrating the combined dichloromethane filtrates and azeotroping with toluene (2×1.5 L) to remove residual water. The product was further dried under high vacuum at 35° C. to give Intermediate 1 as a yellow solid (2.2 kg).

Step 2—Three runs were carried out in parallel and combined in the work-up. Intermediate 1 (733 g, 2.8 mol, 1.0 eq) was dissolved in THF (13.8 L) and placed under nitrogen and the solution was cooled to below −70° C. (CO$_2$/acetone bath) before adding ethylmagnesium bromide (3.0M in Et$_2$O, 1.6 L, 4.8 mol, 1.7 eq) in 100 ml portions, keeping the internal temperature below −70° C., over a period of approximately two hours. The reaction mixture was then stirred at −78° C. for one hour, quenched by the dropwise addition of sat NH$_4$Cl (3 L) and stirred overnight. The organic layer was then removed, the aqueous layer was re-extracted with EtOAc (3×2 L), and the organic extracts were combined and washed with saturated brine (2 L). The combined organics from three runs were combined and evaporated to dryness to give (R)-(+)-2-methyl-propane-2-sulfinic acid [1-(4-chloro-2-fluoro-phenyl)-propyl]-amide as a pale yellow solid (2491.0 g, 101.6%).

Step 3—Two runs were put on in parallel and combined in the workup. (R)-(+)-2-Methyl-propane-2-sulfinic acid [1-(4-chloro-2-fluoro-phenyl)-propyl]-amide (1245.5 g, 4.27 mol, 1.0 eq) from Step 2 was dissolved in methanol (5.5 L) and placed under nitrogen before adding 4 M HCl in 1,4-dioxane (1.3 L, 5.2 mol, 1.22 eq) over approximately 20 minutes and allowing the reaction mixture to return to room temperature over one hour. The combined reaction mixtures from two runs were combined and the solvent was evaporated to give a semi-solid (2881 g) which was dried overnight under high vacuum to give a pale yellow solid (2520.1 g). The solid was split into two equal portions and to each was added petrol (40-60) (2.2 L) and diethyl ether (2.2 L). The suspended solids in each case were stirred for one hour, then isolated by filtration, washed with petrol (700 ml) and air dried (1909.7 g). The solids were then stirred with 2M NaOH (7 L), the resulting mixture was extracted with ethyl acetate (2×2.75 L) and the combined organic extracts were washed with saturated brine (2 L) and then were evaporated to give 1-(4-chloro-2-fluoro-phenyl)-propylamine as a yellow oil (1493 g).

Step 4—Three runs were carried out in parallel and combined in the work-up. A mixture of 1-(4-chloro-2-fluoro-phenyl)-propylamine (497.6 g, 2.65 mol, 1.0 eq) from Step 3, ethanol and water (3.1 L ethanol/1.3 L water) and L-aspartic acid (353 g, 2.65 mol, 1.0 eq) was heated to 72° C. (oil bath) for 1 hour and then allowed to cool to room temperature. The resulting precipitate was filtered off, washed with ethanol (2 L) and air dried to give a white solid (4381.6 g-contains solvent, dry weight estimated by $^1$H NMR at 2674.2 g), which was split into four. To each of the four portions was added a mixture of ethanol and water (11.9 L EtOH, 4.9 L H$_2$O) and the resulting mixture was then stirred at room temperature overnight before isolating the solid by filtration, washing with ethanol, and drying the solid in a vacuum oven overnight at 40° C., to give (R)-1-(4-chloro-2-fluoro-phenyl)-propylamine as the aspartate salt, a white solid (1409.2 g). $^1$H NMR (400 MHz, DMSO-d6): 7.56 (1H, t), 7.34 (1H, dd), 7.29 (1H, dd), 4.03 (1H, t), 3.68 (1H, dd), 2.67 (1H, dd), 2.38 (1H, dd), 1.69-1.49 (2H, m), 0.80 (3H, t).

Step 5—To (R)-1-(4-chloro-2-fluoro-phenyl)-propylamine aspartate salt (1409.2 g, 4.39 mol, 1.0 eq) in THF (7.0 L) was added 2 M NaOH (3.5 L, 7.03 mol, 1.6 eq), and the mixture was stirred at room temperature for one hour before adding sat brine (1.8 L) to the mixture. The organic layer was removed, the aqueous layer was re-extracted with THF (2.2 L) and the organic extracts were combined before adding 2 M NaOH (3.5 L, 7.03 mol, 1.6 eq), then Boc$_2$O (1150.6 g, 5.27 mol, 1.2 eq) in THF (1.3 L). The resulting mixture was stirred at room temperature overnight, the organic layer was removed and the aqueous layer was re-extracted with EtOAc (3 L). The organic extracts were combined, washed with sat brine (2.0 L), then evaporated to dryness at 40° C. to give crude product as a white solid which was dried a vacuum oven at room temperature (1393 g).

A mixture of the crude product (1393 g), IPA (6.0 L) and water (1.2 L) was heated to 50° C. (oil bath) for 1 hour and then allowed to cool to room temperature with stirring overnight. Water (4.8 litres in two batches) was added to the mixture and the precipitate that formed was filtered off and washed with IPA/water (1:1, 2.4 L in total) to give Intermediate 2 as a white solid.

Step 6—To a stirred solution of Intermediate 2 (174.8 g, 0.607 mol) in THF (3.5 L) at −78° C. under a nitrogen atmosphere was added n-butyllithium solution (2.76 M in hexanes, 554 mL, 1.519 mol) dropwise over 210 min, the temperature being kept at <−70° C.). The solution was stirred at −78° C. for 40 min and then ethyl 6-chloropyridine-3-carboxylate (124 g, 0.668 mol) was added dropwise as a solution in THF (120 mL). The reaction mixture was stirred at −78° C. for 10 min, and then quenched by the addition of water (1 L) at −78° C. The mixture was allowed to warm up to room temperature and the phases were separated. The aqueous phase was extracted with EtOAc (2×800 mL) and the combined organic phases were washed with brine (800 mL) and concentrated under vacuum at 40° C. to give 254.4 g of crude material as a brown oil. The crude material was dissolved in heptane (1 L) and toluene (300 mL) and the mixture was heated, block temp 130° C., hot filtered to clarify using a GFA paper. The solution was then cooled slowly to room temperature overnight with stirring. The solid formed was filtered under vacuum and the cake washed with~200 mL of heptane, to give 207 g of tert-butyl N-[(1R)-1-[4-chloro-3-(6-chloropyridine-3-carbonyl)-2-fluorophenyl]propyl]-carbamate as a yellow solid (80% yield).

Step 7—To a solution of tert-butyl N-[(1R)-1-[4-chloro-3-(6-chloropyridine-3-carbonyl)-2-fluorophenyl]propyl]-carbamate (82.8 g, 194 mmol) from Step 6 in DMSO (5 vol) was added 4-methoxybenzylamine (53.1 g, 2 equi Vol). The mixture was heated to 50° C. (external temp) overnight then allowed to cool. The mixture was diluted with EtOAc (30 vol) and washed with 5% citric acid (5 vol), water (5 vol) and brine (5 vol) and concentrated to furnish tert-butyl N-[(1R)-1-[4-chloro-2-fluoro-3-(6-{[(4-methoxyphenyl)methyl]amino}pyridine-3-carbonyl)phenyl]propyl]carbamate as a brown oil, 109 g. m/z: 528.

Step 8—To a solution of the tert-butyl N-[(1R)-1-[4-chloro-2-fluoro-3-(6-{[(4-methoxyphenyl)methyl]-amino}pyridine-3-carbonyl)phenyl]propyl]carbamate (109 g) in dichloromethane (2 vol) was carefully added trifluoroacetic acid (1 vol) at room temperature. The dichloromethane was removed under vacuum, additional trifluoroacetic acid (2 vol) was added and the mixture was stirred for 10 minutes before increasing the temperature to 70° C. and stirring overnight. The mixture was allowed to cool then poured slowly into a stirred mix of TBME (15 vol) and water (15 vol). The phases were separated and the remaining emulsion was filtered through GFA paper. The TBME layer was extracted into 2M HCl (2×3 vol) and the combined acidic extracts were basified (~pH 12) and extracted with TBME (5×5 vol). The combined organic liquors were dried (Na$_2$SO$_4$) and concentrated to produce an oil/foam. The material was triturated with EtOAc to give 5-{3-[(1R)-1-aminopropyl]-6-chloro-2-fluorobenzoyl}pyridin-2-amine as a fine yellow powder 53.5 g, 84%. (Data for this compound are in Example 1).

Step 9—To a solution of (4R)-4-benzyl-3-(but-2-enoyl)-1,3-oxazolidin-2-one (105 g, 427 mmol) in THF (821 mL) at 15° C. was added lithium perchlorate (56.8 g, 534 mmol) (water bath was removed after the initial exotherm). The mixture was stirred at room temperature of 1 hour before the 5-{3-[(1R)-1-aminopropyl]-6-chloro-2-fluorobenzoyl}pyridin-2-amine (82.1 g, 267 mmol) from Step 8 was added and the mixture was stirred at room temperature. After 3 days the mixture was concentrated, diluted with EtOAc (15 Vol), washed with 4:1 H$_2$O:brine (15V, ×1), 1:9 brine: 5% AcOH solution (15V, ×2), saturated NaHCO$_3$ solution (15V, ×1; after neutralisation 3V of brine was also added to aid separation), dried (Na$_2$SO$_4$), filtered and concentrated. The residue was taken into EtOAc (5 Vol) and TBME (15 Vol) then 4M HCl in 1,4-dioxane (133 mL, 534 mmol) was added forming the HCl salt as a pale yellow precipitate. The solid was collected by filtration, washing with TBME then with petrol. The solid material was dried at 40° C. under vacuum providing 167.3 g (100.2%) in a ratio of 7.02:1 in favour of the desired (4R)-3-[(3S)-3-{[(1R)-1-[3-(6-aminopyridine-3-carbonyl)-4-chloro-2-fluorophenyl]propyl]amino}butanoyl]-4-benzyl-1,3-oxazolidin-2-one hydrochloride diastereomer. m/z: 553.

Step 10—The process was carried out in two parallel reactions: ammonia gas was bubbled through a rapidly stirred suspension of (4R)-3-[3-{[(1R)-1-[3-(6-aminopyridine-3-carbonyl)-4-chloro-2-fluorophenyl]propyl]amino}butanoyl]-4-benzyl-1,3-oxazolidin-2-one hydrochloride (189 g, 302 mmol) in 2-propanol (2840 mL) at 15° C. for 1 hour; then the reaction was allowed to stir at room temperature. The re-saturation of the solution with ammonia at 15° C. was repeated after 7 hours and the mixture was allowed to stir at room temperature overnight. This process was repeated over an additional 2 days before the starting material was fully consumed. The reaction was concentrated and the residue was taken into EtOAc (10 Vol) and washed with 1:1 brine:water (8 Vol). The desired product was extracted into 1M HCl solution (7.5 Vol) and water (2.5 Vol), the EtOAc was discarded, the aqueous solution was made basic (pH~11) by the careful addition of 50% NaOH solution and the product was extracted into EtOAc (8V, ×2). The combined organic extracts were washed with brine (2.5 Vol), dried (Na$_2$SO$_4$) and filtered and concentrated providing 247 g (combined) LCMS UV: 89.2% pure and a diastereomer ratio of 88.4:11.6 in favour of the desired (3S)-3-{[(1R)-1-[3-(6-aminopyridine-3-carbonyl)-4-chloro-2-fluorophenyl]propyl]amino}-butanamide diastereomer. m/z: 393.

Step 11—To a stirred solution of 3-{[(1R)-1-[3-(6-aminopyridine-3-carbonyl)-4-chloro-2-fluorophenyl]propyl]amino}butanamide (237 g, 603 mmol) in EtOH (1900 mL) at 78° C. was added (+)-O-acetyl-L-mandelic acid (117 g, 603 mmol). The mixture was kept at 78° C. for 10 minutes then allowed to cool to room temperature (with stirring) providing a precipitate. After stirring overnight the solid was collected by filtration, washed with EtOH (1.25 Vol), then Et$_2$O (1.7 Vol) and dried at 40° C. under vacuum providing (3S)-3-{[(1R)-1-[3-(6-aminopyridine-3-carbonyl)-4-chloro-2-fluorophenyl]propyl-amino}butanamide (+)-O-acetyl-L-mandelic acid salt (206 g) diastereomer ratio of 97.5:2.5 in favour of the desired diastereomer. $^1$H NMR (400 MHz, DMSO-d6): 8.15 (1H, d), 7.78 (1H, dd), 7.64 (1H, t), 7.52-7.37 (6H, m), 7.31 (3H, d), 6.79 (1H, s), 6.54 (1H, d), 5.83-5.73 (1H, m), 4.01 (1H, t), 2.87-2.69 (1H, m), 2.62-2.52 (1H, m), 2.22-2.01 (2H, m), 2.12 (3H, s), 1.81-1.66 (1H, m), 1.66-1.50 (1H, m), 0.95 (3H, d), 0.78 (3H, t).

Step 12—At room temperature (3S)-3-{[(1R)-1-[3-(6-aminopyridine-3-carbonyl)-4-chloro-2-fluorophenyl]-propyl]amino}butanamide (+)-O-acetyl-L-mandelic acid salt (94 g, 160 mmol) was suspended in EtOAc (752 mL) and sat NaHCO$_3$ (752 mL) was added with rapid stirring. The mixture was stirred for 1 hour, the phases were separated and the aqueous layer was further extracted into EtOAc (3×5 Vol). The combined organic extracts were dried (Na$_2$SO$_4$), filtered and concentrated to approximately 6 volumes. In a cool bath (10° C.) water (113 mL) was added followed by the slow addition of HCl in water (2.030 M, 78.9 mL, 160 mmol). The phases were separated and the EtOAc layer was extracted into water (% Vol). The combined aqueous extracts were placed on a rotary evaporator at 22° C. and the pressure was gradually reduced to 25 mbar for 1 hour to remove the majority of dissolved EtOAc. The solution was freeze-dried and subsequently ground to a pale-yellow powder.

A second batch (82 g) of (3S)-3-{[(1R)-1-[3-(6-aminopyridine-3-carbonyl)-4-chloro-2-fluorophenyl]propyl]amino}butanamide (+)-O-acetyl-L-mandelic acid salt was treated in the same manner and both batches were combined to give 151 g of (3S)-3-{[(1R)-1-[3-(6-aminopyridine-3-carbonyl)-4-chloro-2-fluorophenyl]propyl]amino}butanamide hydrochloride.

From step 10, 378 g (0.604 mol) of (4R)-3-[3-{[(1R)-1-[3-(6-aminopyridine-3-carbonyl)-4-chloro-2-fluorophenyl]propyl]amino}butanoyl]-4-benzyl-1,3-oxazolidin-2-one hydrochloride provided 151.1 g of (3S)-3-{[(1R)-1-[3-(6-aminopyridine-3-carbonyl)-4-chloro-2-fluorophenyl]propyl]amino}-butanamide hydrochloride (58%).

(3S)-3-{[(1R)-1-[3-(6-aminopyridine-3-carbonyl)-4-chloro-2-fluorophenyl]propyl]amino}butanamide hydrochloride (120 g, 280 mmol) was converted to the free-base by partition between EtOAc and saturated NaHCO$_3$ solution and stirring for 10 minutes. The phases were separated and the aqueous layer was extracted into EtOAc (×1). The combined organic extracts were dried (Na$_2$SO$_4$), filtered and concentrated. The free-base was dissolved in acetonitrile (3.5 Vol) at 100° C. (external temperature), then left to cool to room temperature. After stirring overnight the solid was collected by filtration and dried providing (3S)-3-{[(1R)-1-[3-(6-aminopyridine-3-carbonyl)-4-chloro-2-fluorophenyl]propyl]amino}butanamide as a white crystalline solid, 91.7 g, 84%. m/z: 393. $^1$H NMR (400 MHz, DMSO-d6): 8.14 (1H, d), 7.77 (1H, dd), 7.61 (1H, t), 7.44 (1H, d), 7.37-7.16 (3H, m), 6.73 (1H, s), 6.54 (1H, dd), 4.00-3.87 (1H, m), 2.77-2.63 (1H, m), 2.33-2.23 (1H, m), 2.09 (1H, dd), 2.04 (1H, dd), 1.76-1.61 (1H, m), 1.61-1.46 (1H, m), 0.92 (3H, d), 0.79 (3H, t).

Example 82

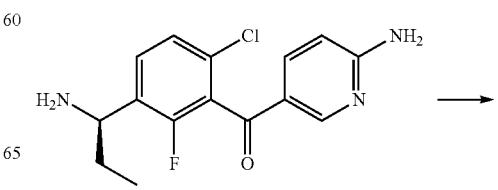

-continued

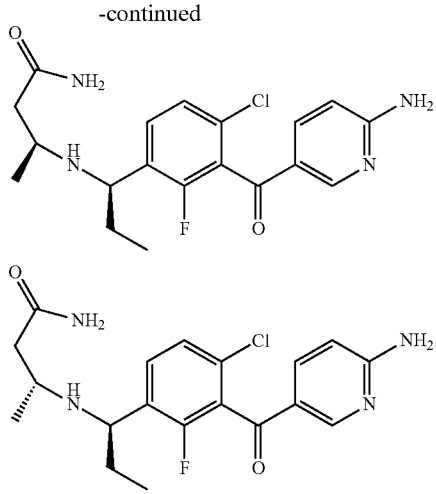

To a solution of Example 1 free base (176 mg, 0.57 mmol) and acetoacetamide (58 mg, 0.57 mmol) in DCE (5 ml), was added glacial acetic acid (0.04 ml, 0.5 mmol) and sodium triacetoxyborohydride (164 mg, 0.5 mmol). The resulting mixture was stirred at room temperature for 18 hours, then diluted with DCM and washed with sat. sodium hydrogen carbonate. The organic fraction was dried over sodium sulphate, filtered and concentrated. The diastereoisomers were separated by preparative HPLC to give the (R,R) product (23 mg) (Example 82) and the (S,R) isomer (Example 81) in free base form. Each free base was then treated with sufficient hydrochloric acid to form the di-hydrochloride salt.

Example 87

(3R)—N-(2-Aminoethyl)-3-{[(1R)-1-(3-benzoyl-4-chloro-2-fluorophenyl)propyl]-amino}butanamide To (2-{(S)-3-[(R)-1-(3-benzoyl-4-chloro-2-fluoro-phenyl)-propylamino]-butyrylamino}-ethyl)-carbamic acid tert-butyl ester (13 mg, 0.025 mmol) residue was added hydrogen chloride in ethyl acetate (2N, 2 ml). The mixture was stood at room temperature for 20 minutes, diethyl ether was added to precipitate solids. These were isolated by filtration and dried in a vacuum oven to furnish the desired material as a white solid Example 113

3-{[(1R)-1-{4-Chloro-2-fluoro-3-[(pyridin-3-yl)carbonyl]phenyl}propyl]amino}-3-methylbutanamide Step 1 Example 2 (0.582 g, 1.66 mmol) converted to the free-base by partition between DCM, 1M NaOH solution and brine the phases were separated and the aqueous layer was extracted into DCM (×2). Combined organic extracts were dried (Na2SO4), filtered and concentrated. A mixture of the residue and 3,3-dimethylacrylic acid (0.166 g, 1.66 mmol) in pyridine (0.83 mL), under nitrogen was stirred at 130° C. for 4 days before it was concentrated. Preparative HPLC gave 3-{[(1R)-1-{4-chloro-2-fluoro-3-[(pyridin-3-yl)carbonyl]phenyl}propyl]amino}-3-methylbutanoic acid, 0.023 g, 3%. MS: [M+H]+ 393.

Step 2 To a stirred solution of 3-{[(1R)-1-{4-chloro-2-fluoro-3-[(pyridin-3-yl)carbonyl]phenyl}-propyl]amino}-3-methylbutanoic acid (0.023 g, 0.0585 mmol), iPr2NEt (0.0714 mL, 0.41 mmol) and ammonium chloride (0.0157 g, 0.293 mmol) in DMF (0.351 mL) at 0° C. was added HATU (0.0334 g, 0.0878 mmol). The mixture was allowed to warm to room temperature and stirred for 1 hour. The mixture was poured into EtOAc and washed with water (×3). The organic extract was dried (Na2SO4), filtered and concentrated. The material was converted to the HCl salt and triturated with EtOAc providing 3-{[(1R)-1-{4-chloro-2-fluoro-3-[(pyridin-3-yl)carbonyl]phenyl}propyl]amino}-3-methylbutanamide, 0.013 g, 52%.

Example 131 and Example 132

1-[(1R)-1-{[(1R)-1-{4-chloro-2-fluoro-3-[(pyridin-3-yl)carbonyl]phenyl}-propyl]-amino}ethyl]-cyclopropane-1-carboxamide (Example 131) and 1-[(1S)-1-{[(1R)-1-{4-chloro-2-fluoro-3-[-(pyridin-3-yl)carbonyl]phenyl}propyl]amino}ethyl]cyclopropane-1-carboxamide (Example 132)

Step 1 A stirred suspension of tert-butyl acetoacetate (2.1 mL, 12.6 mmol), 1,2-dibromoethane (1.14 mL, 13.3 mmol) and potassium carbonate (3.49 g, 25.3 mmol) in acetone (50.6 mL) was heated to 55° C. over a weekend. Upon cooling the mixture was diluted with Et2O and washed with water (×2). The organic phase was dried (Na2SO4), filtered and concentrated. Biotage column (40+M) eluting with a gradient of 0% Et2O/petrol to 20% Et2O/petrol gave tert-butyl 1-acetylcyclopropane-1-carboxylate, 0.78 g, 29%. $^1$H NMR (400 MHz, CDCl$_3$): 2.46 (3H, s), 1.51 (9H, s), 1.43-1.38 (4H, m).

Step 2 Example 2 (0.325 g, 1.08 mmol) converted to the free-base by partition between DCM, 1M NaOH solution and brine the phases were separated and the aqueous layer was extracted into DCM (×2). Combined organic extracts were dried (Na2SO4), filtered and concentrated. A mixture of the residue, tert-butyl 1-acetylcyclopropane-1-carboxylate (0.199 g, 1.08 mmol) in acetic acid (0.0927 mL) and 1,2-dichloroethane (5.4 mL) was stirred at room temperature for 20 minutes before sodium triacetoxyborohydride (0.572 g, 2.7 mmol) was added and the mixture was stirred at room temperature overnight. Saturated NaHCO3 solution was added the phases were separated and the aqueous phase was extracted into DCM (×2). Combined organic extracts were dried (Na2SO4), filtered and concentrated. Biotage column (25+M) eluting with a gradient of 10% EtOAc/petrol to 60% EtOAc gave tert-butyl 1-(1-{[(1R)-1-{4-chloro-2-fluoro-3-[(pyridin-3-yl)carbonyl]phenyl}propyl]amino}ethyl)cyclopropane-1-carboxylate, 0.234 g, 47%. MS: [M+H]+461.2.

Step 3 A solution of tert-butyl 1-0-{[(1R)-1-{4-chloro-2-fluoro-3-[(pyridin-3-yl)carbonyl]phenyl}-propyl]amino}ethyl)cyclopropane-1-carboxylate (0.234 g, 0.508 mmol) in TFA (0.711 mL) and DCM (3.55 mL) was stirred at room temperature for 3 hours, then left to stand at 5° C. over a weekend before the mixture was concentrated providing 1-(1-{[(1R)-1-{4-chloro-2-fluoro-3-[(pyridin-3-yl)carbonyl]phenyl}propyl]amino}ethyl)-cyclopropane-1-carboxylic acid, 0.17 g, 83%. MS: [M−NH2]+391.

Step 4 1-[(1R)-1-{[(1R)-1-{4-chloro-2-fluoro-3-[(pyridin-3-yl)carbonyl]phenyl}-propyl]-amino}ethyl]-cyclopropane-1-carboxamide (Example 131) and 1-[(1S)-1-{[(1R)-1-{4-chloro-2-fluoro-3-[(pyridin-3-yl)carbonyl]phenyl}propyl]amino}ethyl]cyclopropane-1-carboxamide (Example 132) were prepared from 1-(1-{[(1R)-1-{4-chloro-2-fluoro-3-[(pyridin-3-yl)carbonyl]phenyl}-propyl]amino}ethyl)cyclopropane-1-carboxylic acid according to Example 81, Step 3.

Example 138

(3S)-3-{[(1R)-1-{3-[(5-aminopyrazin-2-yl)carbonyl]-4-chloro-2-fluorophenyl}propyl]-amino}butanamide Prepared according to Example 82 using Example 3. The (semi-) preparative stereoselective chromatography was carried out using a pre-packed Chiralpak AD-H column (250 mm×20 mm I.D., $d_p$=5 µm), produced by Chiral Technologies Europe (IIIkirch, France). Mobile phase elution was made isocratically using n-hepane/2-propanol (80/20 v/v) at a flow of 19 ml/min.

Example 144

4-({3-[(1R)-1-{[(2S)-1-Carbamoylpropan-2-yl]amino}propyl]-6-chloro-2-fluorophenyl}carbonyl)-benzoic acid To (3S)-3-{[(1R)-1-{4-chloro-3-[(4-cyanophenyl)carbonyl]-2-fluorophenyl}propyl]amino}-butanamide (compound of Example 91) (0.024 g, 0.06 mmol) added EtOAc (0.1 ml) and 6M HCl (0.1 ml) stirred at ambient 48 hours, evaporated down, residue dissolved in DMSO (0.1 ml) treated with K2CO3 (spatula end) stirred ambient for 16 hours, some primary amide product visible, further DMSO (0.1 ml) and 2M NaOH (0.2 ml) added stirred ambient 16 hours to give predominantly the acid. Reaction products purified by Prep HPLC to give 4-({3-[(1R)-1-{[(2S)-1-carbamoylpropan-2-yl]amino}propyl]-6-chloro-2-fluorophenyl}carbonyl)-benzoic acid (0.09 g).

Example 146

4-({3-[(1R)-1-{[(2S)-1-Carbamoylpropan-2-yl]amino}propyl]-6-chloro-2-fluorophenyl}carbonyl)-benzamide To (3S)-3-{[(1R)-1-{4-chloro-3-[(4-cyanophenyl)carbonyl]-2-fluorophenyl}propyl]amino}-butanamide (compound of Example 91) (0.016 g, 0.04 mmol) added DMSO (1 ml) treated with $K_2CO_3$ (0.027 g, 0.2 mmol) stirred ambient for 2 hours, further $K_2CO_3$ (0.027 g, 0.2 mmol) added left stirring ambient for 16 hours. Reaction purified by Prep HPLC to give 4-({3-[(1R)-1-{[(2S)-1-carbamoylpropan-2-yl]amino}propyl]-6-chloro-2-fluorophenyl}carbonyl)-benzamide (1 mg).

Example 154

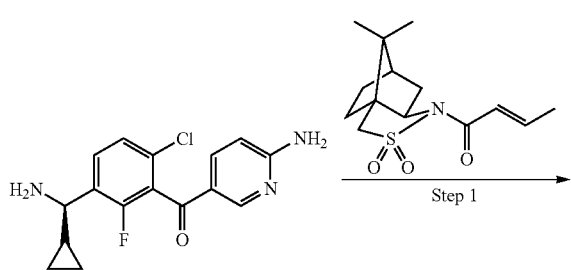

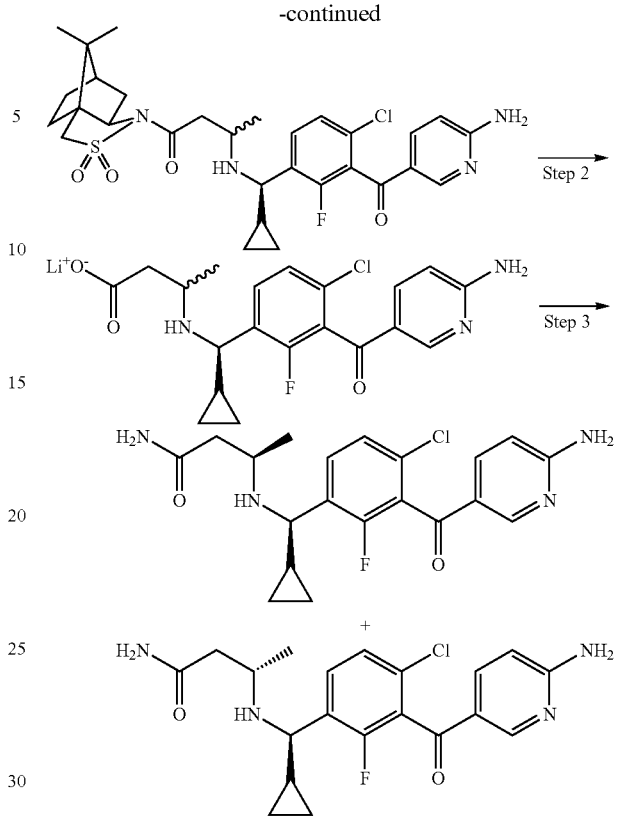

Step 1 Example 47 (5-({3-[(R)-amino(cyclopropyl)methyl]-6-chloro-2-fluorophenyl}carbonyl)pyridin-2-amine) hydrochloride was partitioned between ethyl acetate and sodium bicarbonate solution. The organic liquors were taken, dried (MgSO₄) and concentrated to furnish the free base as an oil (3.82 g, 12 mmol). To this oil was added tetrahydrofuran (20 ml), (N-crotonyl)-(2R)-bornane-10,2-sultam (4.1 g, 14.4 mmol) and lithium perchlorate (1.78 g, 16.8 mmol). The mixture was stirred at room temperature for 36 hours. Additional sultam (0.2 g) and lithium perchlorate (90 mg) were added and the reaction was stirred at room temperature for a further 3 days. Ethyl acetate was then added and the mixture was washed with water and brine, dried (MgSO₄) and concentrated. The desired product was obtained as a foam (7.2 g). [M+H] 603

Step 2 The product from Step 1 (7.2 g, 12 mmol) was dissolved in a tetrahydrofuran/water mixture (4:1, 200 ml) and lithium hydroxide (0.76 g, 18 mmol) was added. The mixture was stirred at room temperature for 48 hours before the mixture was concentrated to dryness. The crude lithium salt was used without further purification. {M+H} 406

Step 3 To the crude product from Step 2 (theory 12 mmol) dissolved in N,N-dimethylformamide (140 ml) and cooled to 0° C. was added ethyldiisopropylamine (25 ml, 144 mmol), ammonium chloride (3.19 g, 60 mmol) and O-(7-Azabenzotriazol-1-yl)-N,N,N',N'-tetramethyluronium hexafluorophosphate (HATU, 6.81 g, 18 mmol). The mixture was stirred at this temperature for 1 hour before warming to room temperature. Due to incomplete reaction, additional reagents were added (5%) and the mixture was stirred until no further change observed by LCMS. Water was then added and the mixture was extracted twice with ethyl acetate. The combined organic liquors were washed with water and brine, dried (MgSO₄) and concentrated. Further product was obtained by re-extracting the aqueous fractions. The crude material was purified first on silica eluting with 0-20% methanol/ethyl acetate furnishing the diastereoisomeric mixture of products (3.61 g). This mixture was separated by chiral preparative chromatography using a pre-packed Chiralpak AD-H column (250 mm×20 mm I.D., $d_p$=5 μm), produced by Chiral Technologies Europe (Illkirch, France). Mobile phase elution was made isocratically using n-heptane/2-propanol (80/20 v/v) at a flow of 19 ml/min furnishing 1.7 g of the S,R-diasteroisomer (Example 154)

Example 162

3-{[(1R)-1-{4-Chloro-2-fluoro-3-[(pyridin-3-yl)carbonyl]phenyl}propyl]amino}propanamide (1R)-1-{4-chloro-2-fluoro-3-[(pyridin-3-yl)carbonyl]phenyl}propan-1-amine (0.1 g, 0.34 mmol) and 3-bromopropionamide (0.052 g, 0.34 mmol) heated in a microwave tube at 120° C., 150 W for 30 minutes. Reaction purified by Prep HPLC using Basic 0A3 system, followed by silica column (Biotage SP4) eluting 0-10% MeOH in EtOAc to give 3-{[(1R)-1-{4-chloro-2-fluoro-3-[(pyridin-3-yl)carbonyl]phenyl}propyl]amino}propanamide (0.001 g).

Example 163

2-{[(1R)-1-{4-Chloro-2-fluoro-3-[(pyridin-3-yl)carbonyl]phenyl}propyl]amino}ethan-1-ol To (3-{(R)-1-[2-(tert-Butyl-dimethyl-silanyloxy)-ethylamino]-propyl}-6-chloro-2-fluoro-phenyl)-pyridin-3-yl-methanone (0.176 g, 0.39 mmol) in THF (3 ml) at 0° C. added TBAF [1M] (90.43 ml, 0.43 mmol) dropwise stirred at 0° C. for 1 hour, diluted with water, THF evaporated off and reaction mixture extracted with DCM. The organic phase was separated and dried (Na$_2$SO4), filtered and concentrated, purified by Prep HPLC to give 2-{[(1R)-1-{4-chloro-2-fluoro-3-[(pyridin-3-yl)carbonyl]phenyl}propyl]amino}ethan-1-ol (0.129 g).

Example 164

2-{[(1R)-1-{4-Chloro-2-fluoro-3-[(pyridin-3-yl)carbonyl]phenyl}propyl]amino}-acetamide Example 2 hydrochloride (110 mg, 0.55 mmol) was partitioned between DCM (15 mL) and water (15 mL) with enough NaOH (5M) added to bring the pH to ~12. Organic layer was isolated by phase separator and concentrated. The residue was dissolved in DCE (2 mL) and bromoacetamide (83 mg, 0.60 mmol, 1.1 eq.) was added. The reaction mixture was heated in the microwave at 100 degC for 3 h. Partitioned between DCM (10 mL) and water (10 mL) and the organic phase washed with brine (10 mL) before it was dried (MgSO4), filtered and concentrated to give crude material (~174 mg). The crude was purified by preparative LC-MS, followed by trituration with Et$_2$O to give 2-{[(1R)-1-{4-chloro-2-fluoro-3-[(pyridin-3-yl)carbonyl]phenyl}propyl]amino}-acetamide (2.0 mg, 1% yield).

Example 167

3-{[(1R)-1-(3-Benzoyl-4-chloro-2-fluorophenyl)propyl]amino}-propanamide

To (1R)-1-(3-benzoyl-4-chloro-2-fluorophenyl)propan-1-amine (0.1 g, 0.34 mmol) in a microwave tube was added ethanol (0.4 ml) water (0.4 ml), acrylamide (0.025 g, 0.35 mmol) and MnCl$_2$ (0.056 g, 0.28 mmol) heated 100° C., 200 W for a total of 1 hour. The reaction was diluted with MeOH and filtered and filtrate evaporated then purified by Prep HPLC to give 3-{[(1R)-1-(3-benzoyl-4-chloro-2-fluorophenyl)propyl]amino}-propanamide (0.047 g).

Example 168

1-({[(1R)-1-{4-Chloro-2-fluoro-3-[(pyridin-3-yl)carbonyl]phenyl}propyl]amino}methyl)-cyclopropane-1-carboxamide Step 1 A stirred suspension of tert-butyl ethyl malonate (2.01 mL, 10.6 mmol), 1,2-dibromoethane (1.01 mL, 11.7 mmol), potassium carbonate (3.67 g, 26.6 mmol) and 1-butyl-3-methylimidazolium tetrafluoroborate (0.198 mL, 1.06 mmol) in DMF (26.6 mL) was heated to 55° C. for 20 hours. Upon cooling the mixture was filtered and the solid residue was washed with Et$_2$O. The mixture was diluted with Et$_2$O and washed with water (×2). The organic phase was dried (Na2SO4), filtered and concentrated giving 1-tert-butyl 1-ethyl cyclopropane-1,1-dicarboxylate which was used without further purification, 2.24 g.

Step 2 To a stirred solution of 1-tert-butyl 1-ethyl cyclopropane-1,1-dicarboxylate (0.5 g, 2.33 mmol) in THF (11.7 mL) at −78° C. was added lithium tri-tert-butoxyaluminum hydride solution (11.7 mL, 11.7 mmol) dropwise. The mixture was warmed to room temperature and stirred overnight before it was quenched at 0° C. by the addition of a saturated solution of potassium sodium tartrate. EtOAc was added the phases were separated and the aqueous phase was extracted into EtOAc (×2). Combined organic extracts were dried (Na2SO4), filtered and concentrated providing tert-butyl 1-(hydroxymethyl)-cyclopropane-1-carboxylate which was used without further purification, 0.438 g.

Step 3 To a stirred suspension of tert-butyl 1-(hydroxymethyl)cyclopropane-1-carboxylate (0.16 g, 0.929 mmol) and sodium hydrogen carbonate (0.312 g, 3.72 mmol) in DCM (5.57 mL) at room temperature was added Dess-Martin periodinane (0.788 g, 1.86 mmol). The mixture was stirred at room temperature for 1 hour before it was quenched by the addition of a 1:1 mixture of saturated NaHCO$_3$ solution and saturated Na$_2$S$_2$O$_3$ solution. After stirring for an additional 1 hour the phases were separated and the aqueous phase was extracted into DCM (×2). Combined organic extracts were dried (Na$_2$SO$_4$), filtered and concentrated giving tert-butyl 1-formylcyclopropane-1-carboxylate which was used without further purification, 0.141 g.

Step 4 Example 2 (0.25 g, 0.83 mmol) was converted to the free-base by partition between DCM, 1M NaOH solution and brine the phases were separated and the aqueous layer was extracted into DCM (×2). Combined organic extracts were dried (Na$_2$SO$_4$), filtered and concentrated. A mixture of the residue, tert-butyl 1-formylcyclopropane-1-carboxylate (0.141 g, 0.83 mmol) in acetic acid (0.0713 mL) and 1,2-dichloroethane (4.15 mL) was stirred at room temperature for 20 minutes before sodium triacetoxyborohydride (0.44 g, 2.08 mmol) was added and the mixture was stirred at room temperature overnight. Saturated NaHCO$_3$ solution was added the phases were separated and the aqueous phase was extracted into DCM (×2). Combined organic extracts were dried (Na$_2$SO$_4$), filtered and concentrated. Biotage column (25+M) eluting with a gradient of 20% EtOAc/petrol to 100% EtOAc gave tert-butyl 1-({[(1R)-1-{4-chloro-2-fluoro-3-[(pyridin-3-yl)carbonyl]phenyl}propyl]amino}methyl)cyclopropane-1-carboxylate, 0.215 g, 58%. MS: [M+H]+447.2.

Step 5 1-({[(1R)-1-{4-Chloro-2-fluoro-3-[(pyridin-3-yl)carbonyl]phenyl}propyl]amino}methyl)-cyclopropane-1-carboxylic acid was prepared from tert-butyl 1-({[(1R)-1-{4-chloro-2-fluoro-3-[(pyridin-3-yl)carbonyl]phenyl}propyl]amino}methyl)cyclopropane-1-carboxylate according to Example 131, Step 3, 0.17 g.

Step 6 1-({[(1R)-1-{4-chloro-2-fluoro-3-[(pyridin-3-yl)carbonyl]phenyl}propyl]amino}methyl)-cyclopropane-1-carboxamide was prepared from 1-({[(1R)-1-{4-chloro-2-fluoro-3-[(pyridin-3-yl)carbonyl]phenyl}propyl]amino}methyl)cyclopropane-1-carboxylic acid according to Example 81, Step 3.

Example 172

3-{(R)-1-[4-Chloro-2-fluoro-3-(pyridine-3-carbonyl)-phenyl]-propylamino}-2,2-dimethyl-propionamide Step 1 To a solution of diisopropylamine (2.94 mL, 20.8 mmol) in THF (20 mL) under nitrogen at 0° C. was added nBuLi (2.5M in hexanes, 8.32 mL, 20.8 mmol, 1 eq.) and the solution stirred at 0° C. for 30 min. The solution was cooled to −78° C. and then a solution of isobutylisobutyrate (3.49 mL, 20.8 mmol) in THF (6 mL) was added dropwise and then the reaction stirred at −78° C. for 1 h. TMS-Cl (3.19 mL, 25 mmol) was then added dropwise and the reaction allowed to warm to room temperature over 3 h. The reaction was quenched with ice-water (20 mL) and EtOAc (20 mL) was added. The organic phase was washed with water (10 mL) and then brine (10 mL) before it was dried (MgSO4), filtered and concentrated to give (1-isobutoxy-2-methyl-propenyloxy)-trimethyl-silane (3.5 g) used crude in the next reaction.

Step 2 To a solution of DMF (2.86 mL, 37 mmol, 8 eq.) in DCM (5 mL) at 0° C. was added POCl$_3$ (0.84 mL, 9.2 mmol, 2 eq.) in DCM (3 mL) under nitrogen and then the reaction stirred for 30 min. (1-isobutoxy-2-methyl-propenyloxy)-trimethyl-silane (1 g, 4.62 mmol, 1 eq.) was then added and the reaction stirred for 18 h. The mixture was diluted with DCM (15 mL) and then washed with sodium bicarbonate (2×15 mL) and brine (15 mL) before it was dried (MgSO4), filtered and concentrated to give 2,2-dimethyl-3-oxo-propionic acid isobutyl ester (800 mg)—used crude in subsequent reactions Step 3 Example 2 (379 mg, 1.15 mmol) was partitioned between DCE (8 mL) and water (5 mL) which was basified to pH12 with 5M NaOH. The organic phase was isolated by phase separator and then 2,2-Dimethyl-3-oxo-propionic acid isobutyl ester (396 mg, 2.3 mmol, 2 eq.), NaBH(OAc)$_3$ (487 mg, 2.3 mmol, 2 eq.) and AcOH (132 µL, 2.3 mmol, 2 eq.) was added and the reaction stirred for 3 h. Partitioned between DCM (15 mL) and water (10 mL) basified to pH 10 with addition of 5M NaOH. Organic phase was then washed with brine (10 mL) before it was dried (MgSO$_4$), filtered and concentrated to give crude 3-{(R)-1-[4-Chloro-2-fluoro-3-(pyridine-3-carbonyl)-phenyl]-propylamino}-2,2-dimethyl-propionic acid isobutyl ester (0.5 g, assume 1.15 mmol for next reaction). Used crude in next reaction. LCMS of reaction mixture before work up −[MH]=449, 73%.

Step 4 A mixture of crude 3-{(R)-1-[4-Chloro-2-fluoro-3-(pyridine-3-carbonyl)-phenyl]-propylamino}-2,2-dimethyl-propionic acid isobutyl ester (assumed 1.15 mmol), NaOH (aq., 5M, 230 µL. 1.15 mmol) and THF (3 mL) was stirred at room temperature overnight. Only partial reaction. A further 1 eq. of NaOH was added, stirred for 8 h, and then another 2 eq. NaOH added and stirred overnight. LCMS: [MH]+ 393, 73%. Concentrated to give crude 3-{(R)-1-[4-Chloro-2-fluoro-3-(pyridine-3-carbonyl)-phenyl]-propylamino}-2,2-dimethyl-propionic acid and used directly in next reaction.

Step 5 To a solution of crude 3-{(R)-1-[4-Chloro-2-fluoro-3-(pyridine-3-carbonyl)-phenyl]-propylamino}-2,2-dimethyl-propionic acid (1.15 mmol) in DMF (7 mL) was added ammonium chloride (315 mg, 5.8 mmol, 5 eq), DIPEA (1.41 mL, 8.1 mmol, 7 eq.) and then HATU (661 mg, 1.74 mmol, 1.5 eq.) and the reaction stirred for 18 h. The mixture was partitioned between EtOAc (20 mL) and water (20 mL). The aqueous was extracted with further EtOAc (20 mL) and then the combined organic phase washed with water (3×20 mL) and brine (20 mL) before it was dried (MgSO$_4$), filtered and concentrated. Purified by prepHPLC, basic conditions, and then concentrated. Dissolved in DCM and 1.1 eq. 2 M HCl in Et$_2$O was added. Concentrated and dried in a vacuum oven to give 3-{(R)-1-[4-Chloro-2-fluoro-3-(pyridine-3-carbonyl)-phenyl]-propylamino}-2,2-dimethyl-propionamide (26 mg, 0.06 mmol).

Example 174

2R)-3-{[(1R)-1-{4-chloro-2-fluoro-3-[(pyridin-3-yl)carbonyl]phenyl}-propyl]amino}-2-methylpropanamide HCl (1:1

To 3-{(R)-1-[4-Chloro-2-fluoro-3-(pyridine-3-carbonyl)-phenyl]-propylamino}-2-methyl-propionic acid ethyl ester (0.22 g, 0.54 mmol) in THF: water [4:1] 95 ml) added lithium hydroxide (0.032 g, 1.35 mmol) stirred at ambient for 48 hours, evaporated to dryness, MS: [M+H] 379. To the crude reaction mixture was added DMF(6 ml), ammonium chloride (0.145 g, 2.65 mmol), diisopropylethylamine (1.13 ml, 6.47 mmol) and HATU (0.309, 0.8 mmol) stirred at ambient for 16 hours. Reaction diluted with water and extracted with EtOAc, The organic phase was separated and dried (Na2SO4), filtered and concentrated, purified by Prep HPLC to give the (R,R) product (0.02 g).

Example 179

2-{11-(3-Benzoyl-4-chloro-2-fluorophenyl)-propyl]amino}-2-methylpropan-1-ol

Step 1 Intermediate 11 (1.95 g; 7.4 mmol) was dissolved in dry THF (30 ml) under N$_2$ then cooled to 0° C. To this was added dropwise a solution of 3M ethylmagnesium bromide (2.7 ml; 1.1 equiv.) then allowed to warm to room temperature. Starting material was still present so a further 1 ml of 3M ethylmagnesium bromide solution was added and stirred for 30 minutes. The reaction was treated with brine (30 ml) then extracted with EtOAc (×2). The EtOAc layer was separated, dried (Na$_2$SO$_4$), filtered and evaporated. The crude material was purified by flash column chromatography, with gradient elution from 0 to 50% EtOAc/petroleum ether. Product containing fractions were combined and evaporated to give 760 mg of [6-chloro-2-fluoro-3-(1-hydroxy-propyl)-phenyl]-phenyl-methanone. $^1$H NMR (400 MHz, DMSO-d6): 7.82-7.54 (5H, m), 7.50 (1H, d), 7.44-7.18 (1H, m), 5.48 (1H, d), 4.80-4.70 (1H, m), 1.72-1.54 (2H, m), 0.92-0.81 (3H, m).

Step 2 [6-Chloro-2-fluoro-3-(1-hydroxy-propyl)-phenyl]-phenyl-methanone (760 mg; 2.6 mmol) was dissolved in DCM (20 ml), treated with triphenylphosphine (1.095 g; 1.6 equiv.) and carbon tetrabromide (1.275 g; 1.5 equiv.) and stirred at room temperature overnight. The reaction mixture was evaporated then purified by flash column chromatography eluting with 0 to 20% EtOAc/petroleum ether. Product containing fractions were combined and evaporated to give 650 mg of [3-(1-Bromo-propyl)-6-chloro-2-fluoro-phenyl]-phenyl-methanone as a colourless gum. $^1$H NMR (400 MHz, DMSO-d6): 7.89-7.69 (4H, m), 7.69-7.54 (3H, m), 5.34 (1H, dd), 2.38-2.12 (2H, m), 0.99 (3H, t).

Step 3 A solution of [3-(1-bromo-propyl)-6-chloro-2-fluoro-phenyl]-phenyl-methanone (50 mg; 0.14 mmol) and 2-methyl-2-aminopropanol (30 µl; 2 equiv.) in DMF (1 ml) was stirred at room temperature for 72 hours then partitioned between Et$_2$O and brine. The Et$_2$O later was separated, dried (Na$_2$SO$_4$), filtered and evaporated. The crude material was purified by flash column chromatography using gradient elution from 0-10% MeOH/DCM. Product containing fractions were combined, treated with saturated HCl/EtOAc then evaporated. The residue was triturated with Et$_2$O, the solid collected by filtration, washed with Et$_2$O and sucked dry to give 55 mg of 2-{[1-(3-benzoyl-4-chloro-2-fluorophenyl)-propyl]amino}-2-methylpropan-1-ol as a white solid.

Example 180

3-{[(1R)-1-{3-[(6-Aminopyridin-3-yl)carbonyl]-4-chloro-2-fluorophenyl}propyl]amino}propanamide Example 1 (200 mg, 0.58 mmol) was partitioned between DCM (5 mL) and water (3 mL) basified to pH 12 with 5M NaOH. The organic phase was isolated by phase separator and blown down into a microwave vial. Acrylamide (41 mg, 0.58 mmol, 1 eq.) and MnCl$_2$.4H$_2$O (57 mg, 0.29 mmol, 0.5 eq.) was heated in ethanol (0.9 mL) and water (0.1 mL) in the microwave at 100 degC for 30 min. Only partial reaction, so further acrylamide and MnCl$_2$ (same amounts) were added and the reaction heated for 30 min at 100° C. Still not complete so reaction heated as is for another 30 min at 100° C. The mixture then partitioned between EtOAc (15 mL) and water (10 mL) (plus drop of 5M NaOH) and then the aqueous extracted with further EtOAc (15 mL). Combined organics were washed with water (10 mL) and brine (10 mL) and then dried (MgSO+), filtered and concentrated. Purified by chiral HPLC normal phase, eluting EtOH and heptane. Concentrated and then dissolved in DCM (2 mL) and 1.1 eq. 2M HCl in Et$_2$O added. Concentrated and dried in a vacuum oven to give 3-{[(1R)-1-{3-[(6-aminopyridin-3-yl)carbonyl]-4-chloro-2-fluorophenyl}propyl]amino}-propanamide (56 mg, 0.15 mmol, 25%) as an HCl salt and white solid.

Example 183

3-{[(1R)-1-{3-[(5-Aminopyrazin-2-yl)carbonyl]-4-chloro-2-fluorophenyl}propyl]amino}propanamide A suspension of Example 3 (0.15 g, 0.486 mmol), manganese(II) chloride tetrahydrate (0.0721 g, 0.364 mmol) and acrylamide (0.0518 g, 0.729 mmol) in ethanol (0.632 mL) and water (0.158 mL) was heated in the microwave at 100° C. for 2.5 hours. The mixture was filtered and concentrated. The residue was partitioned between EtOAc and water, the phases separated and the organic phase was dried (Na$_2$SO$_4$), filtered and concentrated. The residue was purified by preparative HPLC providing 3-{[(1R)-1-{3-[(5-aminopyrazin-2-yl)carbonyl]-4-chloro-2-fluorophenyl}propyl]-amino}propanamide which was converted to the HCl salt, 0.05 g, 25%.

Example 184

1-[1-(3-Benzoyl-4-chloro-2-fluorophenyl)-propylamino]-cyclopropanecarboxylic acid amide.HCl Step 1 A solution of [3-(1-bromopropyl)-6-chloro-2-fluorophenyl]-phenyl-methanone (75 mg; 0.14 mmol), triethylamine (90 µl; 2.5 equiv.) and 1-amino-cyclopropane-1-carboxylic acid ethyl ester. HCl (30 mg; 1.2 equiv.) in DCM (3 ml) was stirred at room temperature for 72 hours then partitioned between EtOAc and brine. The EtOAc later was separated, dried (Na$_2$SO$_4$), filtered and evaporated. The crude material was purified by flash column chromatography using gradient elution from 0-50% EtOAc/petroleum ether. Product containing fractions were combined and evaporated to give 30 mg of 1-[1-(3-benzoyl-4-chloro-2-fluorophenyl)-propylamino]-cyclopropanecarboxylic acid ethyl ester as a white solid.

Step 2 A solution of 1-[1-(3-benzoyl-4-chloro-2-fluorophenyl)-propylamino]-cyclopropane-carboxylic acid ethyl ester (30 mg) in MeOH/2M NaOH (2 ml/2 ml) was heated at 45° C. overnight. The reaction was cooled, evaporated, diluted with saturated NH$_4$Cl solution then extracted with EtOAc (×2). The combined organics were dried (Na$_2$SO$_4$), filtered and evaporated and used without further purification.

Step 3 The crude acid (from step 2) was dissolve in DMF (2 ml) then treated with NH$_4$Cl (13 mg; 3 equiv.), NEt$_3$ (35 µl; 3 equiv.), HOBt (13 mg; 1.2 equiv.) and EDC (19 mg; 1.2 equiv.) then stirred at room temperature overnight. The reaction was evaporated and partitioned between EtOAc and saturated NaHCO$_3$ solution. The EtOAc later was separated, dried (Na$_2$SO$_4$), filtered and evaporated. The crude material was purified by flash column chromatography using gradient elution from 0-1000% EtOAc/petroleum ether. Product containing fractions were combined, treated with saturated HCl/EtOAc then evaporated. The residue was triturated with Et$_2$O, the solid collected by filtration, washed with Et$_2$O and sucked dry to give 22 mg of 1-[1-(3-benzoyl-4-chloro-2-fluorophenyl)-propylamino]-cyclopropanecarboxylic acid amide.HCl as a white solid.

Example 193

[3-(1-Amino-propyl)-6-chloro-2-fluoro-phenyl]-(4-hydroxy-phenyl)-methanone

Step 1-2 Intermediate 2 was reacted with n-butyl lithium and 4-(benzyloxy)benzaldehyde following the methods described in Steps 1 and 2 of the synthesis for Example 51 to give tert-butyl N-[(1R)-1-(3-{[4-(benzyloxy)phenyl]carbonyl}-4-chloro-2-fluorophenyl)propyl]-carbamate. [M–H]$^-$ 496

Step 3 Boron trichloride (1M in dichloromethane, 10 ml) was added to a solution of tert-butyl N-[(1R)-1-(3-{[4-(benzyloxy)phenyl]carbonyl}-4-chloro-2-fluorophenyl)propyl]carbamate (1.53 g, 3.07 mmol) in dichloromethane (50 ml) in an ice/water bath. The mixture was stirred for 30 minutes then the reaction mixture was poured onto ice/water. The aqueous was basified with saturated sodium bicarbonate and then extracted with dichloromethane (×2). The organic liquors were concentrated and then treated with 2N hydrochloric acid in ethyl acetate to remove protecting group. The residue was concentrated and re-concentrated from ethyl acetate. A solid was obtained from ethyl acetate/diethyl ether mixtures which was isolated by filtration and dried in a vacuum oven to furnish the title compound as an off-white solid (481 mg).

Example 197

6-({3-[(1R)-1-Aminopropyl]-6-chloro-2-fluorophenyl}carbonyl)pyridazin-3-amine

Steps 1 and 2 tert-Butyl N-[(1R)-1-{4-chloro-3-[(6-chloropyridazin-3-yl)carbonyl]-2-fluorophenyl}propyl]carbamate was prepared from intermediate 2 by the method of Example 51 using 6-chloropyridazine-3-carbaldehyde.

Step 3 and 4 6-({3-[(1R)-1-aminopropyl]-6-chloro-2-fluorophenyl}carbonyl)pyridazin-3-amine was prepared according to step 2 and 3 of Example 1.

Example 218

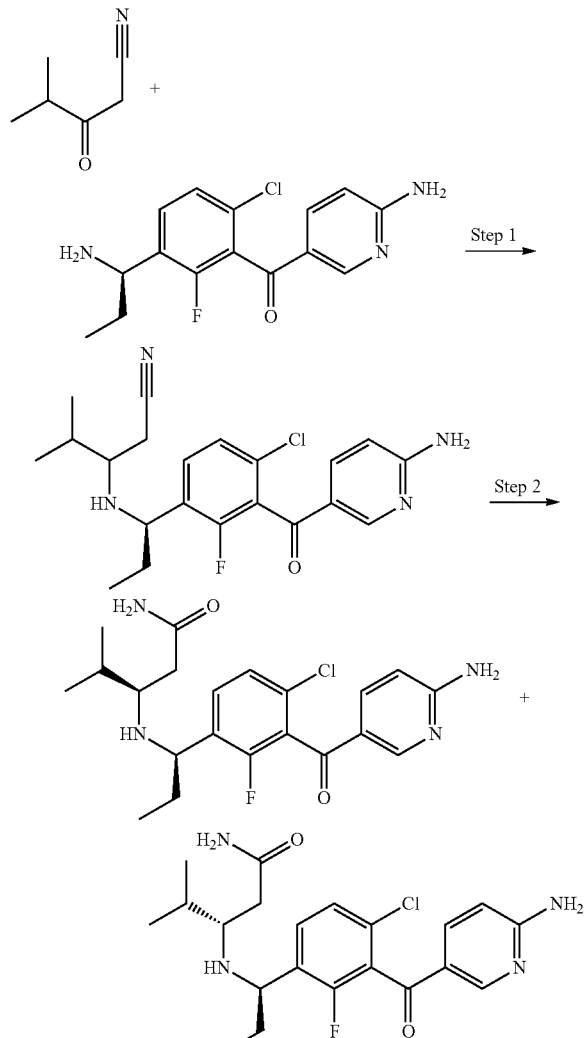

Step 1 Example 1 (0.28 g, 0.91 mmol) converted to the free-base by partition between DCM, 1M NaOH solution and brine the phases were separated and the aqueous layer was extracted into DCM (×2). Combined organic extracts were dried (Na₂SO₄), filtered and concentrated. A mixture of the residue, 4-methyl-3-oxopentanenitrile (0.202 g, 1.82 mmol) in acetic acid (5.46 mL) and 1,2-dichloroethane (1.82 mL) was stirred at 40° C. overnight. Imine formation was incomplete, therefore additional 4-methyl-3-oxopentanenitrile (1 eq) was added and heating was continued for 24 hours, this was repeated an additional 2 times. Sodium borohydride (0.231 g, 1.09 mmol) was added carefully, portionwise and the mixture was stirred overnight. Water was added and the mixture was neutralised by the addition of Na₂CO₃ followed by NaHCO₃. The phases were separated and the aqueous phase was extracted into DCM (×2). The combined organic extracts were dried (Na₂SO₄), filtered and concentrated to give 3-{[(1R)-1-{3-[(6-aminopyridin-3-yl)carbonyl]-4-chloro-2-fluorophenyl}-propyl]amino}-4-methylpentanenitrile which was used without further purification. MS:[M+H]+ 403.

Step 2 To a rapidly stirred solution of crude 3-{[(1R)-1-{3-[(6-aminopyridin-3-yl)carbonyl]-4-chloro-2-fluorophenyl}propyl]amino}-4-methylpentanenitrile (0.911 mmol) in toluene (2.91 mL) and water (0.145 mL) at 0° C. was added sulfuric acid (0.966 mL). The reaction mixture was allowed to warm to room temperature and stirred overnight. The mixture was made neutral by the addition of saturated Na₂CO₃ solution followed by saturated NaHCO₃ solution and was extracted into EtOAc (×2). The combined organic extracts were dried (Na2SO4), filtered and concentrated. The residue was purified by chiral preparative HPLC to give (3R)-3-{[(1R)-1-{3-[(6-aminopyridin-3-yl)carbonyl]-4-chloro-2-fluorophenyl}propyl]amino}-4-methylpentanamide which was converted to the HCl salt, 0.0656 g and (3S)-3-{[(1R)-1-{3-[(6-aminopyridin-3-yl)carbonyl]-4-chloro-2-fluorophenyl}propyl]-amino}-4-methylpentanamide which was also converted to the HCl salt, 0.0259 g.

Example 222

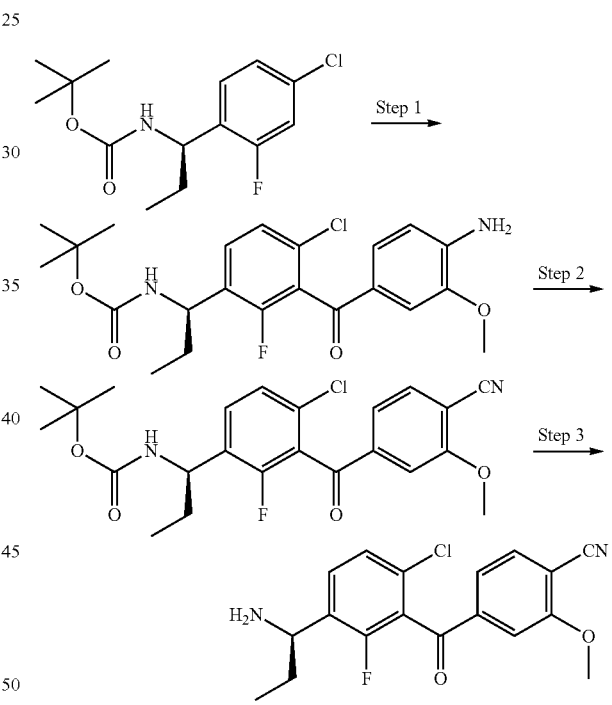

Step 1 As Example 1 step 1 using methyl 4-bromo-3-methoxybenzoate

Step 2 {(R)-1-[3-(4-Bromo-3-methoxy-benzol)-4-chloro-2-fluoro-phenyl]-propyl}-carbamic acid tert-butyl ester (0.1 g, 0.2 mmol) in dry DMF (3 ml) treated with Zinc cyanide (0.012 g, 0.1 mmol), Pd₂(dba)₃ (0.009 g, 0.01 mmol) and dppf (0.013 g, 0.024 mmol), N₂ bubbled through for 2 mins, poly (methylhydrosiloxane) (0.015 ml) added and reaction heated to 100° C. for 1 hour. Reaction cooled to RT, mixture was partitioned between EtOAc) and sat. bicarbonate, the organic phase washed with further bicarbonate then brine, dried (Na₂SO₄), filtered and the solvent removed in vacuo. Purified by silica column to give {(R)-1-[4-Chloro-3-(4-cyano-3-methoxy-benzoyl)-2-fluoro-phenyl]-propyl}-carbamic acid tert-butyl ester (57 mg).

Step 3 As Example 1 step 3

Example 240

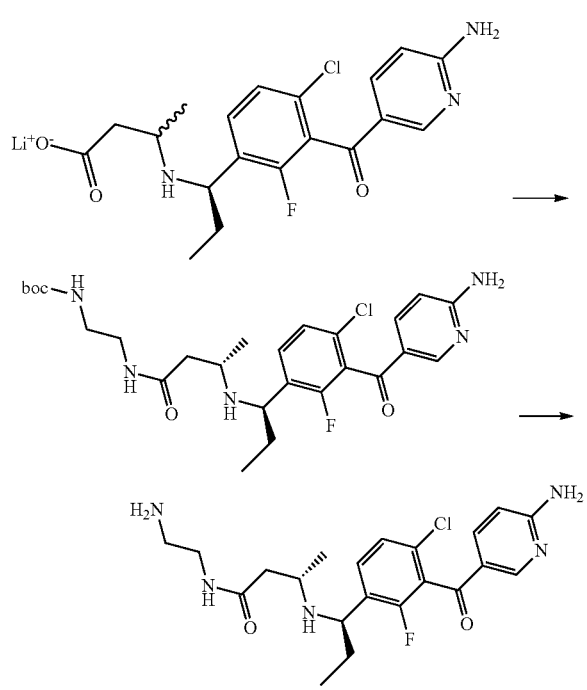

The lithium salt of 3-{(R)-1-[3-(6-amino-pyridine-3-carbonyl)-4-chloro-2-fluoro-phenyl]-propylamino}-butyric acid [as prepared in Example 81 step 2 (0.5 mmol) was dissolved in DMF (7 ml), treated with tert-butyl N-(2-aminoethyl)carbamate (120 mg; 1.5 equiv.) followed by HATU (210 mg; 1.5 equiv.), stirred at room temperature overnight, and then evaporated. The crude mixture was partitioned between EtOAc and saturated NaHCO₃ solution, the two layers were separated then the organic phase was dried (Na₂SO₄), filtered and evaporated. Preparative stereoselective chromatography was carried out using a pre-packed Chiralpak AD-H column (250 mm×20 mm I.D., $d_p$=5 μm), produced by Chiral Technologies Europe (Illkirch, France). Mobile phase elution was made isocratically using n-heptane/2-propanol/diethylamine (80/20/0.2 v/v) at a flow rate of 19 ml/min. The major (fast eluting) diastereoisomer (52 mg) was isolated. The BOC protected amine (51 mg) was dissolved in EtOAc, treated with saturated HCl/EtOAc, stirred at room temperature overnight then evaporated to give the title compound (44 mg) as a white solid. The same procedure was followed also for the other isolated diastereoisomer (slow eluting). BOC deprotection yielded 26 mg of Example 241.

Example 242

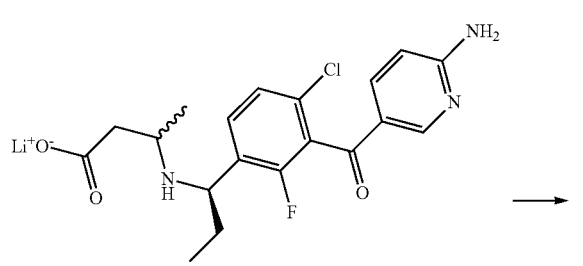

The lithium salt of 3-{(R)-1-[3-(6-amino-pyridine-3-carbonyl)-4-chloro-2-fluoro-phenyl]-propylamino}-butyric acid [as prepared in Example 80 step 2] (0.5 mmol) was dissolved in DMF (7 ml), treated with ethanolamine (45 μl; 1.5 equiv.) followed by HATU (210 mg; 1.5 equiv.), stirred at room temperature overnight then evaporated. The crude mixture was partitioned between EtOAc and saturated NaHCO₃ solution, the two layers were separated then the organic phase was dried (Na₂SO₄), filtered and evaporated. Preparative stereoselective chromatography was carried out using a pre-packed Chiralpak AD-H column (250 mm×20 mm I.D., $d_p$=5 μm), produced by Chiral Technologies Europe (Illkirch, France). Mobile phase elution was made isocratically using n-hepane/2-propanol/diethylamine (80/20/0.2 v/v) at a flow of 19 ml/min. The main diastereoisomer (fast eluting) was dissolved in EtOAc and saturated HCl in EtOAC was added. The resulting solid was collected by filtration, washed with Et₂O and sucked dry to give the title compound (37 mg). The same procedure was followed also for the other slower running diastereoisomer. After formation of the HCl salt, the solid was filtered off to give the minor compound (12 mg).

Examples 250 & 251

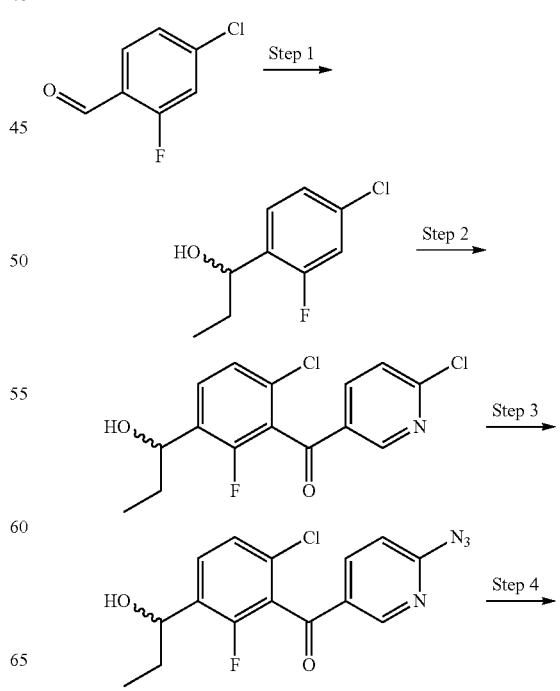

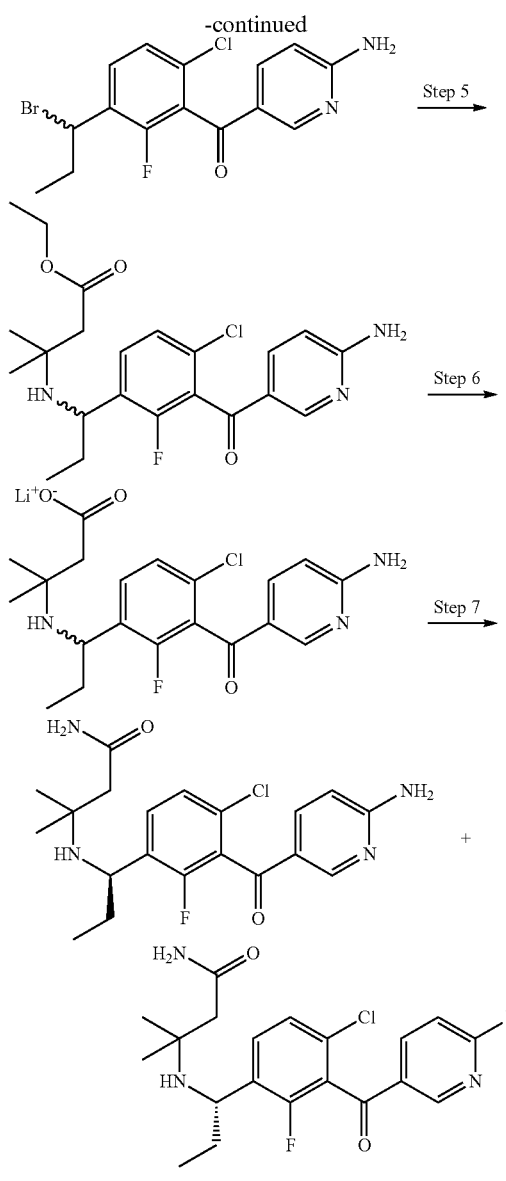

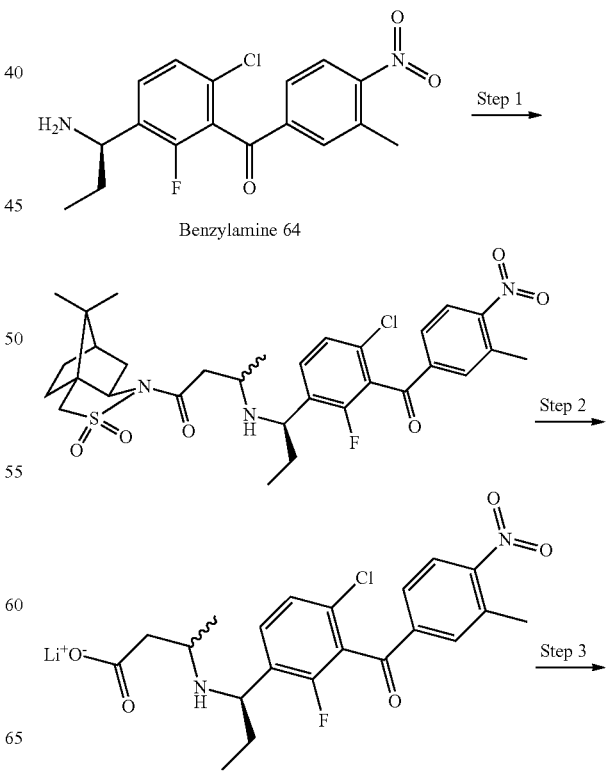

chloro-2-fluorophenyl}propan-1-ol (1.1 g, 3.4 mmol) in dichloromethane (25 ml) and the mixture was stirred at room temperature for 4 hours. Carbon tetrabromide (1.37 g, 4.1 mmol) was then added. After 3 hours the brominated Staudinger intermediate had formed. Dilute hydrochloric acid was added and the mixture was stirred vigorously overnight. No hydrolysis had occurred; the mixture was basified with saturated sodium bicarbonate and the dichloromethane layer was separated. The organic liquors were concentrated and then treated with tetrahydrofuran/2N aqueous hydrochloric acid. After 3 hours, hydrolysis was complete. The mixture was basified with saturated sodium bicarbonate solution and extracted twice with ethyl acetate. The combined organic liquors were washed with brine, dried (MgSO$_4$) and concentrated. The residue was purified on silica eluting with 40-60% ethyl acetate/petrol furnishing the desired material as a yellow oil (0.776 g). [M+H]$^+$ 371

Step 5 A mixture of 5-{[3-(1-bromopropyl)-6-chloro-2-fluorophenyl]carbonyl}pyridin-2-amine (300 mg, 0.81 mmol), ethyl 3-amino-3-methylbutanoate hydrochloride (700 mg, 3.9 mmol), potassium carbonate (1.1 g, 8.1 mmol) and acetonitrile (4 ml) was heated to 60° C. over the weekend. The reaction mixture was allowed to cool, water was added and the mixture was extracted with ethyl acetate (×2). The organic liquors were washed with brine, were dried (MgSO$_4$) and concentrated. The residue was purified on silica eluting with 30-60% ethyl acetate/petrol to give the product as an oil (100 mg). [M+H]$^+$ 436

Step 6 & 7 Hydrolysis and amide formation were conducted as per Example 81 Steps 2 and 3. Separation of enantiomers by prep HPLC gave the 2 products.

Example 259

Step 1 1-(4-chloro-2-fluorophenyl)propan-1-ol was prepared according to Step 1 of Example 179 using 4-chloro-2-fluoro-benzaldehyde in place of Intermediate 11. 1H NMR (400 MHz, CDCl3): 7.43 (1H, t), 7.17 (1H, dd), 7.07 (1H, dd), 4.94 (1H, t), 1.83-1.75 (2H, m), 0.96 (3H, t).

Step 2 1-{4-chloro-3-[(6-chloropyridin-3-yl)carbonyl]-2-fluorophenyl}propan-1-ol prepared according to Example 1 Step 1. [M+H]$^+$ 328

Step 3 To a solution of 1-{4-chloro-3-[(6-chloropyridin-3-yl)carbonyl]-2-fluorophenyl}propan-1-ol (2.624 g, 8.00 mmol) in dimethylformamide (20 ml) was added sodium azide (779 mg, 12 mmol). The mixture was stirred at room temperature for 7 hours before addition of aqueous ammonium chloride solution. The mixture was extracted twice with ethyl acetate. The purple organic liquors were washed with brine, dried (MgSO$_4$) and concentrated. The residue was purified on silica eluting with 20-60% ethyl acetate/petrol to furnish 1.147 g of the desired material as a colourless oil. [M+H]$^+$ 335

Step 4 Triphenylphosphine (2.70 g, 10.3 mmol) was added to a solution of 1-{3-[(6-azidopyridin-3-yl)carbonyl]-4-

177

-continued

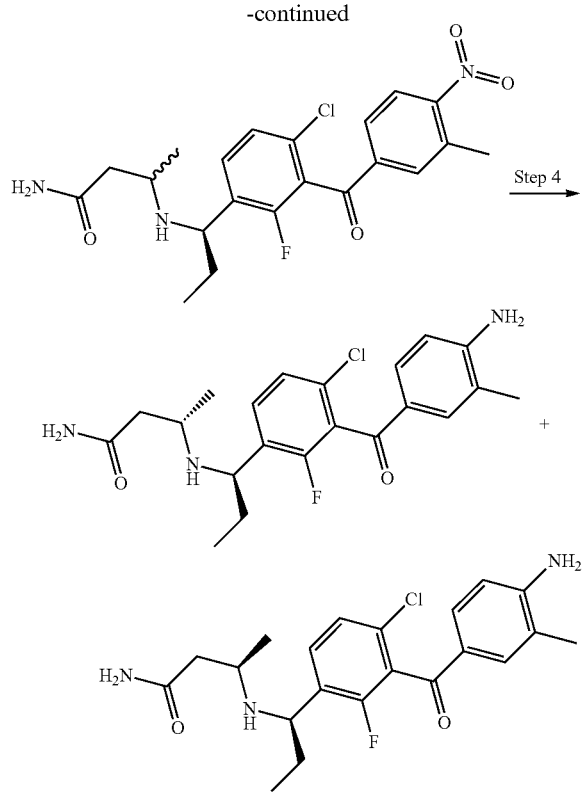

Steps 1-3 Steps 1 to 3 were carried out following the procedures described in Example 81 but using Example 64.

Step 4 The crude residue from step 3 (200 mg, 0.46 mmol) was dissolved in acetic acid (10 mL) and zinc dust (300 mg, 4.60 mmol) was added. The reaction mixture was stirred for 1 hour, and then an extra 5 eq. of zinc dust (150 mg) were added. After 30 minutes, the mixture was concentrated under reduced pressure and the residual acetic acid was quenched with a saturated solution of NaHCO$_3$ (100 mL), then extracted with EtOAc (3×100 mL). The combined organic phase was washed with brine (20 mL) before drying (Na$_2$SO4), filtering and concentrating. (Semi-preparative stereoselective chromatography was carried out using a prepacked Chiralpak AD-H column (250 mm×20 mm I.D., d$_p$=5 μm), produced by Chiral Technologies Europe (Illkirch, France). Mobile phase elution was made isocratically using n-hepane/2-propanol/Diethylamine (80/20/0.2 v/v) at a flow of 19 ml/min. The main diastereoisomer was dissolved in EtOAc and then 1.1 eq. 2M HCl in ether added. The solid was filtered off to give the title compound (18 mg) [M+H]+405 for $^{35}$Cl. The same procedure was followed also for the other isolated diastereoisomer. After formation of the HCl salt, the solid was filtered off to give the minor compound (16 mg) [M+H]+ 405 for $^{35}$Cl.

Examples 263 & 264

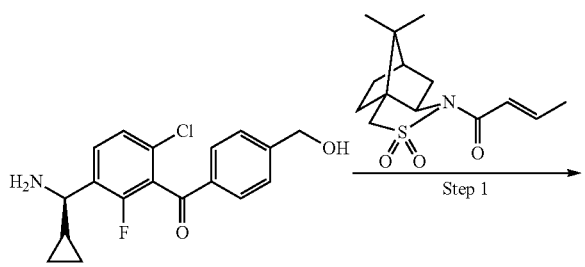

178

-continued

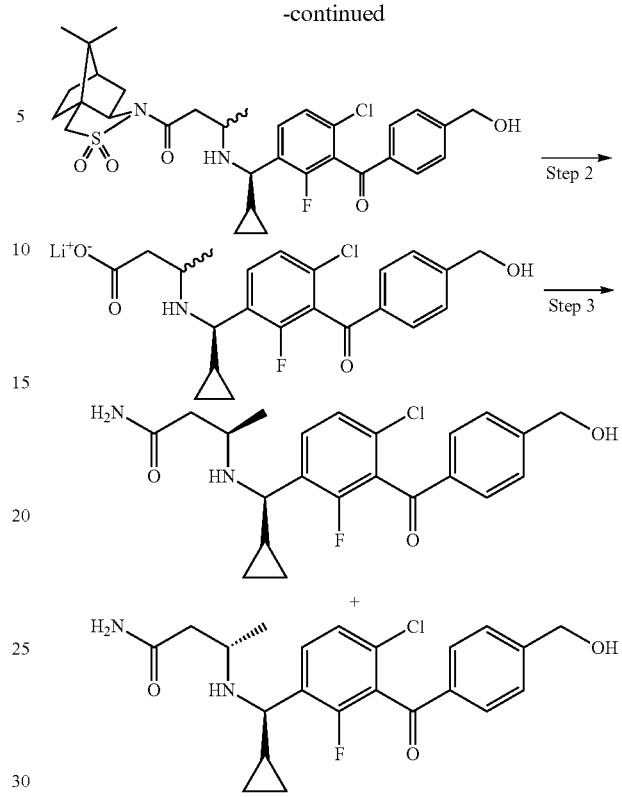

Step 1 Example 68 ([4-({3-[(R)-amino(cyclopropyl)methyl]-6-chloro-2-fluorophenyl}-carbonyl)phenyl]methanol hydrochloride) was partitioned between ethyl acetate and sodium bicarbonate solution. The organic liquors were taken, dried (MgSO$_4$) and concentrated to furnish the free base as an oil (117 mg, 0.35 mmol). To the oil was added tetrahydrofuran (2 ml), (N-crotonyl)-(2R)-bornane-10,2-sultam (119 mg, 0.42 mmol) and lithium perchlorate (52 mg, 0.49 mmol). The mixture was stirred at room temperature for 2 weeks. Water was then added and the mixture was extracted twice with ethyl acetate. The combined liquors were washed with brine, dried (MgSO$_4$) and concentrated. The residue was purified on silica eluting with 10-70% ethyl acetate/petrol furnishing the desired product as an oil (158 mg). [M+H] 617

Step 2 The product from Step 1 (158 mg, 0.256 mmol) was stirred at room temperature in a mixture of tetrahydrofuran (5 ml) and 1M aqueous lithium hydroxide (0.75 ml). After overnight stirring, the mixture was concentrated in vacuo and used crude in the following reaction.

Step 3 The crude product from Step 2 (lithium 3-{[(R)-(4-chloro-2-fluoro-3-{[4-(hydroxymethyl)-phenyl]carbonyl}phenyl)(cyclopropyl)methyl]amino}butanoate, assumed 0.256 mmol) was mixed with ammonium chloride (68 mg, 1.3 mmol), triethylamine (0.25 ml, 1.8 mmol) in N,N-dimethylformamide (2 ml). At room temperature, HATU (146 mg, 0.38 mmol) was added and the mixture was stirred overnight. The reaction mixture was then concentrated to remove the solvent, water was added and the mixture was extracted twice with ethyl acetate. The combined liquors were washed with brine, dried (MgSO$_4$) and concentrated to furnish the crude product which was purified first on silica eluting with 0-10% ammonia in methanol/dichloromethane and then by chiral preparative HPLC using the method described in Example 81 Step 3. Hydrochloride salts of the clean diastereoisomers were prepared using hydrogen chloride in ethyl acetate/diethyl ether and these were collected by filtration and dried in a vacuum oven. The S-diastereoisomer (Example 263, 45 mg) and R-diastereoisomer (Example 264, 5 mg) were thus obtained.

Examples 267 and 220

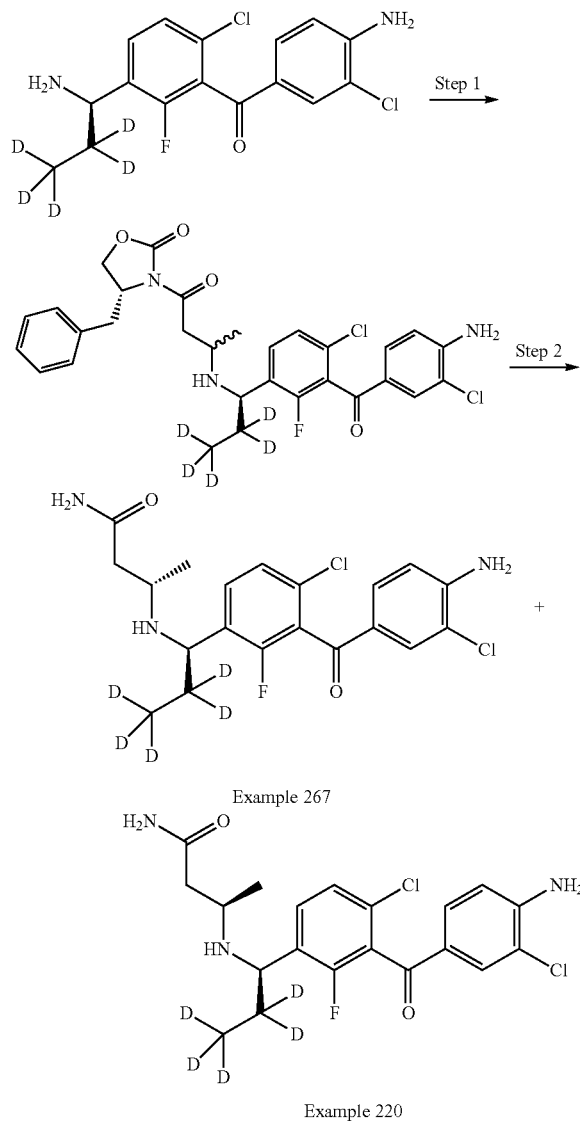

Example 267

Example 220

Step 1 To a solution of Example 78 (216 mg, 0.62 mmol) in THF (0.5 mL) was added lithium perchlorate (93 mg, 0.87 mmol, 1.4 eq.) and the (R)-4-benzyl-3-((E)-but-2-enoyl)-oxazolidin-2-one (184 mg, 0.75 mmol, 1.2 eq.). The reaction mixture was stirred at room temperature for 18 h. The reaction mixture was partitioned between EtOAc (15 mL) and water (10 mL) and then the organic phase washed with brine (5 mL), dried (MgSO$_4$), filtered and concentrated to give crude intermediate (308 mg) which was used directly in the next step. [M+H]+ 591

Step 2 To a solution of the intermediate from step 1 (assumed 0.62 mmol) in NMP (3 mL) at 0° C. was added 880 ammonia (3 mL) and the reaction mixture was stirred for 2 hours at room temperature by which time reaction was almost complete. The mixture was left to stand over the weekend, partitioned between EtOAc (25 mL) and water (25 mL) and the aqueous phase was extracted with further EtOAc (20 mL). The combined organic phases were washed with water (2×30 mL) and then brine (20 mL) before drying (MgSO$_4$), filtering and concentrating. The product was purified by SCX cartridge, washed with MeOH and then eluted with ~0.2 M NH$_3$ in MeOH, before concentrating. The resulting mixture of diastereoisomers was separated by chiral HPLC, using a Chiralpak AD-H column, eluting 80:20:0.2 Heptane:IPA:diethylamine. Each diastereoisomer was concentrated and then dissolved in DCM and 1.1 eq. HCl in Et$_2$O was added before removal of the solvent and drying in a vacuum oven to give the HCl salt of Examples 267 and 220.

Example 273

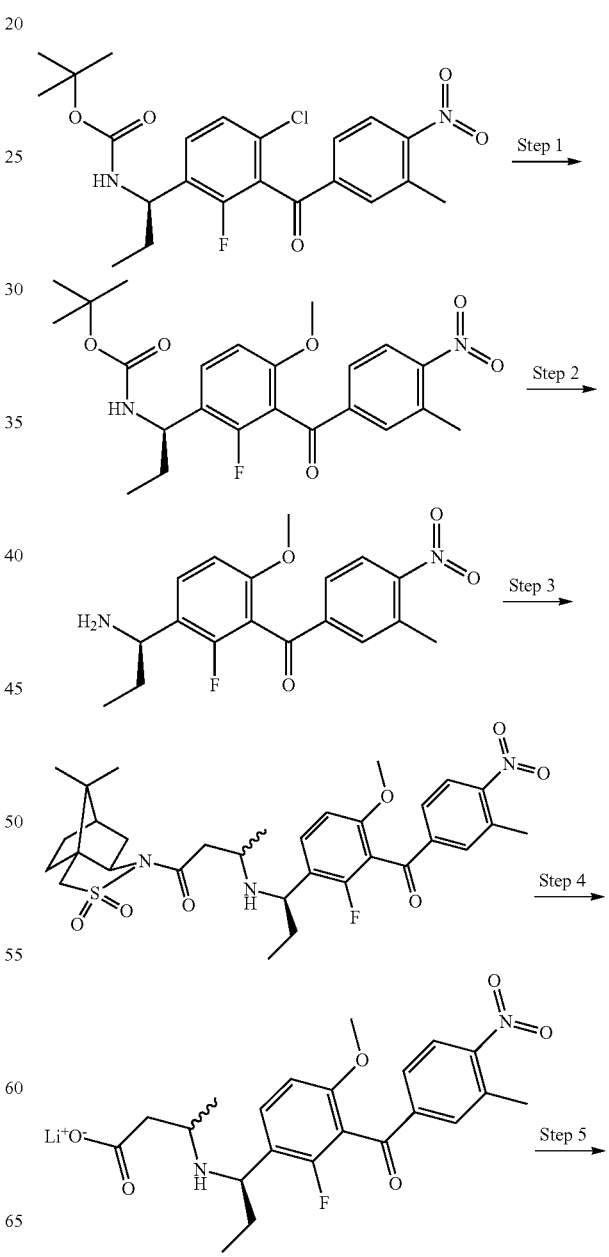

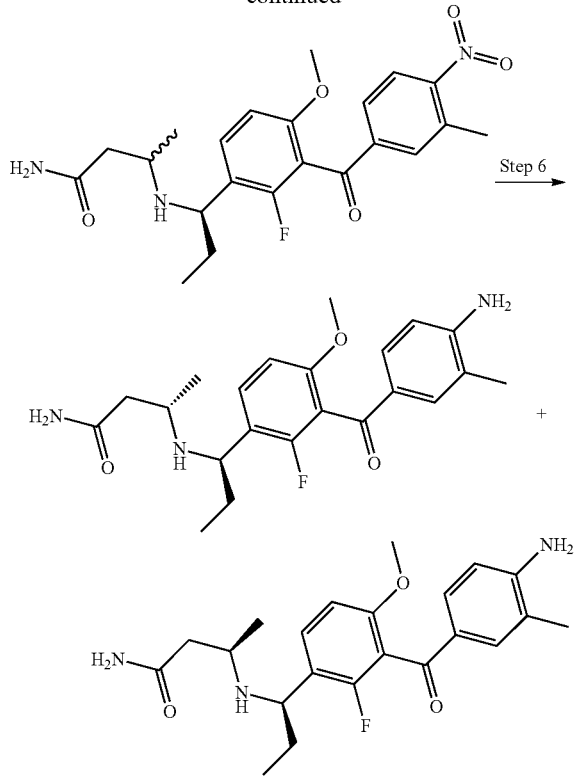

Step 1 To a stirred mixture of tert-butyl N-[(1R)-1-{4-chloro-2-fluoro-3-[(3-methyl-4-nitrophenyl)carbonyl]phenyl}propyl]carbamate (500 mg, 1.11 mmol), potassium hydroxide (249 mg, 4.44 mmol) 2-di-tert-butylphosphino-2', 4',6'-triisopropylbiphenyl (38 mg, 0.089 mmol) and tris(dibenzylideneacetone)dipalladium(0) (20.3 mg, 0.022 mmol) under vacuum, was added 1,4-dioxane (1.3 mL) followed by water (0.9 mL). The microwave vial was filled with nitrogen, evacuated and refilled with nitrogen twice before the tube was sealed and heated in the microwave at 120° C. for 40 min. Cetyltrimethylammonium bromide (40 mg, 0.11 mmol) and iodomethane (237 mg, 1.67 mmol) were added and the vial was heated in the microwave at 100° C. for 2 h. After this time, water (3 mL) was added and the mixture was extracted with EtOAc (3×5 mL). The combined organic phase was washed with brine (20 mL) before it was dried (Na$_2$SO$_4$), filtered and concentrated. Biotage column (25+M) eluting with a gradient of 10% EtOAc/petrol to 60% EtOAc/petrol gave the desired product (408 mg, 82% yield).

Step 2 Carried out according to the procedures described for Intermediate 2 step 3.

Step 3-6 Steps 3-6 carried out following the procedures of Example 259, steps 1-4.

Example 281

(3S)-3-{[3-benzoyl-4-chloro-2-fluorophenyl)methyl]-amino}butanamide

Step 1 To a solution of 3-benzoyl-4-chloro-2-fluoro-benzaldehyde (Intermediate 10, 337 mg, 1.29 mmol) in dichloroethane (5 ml) was sequentially added (S)-3-amino-butyric acid ethyl ester hydrochloride (237 mg, 1.41 mmol), triethylamine (0.196 ml, 1.41 mmol), sodium triacetoxyborohydride (818 mg, 3.86 mmol) and glacial acetic acid (0.159 ml 2.57 mmol). The mixture was stirred for 2 days then dilute sodium bicarbonate was added. After stirring for 10 minutes, the mixture was extracted with ethyl acetate. The organic liquors were washed with water and brine, dried (MgSO$_4$) and concentrated. The residue was purified by silica chromatography eluting with 20-100% ethyl acetate/petroleum ether furnishing (3S)-3-(3-benzoyl-4-chloro-2-fluoro-benzylamino)-butyric acid ethyl ester as a colourless oil (203 mg). MS: [M+H] 378

Step 2 A mixture of (3S)-3-(3-benzoyl-4-chloro-2-fluoro-benzylamino)-butyric acid ethyl ester (203 mg, 0.537 mmol), lithium hydroxide solution (1 M aqueous, 0.806 ml) and methanol (3 ml) was stirred at room temperature. Additional lithium hydroxide (0.4 ml) was added after 4 hours and the reaction left overnight. The mixture was concentrated and used crude in the following amide coupling.

Step 3 The residue from step 2 above was dissolved in dimethylformamide (4 ml). To half of this solution (ca. 0.27 mmol) was added ammonium chloride (73 mg, 1.35 mmol), diisopropylamine (0.328 ml), O-(7-azabenzotriazol-1-yl)-1,1,3,3-tetramethyluronium hexafluorophosphate (HATU, 153 mg). The mixture was stirred at room temperature. After 3 hours ethyl acetate was added and the mixture was washed with water, lithium chloride solution and brine, dried (MgSO$_4$) and concentrated. The residue was purified on silica eluting with 0-20% ethyl acetate/petroleum ether. The residue was salted by addition of hydrogen chloride in ethyl acetate to a diethyl ether solution to the product furnishing (3S)-3-{[(3-benzoyl-4-chloro-2-fluorophenyl)methyl]amino}butanamide hydrochloride as a white solid (62 mg).

Example 282

(3S)—N-(2-aminoethyl)-3-{[(3-benzoyl-4-chloro-2-fluorophenyl)methyl]-amino}butanamide Steps 1-3 As for Example 281 using tert-butyl N-(2-aminoethyl)carbamate in Step 3. [M+H]+ 492

Step 4 A mixture of {2-[(S)-3-(3-benzoyl-4-chloro-2-fluoro-benzylamino)-butyrylamino]-ethyl}-carbamic acid tert-butyl ester (92 mg) and 2N hydrogen chloride in ethyl acetate (2 ml) was allowed to stand at room temperature for 60 minutes. The mixture was concentrated and re-concentrated from methanol (×2). Ethyl acetate was added to the residue and a solid produced by scratching. The material was obtained by filtration and was dried in a vacuum oven furnishing the desired compound as a white solid (56.1 mg).

Example 283

N-[(1R)-1-{4-chloro-2-fluoro-3-[(pyridin-3-yl)carbonyl]phenyl}propyl]oxan-4-amine To a solution of the compound of Example 2 (158 mg, 0.54 mmol) and oxan-4-one (59.6 mg, 0.59 mmol) in DCE (3 ml), was added glacial acetic acid (0.08 ml, 1.35 mmol) and sodium triacetoxyborohydride (286 mg, 1.35 mmol). The resulting mixture was stirred at room temperature for 18 hours, then diluted with DCM and washed with sat. sodium hydrogen carbonate. The organic fraction was dried over sodium sulphate, filtered and concentrated. The residue was purified via preparative LC-MS. The residue was salted by addition of hydrogen chloride in diethyl ether to a ethyl acetate solution of the product furnishing N-[(1R)-1-{4-chloro-2-fluoro-3-[(pyridin-3-yl)carbonyl]phenyl}propyl]oxan-4-amine as a white solid (48 mg).

Example 286

N-[(1S)-1-{4-chloro-2-fluoro-3-[(pyridin-3-yl)carbonyl]phenyl}propyl]-2,5-dihydro-1H-pyrrole-3-carboxamide To (1S)-1-{4-chloro-2-fluoro-3-[(pyridin-3-yl)carbonyl]phenyl}propan-1-amine (0.1 g, 0.3 mmol) (Example 26) in DCM was added 1-tert-butyl 3-ethyl 1H-pyrrole-1,3(2H,5H)-dicarboxylate (0.065, 0.3 mmol), 1-ethyl-3-(3-dimethylaminopropyl)carbodiimide (0.07 mg, 0.36 mmol), 1-hydroxy-7-azabenzotriazole (0.049 g, 0.36 mmol) and triethylamine (0.085 ml, 0.6 mmol), then stirred at ambient for 18 hours. The reaction was diluted with DCM washed with 5% citric acid, sat. sodium bicarbonate then brine. The organic extract was dried (Na2SO4), filtered and concentrated to give 3-{(S)-1-[4-Chloro-2-fluoro-3-(pyridine-3-carbonyl)-phenyl]-propylcarbamoyl}-2,5-dihydro-pyrrole-1-carboxylic acid tert-butyl ester (0.125 g). MS: [M+H]$^+$ 488.

3-{(S)-1-[4-Chloro-2-fluoro-3-(pyridine-3-carbonyl)-phenyl]-propylcarbamoyl}-2,5-dihydro-pyrrole-1-carboxylic acid tert-butyl ester (0.125 g, 0.26 mmol) treated with saturated HCl/EtOAc stirred at ambient for 1 hour, solid filtered off then purified by Prep HPLC to give N-[(1S)-1-{4-chloro-2-fluoro-3-[(pyridin-3-yl)carbonyl]phenyl}propyl]-2,5-dihydro-1H-pyrrole-3-carboxamide (0.062 g), MS: [M+H] 388

Example 288

[(1R)-1-{4-chloro-2-fluoro-3-[pyridin-3-yl)carbonyl]phenyl}propyl](1H-imidazol-5-ylmethyl)amine To (6-Chloro-2-fluoro-3-{(R)-1-[(3-trityl-3H-imidazol-4-ylmethyl)-amino]-propyl}-phenyl)-pyridin-3-yl-methanone (0.208 g, 0.33 mmol) suspended in acetone (2 ml) treated with saturated HCl/EtOAc, ethanol added till all in solution stirred at ambient for 18 hours, concentrated then purified by Prep HPLC to give [(1R)-1-{4-chloro-2-fluoro-3-[(pyridin-3-yl)carbonyl]phenyl}propyl](1H-imidazol-5-ylmethyl)amine (0.07 g), MS: [M+H] 373

Example 289

[(1R)-1-{4-chloro-2-fluoro-3-[pyridin-3-yl)carbonyl]phenyl}propyl](methyl)amine

Step 1 To a stirred solution of Example 2 (0.233 mL, 0.664 mmol), iPr2NEt (0.463 mL, 2.66 mmol) and formic acid (0.0301 mL, 0.797 mmol) in DMF (3.98 mL) at 0° C. was added HATU (0.379 g, 0.996 mmol). The mixture was allowed to warm to room temperature and stirred for 1 hour. The mixture was concentrated and the residue was partitioned between water and CHCl3 and extracted into CHCl3 (×2). The combined organic extracts were dried (Na2SO4), filtered and concentrated providing N-[(1R)-1-{4-chloro-2-fluoro-3-[(pyridin-3-yl)carbonyl]phenyl}propyl]formamide which was used without further purification, 0.128 g. MS: [M+H]+ 321.

Step 2 To a stirred solution of N-[(1R)-1-{4-chloro-2-fluoro-3-[(pyridin-3-yl)carbonyl]phenyl}propyl]formamide (0.128 g, 0.399 mmol) in THF (2 mL) at room temperature was added BH3 in THF (1 M soln, 0.998 mL, 0.998 mmol) dropwise. The mixture was stirred at 50° C. overnight before it was quenched at 0° C. by the addition of excess MeOH followed by piperazine (0.352 g, 4.09 mmol). The mixture was stirred at room temperature for 1 hour before the solvents were removed under vacuum. The residue was taken into EtOAc, washed with water (×2), brine, dried (Na2SO4), filtered and concentrated providing {6-chloro-2-fluoro-3-[(1R)-1-(methylamino)propyl]-phenyl}(pyridin-3-yl)methanol which was used without further purification, 0.123 g, 100%. MS: [M+H]+ 309.

Step 3 A stirred suspension of {6-chloro-2-fluoro-3-[(1R)-1-(methylamino)propyl]-phenyl}(pyridin-3-yl)methanol (0.123 g, 0.398 mmol) and manganese(IV) oxide (0.693 g, 7.97 mmol) in toluene (1.99 mL) and 1,2-dichloroethane (1.99 mL) was heated at 100° C. for 2.5 hours. Upon cooling, the mixture was filtered; the residual solids were washed with DCM (×2) and concentrated. Preparative HPLC gave [(1R)-1-{4-chloro-2-fluoro-3-[(pyridin-3-yl)carbonyl]phenyl}propyl](methyl)amine which was converted to the HCl salt, 0.012 g, 9%.

Example 294

N-[(1S)-1-{4-chloro-2-fluoro-3-[(pyridin-3-yl)carbonyl]phenyl}propyl]piperidine-3-carboxamide Step 1 To a solution of Example 26 (140 mg, 0.43 mmol), 1-[(tert-butoxy)-carbonyl]-piperidine-3-carboxylic acid (98 mg, 0.43 mmol) and diisopropyl-ethylamine (0.37 ml, 2.14 mmol) in dimethylformamide (1.5 ml) was added O-(7-azabenzotriazol-1-yl)-1,1,3,3-tetramethyl-uronium hexafluorophosphate (HATU, 244 mg, 0.64 mmol). The mixture was stirred at room temperature for 18 hours, then ethyl acetate was added and the mixture was washed with water, and brine, dried (MgSO$_4$) and concentrated to give crude material (~220 mg), which was used in Step 2 without further purification. m/z: 503 (Molecular ion).

Step 2
To a solution of tert-butyl 3-{[(1S)-1-{4-chloro-2-fluoro-3-[(pyridin-3-yl)carbonyl]phenyl}-propyl]carbamoyl}piperidine-1-carboxylate (220 mg, 0.44 mmol) in DCM (3 mL) was added 4M HCl in dioxane (0.44 mL, 1.75 mmol, 4 eq) and the reaction stirred for 18 h. The mixture was concentrated and then triturated with diethyl ether (~5 mL) and the pale green solid filtered off and dried in a vacuum oven to give N-[(1S)-1-{4-chloro-2-fluoro-3-[(pyridin-3-yl)carbonyl]phenyl}propyl]piperidine-3-carboxamide as a white solid (80.0 mg).

Example 296

N-[(1R)-1-{4-chloro-2-fluoro-3-[(pyridin-3-yl)carbonyl]phenyl}propyl]cyclopropanamine The compound of Example 2 (0.25 g, 0.83 mmol) converted to the free-base by partition between DCM, 1M NaOH solution and brine the phases were separated and the aqueous layer was extracted into DCM (×2). Combined organic extracts were dried (Na2SO4), filtered and concentrated. A mixture of the residue, (1-ethoxycyclopropoxy)-trimethylsilane (0.167 mL, 0.83 mmol) in acetic acid (4.98 mL) and DCM (1.66 mL) was stirred at 40° C. for 5 hours. At room temperature sodium triacetoxyborohydride (0.211 g, 0.996 mmol) was added and the mixture was stirred for 30 minutes. The mixture was cooled in an ice bath and a concentrated solution of aqueous NaOH (3.4 g) was added slowly followed by saturated NaHCO3 solution to neutralize the acetic acid. EtOAc was added, the phases were separated and the aqueous layer was extracted into EtOAc (×2). Combined organic extracts were dried (Na2SO4), filtered and concentrated. Preparative HPLC gave N-[(1R)-1-{4-chloro-2-fluoro-3-[(pyridin-3-yl)carbonyl]phenyl}-propyl]cyclopropanamine which was converted to the HCl salt.

Example 302

1-[(1S)-1-{4-chloro-2-fluoro-3-[pyridin-3-yl)carbonyl]phenyl}propyl]quanidine To a solution of [3-((S)-1-Amino-propyl)-6-chloro-2-fluoro-phenyl]-pyridin-3-yl-methanone (100 mg, 0.3 mmol) (Example 26) in dimethylformamide (2 ml) was added 1H-pyrazole-carboxamidine hydrochloride (50 mg, 0.33 mmol) and diisopropylethylamine (0.116 ml, 0.66 mmol). The mixture was stirred at room temperature overnight before removal of the solvent in vacuo. Ethyl acetate and water was added to the residue; the aqueous layer was removed and concentrated to furnish crude product. This was purified on silica eluting with 0-20% methanol/dichloromethane to furnish the title compound as the free base. This was converted to the hydrochloride salt through treatment with hydrogen chloride/ethyl acetate and diethyl ether trituration.

Example 307

5-({6-chloro-2-fluoro-3-[(1R)-1-(methylamino)propyl]-phenyl}carbonyl)pyridin-2-amine A mixture of [3-((R)-1-Amino-propyl)-6-chloro-2-fluoro-phenyl]-(6-amino-pyridin-3-yl)-methanone (100 mg, 0.29 mmol), paraformaldehyde (26 mg, 0.87 mmol), sodium triacetoxyborohydride (92 mg, 0.44 mmol) and acetic acid (67 µL, 1.16 mmol) in DCM (0.5 mL) was stirred for 18 h. Chromatographic analysis showed mainly bis-addition peaks, but a small peak for product. Further DCM (5 mL) and water (5 mL) were added and the mixture was made basic with a few drops of 5M NaOH. Separated and aqueous extracted with further DCM (5 mL). The combined organic phase was washed with brine (4 mL), dried ($MgSO_4$), filtered and concentrated. Purified by prep LCMS (basic 3) and concentrated to give (6-Amino-pyridin-3-yl)-[6-chloro-2-fluoro-3-((R)-1-methylamino-propyl)-phenyl]-methanone (3 mg). Dissolved in d6-DMSO (160 uL) and concentration determined by NMR—53 mM. Used as solution for assays. [MH]+ 322.

Characterising Data

The compounds set out in Table 2 below were prepared using the methods described above, or methods similar or analogous thereto, as indicated. The numbers in the first column of the table are the Example numbers.

TABLE 2

| | Structure | Name | Salt | NMR Data / MS Data | Method |
|---|---|---|---|---|---|
| 81 | 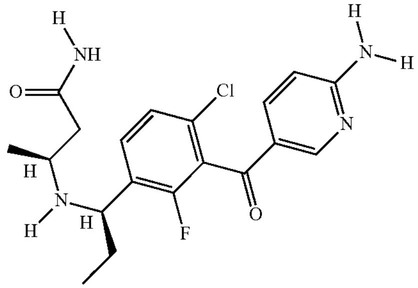 | (3S)-3-{[(1R)-1-{3-[(6-aminopyridin-3-yl)carbonyl]-4-chloro-2-fluorophenyl}propyl]-amino}butanamide | HCl (1:2) | 1H NMR (400 MHz, Me-d3-OD): 8.38 (2H, s), 7.81 (1H, t), 7.63 (1H, d), 7.16 (1H, dd), 3.55-3.45 (1H, m), 2.70-2.58 (2H, m), 2.26-2.09 (2H, m), 1.42 (3H, d), 0.93 (3H, t). m/z: 393 | Example 81 or Example 82 followed by treatment with HCl to form di-hydrochloride salt |
| 82 | 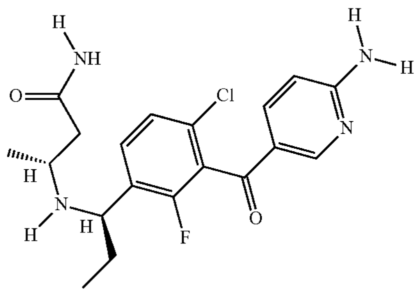 | (3R)-3-{[(1R)-1-{3-[(6-aminopyridin-3-yl)carbonyl]-4-chloro-2-fluorophenyl}propyl]-amino}butanamide | HCl (1:2) | 1H NMR (400 MHz, Me-d3-OD): 8.37-8.28 (2H, m), 7.79 (1H, t), 7.64 (1H, d), 7.11 (1H, d), 4.69 (1H, dd), 3.72-3.64 (1H, m), 2.69-2.61 (2H, m), 2.30-2.23 (1H, m), 2.13-2.04 (1H, m), 0.95 (3H, d), 0.95 (3H, t). m/z: 393 | Example 81 or Example 82 |
| 83 | | (3R)-3-{[(1R)-1-(3-benzoyl-4-chloro-2-fluorophenyl)propyl]-amino}butanamide HCl (1:1) m/z: 377 | | | As Ex 84 |
| 84 | 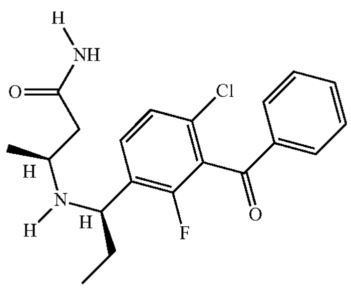 | (3S)-3-{[(1R)-1-(3-benzoyl-4-chloro-2-fluorophenyl)propyl]-amino}butanamide | HCl (1:1) | 1H NMR (400 MHz, DMSO-d6): 9.73 (1H, s), 9.33 (1H, s), 8.04 (1H, t), 7.86-7.76 (3H, m), 7.72 (1H, d), 7.68 (1H, s), 7.62 (2H, t), 7.17 (1H, s), 4.55 (1H, s), 3.28 (1H, s), 2.65 (1H, dd), 2.49-2.40 (1H, m), 2.25-2.13 (1H, m), 2.09-1.96 (1H, m), 1.23 (3H, d), 0.78 (3H, t). m/z: 377 | Prepared according to Example 4 using Example 81 followed by chiral chromatographic separation |

TABLE 2-continued

| | Structure | Name | Salt | NMR Data | MS Data | Method |
|---|---|---|---|---|---|---|
| 85 | 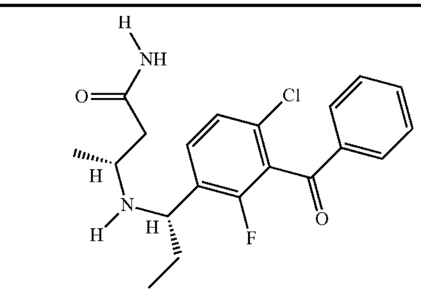 | (3R)-3-{[(1S)-1-(3-benzoyl-4-chloro-2-fluorophenyl)-propyl]-amino}butanamide | HCl (1:1) | 1H NMR (400 MHz, DMSO-d6): 9.53 (1H, d), 9.35-9.26 (1H, m), 8.00 (1H, t), 7.87-7.80 (2H, m), 7.78 (1H, d), 7.75-7.66 (2H, m), 7.62 (2H, t), 7.20 (1H, s), 4.57 (1H, d), 3.44 (1H, d), 2.59-2.52 (1H, m), 2.44-2.34 (1H, m), 2.23-2.13 (1H, m), 2.04-1.93 (1H, m), 1.25 (3H, d), 0.79 (3H, t). | m/z: 377 | Prepared according to Example 81 using Example 6 |
| 86 | 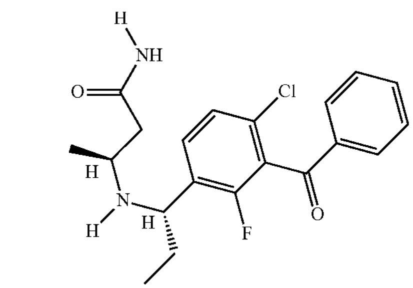 | (3S)-3-{[(1S)-1-(3-benzoyl-4-chloro-2-fluorophenyl)-propyl]amino}butanamide | HCl (1:1) | 1H NMR (400 MHz, DMSO-d6): 9.74 (1H, s), 9.34 (1H, s), 8.04 (1H, t), 7.82 (2H, d), 7.78 (1H, d), 7.72 (1H, d), 7.68 (1H, s), 7.62 (2H, t), 7.17 (1H, s)4.55 (1H, s), 3.28 (1H, s), 2.65 (1H, dd), 2.48-2.38 (1H, m), 2.26-2.13 (1H, m), 2.10-1.96 (1H, m), 1.23 (3H, d), 0.77 (3H, t). | m/z: 377 | Prepared according to Example 81 using Example 6 |
| 87 | 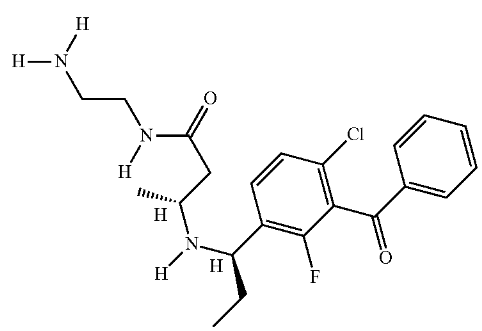 | (3R)-N-(2-aminoethyl)-3-{[(1R)-1-(3-benzoyl-4-chloro-2-fluorophenyl)propyl]-amino}butanamide | HCl (1:2) | 1H NMR (400 MHz, DMSO-d6): 9.98 (1H, s), 9.61 (1H, s), 8.51 (1H, t), 8.20-8.09 (1H, m), 7.99 (3H, s), 7.84 (2H, d), 7.82-7.75 (1H, m), 7.71 (1H, d), 7.62 (2H, t), 4.55 (1H, d), 3.48 (1H, s), 3.30-3.15 (2H, m), 2.85 (2H, s), 2.70 (1H, dd), 2.49-2.41 (1H, m), 2.25 (1H, t), 2.10-1.98 (1H, m), 1.28 (3H, d), 0.77 (3H, t). | m/z: 420 | Prepared according to Example 81 from Example 4; using tert-butyl N-(2-aminoethyl) carbamate in Step 3 followed by deprotection as Example 87 |

TABLE 2-continued

| | Name | Salt | NMR Data | MS Data | Method |
|---|---|---|---|---|---|
| 88 | (3S)-N-(2-aminoethyl)-3-{[(1R)-1-(3-benzoyl-4-chloro-2-fluorophenyl)propyl]-amino}butanamide | HCl (1:2) | 1H NMR (400 MHz, DMSO-d6): 10.03 (1H, s), 9.65 (1H, s), 8.50 (1H, t), 8.22-8.08 (1H, m), 7.98 (3H, s), 7.82 (2H, d), 7.78 (1H, d), 7.72 (1H, d), 7.63 (2H, t), 4.55 (1H, s), 3.33 (1H, obscured by solvent), 3.30-3.19 (2H, m), 2.93-2.73 (3H, m), 2.50 (2H, obscured by solvent), 2.24 (1H, d), 2.14-2.00 (1H, m), 1.23 (3H, d), 0.77 (3H, t). | m/z: 420 | Prepared according to Example 81 from Example 4; using tert-butyl N-(2-aminoethyl) carbamate in Step 3 followed by deprotection as Example 87 |
| 89 | (3S)-N-(2-aminoethyl)-3-{[(1S)-1-(3-benzoyl-4-chloro-2-fluorophenyl)propyl]-amino}butanamide | HCl (1:2) | 1H NMR (400 MHz, DMSO-d6): 9.88 (1H, s), 9.57-9.49 (1H, m), 8.46 (1H, t), 8.12 (1H, t), 7.93 (3H, s), 7.82 (2H, d), 7.78 (1H, d), 7.72 (1H, d), 7.63 (2H, t), 4.60-4.52 (1H, m), 3.31-3.21 (3H, m), 2.86 (2H, s), 2.83-2.73 (1H, m), 2.50 (1H obscured by solvent), 2.26-2.17 (1H, m), 2.11-1.99 (1H, m), 1.23 (3H, d), 0.78 (3H, t). | m/z: 420 | Prepared according to Example 81 from Example 6; using tert-butyl N-(2-aminoethyl) carbamate in Step 3 followed by deprotection as Example 87 |
| 90 | (3S)-3-{[(1R)-1-{4-chloro-3-[(3,4-difluorophenyl)carbonyl]-2-fluorophenyl}propyl]amino}-butanamide | HCl (1:1) | 1H NMR (400 MHz, DMSO-d6): 9.49 (1H, br s), 9.19 (1H, br s), 8.04-7.92 (2H, m), 7.79-7.62 (4H, m), 7.19 (1H, s), 4.61-4.50 (1H, m), 3.43-3.34 (1H, m), 2.67-2.55 (1H, m), 2.42 (1H, d), 2.23-2.09 (1H, m), 2.09-1.94 (1H, m), 1.23 (3H, d), 0.78 (3H, t). | m/z: 413 | Prepared from Example 13 using Example 81. |

TABLE 2-continued

| | Structure | Name | Salt | NMR Data | MS Data | Method |
|---|---|---|---|---|---|---|
| 91 | 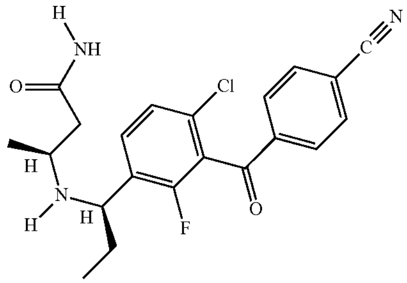 | (3S)-3-{[(1R)-1-{4-chloro-3-[(4-cyanophenyl)carbonyl]-2-fluorophenyl}propyl]amino}-butanamide | HCl (1:1) | 1H NMR (400 MHz, Me-d3-OD): 8.03 (2H, d), 8.00-7.86 (2H, m), 7.86-7.73 (1H, m), 7.63 (1H, d), 4.71-4.64 (1H, m), 3.57-3.45 (1H, m), 2.72-2.52 (2H, m), 2.25-2.05 (2H, m), 1.40 (3H, d), 0.94 (3H, t). | m/z: 402 | Prepared according to Example 9 using Example 81 followed by chiral chromatographic separation |
| 92 | (3R)-3-{[(1R)-1-{4-chloro-3-[(4-cyanophenyl)carbonyl]-2-fluorophenyl}propyl]amino}-butanamide HCl (1:1) m/z: 402 | | | | | |
| 93 | 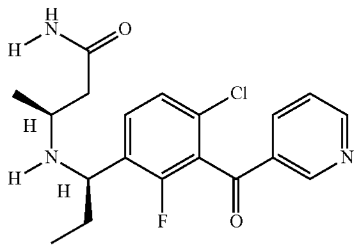 | (3S)-3-{[(1R)-1-{4-chloro-2-fluoro-3-[(pyridin-3-yl)carbonyl]phenyl}propyl]-amino}-butanamide | HCl (1:1) | 1H NMR (400 MHz, Me-d3-OD): 9.22 (1H, s), 9.04 (1H, d), 8.74 (1H, d), 8.04 (1H, dd), 7.86 (1H, t), 7.66 (1H, d), 4.73-4.62 (1H, m), 3.58-3.47 (1H, m), 2.73-2.56 (2H, m), 2.28-2.08 (2H, m), 1.42 (3H, d), 0.94 (3H, t). | m/z: 378 | As Example 91 |
| 94 | (3R)-3-{[(1R)-1-{4-chloro-2-fluoro-3-[(pyridin-3-yl)carbonyl]phenyl}propyl]amino}butanamide HCl (1:1) m/z: 378 | | | | | |
| 95 | 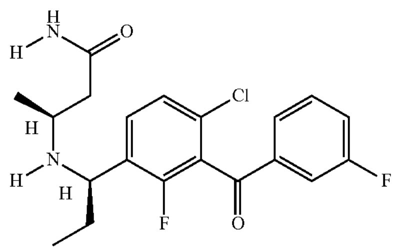 | (3S)-3-{[(1R)-1-{4-chloro-2-fluoro-3-[(3-fluorophenyl)-carbonyl]-phenyl}propyl]-amino}-butanamide | HCl (1:1) | 1H NMR (400 MHz, Me-d3-OD): 7.78 (1H, t), 7.70-7.55 (4H, m), 7.55-7.42 (1H, m), 4.74-4.59 (1H, m), 3.55-3.42 (1H, m), 2.72-2.52 (2H, m), 2.27-2.03 (2H, m), 1.39 (3H, d), 1.00-0.80 (3H, m). | m/z: 395 | Prepared according to Example 7 using Example 81 followed by chiral chromatographic separation |
| 96 | (3R)-3-{[(1R)-1-{4-chloro-2-fluoro-3-[(3-fluorophenyl)-carbonyl]phenyl}propyl]amino}butanamide HCl (1:1) m/z: 395 | | | | | As Ex. 95 |

TABLE 2-continued

| | Structure | Name | Salt | NMR Data | MS Data | Method |
|---|---|---|---|---|---|---|
| 97 | 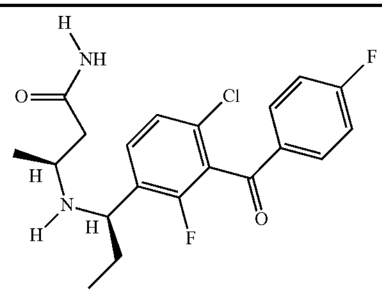 | (3S)-3-{[(1R)-1-{4-chloro-2-fluoro-3-[(4-fluorophenyl)-carbonyl]-phenyl}propyl]-amino}-butanamide | HCl (1:1) | 1H NMR (400 MHz, Me-d3-OD): 7.94 (2H, dd), 7.76 (1H, t), 7.60 (1H, d), 7.33 (2H, t), 4.68 (1H, dd), 3.54-3.42 (1H, m), 2.71-2.53 (2H, m), 2.26-2.05 (2H, m), 1.39 (3H, d), 0.94 (3H, t). | m/z: 395 | Prepared according to Example 8 using Example 8 |
| 98 | (3R)-3-{[(1R)-1-{4-chloro-2-fluoro-3-[(4-fluorophenyl)-carbonyl]phenyl}propyl]amino}butanamide HCl (1:1) m/z: 395 | | | | | As Ex. 97 |
| 99 | 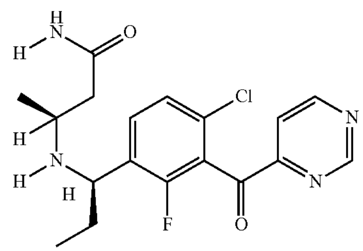 | (3S)-3-{[(1R)-1-{4-chloro-2-fluoro-3-[(pyrimidin-4-yl)carbonyl]phenyl]-propyl]-amino}butanamide | HCl (1:1) | 1H NMR (400 MHz, Me-d3-OD): 9.31 (1H, s), 9.19 (1H, d), 8.19 (1H, dd), 7.78 (1H, t), 7.59 (1H, d), 4.72-4.60 (1H, m), 3.54-3.40 (1H, m), 2.70-2.53 (2H, m), 2.25-2.03 (2H, m), 1.38 (3H, d), 1.00-0.87 (3H, m). | m/z: 379 | Prepared according to Example 10 |
| 100 | (3R)-3-{[(1R)-1-{4-chloro-2-fluoro-3-[(pyrimidin-4-yl)carbonyl]phenyl}propyl]amino}butanamide HCl (1:1) m/z: 379 | | | | | As Ex. 99 |
| 101 | 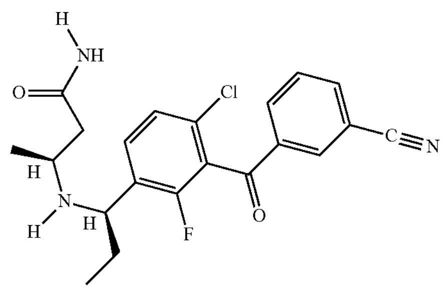 | (3S)-3-{[(1R)-1-{4-chloro-3-[(3-cyanophenyl)carbonyl]-2-fluorophenyl}propyl]amino}-butanamide | HCl (1:1) | 1H NMR (400 MHz, Me-d3-OD): 8.26-8.15 (2H, m), 8.10 (1H, d), 7.86-7.74 (2H, m), 7.63 (1H, d), 4.68 (1H, dd), 3.58-3.46 (1H, m), 2.73-2.52 (2H, m), 2.27-2.08 (2H, m), 1.41 (3H, d), 0.95 (3H, t). | m/z: 402 (Fragment) | Prepared according to Example 81 using Example 18 |
| 102 | (3R)-3-{[(1R)-1-{4-chloro-3-[(3-cyanophenyl)carbonyl]-2-fluorophenyl}propyl]amino}-butanamide HCl (1:1) m/z: 402 | | | | | As Ex. 101 |

TABLE 2-continued

| | Structure | Name | Salt | NMR Data | MS Data | Method |
|---|---|---|---|---|---|---|
| 103 | 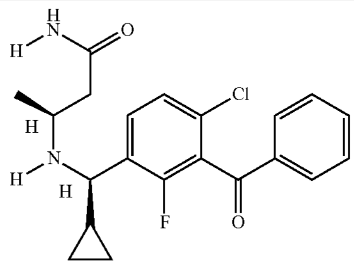 | (3S)-3-{[(R)-(3-benzoyl-4-chloro-2-fluorophenyl)-(cyclopropyl)-methyl]-amino}-butanamide | HCl (1:1) | 1H NMR (400 MHz, Me-d3-OD): 7.86 (2H, d), 7.82 (1H, t), 7.73 (1H, t), 7.63-7.54 (3H, m), 4.03 (1H, d), 3.61-3.46 (1H, m), 2.65 (2H, d), 1.69-1.54 (1H, m), 1.37 (3H, d), 1.04-0.88 (1H, m), 0.84-0.69 (2H, m), 0.53-0.40 (1H, m). | m/z: 389 | Prepared according to Example 81 using Example 11. |
| 104 | 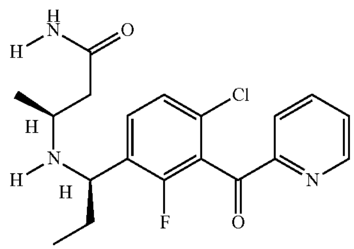 | (3S)-3-{[(1R)-1-{4-chloro-2-fluoro-3-[(pyridin-2-yl)carbonyl]phenyl}-propyl]amino}butanamide | HCl (1:1) | 1H NMR (400 MHz, Me-d3-OD): 8.64 (1H, d), 8.26 (1H, d), 8.16-8.05 (1H, m), 7.78-7.61 (2H, m), 7.55 (1H, m), 4.70-4.59 (1H, m), 3.56-3.40 (1H, m), 2.70-2.53 (2H, m), 2.25-2.00 (2H, m), 1.38 (3H, d), 0.95 (3H, t). | m/z: 378 | Prepared according to Example 81 using Example 14 |
| 105 | (3R)-3-{[(1R)-1-{4-chloro-2-fluoro-3-[(pyridin-2-yl)carbonyl]phenyl}propyl]amino}butanamide HCl (1:1) m/z: 377 | | | | | As Ex. 104 |
| 106 | 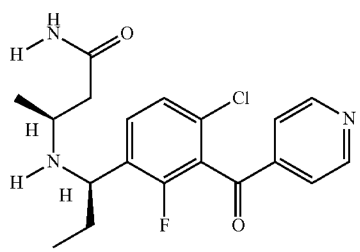 | (3S)-3-{[(1R)-1-{4-chloro-2-fluoro-3-[(pyridin-4-yl)carbonyl]phenyl}-propyl]amino}butanamide | HCl (1:1) | 1H NMR (400 MHz, Me-d3-OD): 9.02 (2H, d), 8.13 (2H, d), 7.88 (1H, t), 7.66 (1H, d), 4.73-4.59 (1H, m), 3.57-3.40 (1H, m), 2.73-2.55 (2H, m), 2.29-2.00 (2H, m), 1.41 (3H, d), 0.94 (3H, t). | m/z: 377 | Prepared according to Example 81 using Example 15 |
| 107 | 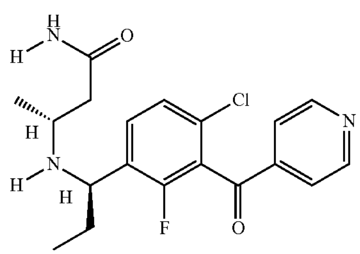 | (3R)-3-{[(1R)-1-{4-chloro-2-fluoro-3-[(pyridin-4-yl)carbonyl]phenyl}-propyl]amino}butanamide | HCl (1:1) | 1H NMR (400 MHz, Me-d3-OD): 8.99 (2H, d), 8.07 (2H, d), 7.86 (1H, t), 7.73-7.61 (1H, m), 4.74-4.62 (1H, m), 3.74-3.63 (1H, m), 2.72-2.56 (2H, m), 2.34-2.18 (1H, m), 2.18-2.01 (1H, m), 1.41 (3H, d), 1.02-0.89 (4H, m). | m/z: 377 | Prepared according to Example 81 using Example 15 |

TABLE 2-continued

| | Structure | Name | Salt | NMR Data | MS Data | Method |
|---|---|---|---|---|---|---|
| 108 | 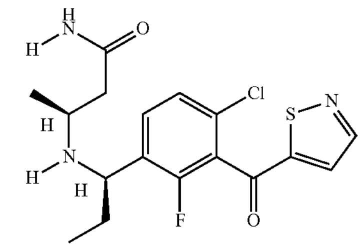 | (3S)-3-{[(1R)-1-{4-chloro-2-fluoro-3-[(1,2-thiazol-5-yl)carbonyl]phenyl}propyl]-amino}butanamide | HCl (1:1) | 1H NMR (400 MHz, Me-d3-OD): 8.69 (1H, d), 7.81 (1H, t), 7.72 (1H, d), 7.64 (1H, d), 4.69 (1H, dd), 3.55-3.41 (1H, m), 2.66 (1H, dd), 2.60 (1H, dd), 2.28-2.06 (2H, m), 1.40 (3H, d), 0.93 (3H, t). | m/z: 384 | Prepared according to Example 81 using Example 16. |
| 109 | 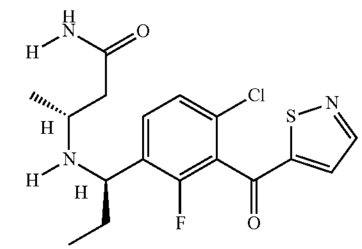 | (3R)-3-{[(1R)-1-{4-chloro-2-fluoro-3-[(1,2-thiazol-5-yl)carbonyl]phenyl}propyl]-amino}butanamide | HCl (1:1) | 1H NMR (400 MHz, Me-d3-OD): 8.69 (1H, d), 7.81 (1H, t), 7.70 (1H, d), 7.65 (1H, d), 4.70 (1H, dd), 3.75-3.62 (1H, m), 2.67 (1H, dd), 2.60 (1H, dd), 2.34-2.19 (1H, m), 2.16-2.03 (1H, m), 1.39 (3H, d), 0.95 (3H, t). | m/z: 384 | Prepared according to Example 81 using Example 16. |
| 110 | 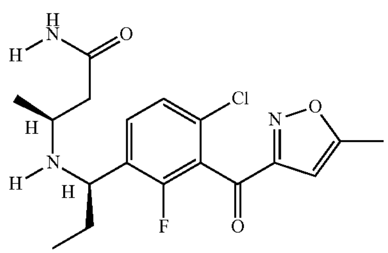 | (3S)-3-{[(1R)-1-{4-chloro-2-fluoro-3-[(5-methyl-1,2-oxazol-3-yl)carbonyl]-phenyl}propyl]-amino}-butanamide | HCl (1:1) | 1H NMR (400 MHz, Me-d3-OD): 7.76 (1H, t), 7.58 (1H, d), 6.73 (1H, s), 4.68 (1H, dd), 3.53-3.39 (1H, m), 2.70-2.58 (2H, m), 2.56 (3H, s), 2.26-2.02 (2H, m), 1.38 (3H, d), 0.92 (3H, t). | m/z: 382 | Prepared according to Example 21 |
| 111 | (3R)-3-{[(1R)-1-{4-chloro-2-fluoro-3-[(5-methyl-1,2-oxazol-3-yl)carbonyl]-phenyl}-propyl]amino}-butanamide HCl (1:1) m/z: 382 | | | | | As Ex. 110 |

TABLE 2-continued

| | Structure | Name | Salt | NMR Data | MS Data | Method |
|---|---|---|---|---|---|---|
| 112 | 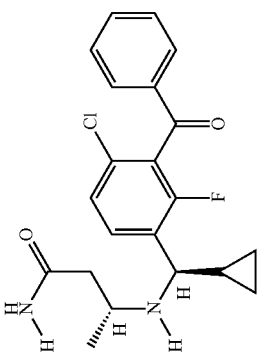 | (3R)-3-{[(R)-(3-benzoyl-4-chloro-2-fluorophenyl)(cyclopropyl)methyl]amino}butanamide | HCl (1:1) | 1H NMR (400 MHz, Me-d3-OD): 7.89-7.84 (2H, m), 7.81 (1H, t), 7.74 (1H, t), 7.63-7.55 (3H, m), 4.10 (1H, d), 3.87-3.76 (1H, m), 2.68 (1H, dd), 2.56 (1H, dd), 1.62-1.49 (1H, m), 1.38 (3H, d), 1.05-0.89 (1H, m), 0.88-0.67 (2H, m), 0.49-0.37 (1H, m). | m/z: 389 | Prepared according to Example 81 using Example 11. |
| 113 | 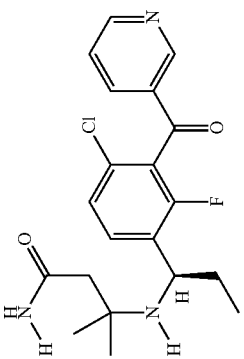 | 3-{[(1R)-1-{4-chloro-2-fluoro-3-[(pyridin-3-yl)carbonyl]-phenyl]-propyl]-amino}-3-methylbutanamide | HCl (1:1) | 1H NMR (400 MHz, Me-d3-OD): 9.13 (1H, d), 9.00 (1H, dd), 8.65 (1H, dt), 7.98 (1H, ddd), 7.85 (1H, t), 7.63 (1H, dd), 4.69 (1H, dd), 2.67 (1H, d), 2.63 (1H, d), 2.26-2.09 (2H, m), 1.50 (3H, s), 1.41 (3H, s), 0.93 (3H, t). | m/z: 392 | Example 113 |
| 114 | | (3R)-3-{[(1R)-1-(3-benzoyl-4-chloro-2-fluorophenyl)-(2,2,3,3,3-D)propyl]amino}-butanamide HCl (1:1) m/z: 382 | | | | As Ex. 115 |
| 115 | 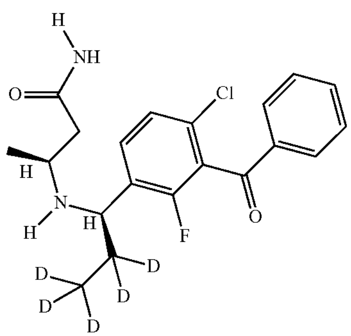 | (3S)-3-{[(1R)-1-(3-benzoyl-4-chloro-2-fluorophenyl)(2,2,3,3,3-D)propyl]amino}-butanamide | HCl (1:1) | 1H NMR (400 MHz, Me-d3-OD): 7.93-7.75 (2H, m), 7.75-7.67 (1H, m), 7.63 (1H, t), 7.56 (2H, t), 7.48-7.38 (1H, m), 4.12 (1H, s), 2.98-2.80 (1H, m), 2.42-2.26 (1H, m), 1.10 (3H, d). | m/z: 382 | Prepared from Example 23 using Example 82. Diastereoisomers were separated by flash column chromatography. |

TABLE 2-continued

| | Structure | Name | Salt | NMR Data | MS Data | Method |
|---|---|---|---|---|---|---|
| 116 | 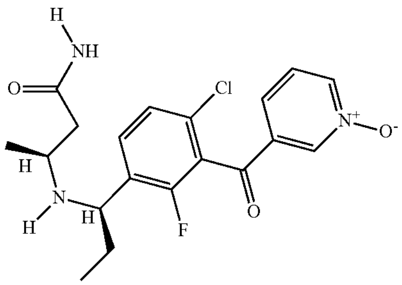 | (S)-3-{(R)-1-[4-Chloro-2-fluoro-3-(1-oxy-pyridine-3-carbonyl)-phenyl]-propylamino}-butyramide | HCl (1:1) | 1H NMR (400 MHz): 9.80 (1H, s), 9.41 (1H, d), 8.56 (2H, d), 8.10 (1H, t), 7.79-7.72 (2H, m), 7.70 (1H, s), 7.68-7.60 (1H, m), 7.18 (1H, s), 4.54 (1H, d), 3.32 (1H, s), 2.67 (1H, dd), 2.49-2.40 (1H, m), 2.26-2.14 (1H, m), 2.09-2.00 (1H, m), 1.24 (3H, d), 0.78 (3H, t). | m/z: 394 | Prepared from Example 25 using Example 82 |
| 117 | | (R)-3-{(R)-1-[4-Chloro-2-fluoro-3-(1-oxy-pyridine-3-carbonyl)-phenyl]propylamino}-butyramide HCl (1:1) m/z: 394 | | | | As Ex. 116 |
| 118 | | (3R)-3-{[(R)-{4-chloro-2-fluoro-3-[(pyridin-3-yl)carbonyl]phenyl}(cyclopropyl)methyl]amino}-butanamide HCl (1:1) m/z: 390 | | | | As Ex. 119 |
| 119 | 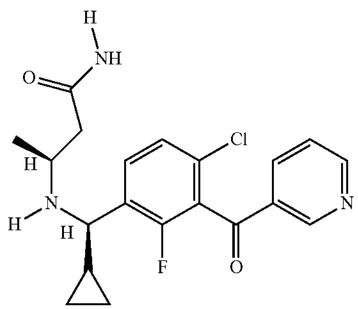 | (3S)-3-{[(R)-{4-chloro-2-fluoro-3-[(pyridin-3-yl)carbonyl]phenyl}(cyclopropyl)methyl]amino}-butanamide | HCl (1:1) | 1H NMR (270 MHz, MeOD-d4): 9.20 (1H, d), 9.00 (1H, dd), 8.77-8.69 (1H, m), 8.01 (1H, dd), 7.87 (1H, t), 7.62 (1H, m), 3.98 (1H, d), 3.60-3.50 (1H, observed sextet), 2.65-2.57 (2H, m), 1.65-1.59 (1H, m), 1.37 (3H, d), 0.97-0.92 (1H, m), 0.78-0.71 (2H, m), 0.46-0.43 (1H, m). | m/z: 390 | Prepared according to Example 81 using Example 28 |
| 120 | | (3R)-3-{[(R)-{4-chloro-2-fluoro-3-[(4-fluorophenyl)carbonyl]phenyl}(cyclopropyl)methyl]amino}butanamide HCl (1:1) m/z: 407 | | | | As Ex. 121 |
| 121 | 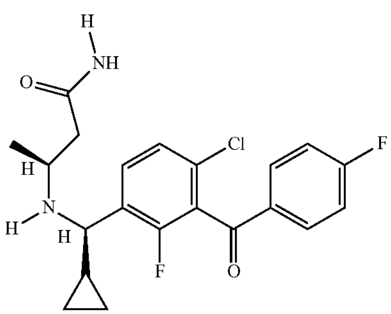 | (3S)-3-{[(R)-{4-chloro-2-fluoro-3-[(4-fluorophenyl)carbonyl]phenyl}(cyclopropyl)methyl]amino}butanamide | HCl (1:1) | 1H NMR (270 MHz, MeOD-d4): 7.95-7.90 (2H, m), 7.80 (1H, t), 7.56 (1H, dd), 7.33-7.27 (2H, m), 3.99 (1H, d), 3.55-3.47 (1H, observed sextet), 2.61 (2H, d), 1.66-1.55 (1H, m), 1.35 (3H, d), 0.99-0.89 (1H, m), 0.80-0.69 (2H, m), 0.46-0.38 (1H, m). | m/z: 407 | Prepared according to Example 81 using Example 27 |

TABLE 2-continued

| | Name | Salt | NMR Data | MS Data | Method |
|---|---|---|---|---|---|
| 122 | 3-({3-[(1R)-1-{[(2S)-1-carbamoylpropan-2-yl]amino}propyl]-6-chloro-2-fluorophenyl}carbonyl)-benzoic acid | HCl (1:1) | 1H NMR (400 MHz, Me-d3-OD): 8.43-8.31 (2H, m), 8.15 (1H, d), 7.86-7.68 (2H, m), 7.64 (1H, d), 4.74-4.64 (1H, m), 3.58-3.47 (1H, m), 2.74-2.53 (2H, m), 2.30-2.04 (2H, m), 1.40 (3H, d), 0.94 (3H, t). | m/z: 421 | Prepared according to Example 82 using Example 59 |
| 123 | 3-({3-[(1R)-1-{[(2R)-1-carbamoylpropan-2-yl]amino}propyl]-6-chloro-2-fluorophenyl}carbonyl)-benzoic acid HCl (1:1) m/z: 421 | | | | As Ex. 122 |
| 124 | (3R)-3-{[(1R)-1-{[4-chloro-2-fluoro-3-[(3-oxo-3,4-dihydro-2H-1,4-benzoxazin-7-yl)carbonyl]phenyl}(2,2,3,3,3-deutero)propyl]amino}-butanamide | HCl (1:1) | 1H NMR (400 MHz, Me-d3-OD): 7.72 (1H, t), 7.59 (1H, d), 7.46 (1H, dd), 7.41 (1H, d), 7.04 (1H, d), 4.68 (2H, s), 4.65 (1H, s), 3.75-3.65 (1H, m), 2.67 (1H, dd), 2.57 (1H, dd), 1.39 (3H, d). | m/z: 453 | Prepared according to Example 81 using Example 70 |
| 125 | 2-{[1-{3-[(6-aminopyridin-3-yl)carbonyl]-4-chloro-2-fluorophenyl}propyl]amino}cyclopentane-1-carboxamide. Cis-stereochemistry at ring junction; absolute stereochemistry not defined | HCl (1:1) | 1H NMR (400 MHz, DMSO-d6): 9.72-9.55 (1H, m), 9.20-9.03 (1H, m), 8.25 (1H, s), 7.94-7.83 (3H, m), 7.65 (2H, d), 7.42 (1H, s), 6.69-6.63 (1H, m), 4.44-4.36 (1H, m), 3.56-3.47 (2H, m), 2.92-2.84 (1H, m), 2.28-2.20 (1H, m), 2.00-1.86 (4H, m), 1.86-1.76 (2H, m), 1.59-1.51 (1H, m), 0.74 (3H, t). | m/z: 419 (Molecular ion) | Prepared as Example 250 using racemic cis ethyl 2-aminocyclopentane-1-carboxylate hydrochloride in step 5 |
| 126 | 2-{[1-{3-[(6-aminopyridin-3-yl)carbonyl]-4-chloro-2-fluorophenyl}propyl]amino}cyclopentane-1-carboxamide. Cis-stereochemistry at ring junction; absolute stereochemistry not defined | HCl (1:1) | 1H NMR (400 MHz, DMSO-d6): 9.92-9.72 (1H, m), 9.49-9.31 (1H, m), 8.31 (1H, s), 8.04-7.85 (4H, m), 7.85-7.76 (1H, m), 7.66 (1H, d), 7.52 (1H, s), 6.74 (1H, d), 4.40-4.30 (1H, m), 3.65-3.60 (1H, m), 2.83 (1H, q), 2.22-2.12 (1H, m), 1.98-1.85 (3H, m), 1.85-1.72 (3H, m), 1.59-1.49 (1H, m), 0.79 (3H, t). | m/z: 419 (Molecular ion) | Prepared as Example 250 using racemic cis ethyl 2-aminocyclopentane-1-carboxylate hydrochloride in step 5 |

TABLE 2-continued

| | Structure | Name | Salt | NMR Data | MS Data | Method |
|---|---|---|---|---|---|---|
| 127 | 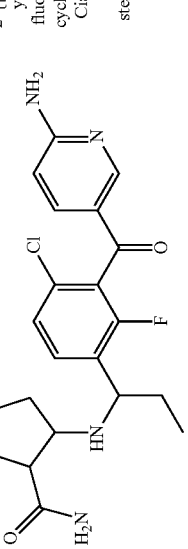 | 2-{[1-{3-[(6-aminopyridin-3-yl)carbonyl]-4-chloro-2-fluorophenyl}propyl]amino}cyclopentane-1-carboxamide. Cis-stereochemistry at ring junction; absolute stereochemistry not defined | HCl (1:1) | 1H NMR (400 MHz, DMSO-d6): 9.79-9.60 (1H, m), 9.18 (1H, s), 8.28 (1H, s), 8.00-7.75 (5H, m), 7.67 (1H, d), 7.43 (1H, s), 6.72 (1H, d), 4.45-4.36 (1H, m), 3.54-3.50 (1H, m), 2.93-2.85 (1H, m), 2.32-2.21 (1H, m), 2.00-1.77 (6H, m), 1.60-1.50 (1H, m), 0.74 (3H, t). | m/z: 419 (Molecular ion) | Prepared as Example 250 using racemic cis ethyl 2-aminocyclopentane-1-carboxylate hydrochloride in step 5 |
| 128 | (3R)-3-{[(R)-{4-chloro-3-[(4-cyanophenyl)-carbonyl]-2-fluorophenyl}(cyclo-propyl)methyl]amino}-butanamide HCl (1:1) m/z: 414 | | | | | As Ex. 129 |
| 129 | 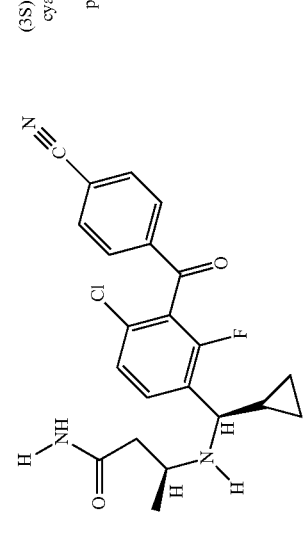 | (3S)-3-{[(R)-{4-chloro-3-[(4-cyanophenyl)-carbonyl]-2-fluorophenyl}(cyclo-propyl)methyl]amino}-butanamide | HCl (1:1) | 1H NMR (270 MHz, MeOD-d4): 8.03-7.93 (4H, m), 7.80 (1H, t), 7.56 (1H, dd), 3.94 (1H, d), 3.50-3.40 (1H, m), 2.65-2.58 (2H, m), 1.63-1.45 (1H, m), 1.31 (3H, d), 0.98-0.84 (1H, m), 0.78-0.62 (2H, m), 0.47-0.35 (1H, m). | m/z: 414 | Prepared according to Example 81 using Example 32 |
| 130 | 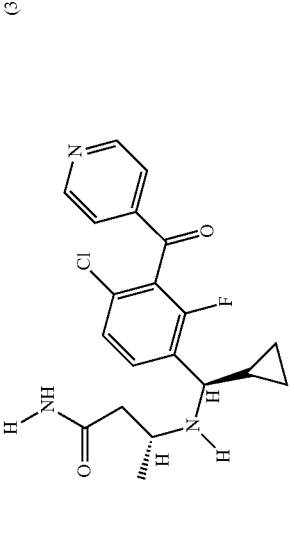 | (3R)-3-{[(R)-{4-chloro-2-fluoro-3-[(pyridin-4-yl)carbonyl]phenyl}-(cyclopropyl)methyl]-amino}butanamide | HCl (1:1) | 1H NMR (400 MHz, DMSO-d6): 9.81 (2H, s), 8.96-8.88 (2H, m), 8.24 (1H, t), 7.81-7.68 (4H, m), 7.22 (1H, s), 4.07-3.95 (1H, m), 3.56 (1H, d), 2.61 (1H, dd), 2.47-2.34 (1H, m), 1.60 (1H, d), 1.28 (3H, d), 0.88-0.72 (2H, m), 0.63-0.52 (1H, m), 0.30-0.20 (1H, m). | m/z: 390 | Prepared according to Example 81 using Example 33 |

TABLE 2-continued

| | Structure | Name | Salt | NMR Data | MS Data | Method |
|---|---|---|---|---|---|---|
| 131 | 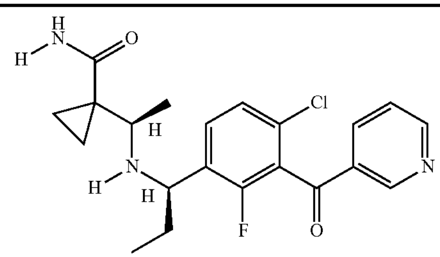 | 1-[(1R)-1-{[(1R)-1-{4-chloro-2-fluoro-3-[(pyridin-3-yl)carbonyl]-phenyl}-propyl]amino}-ethyl]-cyclopropane-1-carboxamide | HCl (1:1) | 1H NMR (400 MHz, Me-d3-OD): 9.15 (1H, d), 9.01 (1H, dd), 8.63 (1H, dt), 7.95 (1H, dd), 7.86 (1H, t), 7.68 (1H, dd), 4.71 (1H, dd), 3.01 (1H, q), 2.33-2.18 (1H, m), 2.12-1.97 (1H, m), 1.48 (3H, d), 1.46-1.40 (1H, m), 1.36-1.27 (1H, m), 1.05-0.89 (5H, m). | m/z: 404 | Example 131 |
| 132 | 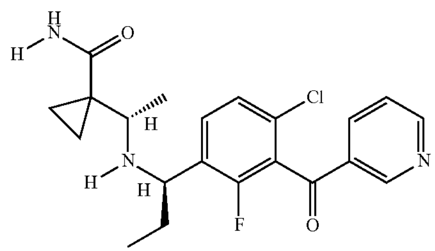 | 1-[(1S)-1-{[(1R)-1-{4-chloro-2-fluoro-3-[(pyridin-3-yl)carbonyl]phenyl}propyl]amino}ethyl]cyclopropane-1-carboxamide | HCl (1:1) | 1H NMR (400 MHz, Me-d3-OD): 9.17 (1H, d), 9.01 (1H, dd), 8.67 (1H, dt), 7.98 (1H, dd), 7.82 (1H, t), 7.66 (1H, dd), 4.68 (1H, dd), 2.96 (1H, q), 2.33-2.19 (1H, m), 2.18-2.04 (1H, m), 1.47 (3H, d), 1.45-1.40 (1H, m), 1.32-1.25 (1H, m), 1.17-1.06 (1H, m), 1.06-0.98 (1H, m), 0.94 (3H, t). | m/z: 404 | Example 132 |
| 133 | 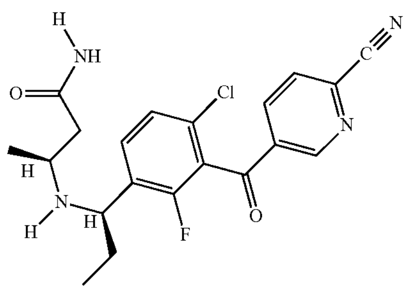 | (3S)-3-{[(1R)-1-{4-chloro-3-[(6-cyanopyridin-3-yl)carbonyl]-2-fluorophenyl}propyl]amino}butanamide | None | 1H NMR (400 MHz, Me-d3-OD): 9.08 (1H, d), 8.39 (1H, d), 8.14-8.05 (1H, m), 7.70 (1H, t), 7.47 (1H, d), 4.07 (1H, dd), 2.91-2.78 (1H, m), 2.26 (2H, d), 1.95-1.79 (1H, m), 1.78-1.62 (1H, m), 1.09 (3H, d), 0.87 (3H, t). | m/z: 403 | Prepared according to Example 82 using Example 34 |

TABLE 2-continued

| | Structure | Name | Salt | NMR Data | MS Data | Method |
|---|---|---|---|---|---|---|
| 134 | 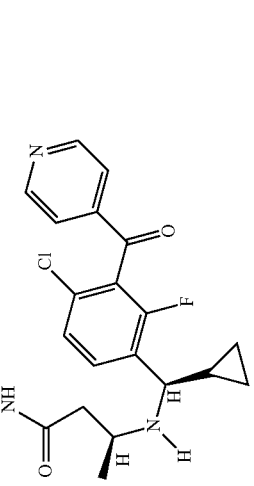 | (3S)-3-{[(R)-{4-chloro-2-fluoro-3-[(pyridin-4-yl)carbonyl]phenyl}-(cyclopropyl)methyl]-amino}butanamide | HCl (1:1) | 1H NMR (400 MHz, CDCl3): 14.48 (2H, d), 13.72-13.64 (2H, m), 12.94 (1H, t), 12.56-12.43 (4H, m), 11.94 (1H, s), 8.80-8.70 (1H, m), 8.20-8.15 (1H, m), 7.49 (1H, dd), 7.24-7.17 (1H, m), 6.38 (1H, s), 5.97 (3H, d), 5.55 (2H, q), 5.36-5.29 (1H, m), 5.06-4.99 (1H, m). | m/z: 390 | Prepared according to Example 81 using Example 33 |
| 135 | 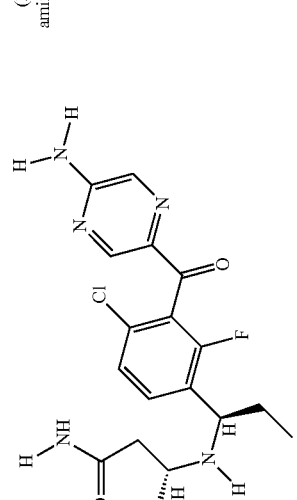 | (3R)-3-{[(1R)-1-{3-[(5-aminopyrazin-2-yl)carbonyl]-4-chloro-2-fluorophenyl}propyl]-amino}butanamide | HCl (1:1) | 1H NMR (400 MHz, DMSO-d6): 9.70 (1H, d), 9.30 (1H, s), 8.72 (1H, d), 7.95 (1H, t), 7.84 (3H, d), 7.70 (1H, s), 7.59 (1H, dd), 7.18 (1H, s), 4.51 (1H, d), 3.47-3.40 (1H, m), 2.59 (1H, dd), 2.40 (1H, dd), 2.25-2.13 (1H, m), 1.99-1.91 (1H, m), 1.24 (3H, d), 0.76 (3H, t). | m/z: 394 | Prepared according to Example 82 using Example 3 |
| 136 | 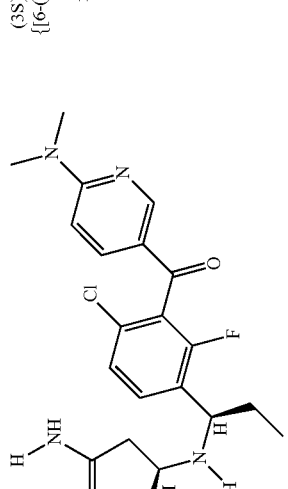 | (3S)-3-{[(1R)-1-(4-chloro-3-{[6-(dimethylamino)pyridin-3-yl]carbonyl}-2-fluorophenyl)propyl]-amino}butanamide | None | 1H NMR (400 MHz, Me-d3-OD): 8.33 (1H, d), 7.96 (1H, dd), 7.59 (1H, t), 7.40 (1H, d), 6.78 (1H, d), 4.08 (1H, dd), 3.22 (6H, s), 2.91-2.76 (1H, m), 2.26 (2H, d), 1.96-1.78 (1H, m), 1.77-1.58 (1H, m), 1.08 (3H, d), 0.86 (3H, t). | m/z: 421 (Fragment) | Prepared according to Example 82 using Example 35 |
| 137 | (3R)-3-{[(1R)-1-(4-chloro-3-{[6-(dimethylamino)pyridin-3-yl]carbonyl}-2-fluorophenyl)propyl]amino}butanamide m/z: 421 | | | | | As Ex. 136 |

TABLE 2-continued

| | Structure | Name | Salt | NMR Data | MS Data | Method |
|---|---|---|---|---|---|---|
| 138 | 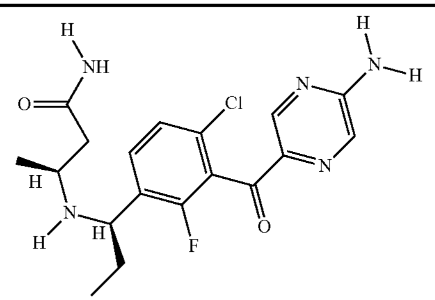 | (3S)-3-{[(1R)-1-{3-[(5-aminopyrazin-2-yl)carbonyl]-4-chloro-2-fluorophenyl}propyl]-amino}butanamide | HCl (1:1) | 1H NMR (400 MHz, DMSO-d6): 10.27 (1H, s), 9.69 (1H, s), 8.72 (1H, s), 8.16-8.05 (1H, m), 8.05-7.64 (4H, m), 7.59 (1H, d), 7.11 (1H, s), 4.45 (1H, s), 3.17 (1H, s), 2.78 (1H, dd), 2.47 (1H, d), 2.23 (1H, s), 2.06-1.94 (1H, m), 1.17 (3H, d), 0.73 (3H, t). | m/z: 394 | Example 138 |
| 139 | 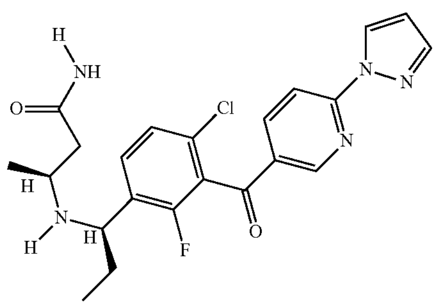 | (3S)-3-{[(1R)-1-(4-chloro-2-fluoro-3-{[6-(1H-pyrazol-1-yl)pyridin-3-yl]carbonyl}phenyl)-propyl]amino}-butanamide | HCl (1:1) | 1H NMR (400 MHz, Me-d3-OD): 8.86 (1H, d), 8.72 (1H, d), 8.41 (1H, dd), 8.17 (1H, d), 7.87 (1H, d), 7.80 (1H, t), 7.65 (1H, d), 6.63 (1H, dd), 4.71 (1H, dd), 3.53-3.47 (1H, m), 2.72-2.54 (2H, m), 2.26-2.08 (2H, m), 1.41 (3H, d), 0.95 (3H, t). | m/z: 444 | Prepared according to Example 82 using Example 37 |
| 140 | (3R)-3-{[(1R)-1-(4-chloro-2-fluoro-3-{[6-(1H-pyrazol-1-yl)pyridin-3-yl]carbonyl}-phenyl)-propyl]amino}-butanamide HCl (1:1) m/z: 444 | | None | | | As Ex. 139 |
| 141 | 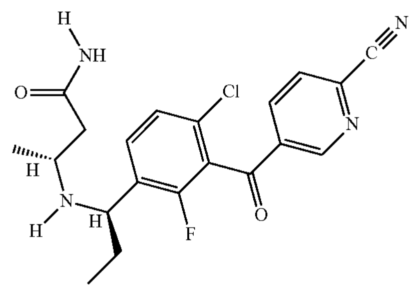 | (3R)-3-{[(1R)-1-{4-chloro-3-[(6-cyanopyridin-3-yl)carbonyl]-2-fluorophenyl}propyl]-amino}butanamide | | 1H NMR (400 MHz, DMSO-d6): 9.12 (1H, d), 8.40 (1H, dd), 8.27 (1H, d), 7.80 (1H, t), 7.56 (1H, d), 7.36 (1H, s), 6.79 (1H, d), 3.93 (1H, t), 2.79-2.66 (1H, m), 2.20 (1H, dd), 1.97 (1H, dd), 1.72-1.47 (2H, m), 0.93 (3H, d), 0.81 (3H, t), −0.50 (1H, s). | m/z: 403 | Prepared according to Example 82 using Example 34 |

TABLE 2-continued

| | Structure | Name | Salt | NMR Data | MS Data | Method |
|---|---|---|---|---|---|---|
| 142 | 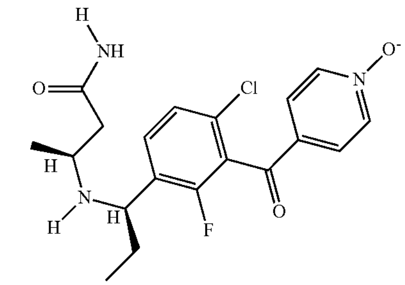 | (S)-3-{(R)-1-[4-Chloro-2-fluoro-3-(1-oxy-pyridine-4-carbonyl)-phenyl]-propylamino}-butyramide | HCl (1:1) | 1H NMR (400 MHz, DMSO-d6): 9.73 (1H, s), 9.32 (1H, s), 8.39 (2H, d), 8.04 (1H, t), 7.82 (2H, d), 7.78-7.67 (2H, m), 7.22 (1H, s), 4.55 (1H, s), 3.29 (1H, s), 2.64 (1H, dd), 2.46 (1H, dd), 2.24-2.12 (1H, m), 2.09-1.96 (1H, m), 1.23 (3H, d), 0.77 (3H, t). | m/z: 394 | Prepared according to Example 116 using ethyl isonicotinate in Step 1 |
| 143 | (R)-3-{(R)-1-[4-Chloro-2-fluoro-3-(1-oxy-pyridine-4-carbonyl)-phenyl]propylamino}-butyramide HCl (1:1) m/z: 394 | | | | | As Ex. 142 |
| 144 | 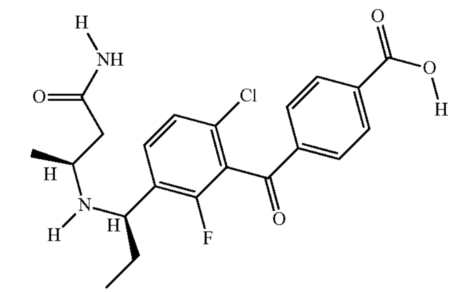 | 4-({3-[(1R)-1-{[(2S)-1-carbamoylpropan-2-yl]amino}propyl]-6-chloro-2-fluorophenyl}carbonyl)-benzoic acid | None | 1H NMR (400 MHz, DMSO-d6): 8.12 (2H, d), 7.88 (2H, d), 7.71 (1H, t), 7.52 (1H, d), 7.34 (1H, s), 6.80 (1H, s), 3.99-3.90 (1H, m), 2.76-2.65 (1H, m), 2.15-2.00 (2H, m), 1.69 (1H, m), 1.63-1.51 (1H, m), 0.93 (3H, d), 0.80 (3H, t). | m/z: 421 | Prepared according to Example 144 |
| 145 | 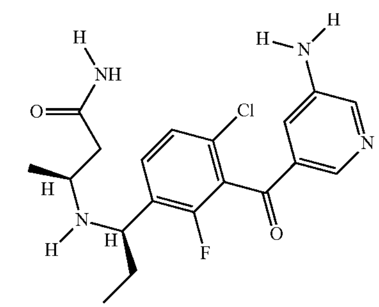 | (3S)-3-{[(1R)-1-{3-[(5-aminopyridin-3-yl)carbonyl]-4-chloro-2-fluorophenyl}propyl]-amino}butanamide | HCl (1:1) | 1H NMR (400 MHz, Me-d3-OD): 8.23 (1H, s), 8.17 (1H, s), 7.79 (1H, t), 7.69-7.58 (2H, m), 4.69 (1H, dd), 3.53-3.46 (1H, m), 2.71-2.54 (2H, m), 2.25-2.07 (2H, m), 1.40 (3H, d), 0.94 (3H, t). | m/z: 393 | Prepared according to Example 81 using Example 45 |

TABLE 2-continued

| | Structure | Name | Salt | NMR Data | MS Data | Method |
|---|---|---|---|---|---|---|
| 146 | 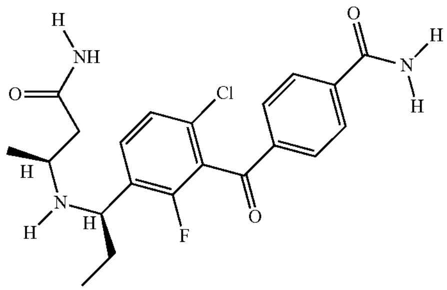 | 4-({3-[((1R)-1-{[(2S)-1-carbamoylpropan-2-yl]amino}propyl]-6-chloro-2-fluorophenyl}carbonyl)-benzamide | None | 1H NMR (400 MHz, DMSO-d6): 8.20 (1H, s), 8.03 (2H, d), 7.84 (2H, d), 7.67 (2H, dd), 7.51 (1H, d), 7.33 (1H, s), 6.78 (1H, s), 3.93 (1H, s), 2.75-2.63 (1H, m), 2.32 (1H, s), 2.16-1.97 (2H, m), 1.76-1.62 (1H, m), 1.62-1.47 (1H, m), 0.92 (3H, d), 0.80 (3H, t). | m/z: 420 | Prepared according to Example 146 |
| 147 | 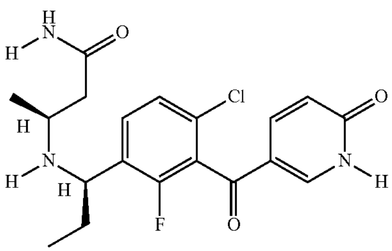 | (3S)-3-{[(1R)-1-{4-chloro-2-fluoro-3-[(6-oxo-1,6-dihydropyridin-3-yl)carbonyl]-phenyl}propyl]amino}-butanamide | HCl (1:1) | 1H NMR (400 MHz, Me-d3-OD): 8.07 (1H, dd), 8.00 (1H, d), 7.74 (1H, t), 7.59 (1H, d), 6.62 (1H, d), 4.66 (1H, dd), 3.51-3.44 (1H, m), 2.70-2.54 (2H, m), 2.25-2.07 (2H, m), 1.41 (3H, d), 0.93 (3H, t). | m/z: 394 | Prepared according to Example 81 using Example 38 |
| 148 | (3R)-3-{[(1R)-1-{4-chloro-2-fluoro-3-[(6-oxo-1,6-dihydropyridin-3-yl)carbonyl]-phenyl}propyl]amino}-butanamide HCl (1:1) m/z: 394 | | | | | As Ex. 147 |
| 149 | 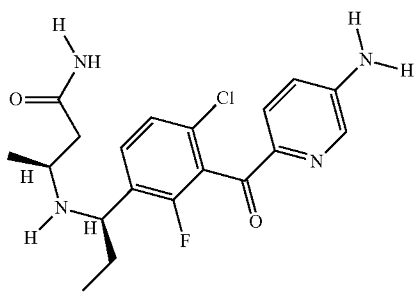 | (3S)-3-{[(1R)-1-{3-[(5-aminopyridin-2-yl)carbonyl]-4-chloro-2-fluorophenyl}propyl]amino}-butanamide | HCl (1:1) | 1H NMR (400 MHz, Me-d3-OD): 8.03-7.98 (2H, m), 7.71 (1H, t), 7.55 (1H, d), 7.23 (1H, dd), 4.67 (1H, dd), 3.57-3.45 (1H, m), 2.69-2.55 (2H, m), 2.25-2.03 (2H, m), 1.38 (3H, d), 0.94 (3H, t). | m/z: 393 | Prepared according to Example 81 using Example 5 |

TABLE 2-continued

| | Structure | Name | Salt | NMR Data | MS Data | Method |
|---|---|---|---|---|---|---|
| 150 | 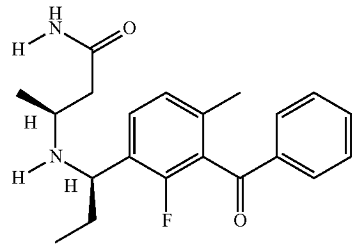 | (3S)-3-{[(1R)-1-(3-benzoyl-2-fluoro-4-methylphenyl)propyl]-amino}butanamide | HCl (1:1) | 1H NMR (400 MHz, Me-d3-OD): 7.87-7.81 (2H, m), 7.71 (1H, tt), 7.62 (1H, t), 7.59-7.53 (2H, m), 7.37 (1H, d), 4.62 (1H, dd), 3.49-3.39 (1H, m), 2.68-2.54 (2H, m), 2.25 (3H, s), 2.23-2.05 (2H, m), 1.37 (3H, d), 0.92 (3H, t). | m/z: 357 | Prepared according to Example 81 using Example 39. |
| 151 | (3R)-3-{[(1R)-1-(3-benzoyl-2-fluoro-4-methylphenyl)propyl]amino}butanamide HCl (1:1) m/z: 357.2 | | | | | |
| 152 | 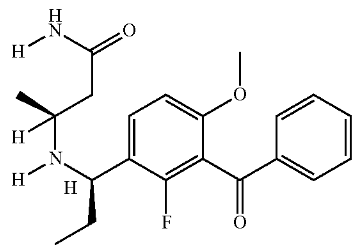 | (3S)-3-{[(1R)-1-(3-benzoyl-2-fluoro-4-methoxyphenyl)propyl]-amino}butanamide | HCl (1:1) | 1H NMR (400 MHz, Me-d3-OD): 7.85-7.79 (2H, m), 7.73-7.65 (2H, m), 7.57-7.50 (2H, m), 7.17 (1H, d), 4.58 (1H, dd), 3.83 (3H, s), 3.49-3.40 (1H, m), 2.68-2.54 (2H, m), 2.24-2.04 (2H, m), 1.38 (3H, d), 0.93 (3H, t). | m/z: 373 | Prepared according to Example 81 using Example 40. |
| 153 | (3R)-3-{[(1R)-1-(3-benzoyl-2-fluoro-4-methoxyphenyl)propyl]amino}butanamide HCl (1:1) m/z: 373 | | | | | |
| 154 | 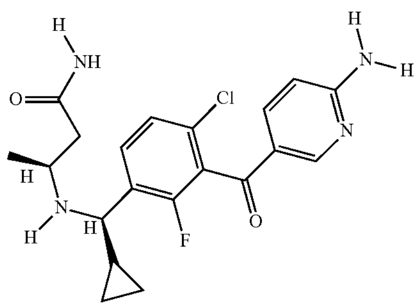 | (3S)-3-{[(R)-{3-[(6-aminopyridin-3-yl)carbonyl]-4-chloro-2-fluorophenyl}(cyclo-propyl)methyl]amino}-butanamide | HCl (1:1) | 1H NMR (400 MHz, Me-d3-OD): 8.36 (1H, d), 8.31 (1H, dd), 7.82 (1H, t), 7.60 (1H, d), 7.08 (1H, d), 4.00 (1H, d), 3.58-3.51 (1H, m), 2.70-2.60 (2H, m), 1.69-1.57 (1H, m), 1.39 (3H, d), 1.03-0.92 (1H, m), 0.82-0.69 (2H, m), 0.51-0.41 (1H, m). | m/z: 405 | Example 154 followed by salt formation |
| 155 | (3R)-3-{[(R)-{3-[(6-aminopyridin-3-yl)carbonyl]-4-chloro-2-fluorophenyl}(cyclo-propyl)methyl]amino}-butanamide HCl (1:1) m/z: 405 | | | | | As Ex. 154 |

TABLE 2-continued

| | Structure | Name | Salt | NMR Data | MS Data | Method |
|---|---|---|---|---|---|---|
| 156 | 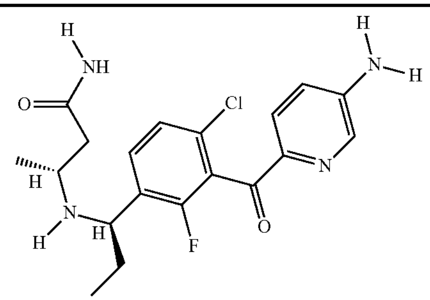 | (3R)-3-{[(1R)-1-{3-[(5-aminopyridin-2-yl)carbonyl]-4-chloro-2-fluorophenyl}propyl]-amino}butanamide | HCl (1:1) | 1H NMR (400 MHz, Me-d3-OD): 8.06 (1H, d), 8.00 (1H, d), 7.73 (1H, t), 7.57 (1H, d), 7.30 (1H, dd), 4.67 (1H, dd), 3.75-3.64 (1H, m), 2.75-2.53 (2H, m), 2.32-2.17 (1H, m), 2.17-2.01 (1H, m), 1.46-1.37 (3H, d), 0.96 (3H, t). | m/z: 393 | Prepared according to Example 81 using Example 5 |
| 157 | 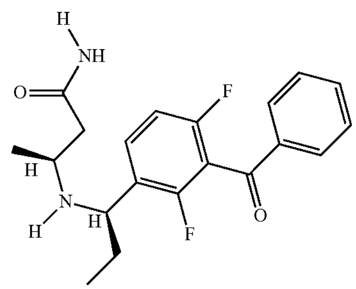 | (3S)-3-{[(1R)-1-(3-benzoyl-2,4-difluorophenyl)propyl]-amino}butanamide | HCl (1:1) | 1H NMR (400 MHz, Me-d3-OD): 7.95-7.80 (3H, m), 7.73 (1H, t), 7.59 (2H, t), 7.36 (1H, t), 4.68 (1H, dd), 3.55-3.39 (1H, m), 2.73-2.54 (2H, m), 2.30-2.05 (2H, m), 1.40 (3H, d), 0.94 (3H, t). | m/z: 361 | Prepared according to Example 81 using Example 43 |
| 158 | (3R)-3-{[(1R)-1-(3-benzoyl-2,4-difluorophenyl)propyl]-amino}butanamide HCl (1:1) m/z: 360 | | | | | As Ex. 157 |
| 159 | 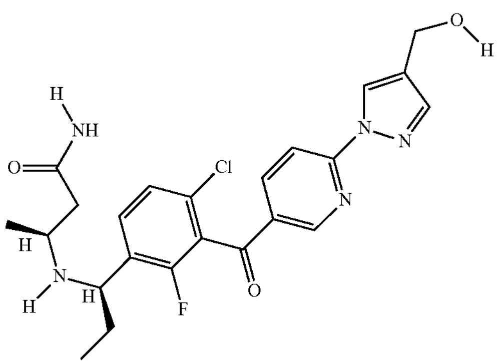 | (3S)-3-{[(1R)-1-[4-chloro-2-fluoro-3-({6-[4-(hydroxymethyl)-1H-pyrazol-1-yl]pyridin-3-yl}carbonyl)phenyl]propyl]amino}-butanamide | HCl (1:1) | 1H NMR (400 MHz, Me-d3-OD): 8.84 (1H, d), 8.65 (1H, s), 8.44-8.35 (1H, m), 8.18-8.10 (1H, m), 7.86 (1H, s), 7.80 (1H, t), 7.64 (1H, d), 4.74-4.65 (1H, m), 4.63 (2H, s), 3.55-3.45 (1H, m), 2.71-2.56 (2H, m), 2.25-2.09 (2H, m), 1.41 (3H, d), 0.95 (3H, t). | 94% by MS m/z: 474 | Prepared according to Example 82 using Example 46 |
| 160 | (3R)-3-{[(1R)-1-[4-chloro-2-fluoro-3-({6-[4-(hydroxymethyl)-1H-pyrazol-1-yl]pyridin-3-yl}carbonyl)phenyl]-propyl]amino}-butanamide HCl (1:1) m/z: 474 | | | | | As Ex. 159 |

TABLE 2-continued

| | Structure | Name | Salt | NMR Data | MS Data | Method |
|---|---|---|---|---|---|---|
| 161 | 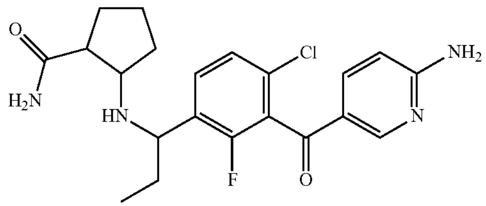 [SMILES: CCC(NC1CCCC1C(N)=O)c1ccc(Cl)c(C(=O)c2ccc(N)nc2)c1F] | 2-{[1-{3-[(6-aminopyridin-3-yl)carbonyl]-4-chloro-2-fluorophenyl}propyl]amino}cyclopentane-1-carboxamide. Cis-stereochemistry at ring junction; absolute stereochemistry not defined | HCl (1:1) | 1H NMR (400 MHz, DMSO-d6): 9.83 (1H, s), 9.40 (1H, s), 8.32 (1H, s), 8.15-7.71 (5H, m), 7.66 (1H, d), 7.52 (1H, s), 6.74 (1H, d), 4.41-4.30 (1H, s), 3.65-3.62 (1H, m), 2.83 (1H, q), 2.22-2.12 (1H, m), 2.03-1.71 (6H, m), 1.59-1.49 (1H, m), 0.79 (3H, t). | m/z: 419 (Molecular ion) | Prepared as Example 250 using racemic cis ethyl 2-aminocyclopentane-1-carboxylate hydrochloride in step 5 |
| 162 | 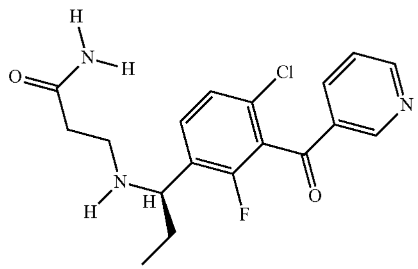 | 3-{[(1R)-1-{4-chloro-2-fluoro-3-[(pyridin-3-yl)carbonyl]phenyl}propyl]amino}-propanamide | HCl (1:1) | 1H NMR (400 MHz, Me-d3-OD): 8.92 (1H, d), 8.85 (1H, dd), 8.33-8.23 (1H, m), 7.77-7.61 (2H, m), 7.51 (1H, d), 4.12 (1H, s), 2.87 (2H, s), 2.48 (2H, t), 2.07-1.90 (1H, m), 1.90-1.75 (1H, m), 0.90 (3H, t) | m/z: 364 | Prepared according to Example 162 |
| 163 | 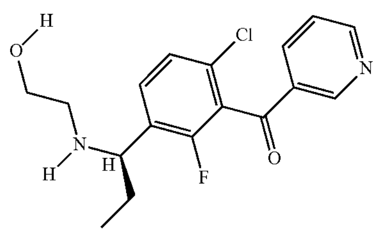 | 2-{[(1 R)-1-{4-chloro-2-fluoro-3-[(pyridin-3-yl)carbonyl]phenyl}propyl]amino}ethan-1-ol | HCl (1:1) | 1H NMR (400 MHz, Me-d3-OD): 9.34-9.15 (1H, m), 9.06 (1H, s), 8.85-8.63 (1H, m), 8.06 (1H, d), 7.86 (1H, t), 7.68 (1H, d), 4.61 (1H, dd), 3.82 (2H, t), 3.22-3.15 (1H, m), 3.13-3.04 (1H, m), 2.34-2.23 (1H, m), 2.16-2.05 (1H, m), 0.93 (3H, t). | m/z: 337 | Prepared according to Example 82 from Example 2: using (tert-butyldimethylsilyloxy)acetaldehyde followed by deprotection as Example 163 |
| 164 | 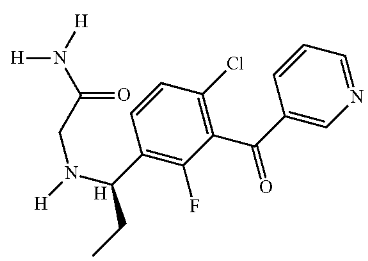 | 2-{[(1R)-1-{4-chloro-2-fluoro-3-[(pyridin-3-yl)carbonyl]phenyl}propyl]amino}acetamide | Trifluoroacetate (1:2) | 1H NMR (400 MHz, DMSO-d6): 10.00 (1H, s), 9.84 (1H, s), 9.02 (1H, s), 8.95 (1H, d), 8.31 (1H, d), 8.13 (1H, t), 7.85 (1H, s), 7.73 (2H, d), 7.54 (1H, s), 6.03 (5H, s), 4.48 (1H, s), 3.63 (2H, s), 2.29-2.16 (1H, s), 2.08-1.99 (1H, m), 0.74 (3H, t). | purity 94% m/z: 349 | Example 164 |

TABLE 2-continued

| | Structure | Name | Salt | NMR Data | MS Data | Method |
|---|---|---|---|---|---|---|
| 165 | 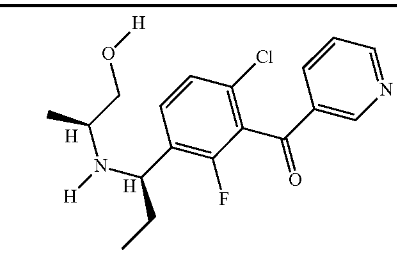 | (2S)-2-{[(1R)-1-{4-chloro-2-fluoro-3-[(pyridin-3-yl)carbonyl]phenyl]-propyl}amino]-propan-1-ol | HCl (1:1) | 1H NMR (400 MHz, Me-d3-OD): 9.17 (1H, s), 9.02 (1H, dd), 8.71-8.62 (1H, m), 7.99 (1H, dd), 7.87 (1H, t), 7.68 (1H, d), 4.71 (1H, dd), 3.79 (1H, dd), 3.29-3.20 (2H, m), 2.31-2.19 (1H, m), 2.19-2.04 (1H, m), 1.34 (3H, d), 0.93 (3H, t) | m/z: 351 | Prepared according to Example 82 using hydroxyacetone and Example 2 |
| 166 | (2R)-2-{[(1R)-1-{4-chloro-2-fluoro-3-[(pyridin-3-yl)carbonyl]phenyl]-propyl]amino}propan-1-ol HCl (1:1) m/z: 351 | | | | | As Ex. 165 |
| 167 | 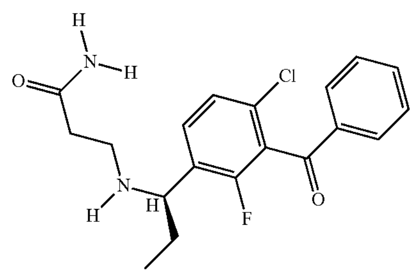 | 3-{[(1R)-1-(3-benzoyl-4-chloro-2-fluorophenyl)propyl]-amino}propanamide | HCl (1:1) | 1H NMR (400 MHz, Me-d3-OD): 7.90-7.81 (2H, m), 7.79-7.68 (2H, m), 7.65-7.53 (3H, m), 4.56 (1H, dd), 3.29-3.17 (2H, m), 2.68 (2H, t), 2.30-2.18 (1H, m), 2.16-2.05 (1H, m), 0.95 (3H, t). | m/z: 363 | Prepared according to Example 167 using Example 4 |
| 168 | 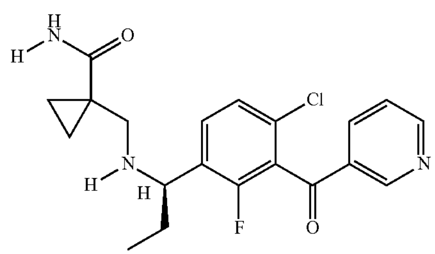 | 1-({[(1R)-1-{4-chloro-2-fluoro-3-[(pyridin-3-yl)carbonyl]phenyl]propyl]amino}methyl)-cyclopropane-1-carboxamide | HCl (1:1) | 1H NMR (400 MHz, Me-d3-OD): 9.22 (1H, d), 9.03 (1H, dd), 8.74 (1H, dt), 8.02 (1H, dd), 7.85 (1H, t), 7.66 (1H, dd), 4.53 (1H, dd), 3.26 (1H, d), 3.07 (1H, d), 2.36-2.20 (1H, m), 2.20-2.06 (1H, m), 1.45-1.30 (2H, m), 1.27-1.19 (1H, m), 1.14-1.04 (1H, m), 0.93 (3H, t). | m/z: 390 | Example 168 |
| 169 | (2R)-2-{[(1R)-1-{4-chloro-2-fluoro-3-[(pyridin-3-yl)carbonyl]phenyl]-propyl]amino}propanamide HCl (1:1) m/z: 364 | | | | | As Ex. 170 |

TABLE 2-continued

| | Structure | Name | Salt | NMR Data | MS Data | Method |
|---|---|---|---|---|---|---|
| 170 | 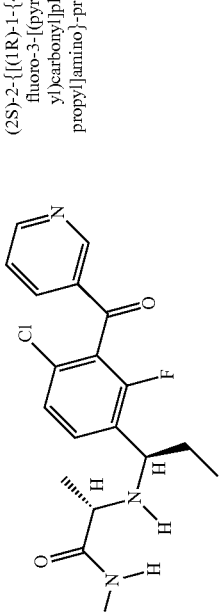 | (2S)-2-{[(1R)-1-{4-chloro-2-fluoro-3-[(pyridin-3-yl)carbonyl]phenyl}-propyl]amino}-propanamide | HCl (1:1) | 1H NMR (400 MHz, DMSO-d6): 10.16 (1H, s), 9.45 (1H, s), 8.96 (2H, d), 8.27 (1H, d), 8.10 (1H, t), 7.96 (1H, s), 7.71 (2H, d), 7.61 (1H, s), 4.35 (1H, s), 3.87 (1H, d), 2.23 (1H, s), 2.15-1.98 (1H, m), 1.44 (3H, d), 0.71 (3H, t). | m/z: 363 | Prepared according to Example 82 using Example 2 and methyl pyruvate |
| 171 | 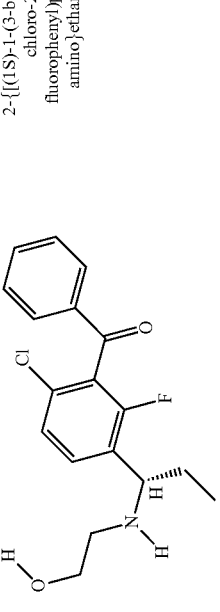 | 2-{[(1S)-1-(3-benzoyl-4-chloro-2-fluorophenyl)propyl]-amino}ethan-1-ol | HCl (1:1) | 1H NMR (400 MHz, Me-d3-OD): 7.90-7.80 (2H, m), 7.80-7.68 (2H, m), 7.65-7.53 (3H, m), 4.57 (1H, dd), 3.80 (2H, t), 3.21-3.11 (1H, m), 3.11-2.99 (1H, m), 2.32-2.19 (1H, m), 2.14-2.04 (1H, m), 0.92 (3H, t). | m/z: 336 | Prepared according to Example 6; using (tert-butyldimethylsilyloxy) acetaldehyde followed by deprotection as Example 163 |
| 172 | 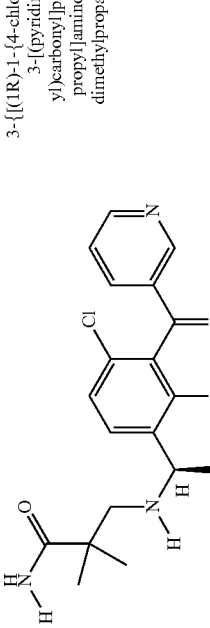 | 3-{[(1R)-1-{4-chloro-2-fluoro-3-[(pyridin-3-yl)carbonyl]phenyl}-propyl]amino}-2,2-dimethylpropanamide | HCl (1:1) | 1H NMR (400 MHz, Me-d3-OD): 9.08 (1H, s), 8.95 (1H, d), 8.54 (1H, d), 7.90-7.77 (2H, m), 7.64 (1H, dd), 4.53 (1H, dd), 3.17-3.00 (2H, m), 2.37-2.23 (1H, m), 2.22-2.08 (1H, m), 1.37 (3H, s), 1.32 (3H, s), 0.93 (3H, t). | m/z: 392 | Example 172 |
| 173 | 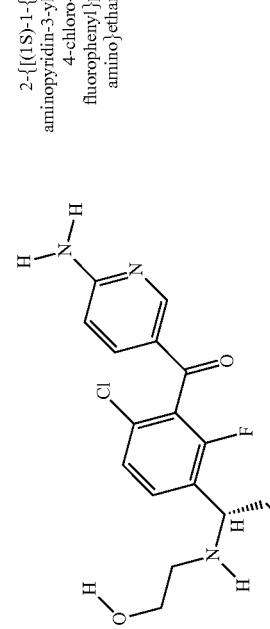 | 2-{[(1S)-1-{3-[(6-aminopyridin-3-yl)carbonyl]-4-chloro-2-fluorophenyl}-propyl]amino}ethan-1-ol | HCl (1:1) | 1H NMR (400 MHz, Me-d3-OD): 8.39-8.30 (2H, m), 7.81 (1H, t), 7.64 (1H, d), 7.15 (1H, t), 4.60 (1H, dd), 3.82 (2H, t), 3.20-3.12 (1H, m), 3.12-3.03 (1H, m), 2.32-2.23 (1H, m), 2.14-2.03 (1H, m), 0.92 (3H, t). | m/z: 352 | Prepared according to Example 82 from Example 31; using (tert-butyldimethylsilyloxy) acetaldehyde followed by deprotection as Example 163 |
| 174 | (2R)-3-{[(1R)-1-{4-chloro-2-fluoro-3-[(pyridin-3-yl)carbonyl]phenyl}-propyl]amino}-2-methylpropanamide HCl (1:1) m/z: 378 | | | | | As Ex. 175 |

TABLE 2-continued

| | Structure | Name | Salt | NMR Data | MS Data | Method |
|---|---|---|---|---|---|---|
| 175 | 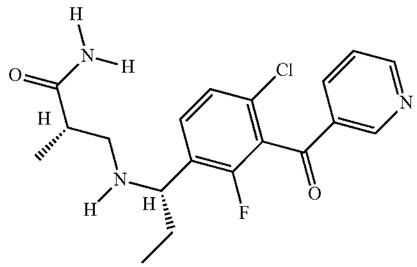 | (2S)-3-{[(1R)-1-{4-chloro-2-fluoro-3-[(pyridin-3-yl)carbonyl]phenyl}-propyl]amino}-2-methylpropanamide | HCl (1:1) | 1H NMR (400 MHz, Me-d3-OD): 9.17 (1H, d), 9.01 (1H, s), 8.76-8.58 (1H, m), 8.06-7.89 (1H, m), 7.83 (1H, t), 7.66 (1H, d), 4.56 (1H, dd), 3.05 (1H, dd), 2.90-2.74 (1H, m), 2.36-2.21 (1H, m), 2.19-2.02 (1H, m), 1.31 (3H, d), 1.00-0.90 (3H, m). | m/z: 378 | Prepared according to Example 82 from Example 2; using formyl-propionic acid ethyl ester followed by Example 174 |
| 176 177 | | 2-{[(1R)-1-(3-benzoyl-4-chloro-2-fluorophenyl)propyl]amino}ethan-1-ol HCl (1:1) m/z: 336 (2S)-2-{[(1S)-1-{3-[(6-aminopyridin-3-yl)carbonyl]-4-chloro-2-fluorophenyl}propyl]amino}propan-1-ol HCl (1:1) m/z: 366 | | | | As Ex. 171 As Ex. 178 |
| 178 | 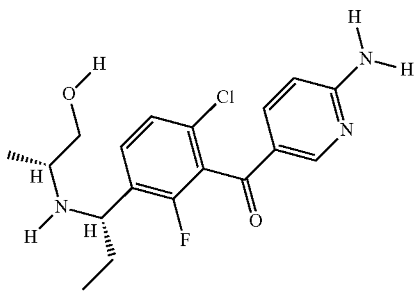 | (2R)-2-{[(1S)-1-{3-[(6-aminopyridin-3-yl)carbonyl]-4-chloro-2-fluorophenyl}propyl]amino}propan-1-ol | HCl (1:1) | 1H NMR (400 MHz, Me-d3-OD): 8.28 (1H, d), 8.22 (1H, dd), 7.77 (1H, t), 7.63 (1H, d), 7.01 (1H, d), 4.69 (1H, dd), 3.79 (1H, dd), 3.22-3.18 (1H, m), 2.33-2.18 (1H, m), 2.08-2.00 (1H, m), 1.35 (3H, d), 0.92 (3H, t). | m/z: 366 | Prepared according to Example 82 using hydroxyacetone and Example 31 |
| 179 | 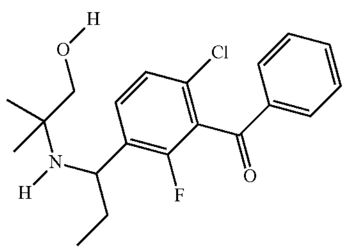 [SMILES: CCC(NC(C)(C)CO)c1ccc(Cl)c(C(=O)c2ccccc2)c1F] | 2-{[1-(3-benzoyl)-4-chloro-2-fluorophenyl)-propyl]amino}-2-methylpropan-1-ol | HCl (1:1) | 1H NMR (400 MHz, DMSO-d6): 8.96-8.85 (1H, m), 8.81-8.71 (1H, m), 7.95 (1H, t), 7.85-7.75 (3H, m), 7.75-7.58 (3H, m), 5.63 (1H, t), 4.60-4.50 (1H, m), 3.48 (1H, dd), 3.44-3.37 (1H, m), 2.27-2.16 (1H, m), 2.09-1.97 (1H, m), 1.24 (3H, s), 1.18 (3H, s), 0.70 (3H, t). | m/z: 364 | Example 179 |

TABLE 2-continued

| | Structure | Name | Salt | NMR Data | MS Data | Method |
|---|---|---|---|---|---|---|
| 180 | 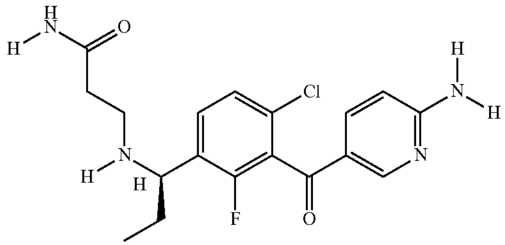 | 3-{[(1R)-1-{3-[(6-aminopyridin-3-yl)carbonyl]-4-chloro-2-fluorophenyl}propyl]-amino}propanamide | HCl (1:1) | 1H NMR (400 MHz, Me-d3-OD): 8.25 (1H, s), 8.06 (1H, dd), 7.73 (1H, t), 7.59 (1H, d), 6.77 (1H, d), 4.56 (1H, dd), 3.31-3.25 (1H, m), 3.25-3.13 (1H, m), 2.69 (2H, t), 2.31-2.17 (1H, m), 2.16-2.02 (1H, m), 0.93 (3H, t). | m/z: 379 | Example 180 |
| 181 | 3-{[(1S)-1-(3-benzoyl-4-chloro-2-fluorophenyl)propyl]-amino}propan-1-ol HCl (1:1) m/z: 350 | | | | | As Ex. 182 |
| 182 | 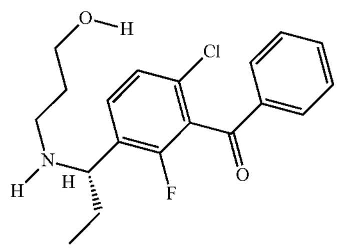 | 3-{[(1S)-1-(3-benzoyl-4-chloro-2-fluorophenyl)propyl]-amino}propan-1-ol | HCl (1:1) | 1H NMR (400 MHz, Me-d3-OD): 7.90-7.80 (2H, m), 7.80-7.66 (2H, m), 7.65-7.53 (3H, m), 4.55 (1H, dd), 3.74-3.63 (2H, m), 3.23-3.13 (1H, m), 3.12-3.02 (1H, m), 2.29-2.17 (1H, m), 2.14-2.04 (1H, m), 1.97-1.84 (2H, m), 0.94 (3H, t). | m/z: 350 | Prepared according to Example 82 from Example 6; using 3-(tert-butyl-dimethyl-silyanyl-oxy)propion-aldehyde)followed by deprotection as Example 163 |
| 183 | 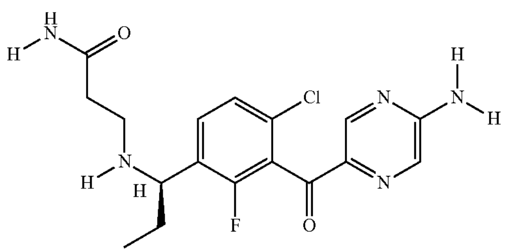 | 3-{[(1R)-1-{3-[(5-aminopyrazin-2-yl)carbonyl]-4-chloro-2-fluorophenyl}propyl]-amino}propanamide | HCl (1:1) | 1H NMR (400 MHz, Me-d3-OD): 8.73 (1H, d), 7.95 (1H, d), 7.66 (1H, t), 7.53 (1H, dd), 4.53 (1H, dd), 3.37-3.16 (2H, m), 2.68 (2H, t), 2.30-2.15 (1H, m), 2.15-2.01 (1H, m), 0.94 (3H, t). | m/z: 380 | Example 183 |
| 184 | 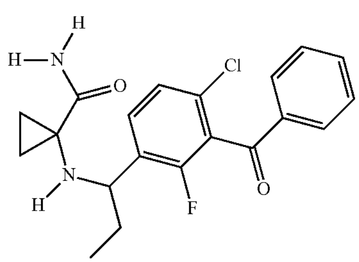 [SMILES: CCC(NC1(C(N)=O)CC1)c1ccc(Cl)c(C(=O)c2ccccc2)c1F] | 1-{[1-(3-benzoyl-4-chloro-2-fluorophenyl)propyl]amino}cyclopropane-1-carboxamide | HCl (1:1) | 1H NMR (400 MHz, Me-d3-OD): 7.83 (2H, d), 7.77-7.60 (2H, m), 7.60-7.45 (2H, m), 7.40 (1H, d), 4.05 (1H, s), 3.07-2.87 (1H, m), 2.36 (1H, dd), 2.31-2.09 (1H, m), 1.08 (3H, d). | m/z: 375 | Example 184 |

TABLE 2-continued

| | Structure | Name | Salt | NMR Data | MS Data | Method |
|---|---|---|---|---|---|---|
| 185 | 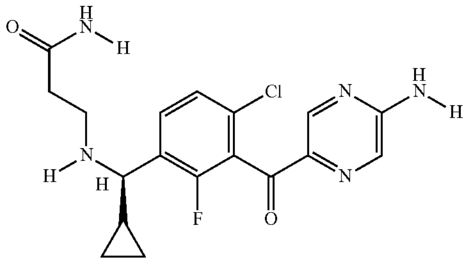 | 3-{[(R)-{3-[(5-aminopyrazin-2-yl)carbonyl]-4-chloro-2-fluorophenyl}(cyclopropyl)methyl]amino}-propanamide | HCl (1:1) | 1H NMR (400 MHz, DMSO-d6): 9.73-9.62 (1H, m), 9.43-9.33 (1H, m), 8.73 (1H, s), 7.98 (1H, t), 7.90-7.74 (3H, m), 7.64-7.53 (2H, m), 7.07 (1H, s), 3.98-3.88 (1H, m), 3.19 (1H, d), 3.08-2.98 (1H, m), 2.64-2.54 (2H, m), 1.53 (1H, d), 0.85-0.71 (2H, m), 0.61-0.51 (1H, m), 0.24-0.14 (1H, m). | m/z: 392 | Prepared as Example 182 using Example 56 |
| 186 | 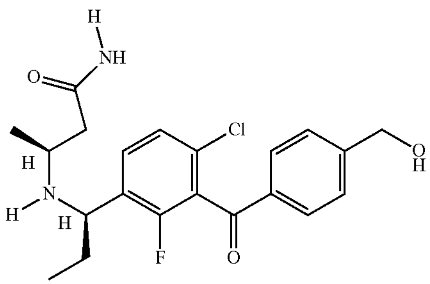 | (3S)-3-{[(1R)-1-(4-chloro-2-fluoro-3-{[4-(hydroxymethyl)-phenyl]carbonyl}phenyl)propyl]amino}-butanamide | HCl (1:1) | 1H NMR (400 MHz, DMSO-d6): 9.54 (1H, s), 9.21 (1H, s), 7.98 (1H, t), 7.77 (2H, d), 7.72 (1H, d), 7.67 (1H, s), 7.54 (2H, d), 7.23-7.15 (1H, m), 5.47-5.39 (1H, m), 4.61 (2H, s), 4.56 (1H, s), 2.61 (1H, dd), 2.47-2.39 (1H, m), 2.22-2.12 (1H, m), 2.06-1.96 (1H, m), 1.23 (3H, d), 0.78 (3H, t). | m/z: 407 | Prepared as Example 81 using Example 50 |
| 187 | | (3R)-3-{[(1R)-1-(4-chloro-2-fluoro-3-{[[4-(hydroxymethyl)-phenyl]-carbonyl]}phenyl)-propyl]amino}butanamide HCl (1:1) m/z: 407 | HCl | 1H NMR (400 MHz, DMSO-d6): 9.49 (1H, s), 9.18 (1H, s), 7.96 (1H, t), 7.80 (1H, s), 7.77-7.61 (4H, m), 7.57 (1H, t), 7.19 (1H, s), 5.36 (1H, s), 4.56 (3H, s), 2.59 (1H, dd), 2.48-2.34 (1H, m), 2.22-2.09 (1H, m), 2.01 (1H, m), 1.22 (3H, d), 0.84-0.69 (3H, m). | m/z: 407 | As Ex. 186 |
| 188 | 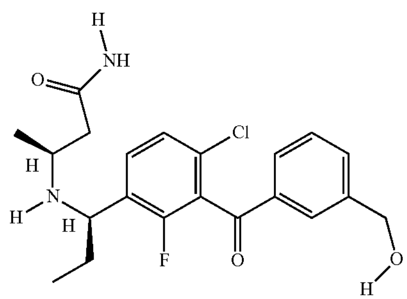 | (3S)-3-{[(1R)-1-(4-chloro-2-fluoro-3-{[3-(hydroxymethyl)phenyl]carbonyl}phenyl)-propyl]amino}butanamide | HCl | | | Prepared as Example 81 using Example 54 |
| 189 | | (3R)-3-{[(1R)-1-(4-chloro-2-fluoro-3-{[[3-(hydroxymethyl)-phenyl]-carbonyl]}phenyl)-propyl]amino}butanamide HCl (1:1) m/z: 407 | | | | As Ex. 188 |

TABLE 2-continued

| | Structure | Name | Salt | NMR Data | MS Data | Method |
|---|---|---|---|---|---|---|
| 190 | 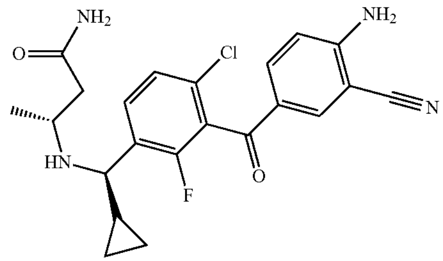 [SMILES: C[C@H](CC(N)=O)N[C@@H](c1ccc(Cl)c(C(=O)c2ccc(N)c(C#N)c2)c1F)C1CC1] | (3R)-3-{[(R)-{3-[(4-amino-3-cyanophenyl)carbonyl]-4-chloro-2-fluorophenyl}(cyclopropyl)methyl]amino}butanamide | HCl (1:1) | 1H NMR (400 MHz, Me-d3-OD): 7.89-7.81 (1H, m), 7.80-7.70 (2H, m), 7.55 (1H, d), 6.91 (1H, d), 4.02 (1H, d), 3.75 (1H, s), 2.72-2.59 (1H, m), 2.54 (1H, dd), 1.51 (1H, s), 1.36 (3H, d), 1.03-0.88 (1H, m), 0.84-0.65 (2H, m), 0.48-0.36 (1H, m). | m/z: 429 | Prepared according to Example 81 from Example 75 |
| 191 | 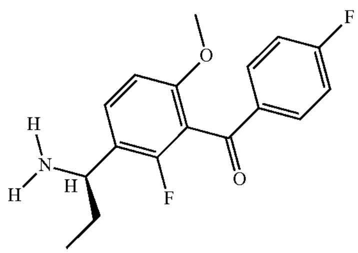 | (1R)-1-{2-fluoro-3-[(4-fluorophenyl)carbonyl]-4-methoxyphenyl}-propan-1-amine | HCl (1:1) | 1H NMR (400 MHz, Me-d3-OD): 7.94-7.83 (2H, m), 7.63 (1H, t), 7.32-7.21 (2H, m), 7.13 (1H, d), 4.44 (1H, dd), 3.82 (3H, s), 2.15-1.96 (2H, m), 0.98 (3H, t). | m/z: 289 [M − NH$_2$]$^+$ | (i) As Example 1 Step 1 using ethyl 4-fluorobenzoate; (ii) as Intermediate 14; and (iii) as Example 1 step 3 |
| 192 | 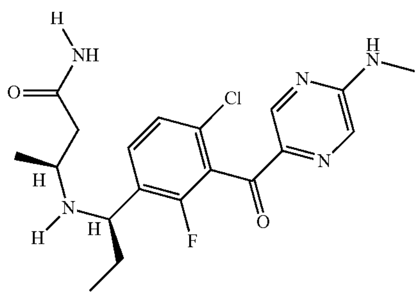 | (3S)-3-{[(1R)-1-(4-chloro-2-fluoro-3-{[5-(methylamino)-pyrazin-2-yl]carbonyl}-phenyl)propyl]-amino}butanamide | HCl (1:1) | 1H NMR (400 MHz, DMSO-d6): 9.83 (1H, s), 9.41-9.31 (1H, m), 8.78 (1H, s), 8.48-8.39 (1H, m), 7.95 (1H, t), 7.88 (1H, s), 7.68 (1H, s), 7.60 (1H, d), 7.13 (1H, s), 4.51 (1H, s), 3.22 (1H, s), 2.92 (3H, d), 2.68 (1H, dd), 2.45 (1H, d), 2.24-2.13 (1H, m), 2.03-1.91 (1H, m), 1.20 (3H, d), 0.75 (3H, t). | m/z: 408 | Prepared as Example 81 using Example 57 |
| 193 | 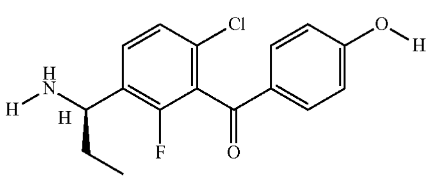 | 4-({3-[(1R)-1-aminopropyl]-6-chloro-2-fluorophenyl}-carbonyl)phenol | HCl (1:1) | 1H NMR (400 MHz, DMSO-d6): 10.85 (1H, s), 8.61 (3H, s), 7.82 (1H, t), 7.66 (2H, d), 7.62 (1H, d), 6.93 (2H, d), 4.40 (1H, dd), 2.09-1.95 (1H, m), 1.95-1.80 (1H, m), 0.83 (3H, t). | m/z: 308 | Example 193 |

TABLE 2-continued

| | Structure | Name | Salt | NMR Data | MS Data | Method |
|---|---|---|---|---|---|---|
| 194 | 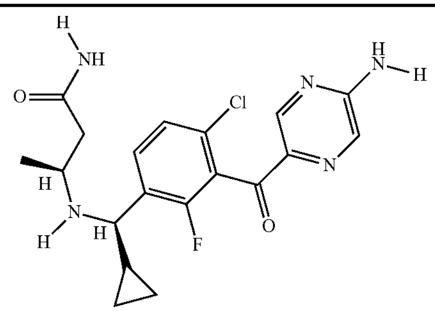 | (3S)-3-{[(R)-{3-[(5-aminopyrazin-2-yl)carbonyl]-4-chloro-2-fluorophenyl}(cyclo-propyl)methyl]amino}-butanamide | HCl (1:1) | 1H NMR (400 MHz, DMSO-d6): 9.58 (1H, s), 9.54-9.45 (1H, m), 8.73 (1H, d), 8.05-7.95 (1H, m), 7.89-7.75 (3H, m), 7.73-7.64 (1H, m), 7.59 (1H, d), 7.14 (1H, s), 3.98-3.88 (1H, m), 3.38-3.29 (1H, m), 2.76-2.66 (1H, m), 2.48-2.40 (2H, m), 1.56 (1H, d), 1.19 (3H, d), 0.78 (2H, t), 0.62-0.52 (1H, m), 0.30-0.21 (1H, m). | m/z: 406 (Molecular ion) | Prepared as Example 138 using Intermediate 6 in place of Intermediate 2 |
| 195 | (3R)-3-{[(R)-{3-[(5-aminopyrazin-2-yl)carbonyl]-4-chloro-2-fluorophenyl}(cyclo-propyl)methyl]amino}-butanamide HCl (1:1) m/z: 406 | | | | | As per Example 194 |
| 196 | 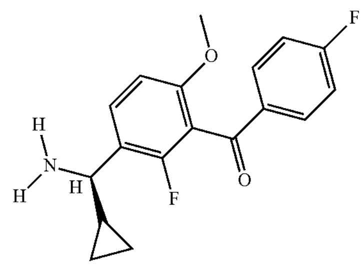 | (R)-cyclopropyl({2-fluoro-3-[(4-fluorophenyl)carbonyl]-4-methoxyphenyl})methanamine | HCl (1:1) | 1H NMR (400 MHz, Me-d3-OD): 7.94-7.84 (2H, m), 7.71 (1H, t), 7.32-7.21 (2H, m), 7.12 (1H, d), 3.82 (3H, s), 1.56-1.46 (1H, m), 0.92-0.83 (1H, m), 0.79-0.70 (1H, m), 0.70-0.59 (1H, m), 0.48-0.39 (1H, m). | m/z: 301 [M – NH2]+ | As Example 191 using intermediate 6 in place of intermediate 2 |
| 197 | 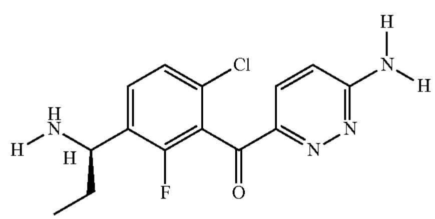 | 6-(3-[(1R)-1-aminopropyl]-6-chloro-2-fluorophenyl}carbonyl)pyridazin-3-amine | HCl (1:1) | 1H NMR (400 MHz, Me-d3-OD): 8.34 (1H, d), 7.69 (1H, t), 7.55 (2H, d), 4.58-4.48 (1H, m), 2.17-1.95 (2H, m), 0.98 (4H, t). | m/z: 309 | Prepared as Example 51 step 1 and 2 using 6-chloropyridazine-3-carbaldehyde, followed by step 2 and 3 as in Example 1 |

TABLE 2-continued

| | Structure | Name | Salt | NMR Data | MS Data | Method |
|---|---|---|---|---|---|---|
| 198 | 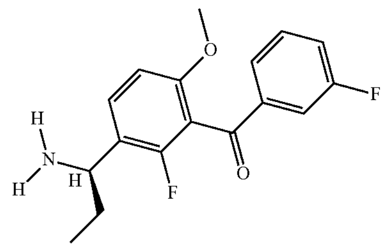 | (1R)-1-{2-fluoro-3-[(3-fluorophenyl)carbonyl]-4-methoxyphenyl}propan-1-amine | HCl (1:1) | 1H NMR (400 MHz, Me-d3-OD): 7.70-7.50 (4H, m), 7.49-7.39 (1H, m), 7.14 (1H, d), 4.45 (1H, dd), 3.82 (3H, s), 2.16-1.96 (2H, m), 0.98 (3H, t). | m/z: 289 [M – NH$_2$]$^+$ | As for Example 40 using methyl 3-fluorobenzoate in anion chemistry |
| 199 | 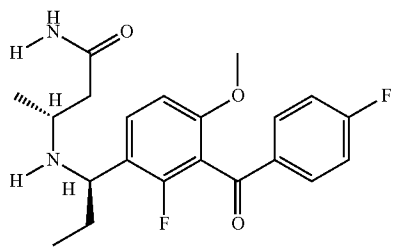 | (3R)-3-{[(1R)-1-{2-fluoro-3-[(4-fluorophenyl)carbonyl]-4-methoxyphenyl}propyl]amino}butanamide | HCl (1:1) | 1H NMR (400 MHz, Me-d3-OD): 7.93-7.83 (2H, m), 7.57 (1H, t), 7.25 (2H, t), 7.02 (1H, d), 4.01 (1H, t), 3.78 (3H, s), 3.06-2.96 (1H, m), 2.37 (1H, dd), 2.25 (1H, dd), 1.92-1.82 (1H, m), 1.76-1.65 (1H, m), 1.09 (3H, d), 0.86 (3H, t). | 88% pure m/z: 391 | Prepared according to Example 191 |
| 200 | 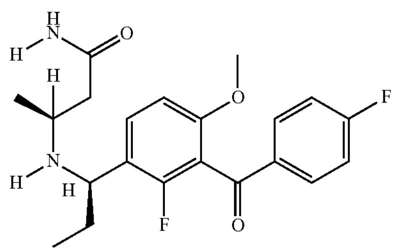 | (3S)-3-{[(1R)-1-{2-fluoro-3-[(4-fluorophenyl)carbonyl]-4-methoxyphenyl}propyl]amino}butanamide | HCl (1:1) | 1H NMR (400 MHz, Me-d3-OD): 7.94-7.85 (2H, m), 7.68 (1H, t), 7.32-7.23 (2H, m), 7.16 (1H, d), 4.59-4.52 (1H, m), 3.83 (3H, s), 3.46-3.39 (1H, m), 2.68-2.47 (2H, m), 2.17-2.05 (2H, m), 1.37 (3H, d), 0.93 (3H, t). | m/z: 391 | Prepared according to Example 81 using Example 191 |
| 201 | 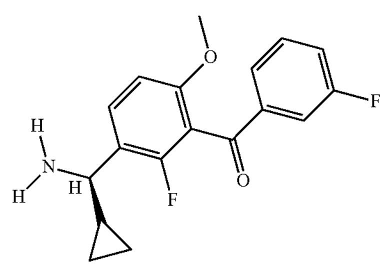 | (R)-cyclopropyl({2-fluoro-3-[(3-fluorophenyl)carbonyl]-4-methoxyphenyl})methanamine | HCl (1:1) | 1H NMR (400 MHz, Me-d3-OD): 7.73 (1H, t), 7.66-7.49 (3H, m), 7.49-7.39 (1H, m), 7.13 (1H, d), 3.82 (3H, s), 3.81-3.75 (1H, m), 1.58-1.46 (1H, m), 0.94-0.82 (1H, m), 0.80-0.70 (1H, m), 0.70-0.59 (1H, m), 0.50-0.39 (1H, m). | m/z: 301 [M – NH$_2$]$^+$ | As Example 196 using methyl 3-fluorobenzoate in step 1 |

TABLE 2-continued

| | Structure | Name | Salt | NMR Data | MS Data | Method |
|---|---|---|---|---|---|---|
| 202 | 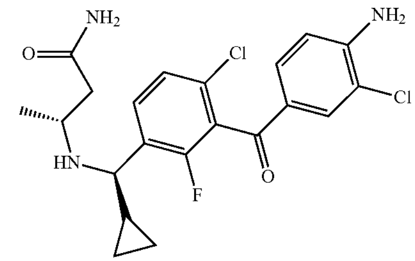 [SMILES: C[C@H](CC(N)=O)N[C@@H](c1ccc(Cl)c(C(=O)c2ccc(N)c(Cl)c2)c1F)C1CC1] | (3R)-3-{[(R)-{3-[(4-amino-3-chlorophenyl)carbonyl]-4-chloro-2-fluorophenyl}(cyclopropyl)methyl]amino}butanamide | HCl (1:1) | 1H NMR (400 MHz, Me-d3-OD): 7.76 (1H, t), 7.65 (1H, s), 7.56 (1H, d), 7.50 (1H, dd), 6.85 (1H, d), 4.09 (1H, d), 3.87-3.75 (1H, m), 2.69 (1H, dd), 2.56 (1H, dd), 1.56 (1H, d), 1.39 (3H, d), 1.05-0.90 (1H, m), 0.87-0.68 (2H, m), 0.49-0.37 (1H, m). | m/z: 438 | Prepared according to Example 76 from Example 76 |
| 203 | 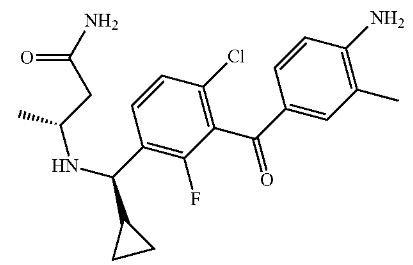 [SMILES: Cc1cc(C(=O)c2c(Cl)ccc([C@H](N[C@H](C)CC(N)=O)C3CC3)c2F)ccc1N] | (3R)-3-{[(R)-{3-[(4-amino-3-methylphenyl)carbonyl]-4-chloro-2-fluorophenyl}(cyclopropyl)methyl]amino}butanamide | HCl (1:1) | 1H NMR (400 MHz, Me-d3-OD): 7.72 (1H, t), 7.54 (1H, d), 7.49 (1H, s), 7.42 (1H, d), 6.68 (1H, d), 4.07 (1H, d), 3.85-3.74 (1H, m), 2.68 (1H, dd), 2.55 (1H, dd), 2.15 (3H, s), 1.62-1.49 (1H, m), 1.38 (3H, d), 1.04-0.89 (1H, m), 0.86-0.68 (2H, m), 0.49-0.38 (1H, m). | m/z: 418 | Prepared according to Example 81 from Example 77 |
| 204 | 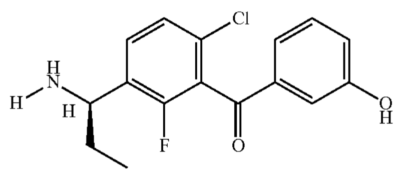 | 3-({3-[(1R)-1-aminopropyl]-6-chloro-2-fluorophenyl}carbonyl)phenol | HCl (1:1) | 1H NMR (400 MHz, DMSO-d6): 10.05 (1H, s), 8.57 (3H, s), 7.84 (1H, t), 7.66 (1H, d), 7.40 (1H, t), 7.24-7.11 (3H, m), 4.42 (1H, dd), 2.08-1.94 (1H, m), 1.94-1.81 (1H, m), 0.83 (3H, t). | m/z: 308 | Prepared as Example 193 using 3-benzyloxy benzyaldehyde in Step 1 |
| 205 | 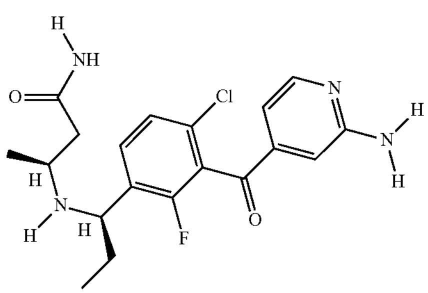 | (3S)-3-{[(1R)-1-{3-[(2-aminopyridin-4-yl)carbonyl]-4-chloro-2-fluorophenyl}propyl]amino}butanamide | HCl (1:1) | 1H NMR (400 MHz, DMSO-d6): 10.02 (1H, s), 9.64 (1H, s), 8.24-8.12 (3H, m), 7.82-7.67 (2H, m), 7.32 (1H, s), 7.16 (1H, s), 7.06 (1H, m), 4.54 (1H, s), 4.24-4.03 (1H, m), 2.76 (1H, dd), 2.47 (1H, d), 2.30-2.16 (1H, m), 2.10-1.98 (1H, m), 1.24 (3H, s), 0.77 (3H, t). | m/z: 393 | Prepared as Example 81 from 4-({3-[(1R)-1-aminopropyl]-6-chloro-2-fluorophenyl}carbonyl)pyridin-2-amine |
| 206 | (3R)-3-{[(1R)-1-{3-[(2-aminopyridin-4-yl)carbonyl]-4-chloro-2-fluorophenyl}propyl]amino}butanamide HCl (1:1) m/z: 392 | | | | | As Ex. 205 |

TABLE 2-continued

| | Structure | Name | Salt | NMR Data | MS Data | Method |
|---|---|---|---|---|---|---|
| 207 | 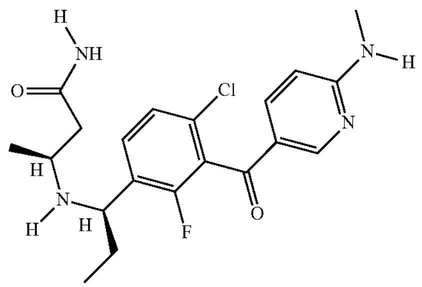 | (3S)-3-{[(1R)-1-(4-chloro-2-fluoro-3-{[6-(methylamino)pyridin-3-yl]carbonyl}phenyl)propyl]amino}butanamide | HCl (1:1) | 1H NMR (400 MHz, Me-d3-OD): 8.24 (1H, d), 7.94-7.84 (1H, m), 7.58 (1H, t), 7.39 (1H, d), 6.60 (1H, d), 4.08 (1H, dd), 2.97 (3H, s), 2.90-2.79 (1H, m), 2.26 (2H, d), 1.93-1.81 (1H, m), 1.75-1.63 (1H, m), 1.08 (3H, d), 0.87 (3H, t). | m/z: 407 | Prepared according to Example 81 using Example 36 |
| 208 209 | | (3R)-3-{[(1R)-1-(4-chloro-2-fluoro-3-{[6-(methylamino)pyridin-3-yl]carbonyl}phenyl)propyl]amino}butanamide HCl (1:1)<br>(3R)-3-{[(R)-cyclopropyl({2-fluoro-3-[(4-fluorophenyl)carbonyl]-4-methoxyphenyl})methyl]amino}butanamide HCl (1:1) | | | | As Ex. 207<br>As Ex. 130 |
| 210 | 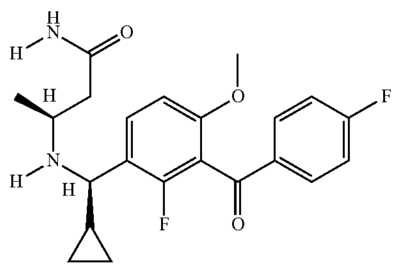 | (3S)-3-{[(R)-cyclopropyl({2-fluoro-3-[(4-fluorophenyl)carbonyl]-4-methoxyphenyl})methyl]amino}butanamide | HCl (1:1) | 1H NMR (400 MHz, Me-d3-OD): 7.96-7.86 (2H, m), 7.74 (1H, t), 7.33-7.22 (2H, m), 7.15 (1H, d), 3.93 (1H, d), 3.83 (3H, s), 3.51 (1H, q), 2.63 (2H, d), 1.65-1.57 (1H, m), 1.36 (3H, d), 0.99-0.90 (1H, m), 0.78-0.68 (2H, m), 0.48-0.40 (1H, m). | m/z: 403 | Prepared according to Example 81 using Example 196 |
| 211 | | (3R)-3-{[(1R)-1-{2-fluoro-3-[(4-fluorophenyl)carbonyl]-4-methoxyphenyl}propyl]amino}butanamide HCl (1:1) m/z: 391 | | | | As Ex. 211 |
| 212 | 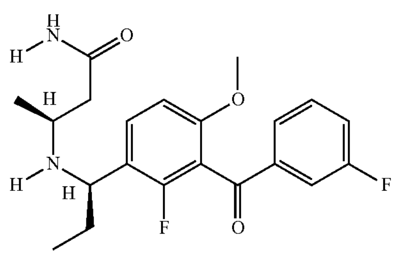 | (3S)-3-{[(1R)-1-{2-fluoro-3-[(3-fluorophenyl)carbonyl]-4-methoxyphenyl}propyl]amino}butanamide | HCl (1:1) | 1H NMR (400 MHz, Me-d3-OD): 7.70 (1H, t), 7.65-7.50 (3H, m), 7.49-7.41 (1H, m), 7.17 (1H, d), 4.57 (1H, dd), 3.83 (3H, s), 3.49-3.41 (1H, m), 2.65-2.54 (2H, m), 2.19-2.05 (2H, m), 1.37 (3H, d), 0.93 (3H, t). | m/z: 391 | Prepared according to Example 81 using Example 198 |

TABLE 2-continued

| | Structure | Name | Salt | NMR Data | MS Data | Method |
|---|---|---|---|---|---|---|
| 213 | 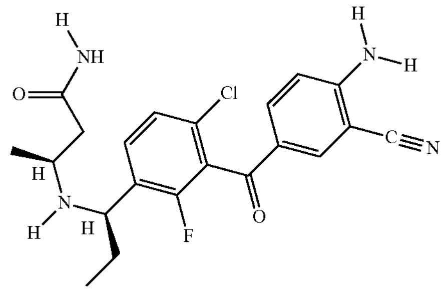 | (3S)-3-{[(1R)-1-{3-[(4-amino-3-cyanophenyl)carbonyl]-4-chloro-2-fluorophenyl}propyl]amino}butanamide | HCl (1:1) | 1H NMR (400 MHz, Me-d3-OD): 7.85 (1H, dd), 7.77 (1H, s), 7.69 (1H, t), 7.55 (1H, d), 6.91 (1H, d), 4.60 (1H, s), 2.66-2.49 (2H, m), 2.21-2.00 (2H, m), 1.36 (3H, d), 0.99-0.84 (3H, m), 1H hidden under solvent peak | m/z: 417 | Prepared according to Example 81 from Example 72 |
| 214 | 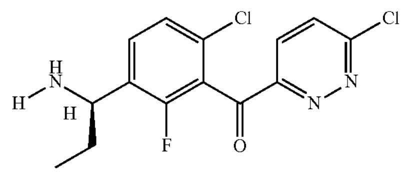 | (1R)-1-{4-chloro-3-[(6-chloropyridazin-3-yl)carbonyl]-2-fluorophenyl}propan-1-amine | HCl (1:1) | 1H NMR (400 MHz, Me-d3-OD): 8.45 (1H, d), 8.17-8.08 (1H, m), 7.70 (1H, t), 7.57 (1H, d), 4.53 (1H, dd), 2.16-1.96 (2H, m), 0.99 (3H, t). | m/z: 327 | Prepared as Example 51 using 6-chloropyridazine-3-carbaldehyde |
| 215 | 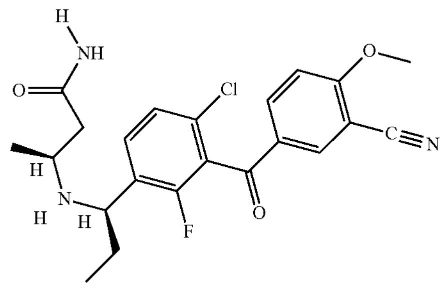 | (3S)-3-{[(1R)-1-{4-chloro-3-[(3-cyano-4-methoxyphenyl)carbonyl]-2-fluorophenyl}propyl]amino}butanamide | HCl (1:1) | 1H NMR (400 MHz, Me-d3-OD): 8.17 (1H, dd), 8.12 (1H, d), 7.75 (1H, t), 7.60 (1H, d), 7.40 (1H, d), 4.65 (1H, dd), 4.10 (3H, s), 3.55-3.41 (1H, m), 2.71-2.50 (2H, m), 2.24-2.05 (2H, m), 1.39 (3H, d), 0.94 (3H, t). | m/z: 432 | Prepared according to Example 81 from Example 73 |
| 216 | 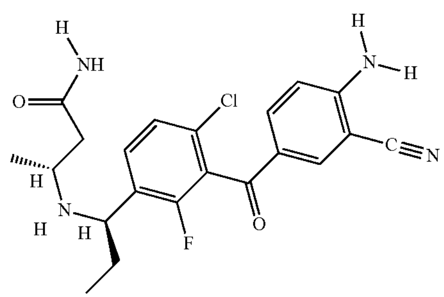 | (3R)-3-{[(1R)-1-{3-[(4-amino-3-cyanophenyl)carbonyl]-4-chloro-2-fluorophenyl}propyl]amino}butanamide | HCl (1:1) | 1H NMR (400 MHz, Me-d3-OD): 7.83 (1H, dd), 7.80-7.65 (2H, m), 7.63-7.53 (1H, m), 6.91 (1H, d), 4.65 (1H, dd), 3.76-3.62 (1H, m), 2.74-2.61 (1H, m), 2.61-2.50 (1H, m), 2.31-2.16 (1H, m), 2.16-1.99 (1H, m), 1.45-1.34 (3H, m), 0.95 (3H, t). | m/z: 417 | Prepared according to Example 81 from Example 72 |

TABLE 2-continued

| | Structure | Name | Salt | NMR Data | MS Data | Method |
|---|---|---|---|---|---|---|
| 217 | | (3R)-3-{[(1R)-1-{4-chloro-3-[(3-cyano-4-methoxyphenyl)carbonyl]-2-fluorophenyl}propyl]amino}butanamide HCl (1:1) m/z: 432 | | | | As Ex. 215 |
| 218 | 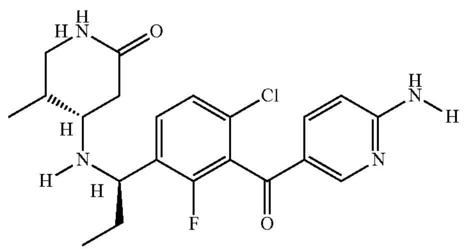 | (3S)-3-{[(1R)-1-{3-[(6-aminopyridin-3-yl)carbonyl]-4-chloro-2-fluorophenyl}propyl]amino}-4-methylpentanamide | HCl (1:1) | 1H NMR (400 MHz, Me-d3-OD): 8.39-8.34 (2H, m), 7.82 (1H, t), 7.62 (1H, dd), 7.13 (1H, dd), 4.71 (1H, dd), 3.48-3.40 (1H, m), 2.69 (1H, dd), 2.50 (1H, dd), 2.42-2.07 (3H, m), 1.06 (3H, d), 1.03 (3H, d), 0.93 (3H, t) | m/z: 421.2 | Example 218 |
| 219 | | (3R)-3-{[(1R)-1-{3-[(6-aminopyridin-3-yl)carbonyl]-4-chloro-2-fluorophenyl}propyl]amino}-4-methylpentanamide HCl (1:1) m/z: 421.0 | | | | As Ex. 218 |
| 220 | 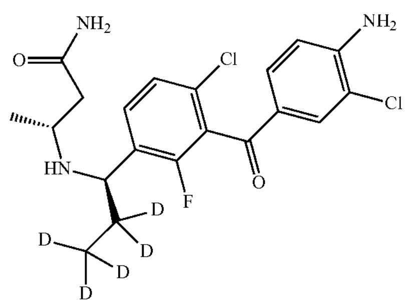 [SMILES: [2H]C([2H])([2H])C([2H])([2H])[C@@H](N[C@H](C)CC(N)=O)c1ccc(Cl)c(C(=O)c2ccc(N)c(Cl)c2)c1F] | (3R)-3-{[(1R)-1-{3-[(4-amino-3-chlorophenyl)carbonyl]-4-chloro-2-fluorophenyl}(2,2,3,3,3-deutero)propyl]amino}butanamide | HCl (1:1) | 1H NMR (400 MHz, Me-d3-OD): 7.75-7.67 (1H, m), 7.65 (1H, s), 7.57 (1H, d), 7.50 (1H, d), 6.85 (1H, d), 4.65 (1H, s), 3.73-3.62 (1H, m), 2.74-2.61 (1H, m), 2.57 (1H, dd), 1.38 (3H, d). | m/z: 431 | From example 78 using method from Example 267 |
| 221 | 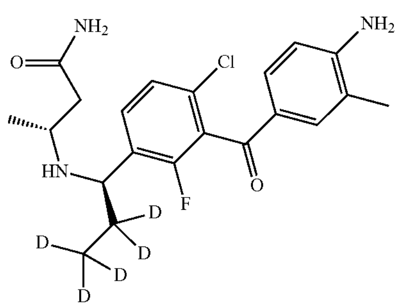 [SMILES: [2H]C([2H])([2H])C([2H])([2H])[C@@H](N[C@H](C)CC(N)=O)c1ccc(Cl)c(C(=O)c2ccc(N)c(C)c2)c1F] | (3R)-3-{[(1R)-1-{3-[(4-amino-3-methylphenyl)carbonyl]-4-chloro-2-fluorophenyl}(2,2,3,3,3-deutero)propyl]amino}butanamide | HCl (1:1) | 1H NMR (400 MHz, Me-d3-OD): 7.67 (1H, t), 7.55 (1H, d), 7.49 (1H, s), 7.42 (1H, d), 6.71 (1H, d), 4.65 (1H, s), 3.73-3.62 (1H, m), 2.68 (1H, dd), 2.58 (1H, dd), 2.16 (3H, s), 1.38 (3H, d). | m/z: 411 | Prepared according to Example 220 |

| | Structure | Name | Salt | NMR Data | MS Data | Method |
|---|---|---|---|---|---|---|
| 222 | 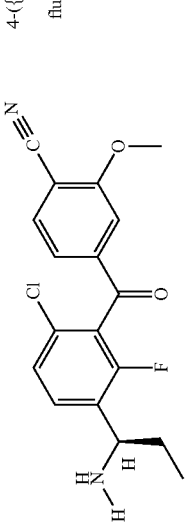 | 4-({3-[(1R)-1-aminopropyl]-6-chloro-2-fluorophenyl}carbonyl)-2-methoxybenzonitrile | HCl (1:1) | 1H NMR (400 MHz, Me-d3-OD): 7.82 (1H, d), 7.76-7.65 (2H, m), 7.59 (1H, d), 7.35 (1H, d), 4.51 (1H, t), 4.05 (3H, s), 2.15-2.01 (2H, m), 0.99 (3H, t) | m/z: 347 (Fragment) | Example 222 |
| 223 | | (3R)-3-{[(R)-cyclopropyl({2-fluoro-3-[(3-fluorophenyl)carbonyl]-4-methoxyphenyl})methyl]amino}butanamide HCl (1:1) m/z: 403 | | | | As Ex. 144 |
| 224 | 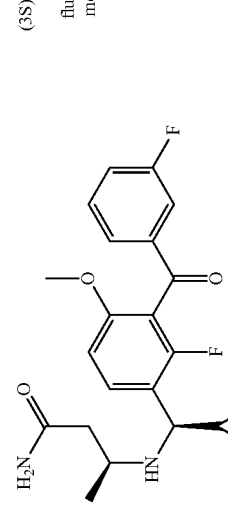 | (3S)-3-{[(R)-cyclopropyl({2-fluoro-3-[(3-fluorophenyl)carbonyl]-4-methoxyphenyl})methyl]amino}butanamide | HCl (1:1) | 1H NMR (400 MHz, Me-d3-OD): 7.76 (1H, t), 7.66-7.50 (3H, m), 7.49-7.39 (1H, m), 7.16 (1H, d), 3.94 (1H, d), 3.83 (3H, s), 3.56-3.46 (1H, m), 2.63 (2H, d), 1.61 (1H, d), 1.36 (3H, d), 1.00-0.89 (1H, m), 0.79-0.67 (2H, m), 0.49-0.39 (1H, m). | m/z: 403 | Prepared according to Example 81 using Example 201 |
| 225 | 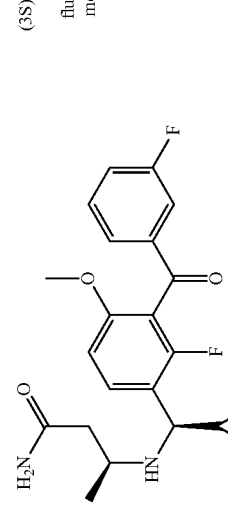 | (3S)-3-{[(1R)-1-{3-[(6-aminopyridin-3-yl)carbonyl]-4-chloro-2-fluorophenyl}propyl]amino}pentanamide | HCl (1:1) | 1H NMR (400 MHz, Me-d3-OD): 8.32 (1H, d), 8.23 (1H, dd), 7.77 (1H, t), 7.60 (1H, dd), 6.97 (1H, d), 4.69 (1H, dd), 3.36-3.28 (1H, m), 2.76 (1H, dd), 2.54 (1H, dd), 2.29-2.07 (2H, m), 2.07-1.92 (1H, m), 1.75-1.61 (1H, m), 1.01 (3H, t), 0.93 (3H, t). | m/z: 407.0 | Prepared according to Example 81 using Example 1 and (N-pent-2-enoyl)-(2R)-bornane-10,2-sultam |
| 226 | | (3R)-3-{[(1R)-1-{3-[(6-aminopyridin-3-yl)carbonyl]-4-chloro-2-fluorophenyl}propyl]amino}pentanamide HCl (1:1) m/z: 407.0 | | | | Example 225 |
| 227 | 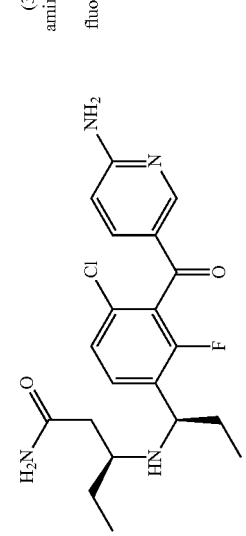 | (3S)-3-{[(1R)-1-{4-chloro-2-fluoro-3-[(3-hydroxyphenyl)carbonyl]phenyl}propyl]amino}butanamide | HCl (1:1) | 1H NMR (400 MHz, DMSO-d6): 10.04 (1H, s), 9.65 (1H, s), 9.27 (1H, d), 8.00 (1H, t), 7.76-7.65 (2H, m), 7.40 (1H, t), 7.25-7.11 (4H, m), 4.56 (1H, s), 3.29 (1H, s), 2.64 (1H, dd), 2.50-2.40 (2H, m), 2.24-2.13 (1H, m), 2.07-1.95 (1H, m), 1.23 (3H, d), 0.77 (3H, t). | m/z: 393 | Prepared as Example 81 using Example 204 in Step 1 |

TABLE 2-continued

| | Structure | Name | Salt | NMR Data | MS Data | Method |
|---|---|---|---|---|---|---|
| 228 | | (3R)-3-{[(1R)-1-{4-chloro-2-fluoro-3-[(3-hydroxyphenyl)carbonyl]phenyl}propyl]amino}butanamide HCl (1:1) m/z: 393 | | | | Prepared as Example 81 using Example 204 in Step 1 |
| 229 | 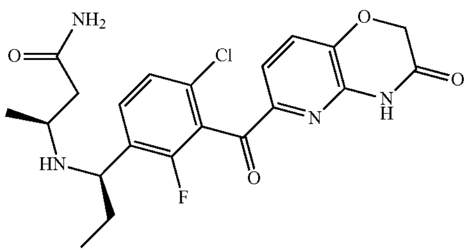 [SMILES: CC[C@@H](N[C@@H](C)CC(N)=O)c1ccc(Cl)c(C(=O)c2ccc3c(n2)NC(=O)CO3)c1F] | (3S)-3-{[(1R)-1-[4-chloro-2-fluoro-3-({3-oxo-2H,3H,4H-pyrido[3,2-b][1,4]oxazin-6-yl}carbonyl)phenyl]propyl]amino}butanamide | HCl (1:1) | 1H NMR (400 MHz, Me-d3-OD): 7.94 (1H, d), 7.70-7.64 (1H, m), 7.51 (2H, d), 4.68-4.57 (1H, m), 3.52-3.48 (1H, m), 2.73-2.54 (2H, m), 2.21-2.07 (2H, m), 1.75-1.55 (1H, m), 1.52-1.42 (1H, m), 1.32 (3H, s), 0.93 (3H, d). | m/z: 449 | Prepared according to Example 81 using Example 58 |
| 230 | 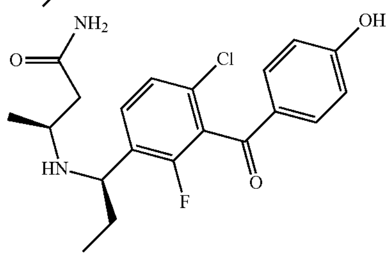 | (3S)-3-{[(1R)-1-{4-chloro-2-fluoro-3-[(4-hydroxyphenyl)carbonyl]phenyl}propyl]amino}butanamide | HCl (1:1) | 1H NMR (400 MHz, DMSO-d6): 10.83 (1H, s), 9.52-9.45 (1H, m), 9.19-9.12 (1H, m), 7.92 (1H, t), 7.72-7.61 (4H, m), 7.18 (1H, s), 6.93 (2H, d), 4.59-4.51 (1H, m), 3.27 (1H, s), 2.60 (1H, dd), 2.47-2.39 (1H, m), 2.20-2.11 (1H, m), 2.04-1.95 (1H, m), 1.23 (3H, d), 0.77 (3H, t). | m/z: 393 | Prepared as Example 81 using Example 193 in Step 1 |
| 231 | | (3R)-3-{[(1R)-1-{4-chloro-2-fluoro-3-[(4-hydroxyphenyl)carbonyl]phenyl}propyl]amino}butanamide HCl (1:1) m/z: 393 | | | | As Ex. 230 |
| 232 | 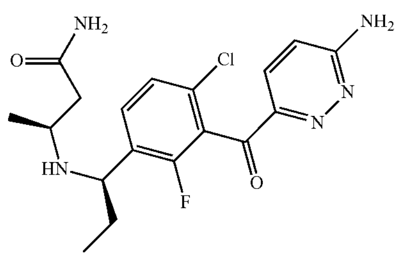 [SMILES: CC[C@@H](N[C@@H](C)CC(N)=O)c1ccc(Cl)c(C(=O)c2ccc(N)nn2)c1F] | (3S)-3-{[(1R)-1-{3-[(6-aminopyridazin-3-yl)carbonyl]-4-chloro-2-fluorophenyl}propyl]amino}butanamide | HCl (1:1) | 1H NMR (400 MHz, Me-d3-OD): 8.38 (2H, s), 7.81 (1H, t), 7.63 (1H, d), 7.16 (1H, d), 4.67 (1H, dd), 3.55-3.45 (1H, m), 2.70-2.58 (2H, m), 2.26-2.09 (2H, m), 1.42 (3H, d), 0.93 (3H, t). | m/z: 393 | Prepared according to Example 81 using Example 197 |
| 233 | | (3R)-3-{[(1R)-1-{3-[(6-aminopyridazin-3-yl)carbonyl]-4-chloro-2-fluorophenyl}propyl]amino}butanamide HCl (1:1) m/z: 393 | | | | As Ex. 232 |

| | Structure | Name | Salt | NMR Data | MS Data | Method |
|---|---|---|---|---|---|---|
| 234 | 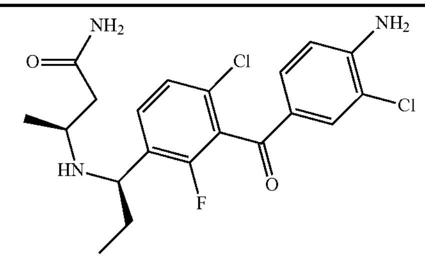 | (3S)-3-{[(1R)-1-{3-[(4-amino-3-chlorophenyl)carbonyl]-4-chloro-2-fluorophenyl}propyl]amino}butanamide | HCl (1:1) | 1H NMR (400 MHz, Me-d3-OD): 7.70 (1H, t), 7.65 (1H, s), 7.56 (1H, d), 7.49 (1H, d), 6.84 (1H, d), 4.64 (1H, d), 3.55-3.38 (1H, m), 2.69-2.51 (2H, m), 2.25-1.99 (2H, m), 1.37 (3H, d), 0.93 (3H, t). | m/z: 427 | Prepared according to Example 81 from Example 74 |
| 235 | 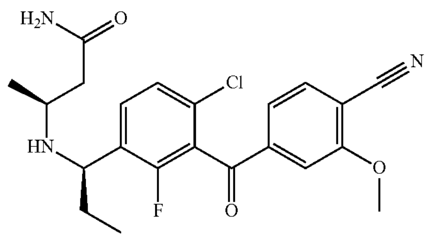 [SMILES: CC[C@@H](N[C@@H](C)CC(N)=O)c1ccc(Cl)c(C(=O)c2ccc(C#N)c(OC)c2)c1F] | (3S)-3-{[(1R)-1-{4-chloro-3-[(4-cyano-3-methoxyphenyl)carbonyl]-2-fluorophenyl}propyl]amino}butanamide | HCl (1:1) | 1H NMR (400 MHz, Me-d3-OD): 7.81 (1H, d), 7.72-7.55 (2H, m), 7.43 (1H, d), 7.37 (1H, dd), 4.08 (1H, dd), 4.02 (3H, s), 2.91-2.77 (1H, m), 2.34-2.10 (2H, m), 1.97-1.77 (1H, m), 1.77-1.60 (1H, m), 1.08 (3H, d), 0.86 (3H, t). | m/z: 432 | Prepared according to Example 222 |
| 236 | (3R)-3-{[(1R)-1-{4-chloro-3-[(4-cyano-3-methoxyphenyl)carbonyl]-2-fluorophenyl}propyl]amino}butanamide HCl (1:1) m/z: 432 | | | | | As Ex. 235 |
| 237 | 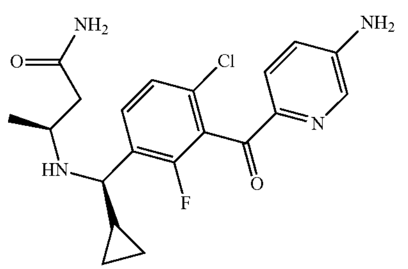 [SMILES: C[C@@H](CC(N)=O)N[C@@H](c1ccc(Cl)c(C(=O)c2ccc(N)cn2)c1F)C1CC1] | (3S)-3-{[(R)-{3-[(5-aminopyridin-2-yl)carbonyl]-4-chloro-2-fluorophenyl}(cyclopropyl)methyl]amino}butanamide | HCl (1:1) | 1H NMR (400 MHz, Me-d3-OD): 7.99 (1H, d), 7.93 (1H, d), 7.69 (1H, t), 7.46 (1H, d), 7.09 (1H, dd), 3.94 (1H, s), 3.58-3.44 (1H, m), 2.58 (2H, s), 1.51 (1H, s), 1.31 (3H, d), 0.91 (1H, d), 0.70 (2H, s), 0.43 (1H, s). | m/z: 405 | Prepared according to Example 81 from Example 61 |

TABLE 2-continued

| | Structure | Name | Salt | NMR Data | MS Data | Method |
|---|---|---|---|---|---|---|
| 238 | 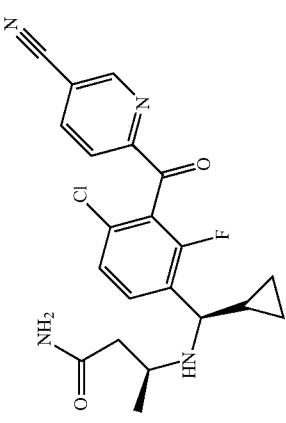 | (3S)-3-{[(R)-{4-chloro-3-[(5-cyanopyridin-2-yl)carbonyl]-2-fluorophenyl}(cyclopropyl)methyl]amino}butanamide | HCl (1:1) | 1H NMR (400 MHz, Me-d3-OD): 8.99 (1H, d), 8.50 (1H, dd), 8.39 (1H, d), 7.80 (1H, t), 7.55 (1H, d), 4.03 (1H, d), 3.58-3.45 (1H, m), 2.70-2.57 (2H, m), 1.58 (1H, s), 1.35 (3H, d), 1.02-0.89 (1H, m), 0.82-0.68 (2H, m), 0.51-0.40 (1H, m). | m/z: 415 | Prepared according to Example 81 from Example 62 |
| 239 | 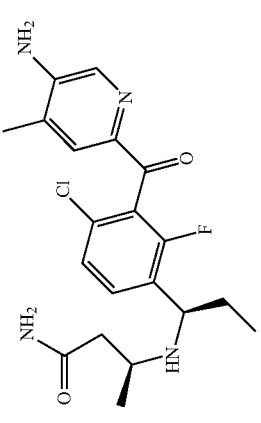 | (3S)-3-{[(1R)-1-{3-[(5-amino-4-methylpyridin-2-yl)carbonyl]-4-chloro-2-fluorophenyl}propyl]amino}butanamide | HCl (1:1) | 1H NMR (400 MHz, Me-d3-OD): 7.93 (1H, s), 7.91-7.85 (1H, m), 7.64 (1H, t), 7.50 (1H, d), 4.64 (1H, dd), 3.59-3.47 (1H, m), 2.68-2.52 (2H, m), 2.26 (3H, s), 2.22-1.98 (2H, m), 1.37 (3H, d), 0.94 (3H, t). | m/z: 407 | Prepared according to Example 81 from Example 71 |
| 240 | 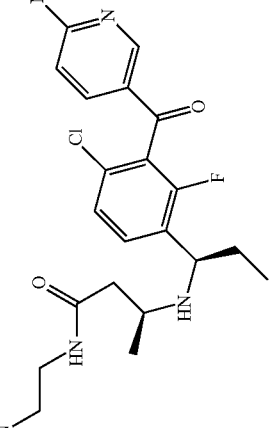 | (3S)-N-(2-aminoethyl)-3-{[(1R)-1-{3-[(6-aminopyridin-3-yl)carbonyl]-4-chloro-2-fluorophenyl}propyl]amino}butanamide | HCl (1:2) | 1H NMR (400 MHz, Me-d3-OD): 8.41-8.28 (2H, m), 7.89 (1H, t), 7.62 (1H, d), 7.10 (1H, d), 4.70 (1H, dd), 3.62-3.40 (4H, m), 3.13-3.02 (2H, m), 2.81-2.62 (2H, m), 2.31-2.09 (2H, m), 1.42 (3H, d), 0.94 (3H, t). | m/z: 436 | Example 240 |

TABLE 2-continued

| | Structure | Name | Salt | NMR Data | MS Data | Method |
|---|---|---|---|---|---|---|
| 241 | 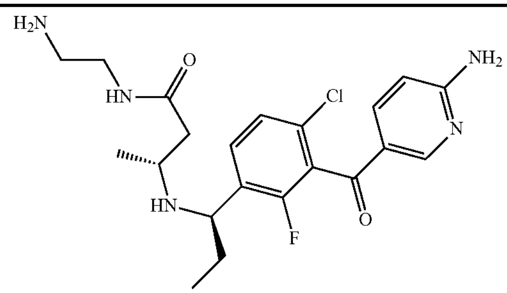 | (3R)-N-(2-aminoethyl)-3-{[(1R)-1-{3-[(6-aminopyridin-3-yl)carbonyl]-4-chloro-2-fluorophenyl}propyl]amino}-butanamide | HCl (1:2) | 1H NMR (400 MHz, Me-d3-OD): 8.41-8.28 (2H, m), 7.84 (1H, t), 7.63 (1H, d), 7.11 (1H, d), 4.71 (1H, dd), 3.83-3.67 (1H, m), 3.55-3.48 (2H, m), 3.10 (2H, t), 2.82-2.60 (2H, m), 2.39-2.25 (1H, m), 2.19-2.03 (1H, m), 1.43 (3H, d), 0.95 (3H, t). | m/z: 436 | As for Example 240 |
| 242 | 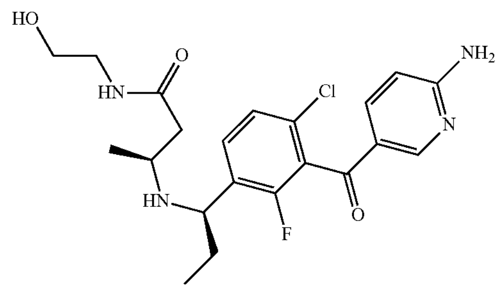 [SMILES: CC[C@@H](N[C@@H](C)CC(=O)NCCO)c1ccc(Cl)c(C(=O)c2ccc(N)nc2)c1F] | (3S)-3-{[(1R)-1-{3-[(6-aminopyridin-3-yl)carbonyl]-4-chloro-2-fluorophenyl}propyl]amino}-N-(2-hydroxyethyl)butanamide | HCl (1:1) | 1H NMR (400 MHz, Me-d3-OD): 8.36-8.23 (2H, m), 7.78 (1H, t), 7.66-7.58 (1H, m), 7.03 (1H, d), 4.72-4.63 (1H, m), 3.61 (2H, t), 3.52-3.49 (1H, m), 3.48-3.41 (1H, m), 3.17-3.12 (1H, m), 2.67-2.56 (2H, m), 2.24-2.09 (2H, m), 1.40 (3H, d), 0.94 (3H, t). | m/z: 437 | Example 242 |
| 243 | (3R)-3-{[(1R)-1-{3-[(6-aminopyridin-3-yl)carbonyl]-4-chloro-2-fluorophenyl}propyl]amino}-N-(2-hydroxyethyl)butanamide HCl (1:1) m/z: 436 | | | | | As Ex. 242 |
| 244 | 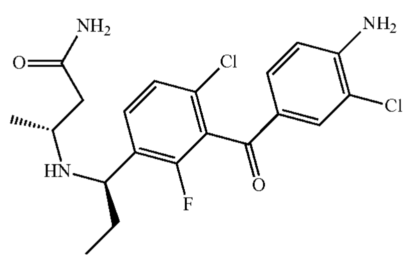 [SMILES: CC[C@@H](N[C@H](C)CC(N)=O)c1ccc(Cl)c(C(=O)c2ccc(N)c(Cl)c2)c1F] | (3R)-3-{[(1R)-1-{3-[(4-amino-3-chlorophenyl)carbonyl]-4-chloro-2-fluorophenyl}propyl]amino}butanamide | HCl (1:1) | 1H NMR (400 MHz, Me-d3-OD): 7.71 (1H, t), 7.66 (1H, s), 7.57 (1H, d), 7.49 (1H, d), 6.85 (1H, d), 4.67 (1H, dd), 3.69 (1H, dd), 2.68 (1H, dd), 2.58 (1H, dd), 2.33-2.18 (1H, m), 2.16-2.00 (1H, m), 1.38 (3H, d), 0.94 (3H, t). | m/z: 427 | Prepared according to Example 81 from Example 74 |

TABLE 2-continued

| | Structure | Name | Salt | NMR Data | MS Data | Method |
|---|---|---|---|---|---|---|
| 245 | 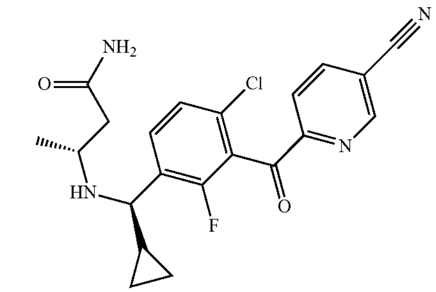 [SMILES: C[C@H](CC(N)=O)N[C@@H](c1ccc(Cl)c(C(=O)c2ccc(C#N)cn2)c1F)C1CC1] | (3R)-3-{[(R)-{4-chloro-3-[(5-cyanopyridin-2-yl)carbonyl]-2-fluorophenyl}(cyclopropyl)methyl]amino}butanamide | HCl (1:1) | 1H NMR (400 MHz, Me-d3-OD): 8.99 (1H, d), 8.50 (1H, dd), 8.39 (1H, d), 7.81 (1H, t), 7.56 (1H, d), 4.09 (1H, d), 3.85-3.73 (1H, m), 2.69 (1H, dd), 2.56 (1H, dd), 1.55 (1H, s), 1.39 (3H, d), 1.05-0.92 (1H, m), 0.92-0.68 (2H, m), 0.49-0.37 (1H, m). | m/z: 415 | Prepared according to Example 81 from Example 62 |
| 246 | 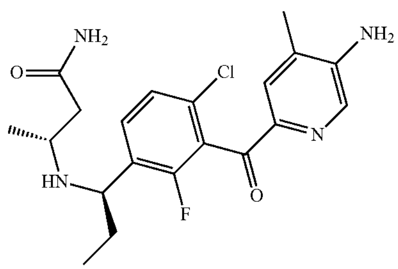 [SMILES: CC[C@@H](N[C@H](C)CC(N)=O)c1ccc(Cl)c(C(=O)c2cc(C)c(N)cn2)c1F] | (3R)-3-{[(1R)-1-{3-[(5-amino-4-methylpyridin-2-yl)carbonyl]-4-chloro-2-fluorophenyl}propyl]amino}butanamide | HCl (1:1) | 1H NMR (400 MHz, Me-d3-OD): 7.93 (1H, s), 7.90 (1H, s), 7.65 (1H, t), 7.51 (1H, d), 4.96-4.73 (16H, m), 4.64 (1H, dd), 3.70 (1H, dd), 3.42-3.21 (13H, m), 2.69 (1H, dd), 2.56 (1H, dd), 2.32-2.16 (4H, m), 2.16-2.00 (1H, m), 1.39 (3H, d), 0.96 (3H, t). | m/z: 407 | Prepared according to Example 81 from Example 71 |
| 247 | 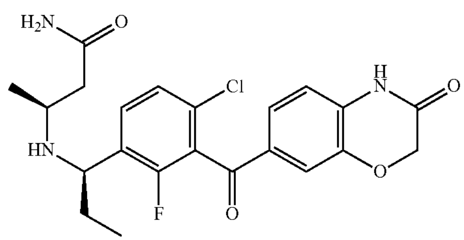 [SMILES: CC[C@@H](N[C@@H](C)CC(N)=O)c1ccc(Cl)c(C(=O)c2ccc3c(c2)OCC(=O)N3)c1F] | (3S)-3-{[(1R)-1-{4-chloro-2-fluoro-3-[(3-oxo-3,4-dihydro-2H-1,4-benzoxazin-7-yl)carbonyl]phenyl}propyl]amino}butanamide | HCl (1:1) | 1H NMR (400 MHz, DMSO-d6): 11.23 (1H, s), 9.72 (1H, s), 9.33 (1H, s), 8.01 (1H, t), 7.69 (2H, d), 7.39 (1H, dd), 7.32 (1H, s), 7.15 (1H, s), 7.05 (1H, d), 4.69 (2H, s), 4.54 (1H, s), 3.28 (1H, s), 2.71-2.59 (1H, m), 2.48-2.39 (1H, m), 2.25-2.13 (1H, m), 2.07-1.95 (1H, m), 1.22 (3H, d), 0.77 (3H, t). | m/z: 448 | Prepared as Example 81 using Example 60 in Step 1 |
| 248 | (3R)-3-{[(1R)-1-{4-chloro-2-fluoro-3-[(3-oxo-3,4-dihydro-2H-1,4-benzoxazin-7-yl)carbonyl]phenyl}propyl]amino}butanamide HCl (1:1) m/z: 448 | | | | | As Ex. 247 |

TABLE 2-continued

| | Structure | Name | Salt | NMR Data | MS Data | Method |
|---|---|---|---|---|---|---|
| 249 | 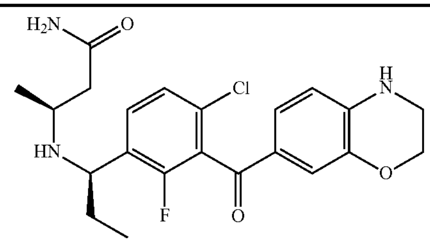 | (3S)-3-{[(1R)-1-{4-chloro-3-[(3,4-dihydro-2H-1,4-benzooxazin-7-yl)carbonyl]-2-fluorophenyl}propyl]amino}butanamide | HCl (1:1) | 1H NMR (400 MHz, DMSO-d6): 9.60-9.51 (1H, m), 9.24-9.15 (1H, m), 7.90 (1H, t), 7.68 (1H, s), 7.64 (1H, d), 7.35-7.26 (1H, m), 7.16 (1H, s), 7.08 (1H, d), 7.03 (1H, s), 6.61 (1H, d), 4.53 (1H, s), 4.17-4.07 (2H, m), 3.41-3.39 (2H, m), 3.27 (1H, s), 2.68-2.57 (1H, m), 2.47-2.39 (1H, m), 2.22-2.12 (1H, m), 2.04-1.93 (1H, m), 1.22 (3H, d), 0.76 (3H, t). | m/z: 434 | Prepared as Example 81 using Example 65 in Step 1 |
| 250 | 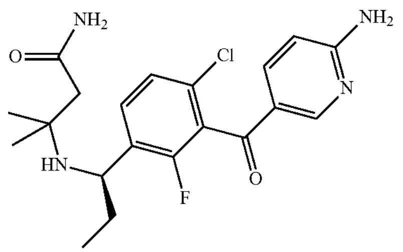 [SMILES: CC[C@@H](NC(C)(C)CC(N)=O)c1ccc(Cl)c(C(=O)c2ccc(N)nc2)c1F] | 3-{[(1S)-1-{3-[(6-aminopyridin-3-yl)carbonyl]-4-chloro-2-fluorophenyl}propyl]amino}-3-methylbutanamide | HCl (1:1) | 1H NMR (400 MHz, DMSO-d6): 9.45 (2H, s), 8.25 (1H, s), 8.01-7.71 (5H, m), 7.64 (1H, d), 7.56 (1H, s), 6.73 (1H, d), 4.68-4.58 (1H, m), 2.57 (2H, s), 2.17-2.01 (2H, m), 1.36 (3H, s), 1.27 (3H, s), 0.76 (3H, t). | m/z: 407 | Example 250 |
| 251 | 3-{[(1S)-1-{3-[(6-aminopyridin-3-yl)carbonyl]-4-chloro-2-fluorophenyl}propyl]amino}-3-methylbutanamide HCl (1:1) m/z: 407 | | | | | Example 251 |
| 252 | 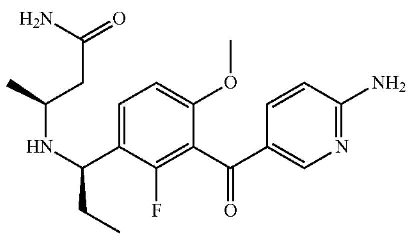 [SMILES: CC[C@@H](N[C@@H](C)CC(N)=O)c1ccc(OC)c(C(=O)c2ccc(N)nc2)c1F] | (3S)-3-{[(1R)-1-{3-[(6-aminopyridin-3-yl)carbonyl]-2-fluoro-4-methoxyphenyl}propyl]amino}butanamide | HCl (1:1) | 1H NMR (400 MHz, Me-d3-OD): 8.30 (2H, d), 7.74 (1H, t), 7.19 (1H, d), 7.10 (1H, d), 4.58 (1H, dd), 3.87 (3H, s), 3.49-3.40 (1H, m), 2.70-2.54 (2H, m), 2.21-2.08 (2H, m), 1.40 (3H, d), 0.92 (3H, t). | m/z: 389 | Prepared according to Example 81 using Example 63 |
| 253 | (3R)-3-{[(1R)-1-{3-[(6-aminopyridin-3-yl)carbonyl]-2-fluoro-4-methoxyphenyl}propyl]amino}butanamide HCl (1:1) m/z: 389 | | | | | As Ex. 252 |

TABLE 2-continued

| | Structure | Name | Salt | NMR Data | MS Data | Method |
|---|---|---|---|---|---|---|
| 254 | 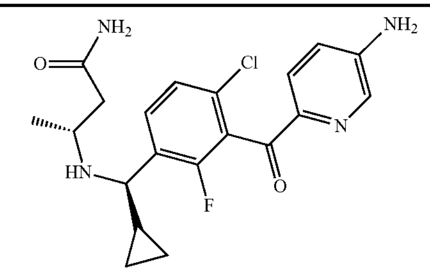 | (3R)-3-{[(R)-{3-[(5-aminopyridin-2-yl)carbonyl]-4-chloro-2-fluorophenyl}(cyclopropyl)methyl]amino}butanamide | HCl (1:1) | 1H NMR (400 MHz, Me-d3-OD): 8.00 (1H, d), 7.92 (1H, d), 7.70 (1H, t), 7.49 (1H, d), 7.10 (1H, dd), 4.05 (1H, d), 3.84-3.70 (1H, m), 2.75-2.59 (1H, m), 2.53 (1H, dd), 1.54 (1H, s), 1.38 (3H, d), 1.03-0.87 (1H, m), 0.87-0.66 (2H, m), 0.50-0.38 (1H, m). | m/z: 405 | Prepared according to Example 81 from Example 61 |
| 255 | 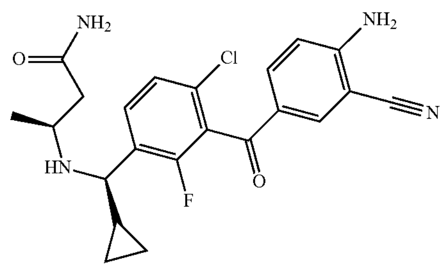 [SMILES: C[C@@H](CC(N)=O)N[C@@H](c1ccc(Cl)c(C(=O)c2ccc(N)c(C#N)c2)c1F)C1CC1] | (3S)-3-{[(R)-{3-[(4-amino-3-cyanophenyl)carbonyl]-4-chloro-2-fluorophenyl}(cyclopropyl)methyl]amino}butanamide | HCl (1:1) | 1H NMR (400 MHz, Me-d3-OD): 7.87 (1H, dd), 7.84-7.71 (2H, m), 7.56 (1H, d), 6.91 (1H, d), 3.99 (1H, d), 3.61-3.47 (1H, m), 2.72-2.56 (2H, m), 1.70-1.54 (1H, m), 1.38 (3H, d), 1.03-0.88 (1H, m), 0.83-0.67 (2H, m), 0.52-0.39 (1H, m). | m/z: 429 | Prepared according to Example 81 from Example 75 |
| 256 | 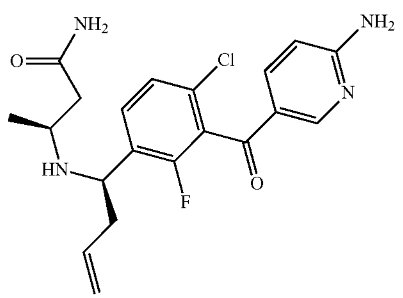 [SMILES: C=CC[C@@H](N[C@@H](C)CC(N)=O)c1ccc(Cl)c(C(=O)c2ccc(N)nc2)c1F] | (3S)-3-{[(1R)-1-{3-[(6-aminopyridin-3-yl)carbonyl]-4-chloro-2-fluorophenyl}but-3-en-1-yl]amino}butanamide | HCl (1:1) | 1H NMR (400 MHz, Me-d3-OD): 8.33 (2H, d), 7.80 (1H, t), 7.61 (1H, d), 7.13 (1H, d), 5.75-5.64 (1H, m), 5.24-5.13 (2H, m), 4.86 (1H, dd), 3.57-3.49 (1H, m), 3.00-2.82 (2H, m), 2.72-2.60 (2H, m), 1.42 (3H, d). | m/z: 405 | Prepared according to Example 81 using Example 67 |
| 257 | | (3R)-3-{[(1R)-1-{3-[(6-aminopyridin-3-yl)carbonyl]-4-chloro-2-fluorophenyl}but-3-en-1-yl]amino}butanamide HCl (1:1) m/z: 405 | | | | As Ex. 256 |

| | Structure | Name | Salt | NMR Data | MS Data | Method |
|---|---|---|---|---|---|---|
| 258 | 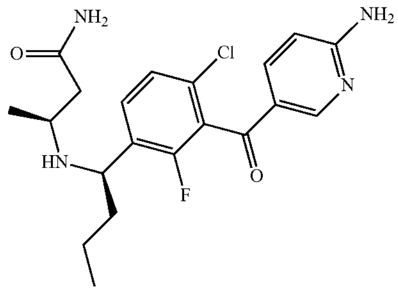 [SMILES: CCC[C@@H](N[C@@H](C)CC(N)=O)c1ccc(Cl)c(C(=O)c2ccc(N)nc2)c1F] | (3S)-3-{[(1R)-1-{3-[(6-aminopyridin-3-yl)carbonyl]-4-chloro-2-fluorophenyl}butyl]amino}butanamide | HCl (1:1) | 1H NMR (400 MHz, Me-d3-OD): 8.36 (2H, d), 7.81 (1H, t), 7.62 (1H, d), 7.13 (1H, d), 4.73 (1H, dd), 3.54-3.43 (1H, m), 2.69-2.58 (2H, m), 2.18-2.05 (2H, m), 1.41 (3H, d), 1.35 (1H, dd), 1.29-1.16 (1H, m), 0.99 (3H, t). | m/z: 407 | Prepared according to Example 81 using Example 66 |
| 259 | 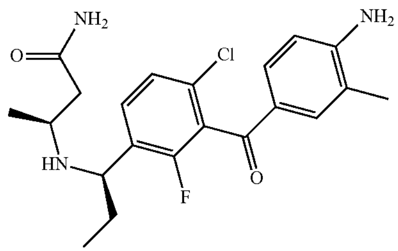 [SMILES: CC[C@@H](N[C@@H](C)CC(N)=O)c1ccc(Cl)c(C(=O)c2ccc(N)c(C)c2)c1F] | (3S)-3-{[(1R)-1-{3-[(4-amino-3-methylphenyl)carbonyl]-4-chloro-2-fluorophenyl}propyl]amino}butanamide | HCl (1:1) | 1H NMR (400 MHz, Me-d3-OD): 7.69 (1H, t), 7.56 (1H, d), 7.52 (1H, s), 7.45 (1H, d), 6.75 (1H, d), 4.68 (1H, dd), 3.54-3.41 (1H, m), 2.71-2.53 (2H, m), 2.18 (3H, s), 1.38 (3H, d), 0.93 (3H, t). | m/z: 406 | Example 259 |
| 260 | (3R)-3-{[(1R)-1-{3-[(4-amino-3-methylphenyl)carbonyl]-4-chloro-2-fluorophenyl}propyl]amino}butanamide HCl (1:1) m/z: 406 | | | | | As Ex. 259 |
| 261 | 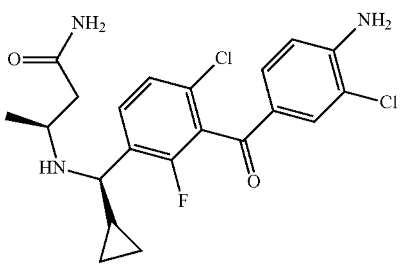 [SMILES: C[C@@H](CC(N)=O)N[C@@H](c1ccc(Cl)c(C(=O)c2ccc(N)c(Cl)c2)c1F)C1CC1] | (3S)-3-{[(R)-{3-[(4-amino-3-chlorophenyl)carbonyl]-4-chloro-2-fluorophenyl}(cyclopropyl)methyl]amino}butanamide | HCl (1:1) | 1H NMR (400 MHz, Me-d3-OD): 7.78 (1H, t), 7.67 (1H, s), 7.55 (1H, d), 7.50 (1H, d), 6.84 (1H, d), 4.03 (1H, d), 3.60-3.46 (1H, m), 2.65 (2H, d), 1.61 (1H, s), 1.37 (3H, d), 1.03-0.90 (1H, m), 0.83-0.69 (2H, m), 0.51-0.40 (1H, m). | m/z: 438 | Prepared according to Example 81 from Example 76 |

TABLE 2-continued

| | Structure | Name | Salt | NMR Data | MS Data | Method |
|---|---|---|---|---|---|---|
| 262 | 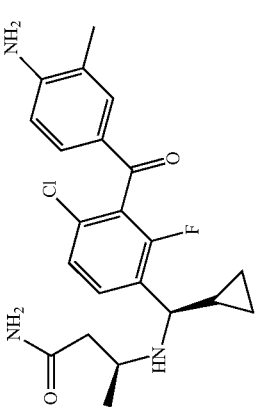 | (3S)-3-{[(R)-{3-[(4-amino-3-methylphenyl)carbonyl]-4-chloro-2-fluorophenyl}-(cyclopropyl)-methyl]-amino}butanamide | HCl (1:1) | 1H NMR (400 MHz, Me-d3-OD): 7.76 (1H, t), 7.58-7.48 (2H, m), 7.48 (1H, s), 7.45 (1H, d), 6.74 (1H, d), 4.03 (1H, d), 3.59-3.46 (1H, m), 2.66 (2H, d), 2.17 (3H, s), 1.68-1.54 (1H, m), 1.37 (3H, d), 1.03-0.89 (1H, m), 0.83-0.68 (2H, m), 0.51-0.39 (1H, m). | m/z: 418 | Prepared according to Example 81 from Example 77 |
| 263 | 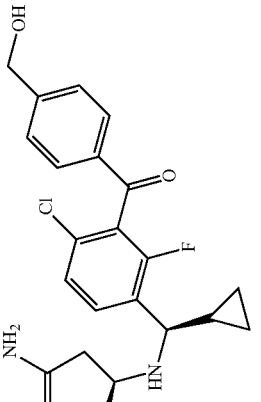 | (3S)-3-{[(R)-(4-chloro-2-fluoro-3-{[4-(hydroxyl-methyl)phenyl]-carbonyl}phenyl)(cyclo-propyl)-methyl]amino}-butanamide | HCl (1:1) | 1H NMR (400 MHz, DMSO-d6): 9.54 (1H, s), 9.46 (1H, s), 8.06 (1H, t), 7.78 (2H, d), 7.69 (2H, m), 7.55 (2H, d), 7.18 (1H, s), 5.50-5.38 (1H, m), 4.61 (2H, s), 4.03-3.94 (1H, m), 3.35 (1H, m), 2.68 (1H, dd), 2.47-2.40 (1H, m), 1.60 (1H, d), 1.22 (3H, d), 0.86-0.73 (2H, m), 0.64-0.54 (1H, m), 0.33-0.23 (1H, m). | m/z: 419 | Example 263 |
| 264 | 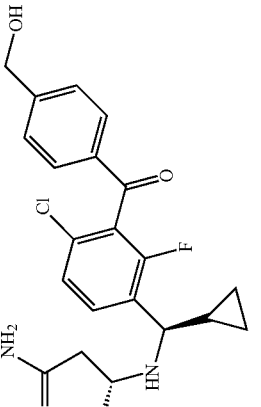 | (3R)-3-{[(R)-(4-chloro-2-fluoro-3-{[4-(hydroxymethyl)phenyl]carbonyl}phenyl)(cyclopropyl)methyl]amino}butanamide | HCl (1:1) | 1H NMR (400 MHz, DMSO-d6): 9.61-9.51 (1H, m), 9.46-9.36 (1H, m), 8.04 (1H, t), 7.78 (2H, d), 7.75-7.65 (2H, m), 7.54 (2H, d), 7.23 (1H, s), 5.47-5.39 (1H, m), 4.61 (2H, s), 4.09-4.02 (1H, m), 3.63-3.54 (1H, m), 2.60-2.54 (1H, m), 2.41 (1H, dd), 1.53 (1H, s), 1.26 (3H, d), 0.88-0.80 (1H, m), 0.80-0.71 (1H, m), 0.64-0.55 (1H, m), 0.31-0.22 (1H, m). | m/z: 419 | Example 263 |

TABLE 2-continued

| | Structure | Name | Salt | NMR Data | MS Data | Method |
|---|---|---|---|---|---|---|
| 265 | 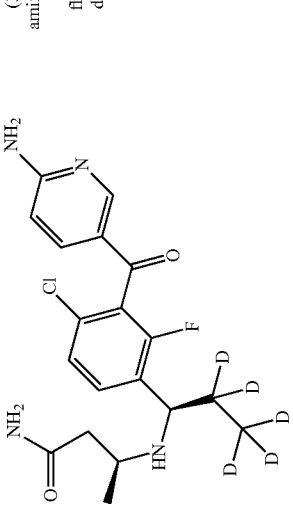 | (3S)-3-{[(1R)-1-{3-[(6-aminopyridin-3-yl)carbonyl]-4-chloro-2-fluorophenyl}(2,2,3,3,3-deuteropropyl]amino}butanamide | HCl (1:1) | 1H NMR (400 MHz, Me-d3-OD): 8.36 (2H, d), 7.80 (1H, t), 7.62 (1H, d), 7.13 (1H, d), 4.66 (1H, s), 3.54-3.45 (1H, m), 2.72-2.56 (2H, m), 1.42 (3H, d). | m/z: 398 | As Example 1 but using D5-ethyl magnesium bromide in step 2 then as Example 81 |
| 266 | | (3R)-3-{[(1R)-1-{3-[(6-aminopyridin-3-yl)carbonyl]-4-chloro-2-fluorophenyl}(2,2,3,3,3-deuteropropyl]amino}butanamide HCl (1:1) m/z: 398 | | | | As Ex. 265 |
| 267 | 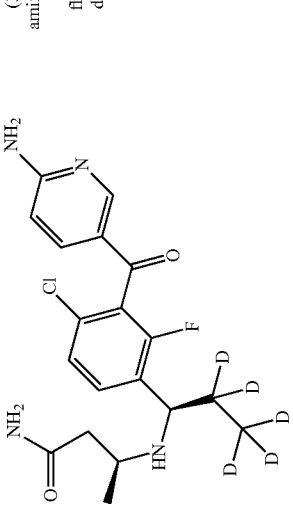 | (3S)-3-{[(1R)-1-{3-[(4-amino-3-chlorophenyl)carbonyl]-4-chloro-2-fluorophenyl}(2,2,3,3,3-deuteropropyl]amino}butanamide | HCl (1:1) | 1H NMR (400 MHz, Me-d3-OD): 7.72 (1H, t), 7.66 (1H, s), 7.57 (1H, d), 7.49 (1H, d), 6.84 (1H, d), 4.66 (1H, s), 3.55-3.40 (1H, m), 2.71-2.54 (2H, m), 1.39 (3H, d). | m/z: 431 | Example 267 |
| 268 | 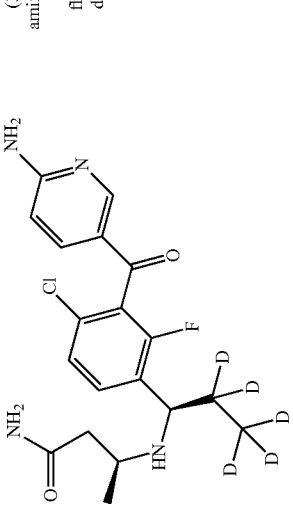 | (3S)-3-{[(1R)-1-{3-[(4-amino-3-methylphenyl)carbonyl]-4-chloro-2-fluorophenyl}(2,2,3,3,3-deuteropropyl]amino}butanamide | HCl (1:1) | 1H NMR (400 MHz, Me-d3-OD): 7.69 (1H, t), 7.55 (1H, d), 7.48 (1H, s), 7.42 (1H, d), 6.69 (1H, d), 4.66 (1H, s), 3.55-3.40 (1H, m), 2.71-2.55 (2H, m), 2.15 (3H, s), 1.39 (3H, d). | m/z: 411 | Prepared according to Example 267 from Example 79 |

TABLE 2-continued

| | Structure | Name | Salt | NMR Data | MS Data | Method |
|---|---|---|---|---|---|---|
| 269 | 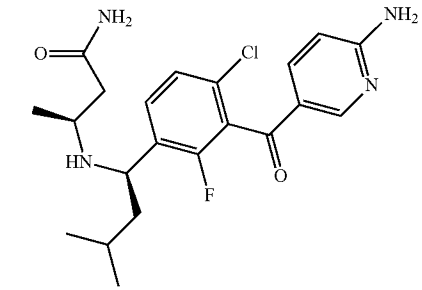 [SMILES: CC(C)C[C@@H](N[C@@H](C)CC(N)=O)c1ccc(Cl)c(C(=O)c2ccc(N)nc2)c1F] | (3S)-3-{[(1R)-1-{3-[(6-aminopyridin-3-yl)carbonyl]-4-chloro-2-fluorophenyl}-3-methylbutyl]amino}-butanamide | HCl (1:1) | 1H NMR (400 MHz, Me-d3-OD): 8.44-8.33 (2H, m), 7.86 (1H, t), 7.68-7.58 (1H, m), 7.17 (1H, d), 4.76-4.66 (1H, m), 3.53-3.44 (1H, m), 2.72-2.58 (2H, m), 2.25-2.11 (1H, m), 1.98-1.87 (1H, m), 1.42 (4H, d), 0.97 (6H, dd). | 6% impurity m/z: 421 | Prepared according to Example 81 from 5-({3-[(1R)-1-amino-3-methylbutyl]-6-chloro-2-fluorophenyl}-carbonyl)pyridin-2-amine which was prepared according to intermediate 2 step 3 and Example 1 steps 1-3 from commercially available (1R)-1-(4-chloro-2-fluorophenyl)-3-methylbutan-1-amine |
| 270 | 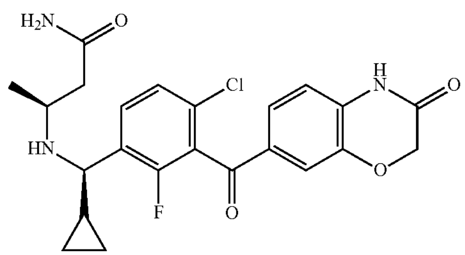 [SMILES: C[C@@H](CC(N)=O)N[C@@H](c1ccc(Cl)c(C(=O)c2ccc3c(c2)OCC(=O)N3)c1F)C1CC1] | (3S)-3-{[(R)-{4-chloro-2-fluoro-3-[(3-oxo-3,4-dihydro-2H-1,4-benzoxazin-7-yl)carbonyl]phenyl}(cyclopropyl)methyl]amino}butanamide | HCl (1:1) | 1H NMR (400 MHz, DMSO-d6): 11.23 (1H, s), 9.51-9.41 (1H, m), 9.41-9.32 (1H, m), 8.02 (1H, t), 7.73-7.64 (2H, m), 7.39 (1H, dd), 7.32 (1H, d), 7.16 (1H, s), 7.06 (1H, d), 4.69 (2H, s), 4.04-3.95 (1H, m), 3.47-3.40 (1H, m), 2.66 (1H, dd), 2.45 (1H, dd), 1.63-1.53 (1H, m), 1.22 (3H, d), 0.86-0.72 (2H, m), 0.63-0.54 (1H, m), 0.32-0.22 (1H, m). | m/z: 460 | Prepared as Example 247 using Intermediate 6 in place of Intermediate 2 |
| 271 | (3R)-3-{[(R)-{4-chloro-2-fluoro-3-[(3-oxo-3,4-dihydro-2H-1,4-benzoxazin-7-yl)carbonyl]phenyl}(cyclopropyl)methyl]amino}butanamide HCl (1:1) m/z: 460 | | | | | As Ex. 270 |
| 272 | 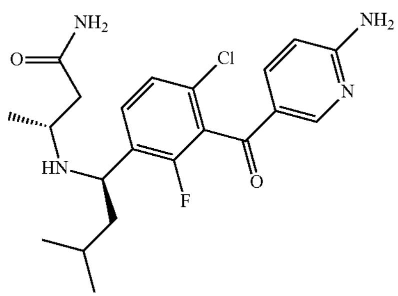 [SMILES: CC(C)C[C@@H](N[C@H](C)CC(N)=O)c1ccc(Cl)c(C(=O)c2ccc(N)nc2)c1F] | (3R)-3-{[(1R)-1-{3-[(6-aminopyridin-3-yl)carbonyl]-4-chloro-2-fluorophenyl}-3-methylbutyl]amino}-butanamide | HCl (1:1) | 1H NMR (400 MHz, Me-d3-OD): 8.39-8.29 (2H, m), 7.85 (1H, t), 7.64 (1H, d), 7.11 (1H, d), 4.80-4.71 (1H, m), 3.71-3.60 (1H, m), 2.66 (2H, d), 2.17-1.93 (2H, m), 1.41 (4H, d), 0.98 (6H, t). m/z: 421 | | Prepared according to Example 81 from 5-({3-[(1R)-1-amino-3-methylbutyl]-6-chloro-2-fluorophenyl}carbonyl)pyridin-2-amine which was prepared according to intermediate 2 step 3 and Example 1 steps 1-3 from commercially available (1R)-1-(4-chloro-2-fluorophenyl)-3-methylbutan-1-amine |

TABLE 2-continued

| | Structure | Name | Salt | NMR Data | MS Data | Method |
|---|---|---|---|---|---|---|
| 273 | 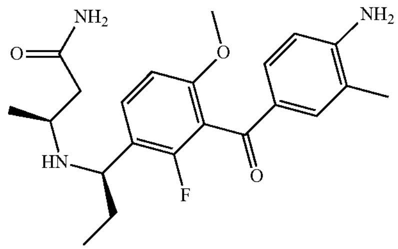 [SMILES: CC[C@@H](N[C@@H](C)CC(N)=O)c1ccc(OC)c(C(=O)c2ccc(N)c(C)c2)c1F] | (3S)-3-{[(1R)-1-{3-[(4-amino-3-methylphenyl)carbonyl]-2-fluoro-4-methoxyphenyl}propyl]amino}butanamide | HCl (1:1) | 1H NMR (400 MHz, Me-d3-OD): 7.67 (1H, t), 7.61 (1H, s), 7.54 (1H, dd), 7.15 (1H, d), 6.95 (1H, d), 4.58 (1H, dd), 3.83 (3H, s), 3.51-3.39 (1H, m), 2.67-2.57 (2H, m), 2.25 (3H, s), 2.22-2.05 (2H, m), 1.38 (3H, d), 0.92 (3H, t). | m/z: 402 | Example 273 |
| 274 | (3R)-3-{[(1R)-1-{3-[(4-amino-3-methylphenyl)carbonyl]-2-fluoro-4-methoxyphenyl}propyl]amino}butanamide HCl (1:1) m/z: 402 | | | | | As Ex. 273 |
| 275 | 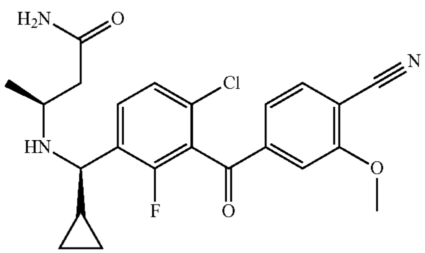 [SMILES: COc1cc(C(=O)c2c(Cl)ccc([C@H](N[C@@H](C)CC(N)=O)C3CC3)c2F)ccc1C#N] | (3S)-3-{[(R)-{4-chloro-3-[(4-cyanophenyl)carbonyl]-2-fluorophenyl}(cyclopropyl)methyl]amino}butanamide | HCl (1:1) | 1H NMR (400 MHz, Me-d3-OD): 7.84 (2H, t), 7.69 (1H, d), 7.60 (1H, dd), 7.42 (1H, dd), 4.05 (3H, s), 4.02 (1H, d), 3.58-3.48 (1H, m), 2.71-2.58 (2H, m), 1.69-1.55 (1H, m), 1.37 (3H, d), 1.04-0.89 (1H, m), 0.83-0.68 (2H, m), 0.52-0.39 (1H, m). | m/z: 444.2 | Prepared according to Example 81 using Example 69 |
| 276 | 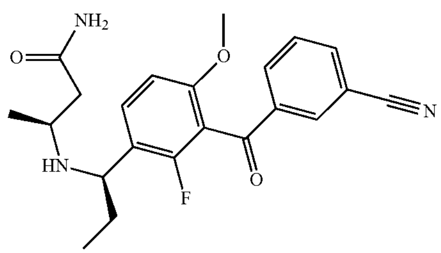 [SMILES: CC[C@@H](N[C@@H](C)CC(N)=O)c1ccc(OC)c(C(=O)c2cccc(C#N)c2)c1F] | (3S)-3-{[(1R)-1-{3-[(3-cyanophenyl)carbonyl]-2-fluoro-4-methoxyphenyl}propyl]amino}butanamide | HCl (1:1) | 1H NMR (400 MHz, Me-d3-OD): 8.20-8.08 (2H, m), 8.04 (1H, d), 7.81-7.68 (2H, m), 7.19 (1H, d), 4.58 (1H, dd), 3.84 (3H, s), 3.54-3.41 (1H, m), 2.71-2.53 (2H, m), 2.25-2.05 (2H, m), 1.40 (3H, d), 0.93 (3H, t). | m/z: 398 | Prepared according to Example 81 from Example 80 |
| 277 | (3R)-3-{[(1R)-1-{3-[(3-cyanophenyl)carbonyl]-2-fluoro-4-methoxyphenyl}propyl]amino}butanamide HCl (1:1) m/z: 398 | | | | | As Ex. 276 |

TABLE 2-continued

| | Structure | Name | Salt | NMR Data | MS Data | Method |
|---|---|---|---|---|---|---|
| 278 | 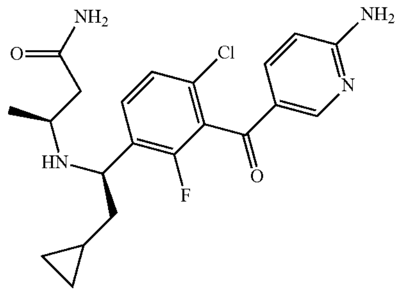 [SMILES: C[C@@H](CC(N)=O)N[C@H](CC1CC1)c1ccc(Cl)c(C(=O)c2ccc(N)nc2)c1F] | (3S)-3-{[(1R)-1-{3-[(6-aminopyridin-3-yl)carbonyl]-4-chloro-2-fluorophenyl}-2-cyclopropylethyl]amino}butanamide | HCl (1:1) | 1H NMR (400 MHz, Me-d3-OD): 8.41-8.31 (2H, m), 7.85 (1H, t), 7.52 (1H, d), 7.15 (1H, d), 4.82-4.76 (1H, m), 3.59-3.47 (1H, m), 2.74-2.55 (2H, m), 2.12-2.04 (2H, m), 1.42 (3H, d), 0.67-0.56 (1H, m), 0.56-0.40 (2H, m), 0.29-0.19 (1H, m), 0.07-0.03 (1H, m). | m/z: 419 | As Example 1 using Intermediate 4 then as Example 1 |
| 279 | (3R)-3-{[(1R)-1-{3-[(6-aminopyridin-3-yl)carbonyl]-4-chloro-2-fluorophenyl}-2-cyclopropylethyl]amino}butanamide HCl (1:1) m/z: 419 | | | | | As Ex. 278 |
| 280 | 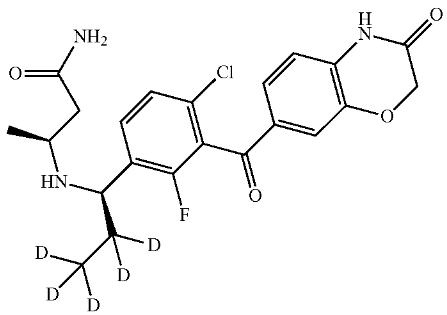 [SMILES: [2H]C([2H])([2H])C([2H])([2H])[C@@H](N[C@@H](C)CC(N)=O)c1ccc(Cl)c(C(=O)c2ccc3c(c2)OCC(=O)N3)c1F] | (3S)-3-{[(1R)-1-{4-chloro-2-fluoro-3-[(3-oxo-3,4-dihydro-2H-1,4-benzoxazin-7-yl)carbonyl]phenyl}(2,2,3,3,3-pentadeutery)propyl]amino}butanamide | HCl (1:1) | 1H NMR (400 MHz, Me-d3-OD): 7.74 (1H, t), 7.63-7.54 (1H, m), 7.50-7.38 (2H, m), 7.04 (1H, d), 4.67 (3H, d), 3.54-3.41 (1H, m), 2.72-2.51 (2H, m), 1.40 (3H, dd). | m/z: 453 | Prepared according to Example 1 using Example 70 |
| 281 | 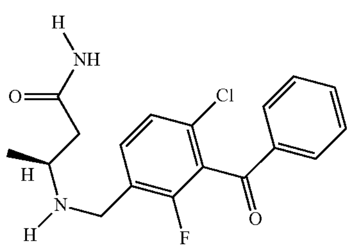 | (3S)-3-{[(3-benzoyl-4-chloro-2-fluorophenyl)methyl]amino}butanamide | HCl (1:1) | 1H NMR (400 MHz, DMSO-d6): 9.40 (1H, d), 9.28 (1H, s), 7.90 (1H, t), 7.84 (2H, d), 7.79 (1H, t), 7.70 (1H, s), 7.67-7.57 (3H, m), 7.17 (1H, s), 4.28 (2H, s), 3.59 (1H, s), 2.66 (1H, dd), 2.47 (1H, d), 1.31 (3H, d). | m/z: 349 (Molecular ion) | Example 281 |

TABLE 2-continued

| | Structure | Name | Salt | NMR Data | MS Data | Method |
|---|---|---|---|---|---|---|
| 282 | 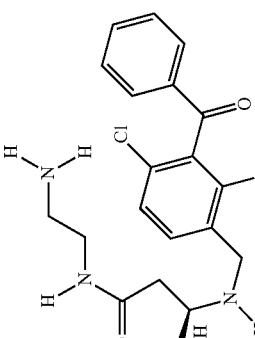 | (3S)-N-(2-aminoethyl)-3-{[(3-benzoyl-4-chloro-2-fluorophenyl)methyl]amino}butanamide | HCl (1:2) | 1H NMR (400 MHz, DMSO-d6, 50degC.): 9.56 (2H, s), 8.51 (1H, s), 8.19-7.92 (4H, m), 7.85 (2H, d), 7.78 (1H, t), 7.67-7.55 (3H, m), 4.28 (2H, s), 3.65 (1H, s), 3.37-3.30 (2H, m), 2.90 (2H, s), 2.85-2.75 (1H, m), 2.63-2.53 (1H, m), 1.35 (3H, d). | m/z: 392 (Molecular ion) | Example 282 |
| 283 | 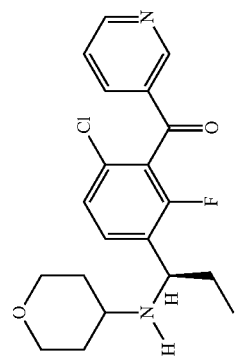 | N-[(1R)-1-{4-chloro-2-fluoro-3-[(pyridin-3-yl)carbonyl]phenyl}propyl]oxan-4-amine | HCl (1:1) | 1H NMR (400 MHz, Me-d3-OD): 9.08 (1H, s), 8.97 (1H, d), 8.55 (1H, d), 7.93-7.80 (2H, m), 7.68 (1H, d), 4.69 (1H, dd), 4.02 (2H, dd), 3.52-3.36 (3H, m), 2.33-2.19 (1H, m), 2.19-1.99 (3H, m), 1.83-1.64 (2H, m), 0.92 (3H, t). | m/z: 376 (Molecular ion) | Example 283 |
| 284 | 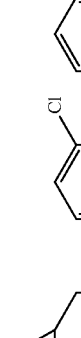 | [(1R)-1-{4-chloro-2-fluoro-3-[(pyridin-3-yl)carbonyl]phenyl]propyl](cyclopropylmethyl)amine | HCl (1:1) | 1H NMR (400 MHz, Me-d3-OD): 9.19 (1H, s), 9.03 (1H, d), 8.70 (1H, d), 8.01 (1H, dd), 7.84 (1H, t), 7.67 (1H, d), 4.58 (1H, dd), 3.03 (1H, dd), 2.86 (1H, dd), 2.34-2.21 (1H, m), 2.15-2.04 (1H, m), 1.21-1.05 (1H, m), 0.92 (3H, t), 0.74 (2H, d), 0.49-0.34 (2H, m). | m/z: 346 (Molecular ion) | Prepared according to Example 283 using Example 2 and cyclopropanecarbaldehyde |
| 285 | 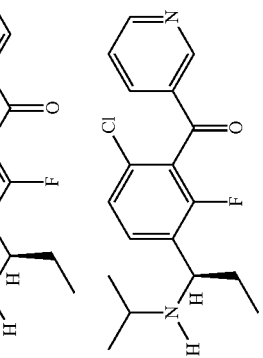 | [(1R)-1-{4-chloro-2-fluoro-3-[(pyridin-3-yl)carbonyl]phenyl]propyl](propan-2-yl)amine | HCl (1:1) | 1H NMR (400 MHz, Me-d3-OD): 8.96 (1H, d), 8.90 (1H, dd), 8.43-8.33 (1H, m), 7.82 (1H, t), 7.73 (1H, dd), 7.66 (1H, d), 4.62 (1H, dd), 3.40-3.34 (1H, m), 2.28-2.14 (1H, m), 2.14-2.04 (1H, m), 1.43-1.20 (7H, m), 0.93 (3H, t). | m/z: 334 (Molecular ion) | Prepared according to Example 283 using Example 2 and acetone |

TABLE 2-continued

| | Structure | Name | Salt | NMR Data | MS Data | Method |
|---|---|---|---|---|---|---|
| 286 | 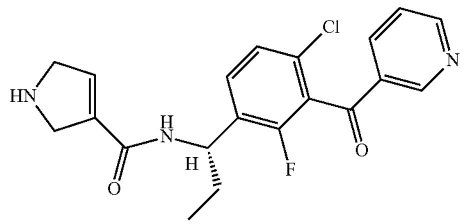 | N-[(1S)-1-{4-chloro-2-fluoro-3-[(pyridin-3-yl)carbonyl]phenyl]propyl]-2,5-dihydro-1H-pyrrole-3-carboxamide | HCl (1:1) | 1H NMR (400 MHz, Me-d3-OD): 8.91-8.81 (2H, m), 8.33-8.23 (1H, m), 7.66 (1H, dd), 7.60 (1H, t), 7.44 (1H, d), 6.74 (1H, s), 5.10 (1H, t), 4.28 (4H, d), 2.04-1.85 (2H, m), 1.01 (3H, t). (DMSO-d6) | m/z: 388 (Molecular ion) | Example 286 |
| 287 | 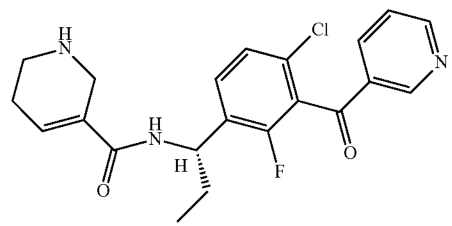 | N-[(1S)-1-{4-chloro-2-fluoro-3-[(pyridin-3-yl)carbonyl]phenyl]propyl]-1,2,5,6-tetrahydropyridine-3-carboxamide | HCl (1:1) | 1H NMR (400 MHz, Me-d3-OD): 9.11 (1H, s), 9.00 (1H, s), 8.64 (1H, s), 7.98 (1H, s), 7.63 (1H, t), 7.46 (1H, d), 6.91 (1H, s), 5.14-5.04 (1H, m), 3.89 (2H, s), 3.37 (2H, s), 2.67-2.56 (2H, m), 2.00-1.84 (2H, m), 1.01 (3H, t). | m/z: 402 (Molecular ion) | Example 286 using 1-(tert-butoxycarbonyl)-1,2,3,6-tetrahydropyridine-3-carboxylic acid |
| 288 | 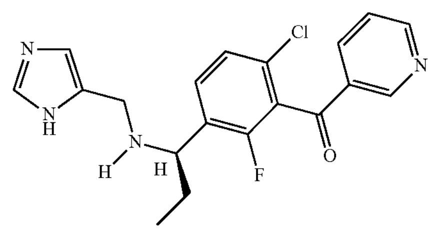 | [(1R)-1-{4-chloro-2-fluoro-3-[(pyridin-3-yl)carbonyl]phenyl]propyl](1H-imidazol-5-ylmethyl)amine | HCl (1:2) | 1H NMR (400 MHz, Me-d3-OD): 9.26 (1H, s), 9.04 (2H, d), 8.78 (1H, d), 8.08-7.93 (2H, m), 7.84 (1H, s), 7.69 (1H, d), 4.71 (1H, dd), 4.55 (1H, d), 4.43 (1H, d), 2.43-2.33 (1H, m), 2.25-2.14 (1H, m), 1.01-0.89 (3H, m). | m/z: 373 (Molecular ion) | Example 283 using 1-trityl-1H-imidazole-4-carboxaldehyde deprotection as Example 8 |
| 289 | 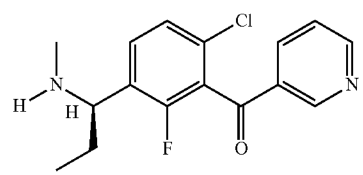 | [(1R)-1-{4-chloro-2-fluoro-3-[(pyridin-3-yl)carbonyl]phenyl]propyl](methyl)amine | HCl (1:1) | 1H NMR (400 MHz, Me-d3-OD): 9.04 (1H, d), 8.95 (1H, dd), 8.48 (1H, dt), 7.83 (1H, ddd), 7.77 (1H, t), 7.66 (1H, dd), 4.50 (1H, dd), 2.72 (3H, s), 2.31-2.18 (1H, m), 2.14-2.00 (1H, m), 0.95 (3H, t). | m/z: 307 (Molecular ion) | Example 289 |

TABLE 2-continued

| | Structure | Name | Salt | NMR Data | MS Data | Method |
|---|---|---|---|---|---|---|
| 290 | 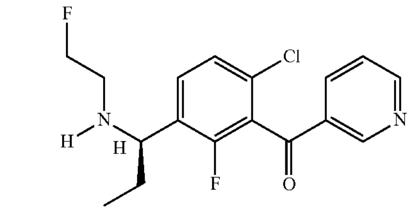 | [(1R)-1-{4-chloro-2-fluoro-3-[(pyridin-3-yl)carbonyl]phenyl}propyl](2-fluoroethyl)amine | HCl (1:1) | 1H NMR (400 MHz, Me-d3-OD): 9.07 (1H, d), 8.96 (1H, dd), 8.52 (1H, dt), 7.90-7.76 (2H, m), 7.68 (1H, dd), 4.84-4.78 (1H, m), 4.73-4.68 (1H, m), 4.63 (1H, dd), 3.55-3.35 (2H, m), 2.35-2.21 (1H, m), 2.17-2.04 (1H, m), 0.94 (3H, t). | m/z: 339 (Molecular ion) | As for Example 289 using fluoroacetic acid in step 1. |
| 291 | 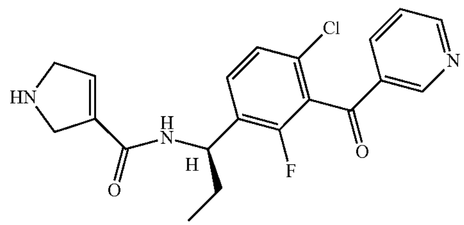 | N-[(1R)-1-{4-chloro-2-fluoro-3-[(pyridin-3-yl)carbonyl]phenyl}propyl]-2,5-dihydro-1H-pyrrole-3-carboxamide | HCl (1:1) | 1H NMR (400 MHz, Me-d3-OD): 9.18 (1H, s), 9.04 (1H, s), 8.91-8.78 (1H, m), 8.72 (1H, d), 8.19-7.97 (1H, m), 7.66 (1H, t), 7.48 (1H, d), 6.77 (1H, s), 5.15-5.06 (1H, m), 4.30 (4H, d), 2.04-1.86 (2H, m), 1.01 (3H, t). | m/z: 388 (Molecular ion) | Example 286 using Example 2 |
| 292 | 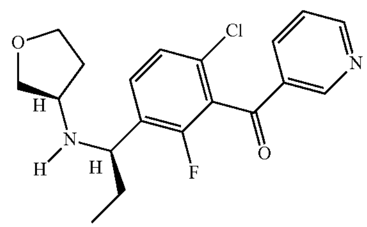 | (3R)-N-[(1R)-1-{4-chloro-2-fluoro-3-[(pyridin-3-yl)carbonyl]phenyl}propyl]oxolan-3-amine | HCl (1:1) | 1H NMR (400 MHz, Me-d3-OD): 8.93-8.78 (2H, m), 8.32-8.21 (1H, m), 7.77-7.58 (2H, m), 7.47 (1H, d), 3.98-3.80 (2H, m), 3.80-3.66 (2H, m), 3.62 (1H, dd), 3.28-3.15 (1H, m), 2.09-1.97 (1H, m), 1.97-1.82 (1H, m), 1.82-1.58 (2H, m), 0.86 (3H, t). | m/z: 363 (Molecular ion) | As Example 283 using 3-oxotetrahydrofuran then separation of diastereoisomers by prep HPLC |
| 293 | 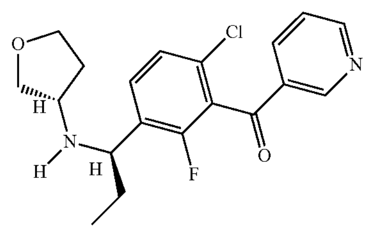 | (3S)-N-[(1R)-1-{4-chloro-2-fluoro-3-[(pyridin-3-yl)carbonyl]phenyl}propyl]oxolan-3-amine | HCl (1:1) | 1H NMR (400 MHz, Me-d3-OD): 8.93-8.79 (2H, m), 8.32-8.22 (1H, m), 7.75-7.60 (2H, m), 7.47 (1H, d), 4.00 (1H, dd), 3.97-3.84 (1H, m), 3.80-3.60 (2H, m), 3.43 (1H, dd), 3.26-3.14 (1H, m), 2.09-1.96 (1H, m), 1.96-1.78 (2H, m), 1.78-1.62 (1H, m), 0.87 (3H, t). | m/z: 363 (Molecular ion) | As Example 283 using 3-oxotetrahydrofuran then separation of diastereoisomers by prep HPLC |

TABLE 2-continued

| | Structure | Name | Salt | NMR Data | MS Data | Method |
|---|---|---|---|---|---|---|
| 294 | 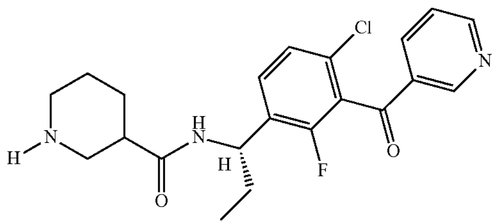 | N-[(1S)-1-{4-chloro-2-fluoro-3-[(pyridin-3-yl)carbonyl]phenyl}propyl]piperidine-3-carboxamide | HCl (1:1) | 1H NMR (400 MHz, Me-d3-OD): 9.08 (1H, d), 8.99 (1H, d), 8.76 (1H, d), 8.59 (1H, t), 8.00-7.89 (1H, m), 7.67-7.54 (1H, m), 7.46 (1H, d), 5.08-4.97 (1H, m), 3.30-3.16 (4H, m), 3.16-3.03 (1H, m), 2.94-2.83 (1H, m), 2.16-2.04 (1H, m), 2.02-1.70 (6H, m), 1.00 (3H, t). | m/z: 403 (Molecular ion) | Example 294 |
| 295 | 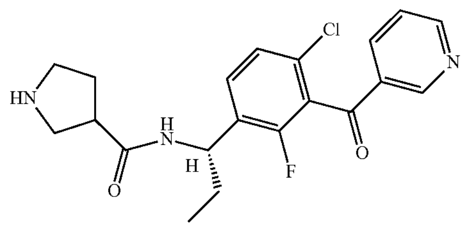 | N-[(1S)-1-{4-chloro-2-fluoro-3-[(pyridin-3-yl)carbonyl]phenyl}propyl]pyrrolidine-3-carboxamide | HCl (1:1) | 1H NMR (400 MHz, Me-d3-OD): 9.10 (1H, s), 9.00 (1H, d), 8.80 (1H, d), 8.62 (1H, dd), 8.02-7.92 (1H, m), 7.67-7.55 (1H, m), 7.47 (1H, d), 5.08-4.91 (1H, m), 3.59-3.49 (1H, m), 3.49-3.34 (3H, m), 2.45-2.29 (1H, m), 2.25-2.13 (1H, m), 2.09-1.97 (1H, m), 1.97-1.80 (2H, m), 1.00 (3H, t). | m/z: 389 (Molecular ion) | Prepared according to Example 294 using Example 26 and 1-[(tert-butoxy)carbonyl]-pyrrolidine-3-carboxylic acid |
| 296 | 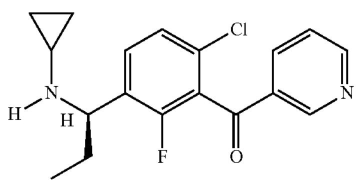 | N-[(1R)-1-{4-chloro-2-fluoro-3-[(pyridin-3-yl)carbonyl]phenyl}propyl]cyclopropanamine | HCl (1:1) | 1H NMR (400 MHz, Me-d3-OD): 9.19 (1H, d), 9.03 (1H, dd), 8.70 (1H, dt), 8.02 (1H, dd), 7.84 (1H, t), 7.67 (1H, dd), 4.68 (1H, dd), 2.81-2.69 (1H, m), 2.36-2.21 (1H, m), 2.21-2.06 (1H, m), 1.04-0.75 (7H, m). | m/z: 333 (Molecular ion) | Example 296 |
| 297 | 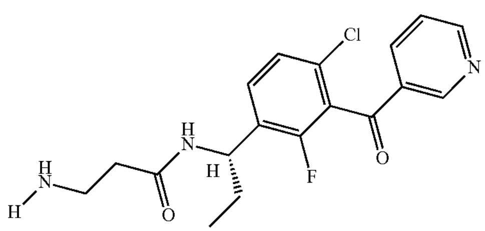 | 3-amino-N-[(1S)-1-{4-chloro-2-fluoro-3-[(pyridin-3-yl)carbonyl]phenyl}propyl]propanamide | HCl (1:1) | 1H NMR (400 MHz, Me-d3-OD): 9.13 (1H, s), 9.02 (1H, dd), 8.70-8.61 (1H, m), 8.01 (1H, dd), 7.61 (1H, t), 7.47 (1H, d), 5.06 (1H, t), 3.19 (2H, t), 2.79-2.62 (2H, m), 1.94-1.79 (2H, m), 0.99 (3H, t). | m/z: 363 (Molecular ion) | Prepared according to Example 294 using Example 26 and 3-{[(tert-butoxy)carbonyl]-amino}propanoic acid |

TABLE 2-continued

| | Structure | Name | Salt | NMR Data | MS Data | Method |
|---|---|---|---|---|---|---|
| 298 | 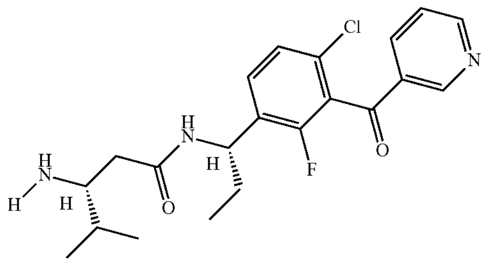 | (3R)-3-amino-N-[(1S)-1-{4-chloro-2-fluoro-3-[(pyridin-3-yl)carbonyl]phenyl}propyl]-4-methylpentanamide | HCl (1:1) | 1H NMR (400 MHz, Me-d3-OD): 8.99 (1H, s), 8.94 (1H, d), 8.53-8.44 (1H, m), 7.85 (1H, dd), 7.60 (1H, t), 7.46 (1H, d), 5.05 (1H, t), 3.41-3.35 (1H, m), 2.76 (1H, dd), 2.51 (1H, dd), 2.00-1.79 (3H, m), 1.12-0.86 (9H, m). | m/z: 405 (Molecular ion) | Prepared according to Example 26 using Example 294 and (3R)-3-[(tert-butoxy)carbonyl]-amino}-4-methylpentanoic acid |
| 299 | 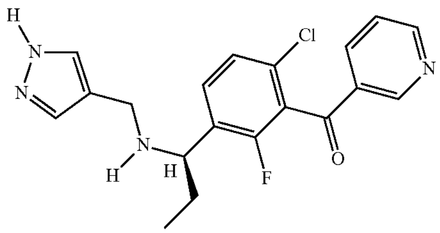 | [(1R)-1-{4-chloro-2-fluoro-3-[(pyridin-3-yl)carbonyl]phenyl}propyl](1H-pyrazol-4-ylmethyl)amine | HCl (1:2) | 1H NMR (400 MHz, Me-d3-OD): 9.29 (1H, s), 9.08 (1H, d), 8.83 (1H, s), 8.12 (1H, s), 7.91-7.81 (3H, m), 7.69 (1H, d), 4.57 (1H, dd), 4.29 (1H, d), 4.22 (1H, d), 2.36-2.26 (1H, m), 2.15-2.01 (1H, m), 0.92 (3H, t). | m/z: 373 (Molecular ion) | As Example 283 using 1H-pyrazole-4-carboxaldehyde |
| 300 | 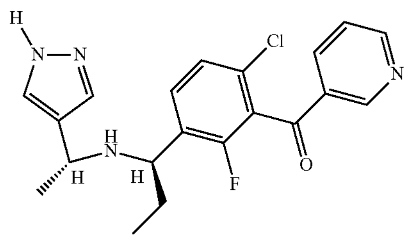 | [(1R)-1-{4-chloro-2-fluoro-3-[(pyridin-3-yl)carbonyl]phenyl}propyl][(1R)-1-(1H-pyrazol-4-yl)ethyl]amine | HCl (1:2) | 1H NMR (400 MHz, Me-d3-OD): 8.89 (1H, d), 8.85 (1H, dd), 8.31-8.23 (1H, m), 7.75-7.63 (2H, m), 7.52-7.41 (3H, m), 3.79 (1H, dd), 3.61 (1H, q), 1.87-1.76 (1H, m), 1.70-1.59 (1H, m), 1.36 (3H, d), 0.79 (3H, t). | m/z: 387 (Molecular ion) | As Example 283 using 4-acetyl pyrazole then separation of diastereoisomers by prep HPLC |
| 301 | 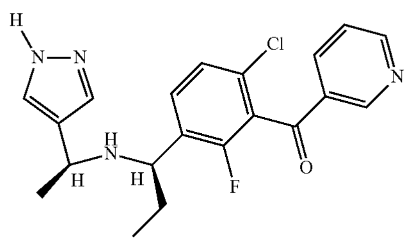 | [(1R)-1-{4-chloro-2-fluoro-3-[(pyridin-3-yl)carbonyl]phenyl}propyl][(1S)-1-(1H-pyrazol-4-yl)ethyl]amine | HCl (1:1) | 1H NMR (400 MHz, Me-d3-OD): 8.92-8.80 (2H, m), 8.28-8.18 (1H, m), 7.74-7.61 (2H, m), 7.49 (2H, d), 7.41 (1H, d), 4.02 (1H, dd), 3.81 (1H, q), 2.00-1.87 (1H, m), 1.76-1.63 (1H, m), 1.37 (3H, d), 0.90-0.75 (3H, m). | m/z: 387 (Molecular ion) | As Example 283 using 4-acetyl pyrazole then separation of diastereoisomers by prep HPLC |

TABLE 2-continued

| | Structure | Name | Salt | NMR Data | MS Data | Method |
|---|---|---|---|---|---|---|
| 302 | 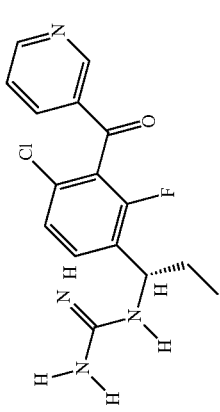 | 1-[(1S)-1-{4-chloro-2-fluoro-3-[(pyridin-3-yl)carbonyl]phenyl}propyl]guanidine | HCl (1:1) | 1H NMR (400 MHz, DMSO-d6): 8.94 (2H, dd), 8.51 (1H, d), 8.29-8.19 (1H, m), 7.75-7.55 (3H, m), 7.35 (3H, s), 4.91-4.79 (1H, m), 1.88-1.71 (2H, m), 0.93 (3H, t). | | Example 302 |
| 303 | 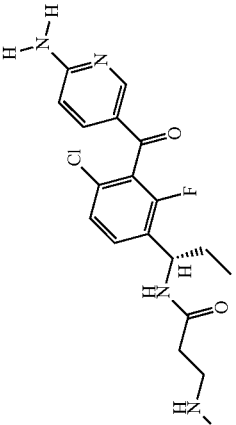 | 3-amino-N-[(1S)-1-{3-[(6-aminopyridin-3-yl)carbonyl]-4-chloro-2-fluorophenyl}propyl]propanamide | HCl (1:1) | 1H NMR (400 MHz, Me-d3-OD): 8.24 (2H, d), 7.55 (1H, t), 7.42 (1H, d), 7.06 (1H, s), 5.05 (1H, t), 3.19 (2H, t), 2.79-2.62 (2H, m), 1.93-1.78 (2H, m), 0.98 (3H, t). | m/z: 379 (Molecular ion) | As Example 286 using Example 31 and BOC-beta-ALA-OH |
| 304 | 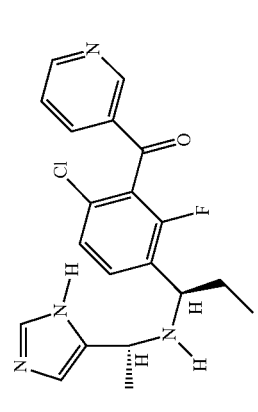 | [(1R)-1-{4-chloro-2-fluoro-3-[(pyridin-3-yl)carbonyl]phenyl}propyl][(1R)-1-(1H-imidazol-5-yl)ethyl]amine | HCl (1:1) | 1H NMR (400 MHz, Me-d3-OD): 9.23 (1H, s), 9.08-8.98 (2H, m), 8.78-8.69 (1H, m), 8.04-7.85 (2H, m), 7.81 (1H, d), 7.68 (1H, d), 4.74 (1H, q), 4.54 (1H, dd), 2.37-2.24 (1H, m), 2.21-2.07 (1H, m), 1.85 (3H, d), 0.90 (3H, t). | m/z: 387 (Molecular ion) | As Example 283 using 4-acetyl imidazole then separation of diastereoisomers by prep HPLC |
| 305 | 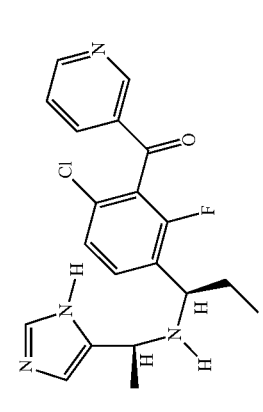 | [(1R)-1-{4-chloro-2-fluoro-3-[(pyridin-3-yl)carbonyl]phenyl}propyl][(1S)-1-(1H-imidazol-5-yl)ethyl]amine | HCl (1:1) | 1H NMR (400 MHz, Me-d3-OD): 9.22 (1H, s), 9.07-8.98 (2H, m), 8.78-8.69 (1H, m), 8.04-7.84 (3H, m), 7.66 (1H, d), 4.79 (1H, d), 4.56 (1H, dd), 2.44-2.29 (1H, m), 2.27-2.09 (1H, m), 1.84 (3H, d), 0.92 (3H, t). | m/z: 387 (Molecular ion) | As Example 283 using 4-acetyl imidazole then separation of diastereoisomers by prep HPLC |

TABLE 2-continued

| | Structure | Name | Salt | NMR Data | MS Data | Method |
|---|---|---|---|---|---|---|
| 306 | 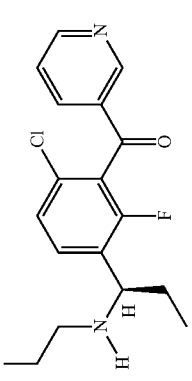 | [(1R)-1-{4-chloro-2-fluoro-3-[(pyridin-3-yl)carbonyl]phenyl]propyl][2-(1H-pyrazol-1-yl)ethyl]amine | HCl (1:1) | 1H NMR (400 MHz, Me-d3-OD): 8.99 (1H, d), 8.92 (1H, dd), 8.40 (1H, dt), 7.81-7.72 (2H, m), 7.70 (1H, d), 7.64 (1H, dd), 7.56 (1H, d), 6.35 (1H, t), 5.51 (1H, s), 4.60 (1H, dd), 4.52 (2H, t), 3.65-3.55 (1H, m), 3.55-3.47 (1H, m), 2.33-2.20 (1H, m), 2.20-2.02 (1H, m), 0.95 (3H, t). | m/z: 387 (Molecular ion) | As for Example 289 using 1H-pyrazol-1-ylacetic acid in step 1. |
| 307 | 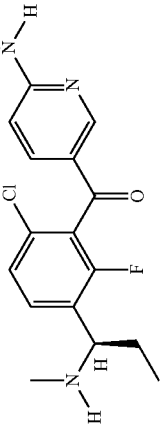 | 5-({6-chloro-2-fluoro-3-[(1R)-1-(methylamino)propyl]phenyl}carbonyl)pyridin-2-amine | None | 1H NMR (400 MHz, DMSOcap): 8.13 (1H, s), 7.78 (1H, d), 7.61 (1H, t), 7.46 (1H, d), 7.32 (2H, s), 6.54 (1H, d), 3.68 (1H, t), 2.12 (3H, s), 1.79-1.62 (1H, m), 1.62-1.45 (1H, m), 0.78 (3H, t). | m/z: 322 (Adduct) | Example 307 |

Biological Activity

Example A

NS3 Protease Assay

The HCV NS3 protease functions have been extensively studied and are considered as potential targets for antiviral therapy: see for example the many references listed in the introductory section of this application. Therefore, the activity of the compounds of the invention as anti-HCV agents was assessed using a full length HCV NS3 protease.

The protease activity of the full length NS3/4a was measured using a FRET-based assay utilizing a peptide substrate derived from the NS4A/B cleavage site (Anaspec) and labelled at one end with a quencher (QXL520) and at the other with a fluorophore (5-FAMsp). NS3/4a (produced in-house by literature methods) was incubated with test compounds and peptide substrate in 50 mM Tris pH8, 20 mM DTT, 1% CHAPS, 10% glycerol and 5% DMSO. The reaction was followed by monitoring the change in fluorescence on a Molecular Devices Gemini plate reader for 30 minutes at room temperature. Initial rates were calculated from the progress curves using SoftMax Pro (Molecular Devices). $IC_{50}$ values were then calculated from replicate curves using Prism GraphPad software.

The compounds of Examples 1, 4, 6, 7, 8, 9, 11, 13, 15, 16, 18, 20, 23, 24, 26, 27, 29, 30, 31, 32, 33, 36, 37, 39, 40, 42, 43, 47, 49, 50, 52, 54, 56, 60 62, 65 to 69, 81-85, 87-93, 95-99, 101, 103, 104, 106, 108-110, 112-116, 119, 125, 126, 128, 132-134, 136, 138, 139, 141, 142, 145-147, 149-154, 157-159, 162, 167, 168, 171, 173, 176-183, 185-190, 192, 193, 200, 202-205, 207, 210, 212-213, 216, 220-222, 224-225, 227, 228, 230, 232, 234, 235, 237-239, 241-244, 247, 249-252, 255-256, 258, 259, 261, 263-265, 267, 268, 270, 273-282, 286, 287, 294, 297, 298, 303 and 307 all have $IC_{50}$ values of less than 1 µM against the protease activity of the full length NS3/4a in the above assay whereas the compounds of Examples 2, 3, 5, 10, 14, 21, 22, 28, 34, 38, 41, 55, 57, 61, 86, 94, 102, 107, 111, 120, 122, 123, 124, 127, 130, 135, 140, 144, 155, 156, 160, 165, 170, 172, 175, 191, 196, 198, 201, 206, 208, 209, 211, 215, 218, 223, 226, 229, 231, 245, 246, 248, 253, 254, 257, 266, 269, 271 284, 285, 288, 289, 291, 302, 304 and 305 all have $IC_{50}$ values of 1-5 µM against the protease activity of the full length NS3/4a in the above assay. The compounds of Examples 12, 19, 25, 45, 46, 51, 100, 105, 118, 131 137, 143, 148, 161, 163, 166, 169, 174, 190, 195, 197, 214, 219, 222, 233, 236, 240, 272, 283, 290, 296, 300, 301 and 306 have $IC_{50}$ values of less than 30 µM or exhibit at least 40% inhibition at a concentration of 100 µM against the protease activity of the full length NS3/4a in the above assay. The individual activities of the compounds of the Examples are set out in the column headed "Assay A" in Table 3 below.

The results demonstrate that compounds of the invention are good inhibitors of the protease activity of the full length NS3/4a of HCV and should therefore exhibit good antiviral activity.

Example B

Replicon Assay

The activities of compounds of the invention against HCV in a cellular environment were analysed using a replicon assay as described below.

Thus, Huh-7 cells persistently infected with an HCV-RNA construct (Bartenschlager, R. Hepatitis C replicons: potential role for drug development. Nature Rev. Drug Discov. 1, 911-916 (2002)) comprising: 5' and 3' non-translated regions (NTR); the non-structural genes NS3 to NS5b; as well as the G418 drug resistance gene, neomycin, (for selection of cells carrying HCV replicon RNA) fused to the firefly Luciferase reporter gene (pFKI3889Iuc-ubi-neo/NS3-3'/ET) were used to determine the cell based antiviral activity of compounds using luciferase activity as an indirect readout of HCV RNA load. In this assay $4 \times 10^{-3}$ huh-7 cells persistently infected with the HCV subgenomic replicon construct above were plated/well in a 96 well tissue culture plate. The cells were allowed to attach overnight in DMEM medium supplemented with 10% FBS 1% NEAA, and 250 µg/ml gentamicin. The following day the medium was replaced with 200 µl/well of fresh medium as described above lacking gentamicin. Semi-log dilutions of compounds in medium were then added to triplicate wells (non-edge) of the cultured cells to give a 0.1% DMSO final concentration. Plates were then incubated at 37° C. in an atmosphere of 5% CO2 and air for 72 h. Following the 72 h incubation, compound CC50 values were determined by adding 20 µl of Alamar Blue™ (Biosource International, Camarillo, Calif., USA) to each well and incubating for 6 h at 37° C. in an atmosphere of 5% $CO_2$ and air. The plate was then read at 535 nm (excitation) and 590 nm (emission) on a SpectraMax Gemini reader (Molecular Devices) to determine the number of viable cells by measuring the conversion of rezasurin (Alamar blue) to resorufin in response to mitochondrial activity. In order to determine the antiviral effect of these compounds $EC_{50}$ values were determined by measuring the luciferase activity of the cells. Alamar blue solution was removed from the wells and replaced with 100 µl/well of medium along with 100 µl/well of Bright-Glo reagent and incubated at room temperature for 5 minutes before transferring 100 µl/well to a white bottom 96 well plate to read in a luminometer as described in the Bright-Glo Luciferase Assay System protocol (promega). The activities of compounds of the invention in the above assay, as defined by the $CC_{50}$ (50% cytotoxicity dose) and the $EC_{50}$ values ($EC_{50}$ luciferase readout), are set out in the column headed "Assay B" in Table 3 below.

TABLE 3

Activities of the Compounds of the Examples in the HCV NS3 Protease Assay (Example A above) and the Replicon Assay (Example B above)

| Compound | Assay A $IC_{50}$ (µM) or % inhibition average | Assay B $EC_{50}$ $CC_{50}$/µM | Compound | Assay A $IC_{50}$ (µM) or % inhibition average | Assay B $EC_{50}$ $CC_{50}$/µM |
|---|---|---|---|---|---|
| Example 1 | 0.089 | | Example 2 | 1.4 | |
| Example 3 | 1.3 | | Example 4 | 0.089 | >10 >10 |
| Example 5 | 55% @ 3 uM | | Example 6 | 80% @ 0.3 uM | |
| Example 7 | 0.38 | | Example 8 | 0.19 | |

TABLE 3-continued

Activities of the Compounds of the Examples in the HCV NS3 Protease Assay
(Example A above) and the Replicon Assay (Example B above)

| Compound | Assay A IC$_{50}$ (µM) or % inhibition average | Assay B EC$_{50}$ CC$_{50}$/µM | Compound | Assay A IC$_{50}$ (µM) or % inhibition average | Assay B EC$_{50}$ CC$_{50}$/µM |
|---|---|---|---|---|---|
| Example 9 | 0.076 | >3 >3 | Example 10 | 3.5 | |
| Example 11 | 0.13 | >3 >3 | Example 12 | 47% @ 30 uM | |
| Example 13 | 0.83 | | Example 14 | 2.5 | |
| Example 15 | 0.84 | | Example 16 | 0.47 | |
| Example 17 | 65% @ 100 uM | | Example 18 | 0.62 | |
| Example 19 | 20 | | Example 20 | 0.82 | |
| Example 21 | 1.0 | | Example 22 | 1.8 | |
| Example 23 | 0.11 | | Example 24 | 0.075 | |
| Example 25 | 59% @ 30 uM | | Example 26 | 0.63 | |
| Example 27 | 0.22 | | Example 28 | 1.5 | |
| Example 29 | 0.50 | | Example 30 | 0.21 | |
| Example 31 | 0.18 | | Example 32 | 0.058 | |
| Example 33 | 0.71 | | Example 34 | 55% @ 3 uM | |
| Example 35 | 30% @ 10 uM | | Example 36 | 0.71 | |
| Example 37 | 0.49 | | Example 38 | 3.6 | |
| Example 39 | 0.73 | | Example 40 | 0.84 | |
| Example 41 | 1.6 | 0.0090 | Example 42 | 0.53 | |
| Example 43 | 0.74 | | Example 44 | 30% @ 100 µM | |
| Example 45 | 50% @ 10 uM | | Example 46 | 64% @ 10 µM | |
| Example 47 | 0.18 | | | — | |
| Example 49 | 0.15 | | Example 50 | 0.21 | |
| Example 51 | 44% @ 3 uM | | Example 52 | 0.77 | |
| — | | | Example 54 | 0.14 | |
| Example 55 | 4.4 | | Example 56 | 0.60 | |
| Example 57 | 4.6 | | Example 58 | 31% @ 10 uM | |
| Example 59 | — | | Example 60 | 0.55 | |
| Example 61 | 1.2 | | Example 62 | 0.32 | |
| Example 63 | — | | Example 64 | 44% @ 0.1 µM | |
| Example 65 | 0.16 | | Example 66 | 0.20 | |
| Example 67 | 0.37 | | Example 68 | 0.21 | |
| Example 69 | 0.052 | 0.033 >1 | Example 70 | — | |
| Example 71 | — | | Example 72 | — | 0.032 |
| Example 73 | — | | Example 74 | — | 0.032 |
| Example 75 | — | | Example 76 | — | |
| Example 77 | — | | Example 78 | — | |
| Example 79 | — | | Example 80 | — | |
| Example 81 | 0.22 | 0.018 >3 | Example 82 | 0.83 | |
| Example 83 | 0.50 | | Example 84 | 0.057 | 0.006 >3 |
| Example 85 | 0.061 | | Example 86 | 1.0 | |
| Example 87 | 54% @ 0.01 uM | | Example 88 | 52% @ 0.01 uM | 0.045 >3 |
| Example 89 | 54% @ 0.03 uM | | Example 90 | 0.13 | 0.38 >3 |
| Example 91 | 0.066 | 0.0012 >10 | Example 92 | 0.34 | |
| Example 93 | 0.14 | 0.51 >3 | Example 94 | 1.0 | |
| Example 95 | 0.085 | 0.041 >3 | Example 96 | 58% @ 0.3 uM | |
| Example 97 | 0.047 | 0.019 >3 | Example 98 | 0.60 | |
| Example 99 | 0.25 | | Example 100 | 14 | |
| Example 101 | 0.11 | 0.16 >3 | Example 102 | 1.2 | |
| Example 103 | 0.077 | 0.0058 >3 | Example 104 | 0.24 | 0.39 >3 |
| Example 105 | 57% @ 30 uM | | Example 106 | 0.11 | 0.057 >3 |
| Example 107 | 1.1 | | Example 108 | 0.070 | 0.27 >3 |
| Example 109 | 0.47 | | Example 110 | 0.17 | 0.51 >3 |
| Example 111 | 3.1 | | Example 112 | 0.62 | |
| Example 113 | 0.093 | 0.18 >3 | Example 114 | 0.75 | |
| Example 115 | 59% @ 0.1 uM | 0.0041 >3 | Example 116 | 0.81 | >3 >3 |

TABLE 3-continued

Activities of the Compounds of the Examples in the HCV NS3 Protease Assay
(Example A above) and the Replicon Assay (Example B above)

| Compound | Assay A IC$_{50}$ (µM) or % inhibition average | Assay B EC$_{50}$ CC$_{50}$/µM | Compound | Assay A IC$_{50}$ (µM) or % inhibition average | Assay B EC$_{50}$ CC$_{50}$/µM |
|---|---|---|---|---|---|
| Example 117 | 16% @ 10 uM | | Example 118 | 41% @ 3 uM | |
| Example 119 | 0.12 | 0.071 >3 | Example 120 | 1.2 | |
| Example 121 | 38% @ 0.03 uM | 0.0099 >3 | Example 122 | 1.4 | |
| Example 123 | 3.2 | | Example 124 | 1.0 | |
| Example 125 | 0.29 | 0.079 >3 | Example 126 | 0.12 | 0.091 >3 |
| Example 127 | 1.6 | >10 | Example 128 | 0.28 | |
| Example 129 | 36% @ 0.03 uM | | Example 130 | 1.5 | |
| Example 131 | 7.9 | | Example 132 | 0.14 | 0.025 >3 |
| Example 133 | 0.12 | >3 >3 | Example 134 | 0.085 | 0.052 >3 |
| Example 135 | 3.4 | | Example 136 | 0.83 | |
| Example 137 | 60% @ 30 uM | | Example 138 | 0.31 | |
| Example 139 | 0.33 | 0.42 >3 | Example 140 | 3.9 | |
| Example 141 | 0.47 | | Example 142 | 0.30 | >3 >3 |
| Example 143 | 59% @ 30 uM | | Example 144 | 1.2 | >3 >3 |
| Example 145 | 0.84 | 1.0 >10 | Example 146 | 56% @ 0.3 uM | |
| Example 147 | 0.39 | 2.1 >10 | Example 148 | 43% @ 10 uM | |
| Example 149 | 0.20 | 0.039 >10 | Example 150 | 0.068 | 0.31 >10 |
| Example 151 | 0.49 | | Example 152 | 0.051 | 0.066 >10 |
| Example 153 | 0.49 | | Example 154 | 0.20 | 0.037 >10 |
| Example 155 | 1.0 | | Example 156 | 2.0 | |
| Example 157 | 0.045 | 0.61 >10 | Example 158 | 0.35 | |
| Example 159 | 0.24 | 0.10 >10 | Example 160 | 4.2 | |
| Example 161 | 60% @ 10 µM | >10 | Example 162 | 0.59 | >3 >3 |
| Example 163 | 62% @ 10 uM | | Example 164 | 37% @ 10 uM | |
| Example 165 | 1.4 | | Example 166 | 6.3 | |
| Example 167 | 0.098 | 0.63 >3 | Example 168 | 0.55 | >3 >3 |
| Example 169 | 53% @ 100 uM | | Example 170 | 55% @ 3 uM | |
| Example 171 | 0.056 | >3 >3 | Example 172 | 1.6 | |
| Example 173 | 0.13 | | Example 174 | 47% @ 30 uM | |
| Example 175 | 1.1 | | Example 176 | 0.29 | >3 >3 |
| Example 177 | 0.18 | >3 >3 | Example 178 | 0.088 | 0.25 >3 |
| Example 179 | 0.063 | 0.3 >3 | Example 180 | 0.14 | 0.27 >3 |
| Example 181 | 0.26 | | Example 182 | 0.038 | |
| Example 183 | 0.50 | 2.2 >10 | Example 184 | 22% @ 10 uM | |
| Example 185 | 0.60 | | Example 186 | 0.11 | |
| Example 187 | 0.66 | | Example 188 | 0.14 | |
| Example 189 | 0.54 | | Example 190 | 0.37 | |
| Example 191 | 1.1 | | Example 192 | 0.63 | |
| Example 193 | 0.31 | | Example 194 | 28% @ 0.3 uM | |
| Example 195 | 6.2 | | Example 196 | 2.3 | |
| Example 197 | 45% @ 10 uM | | Example 198 | 2.4 | |
| Example 199 | 32% @ 100 uM | | Example 200 | 0.078 | |
| Example 201 | 3.0 | | Example 202 | 0.31 | |
| Example 203 | 0.27 | | Example 204 | 0.17 | |
| Example 205 | 0.19 | | Example 206 | 1.2 | |
| Example 207 | 0.37 | | Example 208 | 3.1 | |
| Example 209 | 2.7 | | Example 210 | 0.098 | |
| Example 211 | 47% @ 1 uM | | Example 212 | 0.094 | |
| Example 213 | 0.35 | | Example 214 | 51% @ 10 uM | |
| Example 215 | 1.2 | | Example 216 | 0.48 | |

TABLE 3-continued

Activities of the Compounds of the Examples in the HCV NS3 Protease Assay
(Example A above) and the Replicon Assay (Example B above)

| Compound | Assay A IC$_{50}$ (µM) or % inhibition average | Assay B EC$_{50}$ CC$_{50}$/µM | Compound | Assay A IC$_{50}$ (µM) or % inhibition average | Assay B EC$_{50}$ CC$_{50}$/µM |
|---|---|---|---|---|---|
| Example 217 | 38% @ 30 uM | | Example 218 | 42% @ 1 uM | |
| Example 219 | 7.5 | | Example 220 | 0.26 | |
| Example 221 | 0.36 | | Example 222 | 45% @ 0.03 uM | |
| Example 223 | 3.1 | | Example 224 | 0.081 | 0.19 >3 |
| Example 225 | 0.35 | 0.028 >3 | Example 226 | 1.1 | |
| Example 227 | 0.15 | 0.011 >3 | Example 228 | 0.73 | |
| Example 229 | 1.1 | 1.9 >3 | Example 230 | 0.55 | 0.037 >3 |
| Example 231 | 2.1 | | Example 232 | 0.99 | |
| Example 233 | 40% @ 10 µM | | Example 234 | 0.14 | 0.0028 >1 |
| Example 235 | 0.13 | 0.0088 >1 | Example 236 | 56% @ 1 µM | |
| Example 237 | 0.31 | 0.047 >1 | Example 238 | 0.11 | 0.03 >1 |
| Example 239 | 0.50 | 0.038 >1 | Example 240 | 48% @ 0.03 µM | |
| Example 241 | 0.036 | | Example 242 | 0.49 | 0.098 >1 |
| Example 243 | 0.43 | | Example 244 | 0.38 | |
| Example 245 | 3.4 | | Example 246 | 3.9 | |
| Example 247 | 0.29 | 0.021 >1 | Example 248 | 2.0 | |
| Example 249 | 0.27 | 0.033 | Example 250 | 0.095 | 0.029 >1 |
| Example 251 | 0.30 | >1 >1 | Example 252 | 0.18 | 0.13 >1 |
| Example 253 | 1.4 | | Example 254 | 1.8 | |
| Example 255 | 0.24 | 0.027 >1 | Example 256 | 0.47 | 0.046 >1 |
| Example 257 | 2.0 | | Example 258 | 0.28 | 0.02 >1 |
| Example 259 | 0.11 | 0.021 >1 | Example 260 | 39% @ 0.3 µM | |
| Example 261 | 0.16 | 0.0091 >1 | Example 262 | 32% @ 0.1 µM | 0.0085 >1 |
| Example 263 | 0.11 | 0.004 79 | Example 264 | 0.61 | |
| Example 265 | 0.13 | 0.025 >3 | Example 266 | 1.1 | |
| Example 267 | 0.085 | 0.005 >3 | Example 268 | 0.19 | 0.016 |
| Example 269 | 1.1 | 0.07 >3 | Example 270 | 0.18 | 0.006 >3 |
| Example 271 | 1.1 | | Example 272 | 43% @ 3 µM | |
| Example 273 | 0.14 | 0.027 >3 | Example 274 | 0.56 | |
| Example 275 | 0.13 | 0.0067 >3 | Example 276 | 0.11 | 0.027 >3 |
| Example 277 | 0.73 | | Example 278 | 0.50 | 0.027 >3 |
| Example 279 | 0.39 | | Example 280 | 0.30 | 0.025 >3 |
| Example 281 | 0.45 | | Example 282 | 65% @ 0.01 µM | 3.2 |
| Example 284 | 2.7 | | Example 285 | 2.0 | |
| Example 286 | 0.13 | | Example 287 | 0.14 | |
| Example 288 | 1.4 | | Example 289 | 2.4 | |
| Example 290 | 14 | | Example 291 | 51% @ 3 µM | |
| Example 292 | 4% @ 10 µM | | Example 293 | 11% @ 10 µM | |
| Example 294 | 0.41 | | Example 295 | 38% @ 3 µM | |
| Example 296 | 13 | | Example 297 | 0.15 | |
| Example 298 | 0.064 | | Example 299 | 32% @ 10 µM | |
| Example 300 | 48% @ 30 µM | | Example 301 | 65% @ 10 µM | |
| Example 302 | 1.3 | | Example 303 | 0.065 | |
| Example 304 | 4.7 | | Example 305 | 1.1 | |
| Example 306 | 59% @ 100 µM | | Example 307 | 0.34 | |

Example C

Figure 1B:
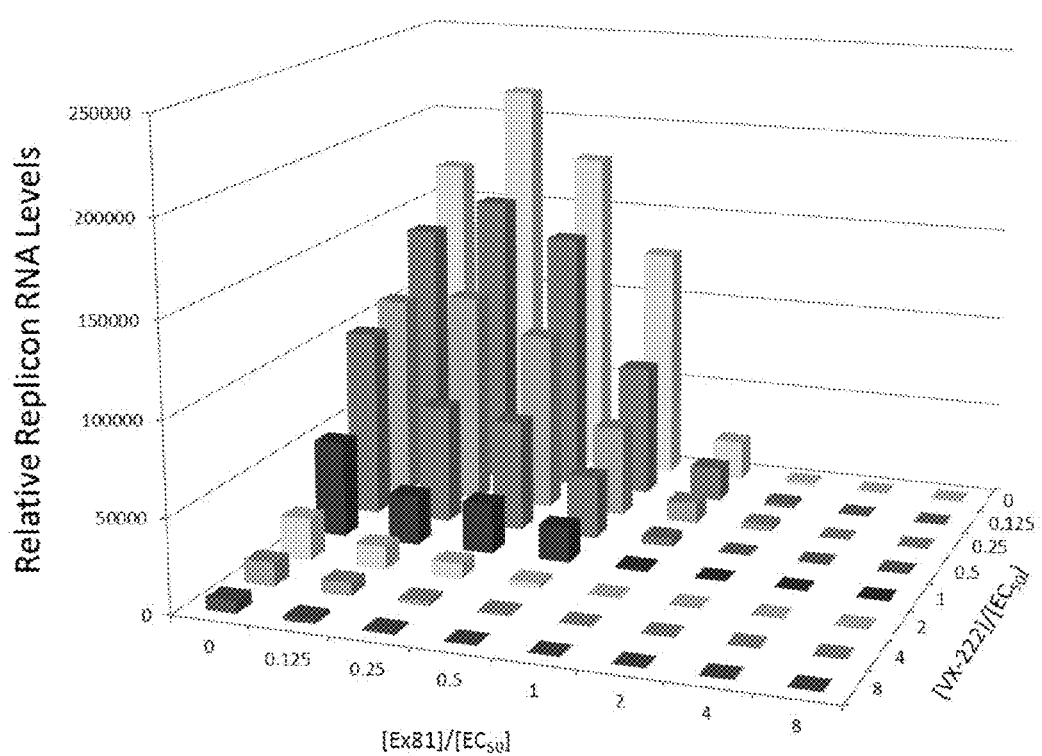

Biological Activities of Combinations of Compounds of the Invention with Other Active Agents The replicon assay described in Example B above was used to determine the reduction in HCV RNA load arising from the use of combinations of compounds of the invention with other active agents. The methods used differed from those set out in Example B only with regard to the compound concentrations tested, where the tested compounds were combined in an 8×8 matrix array using concentrations of 0, 0.125, 0.25, 0.5, 1.0, 2.0, 4.0, and 8.0× the pre-determined $EC_{50}$ of each respective compound tested. The $EC_{50}$s of the compound of Example 81, telaprevir and VX-222 were set as 20 nM, 30 nM, 1.0 nM, and 3.0 nM respectively, in line with previous observations. Lower luminescence values, as a read-out for lower HCV replicon RNA levels were observed in a dose dependent fashion for all of the HCV inhibitors in combination with APHIs tested here (FIG. 1a-b). Synergy plots generated from this data using the Bliss Independence Model also demonstrated additivity or synergy for all compound combinations tested.

The existence of compound resistant HCV replicon quasispecies was analysed using colony forming assays, where the emergence of compound resistant HCV replicon variants can allow production sufficient replicon encoded neomycin for cellular survival in medium containing 1 mg/ml geneticin (Life Technologies). 4,000 replicon bearing cells were plated/well on 12 well plates, and allowed to adhere overnight. The compound of Example 84 ($EC_{50}$=6.0 nM) and either telaprevir or VX-222 were combined in 4×3 arrays using concentrations of 0, 2.5, 5.0 and 10.0× the predetermined $EC_{50}$ of the compound of Example 84 and 0, 2.5 and 5.0 0× the predetermined $EC_{50}$ of the telaprevir or VX-222 at 0.1% DMSO final concentration. The medium used also contained 1 mg/ml geneticin. Plates were then incubated at 37° C. in an atmosphere of 5% CO2 and air for 24 days the medium/compound solution with 1 mg/ml gentamicin was replaced twice every 7 days, before staining surviving colonies with coomasie blue. The emergence of compound resistant colonies was prevented by the compound of Example 84 but was more efficiently eliminated with combinations of the compound of Example 84 and telaprevir or VX-222.

Example D

HCV Helicase Assay

The HCV NS3 NTPase/helicase functions have been extensively studied and are considered as potential targets for antiviral therapy: see for example the many references listed in the introductory section of this application. Therefore, the activity of the compounds of the invention as anti-HCV agents was assessed using an HCV helicase assay.

The helicase assay used is based on the method of Boguszewka-Chachulska, (Febs Letters 567 (2004) 253-258). The assay utilises a DNA substrate, labelled on the 5' end with Cy3 (Cy3-TAGTACCGCCACCCTCAGAAC-CTTTTTTTTTTTTT) annealed to a DNA oligo labelled on the 3' end with Black Hole Quencher (GGTTCTGAGGGTG-GCGGTACTA-BHQ-2). When the labelled strands are separated, the fluorescence increases and the free quencher strand is prevented from re-annealing by binding to a complementary capture strand (TAGTACCGCCACCCTCAGAACC). Each well contains 50 nM HCV NS3 enzyme, 0.25 nM Fluorescence quench annealed DNA oligos, 3.125 uM Capture strand, 2 mM ATP in a buffer containing 30 mM Tris, pH7.5, 10 mM MnCl2, 0.1% Tween 20, 5% glycerol, 0.05% sodium azide. Fluorescence is continuously monitored at 580 nm after excitation at 550 nm.

Functional complex formation assays between the full length protease-helicase and RNA duplex substrates can also be performed by the method described by Ding et al. (Ding, S. C., et al. (2011) *J. Virol.* 85(9), 4343-4353).

Example E

Pharmaceutical Formulations (i) Tablet Formulation

A tablet composition containing a compound of the formula (0) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (0) with 100 mg lactose and optionally 1% by weight of magnesium stearate and filling the resulting mixture into standard opaque hard gelatin capsules.

(iii) Injectable Formulation I

A parenteral composition for administration by injection can be prepared by dissolving a compound of the formula (0) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (0) (e.g. in salt form) (2 mg/ml) and mannitol (50 mg/ml), sterile filtering the solution and filling into sealable 1 ml vials or ampoules.

v) Injectable formulation III

A formulation for i.v. delivery by injection or infusion can be prepared by dissolving the compound of formula (0) (e.g. in a salt form) in water at 20 mg/ml. The vial is then sealed and sterilised by autoclaving.

vi) Injectable formulation IV

A formulation for i.v. delivery by injection or infusion can be prepared by dissolving the compound of formula (0) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (0) with pharmaceutical grade corn oil to give a concentration of 5 mg/ml. The composition is sterilised and filled into a suitable container.

viii) Lyophilised Formulation

Aliquots of formulated compound of formula (0) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

Equivalents

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:
1. A compound of the formula (1):

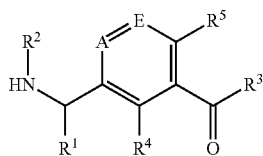

or a salt, N-oxide, tautomer or stereoisomer thereof, wherein:
A is CH;
E is CH;
$R^1$ is selected from;
  an acyclic $C_{1-8}$ hydrocarbon group optionally substituted with one or two substituents $R^6$, wherein one carbon atom of the acyclic $C_{1-8}$ hydrocarbon group may optionally be replaced by a heteroatom or group selected from O, S, $NR^c$, S(O) and $SO_2$, or two adjacent carbon atoms of the acyclic $C_{1-8}$ hydrocarbon group may optionally be replaced by a group selected from $CONR^c$, $NR^cCO$, $NR^cSO_2$ and $SO_2NR^c$ provided that in each case at least one carbon atom of the acyclic $C_{1-8}$ hydrocarbon group remains; and
  a monocyclic carbocyclic or heterocyclic group of 3 to 7 ring members, of which 0, 1, 2, 3 or 4 are heteroatom ring members selected from O, N and S, the carbocyclic or heterocyclic group being optionally substituted with one or two substituents $R^{7a}$;
$R^2$ is $X—R^8$;
X is a $C_{1-8}$ alkanediyl group wherein one carbon atom of the $C_{1-8}$ alkanediyl group may optionally be bonded to a —$CH_2$—$CH_2$— moiety to form a cyclopropane-1,1-diyl group or two adjacent carbon atoms of the $C_{1-8}$ alkanediyl group may optionally be bonded to a —$(CH_2)_n$— moiety, where n is 1 to 5, to form a $C_{3-7}$-cycloalkane-1,2-diyl group;
$R^3$ is a 3- to 10-membered monocyclic or bicyclic carbocyclic or heterocyclic ring containing 0, 1, 2 or 3 heteroatom ring members selected from N, O and S, and being optionally substituted with one or more substituents $R^{13}$;
$R^4$ is selected from hydrogen and a substituent $R^{4a}$;
$R^{4a}$ is selected from halogen; cyano; $C_{1-4}$ alkyl optionally substituted with one or more fluorine atoms; $C_{1-4}$ alkoxy optionally substituted with one or more fluorine atoms; hydroxy-$C_{1-4}$ alkyl; and $C_{1-2}$ alkoxy-$C_{1-4}$ alkyl;
$R^5$ is selected from hydrogen and a substituent $R^{5a}$;
$R^{5a}$ is selected from $C_{1-2}$ alkyl optionally substituted with one or more fluorine atoms; $C_{1-3}$ alkoxy optionally substituted with one or more fluorine atoms; halogen; cyclopropyl; and cyano;
$R^6$ is selected from hydroxy; fluorine; carbamoyl; mono- or di-$C_{1-4}$ alkylcarbamoyl; nitro; amino; mono- or di-$C_{1-4}$ alkylamino; a monocyclic carbocyclic or heterocyclic group of 3 to 7 ring members, of which 0, 1 or 2 are heteroatom ring members selected from O, N and S, the carbocyclic or heterocyclic group being optionally substituted with one or two substituents $R^{7b}$;
$R^{7a}$ and $R^{7b}$ are each independently selected from (=O); (=S); amino; halogen; cyano; hydroxy; $C_{1-4}$ alkyl; hydroxy-$C_{1-4}$ alkyl; amino-$C_{1-4}$ alkyl; mono- and di-$C_{1-4}$ alkylamino-$C_{1-4}$ alkyl;
$R^8$ is selected from a hydroxy group and C(=O)$NR^{10}R^{11}$; provided that when $R^8$ is hydroxy, there are at least two carbon atoms in line between the hydroxy group and the nitrogen atom to which X is attached;
$R^{10}$ is selected from hydrogen and $C_{1-4}$ alkyl;
$R^{11}$ is selected from hydrogen; amino-$C_{2-4}$ alkyl and hydroxy-$C_{2-4}$ alkyl;
$R^{13}$ is selected from halogen; cyano; (=O); (=S); nitro; CH=NOH; and a group $R^a$-$R^b$;
$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$;
$R^b$ is hydrogen; a cyclic group $R^d$; or an acyclic $C_{1-8}$ hydrocarbon group optionally substituted with one or more substituents selected from hydroxy, oxo, halogen, cyano, nitro, carboxy, amino, mono- or di-$C_{1-4}$ alkylamino, and a cyclic group $R^d$; wherein one or two but not all of the carbon atoms of the acyclic $C_{1-8}$ hydrocarbon group may optionally be replaced by O, S, SO, $SO_2$, $NR^c$, $X^1C(X^2)$, $C(X^2)X^1$ or $X^1C(X^2)X^1$; $SO_2NR^c$ or $NR^cSO_2$;
the cyclic group $R^d$ is a monocyclic carbocyclic or heterocyclic group having from 3 to 7 ring members, of which 0, 1, 2 or 3 are heteroatom ring members selected from O, N and S and oxidised forms thereof, the carbocyclic or heterocyclic group being optionally substituted with one or more substituents selected from $R^{14}$;
$R^{14}$ is selected from oxo; halogen; cyano; and $R^a$—$R^e$;
$R^e$ is hydrogen or an acyclic $C_{1-8}$ hydrocarbon group optionally substituted with one or more substituents selected from phenyl; hydroxy; oxo; halogen; cyano; carboxy; amino; mono- or di-$C_{1-4}$ alkylamino; wherein one or two but not all of the carbon atoms of the acyclic $C_{1-8}$ hydrocarbon group may optionally be replaced by O, S, SO, $SO_2$, $NR^c$, $X^1C(X^2)$, $C(X^2)X^1$ or $X^1C(X^2)X^1$; $SO_2NR^c$ or $NR^cSO_2$;
$X^1$ is O or $NR^c$;
$X^2$ is =O or =$NR^c$; and
$R^c$ is hydrogen or $C_{1-4}$ alkyl;
but excluding the compounds 1-(3-benzoylphenyl)-ethylamine and 1-(3-furan-2-oylcarbonylphenyl)-ethylamine.

2. A compound according to claim 1, or a salt, N-oxide, tautomer or stereoisomer thereof, wherein X is a group AA:

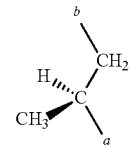

AA where "b" is the point of attachment to $R^8$ and "a" is the point of attachment to the benzylic nitrogen atom.

3. A compound according to claim 1, or a salt, N-oxide, tautomer or stereoisomer thereof, wherein $R^8$ is C(=O)$NH_2$.

4. A compound according to claim 1, or a salt, N-oxide, tautomer or stereoisomer thereof, wherein $R^1$ is ethyl or cyclopropyl.

5. A compound according to claim 1, or a salt, N-oxide, tautomer or stereoisomer thereof, wherein $R^3$ is selected from phenyl and pyridyl each optionally substituted with one or more substituents $R^{13}$.

6. A compound according to claim 1, or a salt, N-oxide, tautomer or stereoisomer thereof, wherein $R^{13}$ is amino.

7. A compound according to claim 1 having the isomeric form (1a):

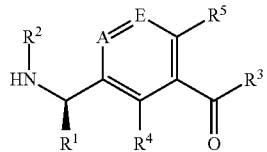

(1a)

or a salt, N-oxide or tautomer thereof, wherein:
- $R^1$ is ethyl or cyclopropyl;
- $R^2$ is X—$R^8$; wherein X is —*CH(CH$_3$)CH$_2$— and the asterisk denotes a chiral centre which is in the S-configuration;
- $R^8$ is C(=O)NR$^{10}$R$^{11}$ where $R^{10}$ and $R^{11}$ are both hydrogen;
- $R^4$ is fluorine;
- $R^5$ is chlorine; and
- $R^3$ is pyridyl substituted with one substituent which is an NH$_2$ group.

8. A compound according to claim 1 having the formula (7):

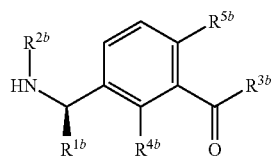

(7)

or a salt, N-oxide or tautomer or stereoisomer thereof, wherein:
- $R^{1b}$ is selected from $C_{1-4}$ alkyl, allyl and cyclopropyl;
- $R^{2b}$ is a group $X^b$—$R^{8b}$;
- $X^b$ is a $C_{1-5}$ alkanediyl group wherein one carbon atom of the $C_{1-4}$ alkanediyl group may optionally be bonded to a —CH$_2$—CH$_2$— moiety to form a cyclopropane-1,1-diyl group or two adjacent carbon atoms of the $C_{1-4}$ alkanediyl group may optionally be bonded to a —CH$_2$—CH$_2$—CH$_2$— moiety to form a cyclopentane-1,2-diyl group;
- $R^{3b}$ is a carbocyclic or heterocyclic ring selected from phenyl, pyridyl, 1-oxypyridyl, pyridonyl, pyrazinyl, pyrimidinyl, pyridazinyl, pyrazolyl, isothiazolyl, thiazolyl, isoxazolyl, pyrido-oxazinonyl and dihydrobenzoxazinyl, each being optionally substituted with one or more substituents $R^{13b}$;
- $R^{4b}$ is halogen;
- $R^{5b}$ is selected from halogen; $C_{1-2}$alkyl; $C_{1-2}$alkoxy; difluoromethoxy; trifluoromethoxy;
- $R^{8b}$ is selected from hydroxy and C(=O)NHR$^{11b}$; provided that when $R^{8b}$ is hydroxy, there are at least two carbon atoms in line between the hydroxy group and the nitrogen atom to which $X^b$ is attached;
- $R^{11b}$ is selected from hydrogen and amino-$C_{2-4}$ alkyl; and
- $R^{13b}$ is selected from halogen, cyano; hydroxy, $C_{1-4}$ alkyl, oxo, $C_{1-4}$alkoxy, hydroxy-$C_{1-4}$ alkyl, $C_{1-4}$acyloxy-$C_{1-4}$ alkyl, $C_{1-4}$ alkylsulfanyl, amino, mono-$C_{1-4}$ alkylamino, di-$C_{1-4}$ alkylamino, pyrazolyl, $C_{1-4}$ alkoxycarbonylpyrazolyl, hydroxy-$C_{1-4}$ alkyl-pyrazolyl, carboxy and, carbamoyl.

9. A compound according to claim 1 having the formula (8):

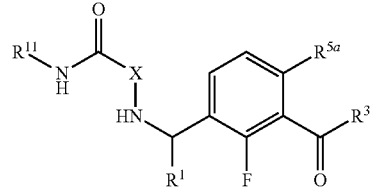

(8)

or a salt, N-oxide, tautomer or stereoisomer thereof, wherein:
- $R^{11}$ is selected from hydrogen, amino-$C_{2-4}$alkyl and hydroxy-$C_{2-4}$alkyl;
- X is selected from —(CH$_2$)$_p$—, —(CH$_2$)$_q$—CH(Alk)-(CH$_2$)$_r$—, —CH(Alk)-W—, —(CH$_2$)$_r$—C(CH$_3$)$_2$—(CH$_2$)$_t$- and —(CH$_2$)$_r$—W—(CH$_2$)$_u$—, where W is a cyclopropane-1,1-diyl group or cyclopentane-1,2-diyl group; each Alk is independently selected from methyl, ethyl and isopropyl; p is 1, 2 or 3; q is 0 or 1; r is 0 or 1; t is 0 or 1 and u is 0 or 1; provided that the total number of carbon atoms contained within X, excluding two of the carbon atoms of any cyclopropane-1,1-diyl group or cyclopentane-1,2-diyl group present, does not exceed 8;
- $R^1$ is selected from ethyl, propyl, cyclopropyl, cyclopropylmethyl and prop-2-en-1-yl;
- $R^{5a}$ is selected from fluorine, chlorine, methyl and methoxy;
- $R^3$ is selected from phenyl, pyridyl, pyrazinyl, pyrimidinyl, isoxazolyl, isothiazolyl, pyrazolyl, 3,4-dihydro-pyrido-oxazine and 3,4-dihydrobenzoxazine, each being unsubstituted or substituted with one or two substituents $R^{13}$; and
- $R^{13}$ is selected from halogen, cyano, hydroxy, $C_{1-4}$alkoxy, $C_{1-4}$ alkyl, hydroxy-$C_{1-4}$ alkyl, amino, mono-$C_{1-4}$ alkylamino, alkylamino, oxo, oxido, pyrazolyl, hydroxy-$C_{1-4}$ alkyl-pyrazolyl, carboxy and carbamoyl.

10. A compound according to claim 1 having the formula (9):

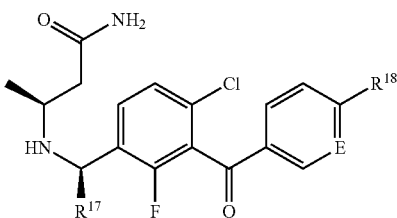

(9)

or a salt, N-oxide, tautomer or stereoisomer thereof, wherein $R^{17}$ is selected from ethyl and cyclopropyl; $R^{18}$ is selected from amino and hydroxymethyl; E is N or C—$R^{19}$; and $R^{19}$ is selected from hydrogen, methyl and chlorine.

11. A compound according to claim 1 which is selected from:
- (3S)-3-{[(R)-(4-chloro-2-fluoro-3-{[4-(hydroxyl-methyl)phenyl]-carbonyl}phenyl)(cyclo-propyl)-methyl]amino}butanamide;
- (3S)-3-{[(1R)-1-(3-benzoyl-4-chloro-2-fluorophenyl)propyl]amino}butanamide;

(3S)-3-{[(1R)-1-{3-[(6-aminopyridin-3-yl)carbonyl]-4-chloro-2-fluorophenyl}propyl]-amino}butanamide;

(3S)-3-{[(R)-{3-[(6-aminopyridin-3-yl)carbonyl]-4-chloro-2-fluorophenyl}(cyclopropyl)-methyl]amino}butanamide;

(3S)-3-{[(R)-{3-[(4-amino-3-chlorophenyl)carbonyl]-4-chloro-2-fluorophenyl}-(cyclopropyl)methyl]-amino}butanamide; and (3S)-3-{[(R)-{3-[(4-amino-3-methylphenyl)carbonyl]-4-chloro-2-fluorophenyl}-(cyclopropyl)methyl]-amino}butanamide; and salts thereof.

12. A pharmaceutical composition comprising a compound as defined in claim 1, or a salt, N-oxide, tautomer or stereoisomer thereof, and a pharmaceutically acceptable excipient.

13. A combination of a compound as defined in claim 1, or a salt, N-oxide, tautomer or stereoisomer thereof, and a further anti-hepatitis C virus agent.

14. A combination of a compound according to claim 1, or a salt, N-oxide, tautomer or stereoisomer thereof, with at least one other therapeutic agent selected from (a) interferons; (b) ribavirin and analogues thereof; (c) other HCV NS3 protease inhibitors; (d) alpha-glucosidase 1 inhibitors; (e) hepatoprotectants; (f) nucleoside or nucleotide inhibitors of HCV NS5B polymerase; (g) non-nucleoside inhibitors of HCV NS5B polymerase; (h) HCV NS5A inhibitors; (i) TLR-7 agonists; (j) cyclophillin inhibitors; (k) HCV IRES inhibitors; (I) pharmacokinetic enhancers; (m) immunoglobulins; (n) immunomodulators; (o) anti-inflammatory agents; (p) antibiotics; (q) HCV NS3 helicase inhibitors; (r) HCV NS4a antagonists; (s) HCV NS4b binding inhibitors; (t) HCV p7 inhibitors; (u) HCV core inhibitors; and (v) HCV entry inhibitors; (w) diacylglycerol acyltransferase type 1 inhibitors (DGAT-1).

15. A combination of a compound according to claim 1, or a salt, N-oxide, tautomer or stereoisomer thereof, with an anti-cancer drug effective in treating hepatocellular carcinoma.

16. A method for the preparation of a compound of the formula (1) as defined in claim 1, or a salt, N-oxide, tautomer or stereoisomer thereof, which method comprises:

(a) when it is required to prepare an intermediate of a compound of the formula (1), wherein, in the intermediate, $R^2$ is hydrogen, the reaction of a compound of the formula (10):

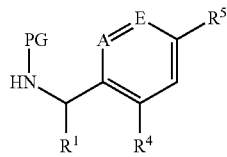

(10)

where PG is a protecting group such as a tert-butyloxycarbonyl (Boc) group, with a basic reagent such as an alkyl lithium (e.g. butyl lithium), followed by reaction with a compound of the formula $R^3$—C(=O)-LG, where LG is a leaving group such as a methoxy or ethoxy group or chloride (i.e. acid chloride), to give a compound of the formula: (11)

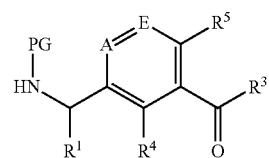

(11)

and thereafter removing the protecting group PG; or (b) when it is required to prepare an intermediate of a compound of the formula (1) wherein, in the intermediate, $R^2$ is hydrogen, the oxidation of a compound of the formula (30):

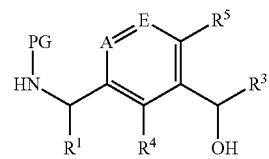

(30)

with a suitable oxidising agent such as manganese dioxide or Dess-Martin periodinane, and thereafter removing the protecting group PG; or (c) when it is required to prepare a compound of the formula (1) wherein $R^3$ is an aminopyridine or aminopyrazine, the reaction of a compound of the formula (31), (32), (33), (34) or (35):

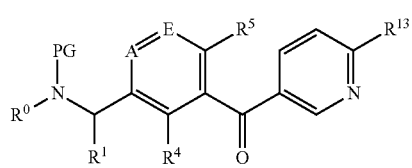

(31)

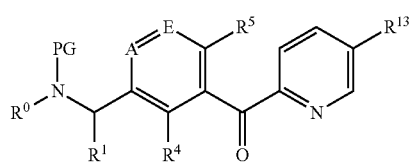

(32)

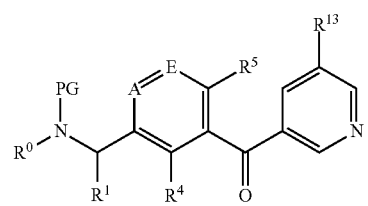

(33)

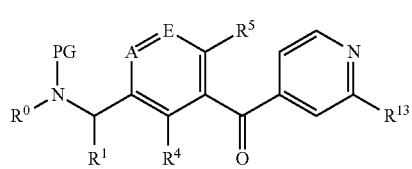

(34)

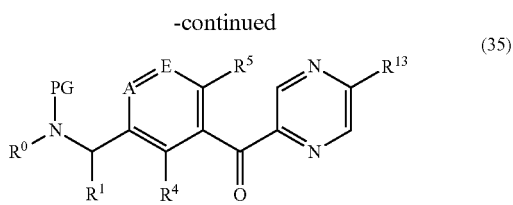

(35)

wherein $R^0$ is hydrogen and $R^{13}$ is bromine or chlorine, with ammonia to give the corresponding compound wherein $R^{13}$ is amino; or (d) when it is required to prepare a compound of the formula (1) wherein $R^2$ is $X$—$R^8$, the reaction of an intermediate compound of formula (1) wherein $R^2$ is hydrogen with an alkylating agent of the formula $LG^1$-$X$—$R^8$, where $LG^1$ is a leaving group, typically in the presence of a base; or (e) when it is required to prepare a compound of the formula (1) wherein $R^2$ is $X$—$R^8$, the reaction of an intermediate compound of formula (1) wherein $R^2$ is hydrogen with an aldehyde or ketone $X''$—$C(\!=\!O)$—$X'$—$R^8$ where $X''$ and $X'$ are residues of the group $X$; in the presence of a reducing agent; or (f) when it is required to prepare a compound of the formula (1) wherein $R^8$ is $C(\!=\!O)NR^{10}R^{11}$, the reaction of an intermediate compound of formula (1) wherein $R^2$ is hydrogen with a compound $X'''$—$C(\!=\!O)NR^{10}R^{11}$ or $X'''$—$C(\!=\!O)M^a$ wherein $M^a$ is a masked amino group or an amino group precursor and $X'''$ contains a double bond conjugated with the carbonyl group of $C(\!=\!O)NR^{10}R^{11}$; or (g) when it is required to prepare a compound of the formula (1) wherein $R^2$ is $X$—$R^8$ and $R^8$ is $C(\!=\!O)NR^{10}R^{11}$, the reaction of a precursor compound containing a group $X$—$R^{8prec}$ wherein $R^{8prec}$ is a precursor group of $C(\!=\!O)NR^{10}R^{11}$ (such as a carboxylic acid group, or cyano group or ester group) with a reagent suitable for converting $R^{8prec}$ into a group $C(\!=\!O)NR^{10}R^{11}$; and thereafter removing any protecting group PG still present; and (h) optionally converting one compound of the formula (1) to another compound of the formula (1).

17. A compound of the formula (1) as defined in claim 1 which is in the form of a salt.

18. A method of treating a hepatitis C virus infection in a subject, which method comprises administering to the subject an effective anti-hepatitis C viral amount of a compound of the formula (1) as defined in claim 1, or a salt, N-oxide, tautomer or stereoisomer thereof.

* * * * *